US007834156B2

(12) United States Patent
Faris et al.

(10) Patent No.: US 7,834,156 B2
(45) Date of Patent: Nov. 16, 2010

(54) 125P5C8: TISSUE SPECIFIC PROTEIN HIGHLY EXPRESSED IN VARIOUS CANCERS

(75) Inventors: Mary Faris, Los Angeles, CA (US); Pia M. Challita-Eid, Encino, CA (US); Steve Chappell Mitchell, Gurnee, IL (US); Daniel E. H. Afar, Fremont, CA (US); Arthur B. Raitano, Los Angeles, CA (US); Aya Jakobovits, Beverly Hills, CA (US)

(73) Assignee: Agensys, Inc., Santa Monica, CA (US)

( * ) Notice: Subject to any disclaimer, the term of this patent is extended or adjusted under 35 U.S.C. 154(b) by 0 days.

(21) Appl. No.: 11/857,405

(22) Filed: Sep. 18, 2007

(65) Prior Publication Data

US 2008/0193458 A1     Aug. 14, 2008

Related U.S. Application Data

(62) Division of application No. 09/809,638, filed on Mar. 14, 2001, now Pat. No. 7,271,240.

(51) Int. Cl.
C07K 1/00 (2006.01)
C07K 14/00 (2006.01)
C07K 16/00 (2006.01)
A61K 35/14 (2006.01)
A61K 36/16 (2006.01)
C12P 21/08 (2006.01)

(52) U.S. Cl. ............... 530/387.9; 530/350; 530/380; 530/386; 530/387.1; 530/387.3; 530/388.1; 530/388.8; 530/391.3; 530/391.7

(58) Field of Classification Search .................. None
See application file for complete search history.

(56) References Cited

U.S. PATENT DOCUMENTS

| 6,783,969 | B1 | 8/2004 | Tang et al. | |
| 2003/0235820 | A1* | 12/2003 | Mack et al. | 435/6 |

FOREIGN PATENT DOCUMENTS

| GB | 2211504 | 7/1989 |
| WO | WO-01/75067 | 10/2001 |
| WO | WO-01/94629 | 12/2001 |
| WO | WO-02/10449 | 2/2002 |
| WO | WO-02/26982 | 4/2002 |
| WO | WO-02/36167 | 5/2002 |
| WO | WO-02/055700 | 7/2002 |
| WO | WO-02/068677 | 9/2002 |
| WO | WO-02/070539 | 9/2002 |
| WO | WO-02/072785 | 9/2002 |
| WO | WO-03/050236 | 6/2003 |

OTHER PUBLICATIONS

GenCore databases, Amino acid and nucleic acid databases, SEQ ID No. 1 and 2, Accession Nos. Q9H720 and AK025164, ten sheets. Mar. 2001 and Sep. 2000.*

Abdel-Malek, J. Cell Physiol. (1988) 136:247.
Abe and Saito, J. Neurochem. (2001) 76:217-223.
Alberts et al., Molecular Biology of the Cell, 3rd edition, Garland Publishing, Inc. (1994) p. 465.
Batra et al., Prostate. (1991) 19:299.
Chen, Current Opinion in Immunology (1999) 11(2):219-222.
Craft et al., Cancer Res. (1999) 59:5030-5036.
Database Uniprot, Accession No. Q9H720 (Mar. 2001).
Davies et al., Science (2000) 290:2295.
Filetti et al., Eur. J. Endocrinol. (1999) 141:443.
Fu et al., EMBO Journal (1996) 15:4392-4401.
Fu et al., Int. J. Cancer (1992) 52(6):987-990.
GenCore databases, Accession No. Q9H720 and AK025164, Mar. 2001 and Sep. 2000.
Gergely et al., Clin. Diagn. Lab. Mannual (1997) 4:70.
Greenbaum et al., Genome Biology (2003) 4(9):117.1-117.8.
Hollo et al., Biochimica et Biophysica Acta (1994) 1191:384.
Howell, Molecular Urology (1999) 3(3):295-302.
Hubert et al., Proc. Natl. Acad. Sci. USA (1999) 96(25):14523-14528.
Ivanov and Ronai, Oncogene (2000) 19:3003.
Jain, Cancer and Metastasis Reviews (1990) 9:253-266.
Janulis et al., J. Biol. Chem. (1999) 274:801.
Kaighn et al., Invest. Urol. (1979) 17(1):16-23.
Klein et al., Nature Med. (1997) 3:402-408.
Krueger et al., Cancer Res. (1999) 59:6010.
Kubota, J. Cell Biochem. (1994) 56(1):4-8.
Lazar et al., Molecular and Cellular Biology (1988) 8(3):1247-1252.
Leith et al., Blood (1995) 86:2329.
Lewin, Genes VI, Oxford University Press, Inc., New York (1997) Chapter 29.
Linsley et al., J. Exp. Med. (1991) 174:561-566.
Mallampalli et al., Biochem. J. (1996) 318:333-341.
McNeil, JNCI 90(12):882-883, Jun. 17, 1998.
Mirza et al. Cell Growth Differ. (2000) 11:279.
Morton and Myszka, Methods in Enzymology (1998) 295:268.
Musil et al., J. Biol. Chem. (2000) 275:25207.
Pemberton et al., J. of Histochemistry and Cytochemistry (1997) 45:1697-1706.
Pinto et al., Clin. Cancer Res. (1996) 2(9):1445-1451.
Prewett et al., Clinical Cancer Research (1998) 4:2957-2966.
Reiter et al., PNAS USA (1998) 95:1735.
Saffran et al., PNAS (2001) 98(5):2658-2663.
Skryma et al., J. Physiol. (2000) 527:71.
Spitzweg et al., Cancer Res. (2000) 60:6526.
Storrie et al., Methods Enzymol. (1990) 182:203-225.
Su et al., PNAS USA (1996) 93:7252.

(Continued)

*Primary Examiner*—Alana M Harris
(74) *Attorney, Agent, or Firm*—Morrison & Foerster LLP

(57) ABSTRACT

A novel gene (designated 125P5C8) and its encoded protein are described. While 125P5C8 exhibits tissue specific expression in normal adult tissue, it is aberrantly expressed multiple cancers including prostate, bladder, kidney and colon cancers. Consequently, 125P5C8 provides a diagnostic and/or therapeutic target for cancers, and the 125P5C8 gene or fragment thereof, or its encoded protein or a fragment thereof used to elicit an immune response.

15 Claims, 10 Drawing Sheets

OTHER PUBLICATIONS

Supplementary Partial European Search Report for EP 02726630.3, Mailed on Jan. 10, 2007, 4 pages.
Tazebay et al., Nat. Med. (2000) 6:871.
Tockman et al., Cancer Res. (1992) 52:2711s-2718s.
Welford, Opt. Quant. Elect. (1991) 23:1.
Lu et al., Nature Biotechnology (2007) 25:117-124.
Kirkin et al., APMIS (1998) 106:665-679.
Chaux et al., Int. J. Cancer (1998) 77:538-542.
Restriction Requirement for U.S. Appl. No. 09/809,638, mailed on Jun. 6, 2002.
Amendment and Response to Restriction Requirement for U.S. Appl. No. 09/809,638, filed Aug. 6, 2002.
Restriction Requirement for U.S. Appl. No. 09/809,638, mailed on Nov. 18, 2002.
Response to Restriction Requirement and Amendment for U.S. Appl. No. 09/809,638, filed Dec. 18, 2002.
Non-Final Office Action for U.S. Appl. No. 09/809,638, mailed on Mar. 7, 2003.
Amendment and Response for U.S. Appl. No. 09/809,638, filed Jul. 11, 2003.
Non-Final Office Action for U.S. Appl. No. 09/809,638, mailed on Oct. 7, 2003.
Amendment in Response for U.S. Appl. No. 09/809,638, filed Feb. 9, 2004.
Final Office Action for U.S. Appl. No. 09/809,638, mailed on May 19, 2004.
Response to Final Office Action for U.S. Appl. No. 09/809,638, filed Jun. 10, 2004.
Non-Final Office Action for U.S. Appl. No. 09/809,638, mailed on Oct. 4, 2004.
Amendment in Response to Non-Final Office Action for U.S. Appl. No. 09/809,638, filed Dec. 7, 2004.
Final Office Action for U.S. Appl. No. 09/809,638, mailed on Feb. 16, 2005.
Amendment After Final Action for U.S. Appl. No. 09/809,638, filed Apr. 18, 2005.
Supplemental Response to Amendment After Final Action for U.S. Appl. No. 09/809,638, filed May 9, 2005.
Advisory Action for U.S. Appl. No. 09/809,638, mailed on Aug. 17, 2005.
Response to Advisory Action and Request for Continued Examination for U.S. Appl. No. 09/809,638, filed Nov. 2, 2005.
Supplemental Response for U.S. Appl. No. 09/809,638, filed Nov. 3, 2005.
Non-Final Office Action for U.S. Appl. No. 09/809,638, mailed on Jan. 3, 2006.
Response to Non-Final Office Action for U.S. Appl. No. 09/809,638, filed Mar. 15, 2006.
Final Office Action for U.S. Appl. No. 09/809,638, mailed on Aug. 4, 2006.
Amendment After Final Action for U.S. Appl. No. 09/809,638, filed Sep. 29, 2006.
Notice of Allowance for U.S. Appl. No. 09/809,638, mailed on Feb. 22, 2007.
Request for Continued Examination for U.S. Appl. No. 09/809,638, filed May 22, 2007.
Notice of Allowance for U.S. Appl. No. 09/809,638, mailed on Jun. 26, 2007.
European Office Action for EP Patent Application No. 02726630.3, mailed on Aug. 27, 2007.
Non-Final Office Action for U.S. Appl. No. 12/235,444, mailed on Mar. 6, 2009, 14 pages.

* cited by examiner

```
GATCACGTGCTGTCGATATCCTTCACATTGCCATGTTCAGTGAGCTGTAGATAATCT
CTGGAGCCAGGTGCTGAAGTGATATATCCCAGAAATATCACTTGATTAGAGCTACTT
TTCAGTAGTTTTGAAACAGCAATAGCCTGCAGTTTCCTGTCGAGGTCATCTTCGTGG
TTCCCAAAGTGTGTCACGACAAAATCCACCAGCTTGCCCGAAATGTTAACGGTCAAT
GTGATGGCTGGTGCGATCTTGCTGTGTTGGCCAGGCTGGTCTCAACGTGCAGATAGA
TC
```

Figure 1

```
       M   T   S   L   W   R   E   I   L   L   E   S   L   L   G   C   V   S
   1   ATG ACC TCG CTG TGG AGA GAA ATC CTC TTG GAG TCG CTG CTG GGA TGT GTT TCT
       W   S   L   Y   H   D   L   G   P   M   I   Y   Y   F   P   L   Q   T
  55   TGG TCT CTC TAC CAT GAC CTG GGA CCG ATG ATC TAT TAC TTT CCT TTG CAA ACA
       L   E   L   T   G   L   E   G   F   S   I   A   F   L   S   P   I   F
 109   CTA GAA CTC ACT GGG CTT GAA GGT TTT AGT ATA GCA TTT CTT TCT CCA ATA TTC
       L   T   I   T   P   F   W   K   L   V   N   K   K   W   M   L   T   L
 163   CTA ACA ATT ACT CCT TTC TGG AAA TTG GTT AAC AAG AAG TGG ATG CTA ACC CTG
       L   R   I   I   T   I   G   S   I   A   S   F   Q   A   P   N   A   K
 217   CTG AGG ATA ATC ACT ATT GGC AGC ATA GCC TCC TTC CAG GCT CCA AAT GCC AAA
       L   R   L   M   V   L   A   L   G   V   S   S   S   L   I   V   Q   A
 271   CTT CGA CTG ATG GTT CTT GCG CTT GGG GTG TCT TCC TCA CTG ATA GTG CAA GCT
       V   T   W   W   S   G   S   H   L   Q   R   Y   L   R   I   W   G   F
 325   GTG ACT TGG TGG TCG GGA AGT CAT TTG CAA AGG TAC CTC AGA ATT TGG GGA TTC
       I   L   G   Q   I   V   L   V   V   L   R   I   W   Y   T   S   L   N
 379   ATT TTA GGA CAG ATT GTT CTT GTT GTT CTA CGC ATG TAT ACT TCA CTA AAC
       P   I   W   S   Y   Q   M   S   N   K   V   I   L   T   L   S   A   I
 433   CCA ATC TGG AGT TAT CAG ATG TCC AAC AAA GTG ATA CTG ACA TTA AGT GCC ATA
       A   T   L   D   R   I   G   T   D   G   D   C   S   K   P   E   E   K
 487   GCC ACA CTT GAT CGT ATT GGC ACA GAT GGT GAC TGC AGT AAA CCT GAA GAA AAG
       K   T   G   E   V   A   T   G   M   A   S   R   P   N   W   L   L   A
 541   AAG ACT GGT GAG GTA GCC ACG GGG ATG GCC TCT AGA CCC AAC TGG CTG CTG GCA
       G   A   A   F   G   S   L   V   F   L   T   H   W   V   F   G   E   V
 595   GGG GCT GCT TTT GGT AGC CTT GTG TTC CTC ACC CAC TGG GTT TTT GGA GAA GTC
       S   L   V   S   R   W   A   V   S   G   H   P   H   P   G   P   D   P
 649   TCT CTT GTT TCC AGA TGG GCA GTG AGT GGG CAT CCA CAT CCA GGG CCA GAT CCT
       N   P   F   G   G   A   V   L   L   C   L   A   S   G   L   M   L   P
 703   AAC CCA TTT GGA GGT GCA GTA CTG CTG TGC TTG GCA AGT GGA TTG ATG CTT CCA
       S   C   L   W   F   R   G   T   G   L   I   W   W   V   T   G   T   A
 757   TCT TGT TTG TGG TTT CGT GGT ACT GGT TTG ATC TGG TGG GTT ACA GGA ACA GCT
       S   A   A   G   L   L   Y   L   H   T   W   A   A   A   V   S   G   C
 811   TCA GCT GCG GGG CTC CTT TAC CTG CAC ACA TGG GCA GCT GCT GTG TCT GGC TGT
       V   F   A   I   F   T   A   S   M   W   P   Q   T   L   G   H   L   I
 865   GTC TTC GCC ATC TTT ACT GCA TCC ATG TGG CCC CAA ACA CTT GGA CAC CTT ATT
       N   S   G   T   N   P   G   K   T   M   T   I   A   M   I   F   Y   L
 919   AAC TCA GGG ACA AAC CCT GGG AAA ACC ATG ACC ATT GCC ATG ATA TTT TAT CTT
       L   E   I   F   F   C   A   W   C   T   A   F   K   F   V   P   G   G
 973   CTA GAA ATA TTT TTC TGT GCC TGG TGC ACA GCT TTT AAG TTT GTC CCA GGA GGT
       V   Y   A   R   E   R   S   D   V   L   L   G   T   M   M   L   I   I
1027   GTC TAC GCT AGA GAA AGA TCA GAT GTG CTT TTG GGG ACA ATG ATG TTA ATT ATC
       G   L   N   M   L   F   G   P   K   K   N   L   D   L   L   L   Q   T
1081   GGG CTG AAT ATG CTA TTT GGT CCT AAG AAA AAC CTT GAC TTG CTT CTT CAA ACA
       K   N   S   S   K   V   L   F   R   K   S   E   K   Y   M   K   L   F
1135   AAA AAC AGT TCT AAA GTG CTT TTC AGA AAG AGT GAA AAA TAC ATG AAA CTT TTT
       L   W   L   L   V   G   V   G   L   L   G   L   G   R   H   K   A
1189   CTG TGG CTG CTT GTT GGT GTG GGA TTG TTG GGA TTA GGA CTA CGG CAT AAA GCC
       Y   E   R   K   L   G   K   V   A   P   T   K   E   V   S   A   A   I
1243   TAT GAG AGA AAA CTG GGC AAA GTG GCA CCA ACC AAA GAG GTC TCT GCT GCC ATC
       W   P   F   R   F   G   Y   D   N   E   G   W   S   S   L   E   R   S
1297   TGG CCT TTC AGG TTT GGA TAT GAC AAT GAA GGG TGG TCT AGT CTA GAA AGA TCA
       A   H   L   L   N   E   T   G   A   D   F   I   T   I   L   E   S   D
1351   GCT CAC CTG CTC AAT GAA ACA GGT GCA GAT TTC ATA ACA ATT TTG GAG AGT GAT
       A   S   K   P   Y   M   G   N   N   D   L   T   M   W   L   G   E   K
```

Figure 2A

```
1405    GCT TCT AAG CCC TAT ATG GGG AAC AAT GAC TTA ACC ATG TGG CTA GGG GAA AAG
         L   G   F   Y   T   D   F   G   P   S   T   R   Y   H   T   W   G   I
1459    TTG GGT TTC TAT ACA GAC TTT GGT CCA AGC ACA AGG TAT CAC ACT TGG GGG ATT
         M   A   L   S   R   Y   P   I   V   K   S   E   H   H   L   L   P   S
1513    ATG GCT TTG TCA AGA TAC CCA ATT GTG AAA TCT GAG CAT CAC CTT CTT CCG TCA
         P   E   G   E   I   A   P   A   I   T   L   T   V   N   I   S   G   K
1567    CCA GAG GGC GAG ATC GCA CCA GCC ATC ACA TTG ACC GTT AAC ATT TCG GGC AAG
         L   V   D   F   V   V   T   H   F   G   N   H   E   D   D   L   D   R
1621    CTG GTG GAT TTT GTC GTG ACA CAC TTT GGG AAC CAC GAA GAT GAC CTC GAC AGG
         K   L   Q   A   I   A   V   S   K   L   L   K   S   S   S   N   Q   V
1675    AAA CTG CAG GCT ATT GCT GTT TCA AAA CTA CTG AAA AGT AGC TCT AAT CAA GTG
         I   F   L   G   Y   I   T   S   A   P   G   S   R   D   Y   L   Q   L
1729    ATA TTT CTG GGA TAT ATC ACT TCA GCA CCT GGC TCC AGA GAT TAT CTA CAG CTC
         T   E   H   G   N   V   K   D   I   D   S   T   D   H   D   R   W   C
1783    ACT GAA CAT GGC AAT GTG AAG GAT ATC GAC AGC ACT GAT CAT GAC AGA TGG TGT
         E   Y   I   M   Y   R   G   L   I   R   L   G   Y   A   R   I   S   H
1837    GAA TAC ATT ATG TAT CGA GGG CTG ATC AGG TTG GGT TAT GCA AGA ATC TCC CAT
         A   E   L   S   D   S   E   I   Q   M   A   K   F   R   I   P   D   D
1891    GCT GAA CTG AGT GAT TCA GAA ATT CAG ATG GCA AAA TTT AGG ATC CCT GAT GAC
         P   T   N   Y   R   D   N   Q   K   V   V   I   D   H   R   E   V   S
1945    CCC ACT AAT TAT AGA GAC AAC CAG AAA GTG GTC ATA GAC CAC AGA GAA GTT TCT
         E   K   I   H   F   N   P   R   F   G   S   Y   K   E   G   H   N   Y
1999    GAG AAA ATT CAT TTT AAT CCC AGA TTT GGA TCC TAC AAA GAA GGA CAC AAT TAT
         E   N   N   H   H   F   H   M   N   T   P   K   Y   F   L   *
2053    GAA AAC AAC CAT CAT TTT CAT ATG AAT ACT CCC AAA TAC TTT TTA TGA AAC
```

Figure 2B

```
  1 MTSLWREILL ESLLGCVSWS LYHDLGPMIY YFPLQTLELT GLEGFSIAFL  50
 51 SPIFLTITPF WKLVNKKWML TLLRIITIGS IASFQAPNAK LRLMVLALGV 100
101 SSSLIVQAVT WWSGSHLQRY LRIWGFILGQ IVLVVLRIWY TSLNPIWSYQ 150
151 MSNKVILTLS AIATLDRIGT DGDCSKPEEK KTGEVATGMA SRPNWLLAGA 200
201 AFGSLVFLTH WVFGEVSLVS RWAVSGHPHP GPDPNPFGGA VLLCLASGLM 250
251 LPSCLWFRGT GLIWWVTGTA SAAGLLYLHT WAAAVSGCVF AIFTASMWPQ 300
301 TLGHLINSGT NPGKTMTIAM IFYLLEIFFC AWCTAFKFVP GGVYARERSD 350
351 VLLGTMMLII GLNMLFGPKK NLDLLLQTKN SSKVLFRKSE KYMKLFLWLL 400
401 VGVGLLGLGL RHKAYERKLG KVAPTKEVSA AIWPFRFGYD NEGWSSLERS 450
451 AHLLNETGAD FITILESDAS KPYMGNNDLT MWLGEKLGFY TDFGPSTRYH 500
501 TWGIMALSRY PIVKSEHHLL PSPEGEIAPA ITLTVNISGK LVDFVVTHFG 550
551 NHEDDLDRKL QAIAVSKLLK SSSNQVIFLG YITSAPGSRD YLQLTEHGNV 600
601 KDIDSTDHDR WCEYIMYRGL IRLGYARISH AELSDSEIQM AKFRIPDDPT 650
651 NYRDNQKVVI DHREVSEKIH FNPRFGSYKE GHNYENNHHF HMNTPKYFL  699
```

Figure 3

```
Score = 1397 bits (3615), Expect = 0.0
Identities = 682/699 (97%), Positives = 683/699 (97%)

Query: 1    MTSLWREILLESLLGCVSWSLYHDLGPMIYYFPLQTLELTGLEGFSIAFLSPIFLTITPF 60
            MTSLWREILLESLLGCVSWSLYHDLGPMIYYFPLQTLELTGLEGFSIAFLSPIFLTITPF
Sbjct: 1    MTSLWREILLESLLGCVSWSLYHDLGPMIYYFPLQTLELTGLEGFSIAFLSPIFLTITPF 60

Query: 61   WKLVNKKWMLTLLRIITIGSIASFQAPNAKLRLMVLALGVSSSLIVQAVTWWSGSHLQRY 120
            WKLVNKKWMLTLLRIITIGSIASFQAPNAKLRLMVLALGVSSSLIVQAVTWWSGSHLQRY
Sbjct: 61   WKLVNKKWMLTLLRIITIGSIASFQAPNAKLRLMVLALGVSSSLIVQAVTWWSGSHLQRY 120

Query: 121  LRIWGFILGQIVLVVLRIWYTSLNPIWSYQMSNKVILTLSAIATLDRIGTDGDCSKPEEK 180
            LRIWGFILGQIVLVVLRIWYTSLNPIWSYQMSNKVILTLSAIATLDRIGTDGDCSKPEEK
Sbjct: 121  LRIWGFILGQIVLVVLRIWYTSLNPIWSYQMSNKVILTLSAIATLDRIGTDGDCSKPEEK 180

Query: 181  KTGEVATGMASRPNWLLAGAAFGSLVFLTHWVFGEVSLVSRWAVSGHPHPGPDPNPFGGA 240
            KTGEVATGMASRPNWLLAGAAFGSLVFLTHWVFGEVSLVSRWAVSGHPHPGPDPNPFGGA
Sbjct: 181  KTGEVATGMASRPNWLLAGAAFGSLVFLTHWVFGEVSLVSRWAVSGHPHPGPDPNPFGGA 240

Query: 241  VLLCLASGLMLPSCLWFRGTGLIWWVTGTASAAGLLYLHTWAAAVSGCVFAIFTASMWPQ 300
            VLLCLASGLMLPSCLWFRGTGLIWWVTGTASAAGLLYLHTWAAAVSGCVFAIFTASMWPQ
Sbjct: 241  VLLCLASGLMLPSCLWFRGTGLIWWVTGTASAAGLLYLHTWAAAVSGCVFAIFTASMWPQ 300

Query: 301  TLGHLINSGTNPGKTMTIAMIFYLLEIFFCAWCTAFKFVPGGVYARERSDVLLGTMMLII 360
            TLGHLINSGTNPGKTMTIAMIFYLLEIFFCAWCTAFKFVPGGVYARERSDVLLGTMMLII
Sbjct: 301  TLGHLINSGTNPGKTMTIAMIFYLLEIFFCAWCTAFKFVPGGVYARERSDVLLGTMMLII 360

Query: 361  GLNMLFGPKKNLDLLLQTKNSSKVLFRKSEKYMKXXXXXXXXXXXXXXXXXXXRHKAYERKLG 420
            GLNMLFGPKKNLDLLLQTKNSSKVLFRKSEKYMK                   RHKAYERKLG
Sbjct: 361  GLNMLFGPKKNLDLLLQTKNSSKVLFRKSEKYMKLFWLLVGVGLLGLGLRHKAYERKLG 420

Query: 421  KVAPTKEVSAAIWPFRFGYDNEGWSSLERSAHLLNETGADFITILESDASKPYMGNNDLT 480
            KVAPTKEVSAAIWPFRFGYDNEGWSSLERSAHLLNETGADFITILESDASKPYMGNNDLT
Sbjct: 421  KVAPTKEVSAAIWPFRFGYDNEGWSSLERSAHLLNETGADFITILESDASKPYMGNNDLT 480

Query: 481  MWLGEKLGFYTDFGPSTRYHTWGIMALSRYPIVKSEHHLLPSPEGEIAPAITLTVNISGK 540
            MWLGEKLGFYTDFGPSTRYHTWGIMALSRYPIVKSEHHLLPSPEGEIAPAITLTVNISGK
Sbjct: 481  MWLGEKLGFYTDFGPSTRYHTWGIMALSRYPIVKSEHHLLPSPEGEIAPAITLTVNISGK 540

Query: 541  LVDFVVTHFGNHEDDLDRKLQAIAVSKLLKSSSNQVIFLGYITSAPGSRDYLQLTEHGNV 600
            LVDFVVTHFGNHEDDLDRKLQAIAVSKLLKSSSNQVIFLGYITSAPGSRDYLQLTEHGNV
Sbjct: 541  LVDFVVTHFGNHEDDLDRKLQAIAVSKLLKSSSNQVIFLGYITSAPGSRDYLQLTEHGNV 600

Query: 601  KDIDSTDHDRWCEYIMYRGLIRLGYARISHAELSDSEIQMAKFRIPDDPTNYRDNQKVVI 660
            KDIDSTDHDRWCEYIMYRGLIRLGYARISHAELSDSEIQMAKFRIPDDPTNYRDNQKVVI
Sbjct: 601  KDIDSTDHDRWCEYIMYRGLIRLGYARISHAELSDSEIQMAKFRIPDDPTNYRDNQKVVI 660

Query: 661  DHREVSEKIHFNPRFGSYKEGHNYENNHHFHMNTPKYFL 699
            DHREVSEKIHFNPRFGSYKEGHNYENNH+FHMNTPKYFL
Sbjct: 661  DHREVSEKIHFNPRFGSYKEGHNYENNHNFHMNTPKYFL 699
```

Figure 4A

```
Score =  261 bits (668), Expect = 1e-68
Identities = 204/705 (28%), Positives = 330/705 (45%), Gaps = 50/705 (7%)

Query:  15  GCVSWSLYHDLGPMIYYFPLQTLELTGLEGFSIAFLSPIFLTITPFWKLVNKKWMLTLLR  74
            G + WS     L   I++FPL + ++G E    + +L PIFL + PF      ++ + L
Sbjct: 279  GFLFWSNVTSLLCSIWHFPLWYMGISGYEAAILGYLGPIFLYL-PFVSEAFTQYGVLLGG 337

Query:  75  IITIGSIASFQAPNAKLRLMVLALGVSSSLIVQAVTWWSGSHLQ-RYLRIWGFILGQIVL 133
            II IG+     Q P +L + +   ++ +    VQ + + + +        W +LG +
Sbjct: 338  IIAIGAYI-VQMPELRLISVAVGTSITVATFVQNLRYITNAETSFSFALTW--LLGLVAS 394

Query: 134  VVLRIWYTSLNPIWSYQMS-----NKVILTLSAIATLDRIGTDGDCSKPEEKKTGEVATG 186
            V+L++ + + NP W           NK   L++ + + +  +       E K+ + +
Sbjct: 395  VILKMGFYTNNPTWVILDERNGGYNKTALVLTVLFGM--LSPYVNSINFEGKRNAQAKS- 451

Query: 189  MASRPNWLLAGAAFGSLVFLTHWVFGEVSLVSRWAVSGHPHP-GPDPNPFGGAVLLCLAS 247
                 AS      L      FGSL+F H +  + S    WA   G+    GP P+G  L C
Sbjct: 452  -ASLIGKLFLAVGFGSLLFGIHQLLTDSSTTIYWAWEGYNESHGPLPWPWGA--LTCTVM 508

Query: 248  GLMLPSCLWFRGTGLIWWVTGTASAAGLLY--LHTWAAAV-SGCVFAIFTASMWPQ---T 301
                     S  + F G  L+ +        S A L    + W   + G ++AI   + P
Sbjct: 509  LFASLSSVKFMGKPLVPCLLLLISTAVLSARSITQWPKYIFGGLLYAIAMLWLVPSYFSA 568

Query: 302  LGHLINSGTNPGKTMTIAMIFYLLEIFFCAWCTAFKFVPGGVYARERSDVLLGTMMLIIG 361
            LG + N             ++    Y++ +      W  A+ FVP G   RE+ + +L       I
Sbjct: 569  LGQVQNIWV-----YVLSFSVYIIFVLAHVWVVAYAFVPMGWVLREKIETVLAFSSTFII 623

Query: 362  LNMLFGPKKNLDLLLQTKNSSKVLFRKSEKYMKXXXXXXXXXXXXXXXXXRHKAYERKLGK 421
            + L    N+ L+    K    +F                            R   R G
Sbjct: 624  IGALTCKNLNIQLVTMGKKFFIYVF-------------FFAVALLSLTARFVYDIRPTGI 670

Query: 422  VAP----TKEVSAAIWPFRFGYDNEGWSSLERSAHLLNETGADFITILESDASKPYMGNN 477
              P    ++ ++A IW    FG DN+ W+S +R  +L+ +    D + +LE+D  +  MGN
Sbjct: 671  PQPYHPDSQLITAGIWTIHFGLDNDMWASEDRMINLIKDMELDVVGLLETDTQRITMGNR 730

Query: 478  DLTMWLGEKLGFYTDFGPSTRYHTWGIMALSRYPIVKSEHHLLPSPEGEIAPAITLTV-N 536
            DLT    L    Y DFGP     HTWG +  LS++PIV S HHLLPSP GE APAI  T+
Sbjct: 731  DLTSKLAHDLNMYADFGPGPNKHTWGCVLLSKFPIVNSTHHHLPSPVGELAPAIHATLQT 790

Query: 537  ISGKLVDFVVTHFGNHEDDLDRKLQAIAVSKLLKSSSNQVIFLGYITSAPGSRDY-LQLT 595
             +   LVD V H G  ED+ DR+LQ+ ++KL+ +++     I L Y+  PG  +Y ++
Sbjct: 791  YNDTLVDVFVFHSGQEEDEEDRRLQSNYMAKLMGNTTRPAILLSYLVVDPGEGNYNTYVS 850

Query: 596  EHGNVKDIDSTDHDRWCEYIMYRGLIRLGYARISHAELSDSEIQMAKFRIPDDPTNYRDN 655
            E   + DID +D DRWCEYI+YRGL R GYAR++    ++D+E+Q+   KF++    +   ++
Sbjct: 851  ETSGMHDIDPSDDDRWCEYILYRGLRRTGYARVARGTITDTELQVGKFQVLSEQA-LVEH 909

Query: 656  QKVVIDHREVSEKIHFNPRFGSYKEGHNYENNHHFHM-NTPKYFL 699
              + ++   +SE  + + +F    G  E H H+ + P+Y L
Sbjct: 910  SDSMYEYGHMSEPEYEDMKFPDKFLGEG-ERGHFYHVFDEPRYYL 953
```

Figure 4B

Figure 5
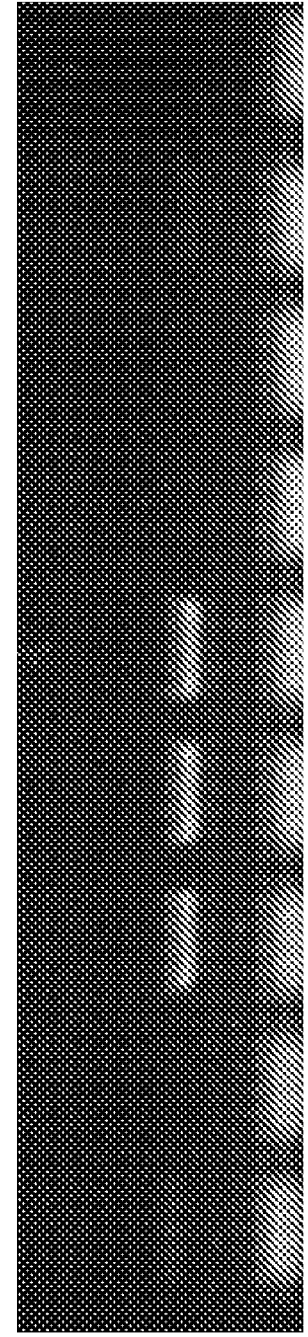
26X
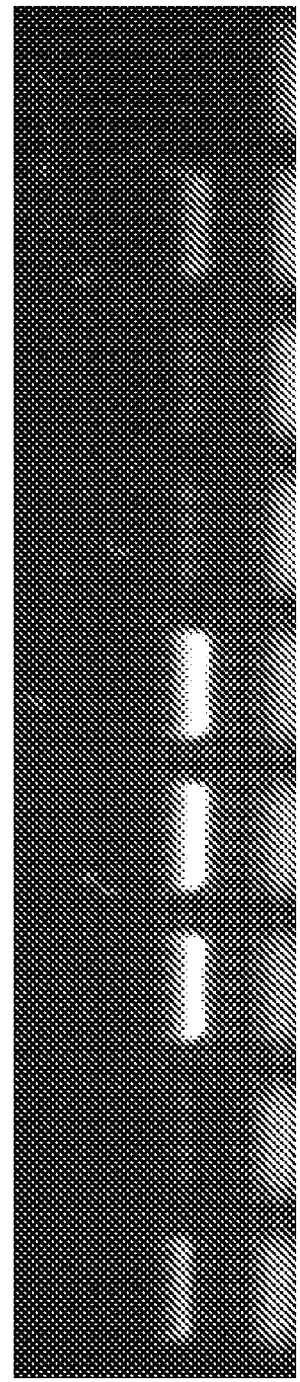
30X

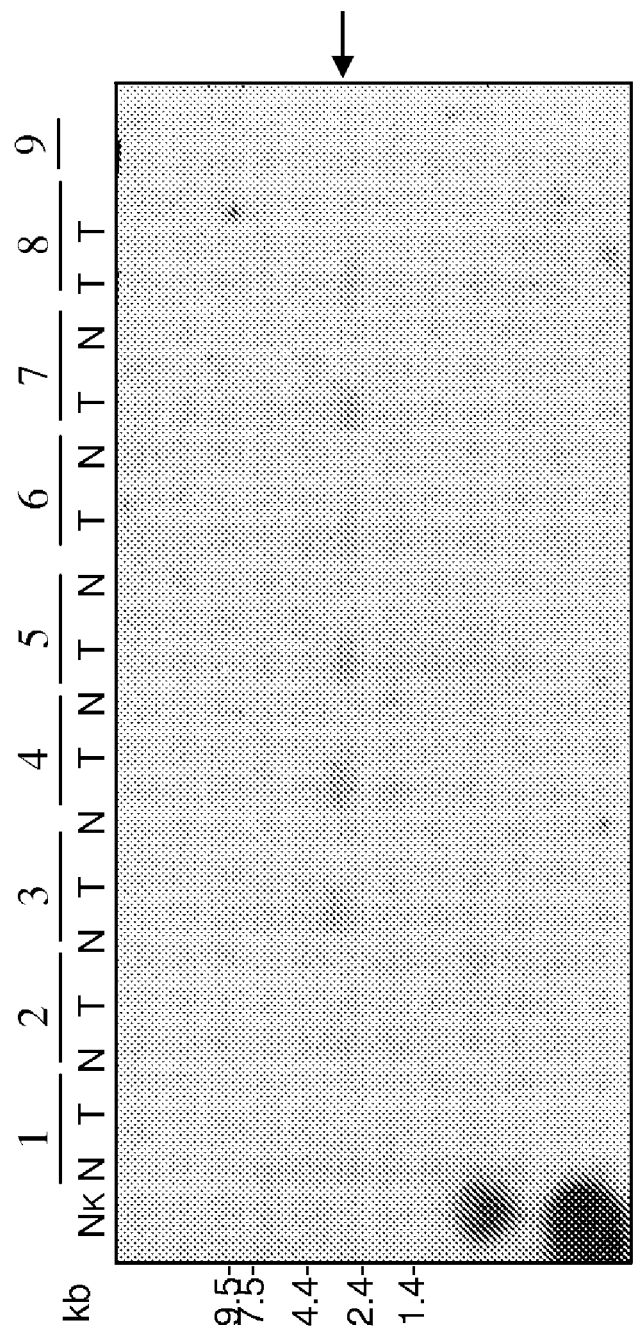

SEQUENCE LISTING

<160> NUMBER OF SEQ ID NOS: 746

<210> SEQ ID NO 1
<211> LENGTH: 2103
<212> TYPE: DNA
<213> ORGANISM: Homo sapiens

<400> SEQUENCE: 1

```
atgacctcgc tgtggagaga aatcctcttg gagtcgctgc tgggatgtgt ttcttggtct     60
ctctaccatg acctgggacc gatgatctat tactttcctt tgcaaacact agaactcact    120
gggcttgaag gttttagtat agcatttctt tctccaatat tcctaacaat tactcctttc    180
tggaaattgg ttaacaagaa gtggatgcta accctgctga ggataatcac tattggcagc    240
atagcctcct tccaggctcc aaatgccaaa cttcgactga tggttcttgc gcttggggtg    300
tcttcctcac tgatagtgca agctgtgact tggtggtcgg aagtcatttg caaaggtac    360 ctcagaattt ggggattcat tttaggacag attgttcttg ttgttctacg catatggtat    420
acttcactaa acccaatctg gagttatcag atgtccaaca aagtgatact gacattaagt    480
gccatagcca cacttgatcg tattggcaca gatggtgact gcagtaaacc tgaagaaaag    540
```

```
aagactggtg aggtagccac ggggatggcc tctagaccca actggctgct ggcagggget     600 gcttttggta gccttgtgtt cctcacccac tgggttttg gagaagtctc tcttgttttcc     660 agatgggcag tgagtgggca tccacatcca gggccagatc ctaacccatt tggaggtgca     720
gtactgctgt gcttggcaag tggattgatg cttccatctt gtttgtggtt tcgtggtact     780
ggtttgatct ggtgggttac aggaacagct tcagctgcgg ggctccttta cctgcacaca     840
tgggcagctg ctgtgtctgg ctgtgtcttc gccatcttta ctgcatccat gtggcccaa      900 acacttggac accttattaa ctcagggaca acccctggga aaaccatgac cattgccatg     960 atatttatc ttctagaaat attttttctgt gcctggtgca cagcttttaa gtttgtccca     1020
ggaggtgtct acgctagaga aagatcagat gtgcttttgg ggacaatgat gttaattatc    1080
gggctgaata tgctatttgg tcctaagaaa aaccttgact tgcttcttca aacaaaaaac    1140
agttctaaag tgcttttcag aaagagtgaa aaatacatga aactttttct gtggctgctt    1200
gttggtgtgg gattgttggg attaggacta cggcataaag cctatgagag aaaactgggc    1260
aaagtggcac caaccaaaga ggtctctgct gccatctggc ctttcaggtt tggatatgac    1320
aatgaagggt ggtctagtct agaaagatca gctcacctgc tcaatgaaac aggtgcagat    1380
ttcataacaa ttttggagag tgatgcttct aagccctata tggggaacaa tgacttaacc    1440
atgtggctag gggaaaagtt gggtttctat acagactttg gtccaagcac aaggtatcac    1500 acttgggga ttatggcttt gtcaagatac ccaattgtga atctgagca tcaccttctt     1560 ccgtcaccag agggcgagat cgcaccagcc atcacattga ccgttaacat ttcgggcaag    1620
ctggtggatt ttgtcgtgac acactttggg aaccacgaag atgacctcga caggaaactg    1680
caggctattg ctgtttcaaa actactgaaa agtagctcta atcaagtgat atttctggga    1740
tatatcactt cagcacctgg ctccagagat tatctacagc tcactgaaca tggcaatgtg    1800
aaggatatcg acagcactga tcatgacaga tggtgtgaat acattatgta tcgagggctg    1860
atcaggttgg gttatgcaag aatctcccat gctgaactga gtgattcaga aattcagatg    1920
gcaaaattta ggatccctga tgaccccact aattatagag acaaccagaa agtggtcata    1980
gaccacagag aagtttctga gaaaattcat tttaatccca gatttggatc ctacaaagaa    2040
ggacacaatt atgaaaacaa ccatcatttt catatgaata ctcccaaata cttttatga    2100 aac                                                                  2103
```

<210> SEQ ID NO 2
<211> LENGTH: 699
<212> TYPE: PRT
<213> ORGANISM: Homo sapiens

<400> SEQUENCE: 2

```
Met Thr Ser Leu Trp Arg Glu Ile Leu Leu Glu Ser Leu Leu Gly Cys
 1               5                  10                  15

Val Ser Trp Ser Leu Tyr His Asp Leu Gly Pro Met Ile Tyr Tyr Phe
             20                  25                  30

Pro Leu Gln Thr Leu Glu Leu Thr Gly Leu Glu Gly Phe Ser Ile Ala
         35                  40                  45

Phe Leu Ser Pro Ile Phe Leu Thr Ile Thr Pro Phe Trp Lys Leu Val
     50                  55                  60

Asn Lys Lys Trp Met Leu Thr Leu Leu Arg Ile Ile Thr Ile Gly Ser
 65                  70                  75                  80

Ile Ala Ser Phe Gln Ala Pro Asn Ala Lys Leu Arg Leu Met Val Leu
```

-continued

```
                85                  90                  95
Ala Leu Gly Val Ser Ser Ser Leu Ile Val Gln Ala Val Thr Trp Trp
                100                 105                 110
Ser Gly Ser His Leu Gln Arg Tyr Leu Arg Ile Trp Gly Phe Ile Leu
            115                 120                 125
Gly Gln Ile Val Leu Val Val Leu Arg Ile Trp Tyr Thr Ser Leu Asn
        130                 135                 140
Pro Ile Trp Ser Tyr Gln Met Ser Asn Lys Val Ile Leu Thr Leu Ser
145                 150                 155                 160
Ala Ile Ala Thr Leu Asp Arg Ile Gly Thr Asp Gly Asp Cys Ser Lys
                165                 170                 175
Pro Glu Glu Lys Lys Thr Gly Glu Val Ala Thr Gly Met Ala Ser Arg
            180                 185                 190
Pro Asn Trp Leu Leu Ala Gly Ala Ala Phe Gly Ser Leu Val Phe Leu
        195                 200                 205
Thr His Trp Val Phe Gly Glu Val Ser Leu Val Ser Arg Trp Ala Val
    210                 215                 220
Ser Gly His Pro His Pro Gly Pro Asp Pro Asn Pro Phe Gly Gly Ala
225                 230                 235                 240
Val Leu Leu Cys Leu Ala Ser Gly Leu Met Leu Pro Ser Cys Leu Trp
                245                 250                 255
Phe Arg Gly Thr Gly Leu Ile Trp Trp Val Thr Gly Thr Ala Ser Ala
            260                 265                 270
Ala Gly Leu Leu Tyr Leu His Thr Trp Ala Ala Val Ser Gly Cys
        275                 280                 285
Val Phe Ala Ile Phe Thr Ala Ser Met Trp Pro Gln Thr Leu Gly His
    290                 295                 300
Leu Ile Asn Ser Gly Thr Asn Pro Gly Lys Thr Met Thr Ile Ala Met
305                 310                 315                 320
Ile Phe Tyr Leu Leu Glu Ile Phe Phe Cys Ala Trp Cys Thr Ala Phe
                325                 330                 335
Lys Phe Val Pro Gly Gly Val Tyr Ala Arg Glu Arg Ser Asp Val Leu
            340                 345                 350
Leu Gly Thr Met Met Leu Ile Ile Gly Leu Asn Met Leu Phe Gly Pro
        355                 360                 365
Lys Lys Asn Leu Asp Leu Leu Leu Gln Thr Lys Asn Ser Ser Lys Val
    370                 375                 380
Leu Phe Arg Lys Ser Glu Lys Tyr Met Lys Leu Phe Leu Trp Leu Leu
385                 390                 395                 400
Val Gly Val Gly Leu Leu Gly Leu Gly Leu Arg His Lys Ala Tyr Glu
                405                 410                 415
Arg Lys Leu Gly Lys Val Ala Pro Thr Lys Glu Val Ser Ala Ala Ile
            420                 425                 430
Trp Pro Phe Arg Phe Gly Tyr Asp Asn Glu Gly Trp Ser Ser Leu Glu
        435                 440                 445
Arg Ser Ala His Leu Leu Asn Glu Thr Gly Ala Asp Phe Ile Thr Ile
    450                 455                 460
Leu Glu Ser Asp Ala Ser Lys Pro Tyr Met Gly Asn Asn Asp Leu Thr
465                 470                 475                 480
Met Trp Leu Gly Glu Lys Leu Gly Phe Tyr Thr Asp Phe Gly Pro Ser
                485                 490                 495
Thr Arg Tyr His Thr Trp Gly Ile Met Ala Leu Ser Arg Tyr Pro Ile
            500                 505                 510
```

Val Lys Ser Glu His His Leu Leu Pro Ser Pro Glu Gly Ile Ala
            515                 520                 525

Pro Ala Ile Thr Leu Thr Val Asn Ile Ser Gly Lys Leu Val Asp Phe
        530                 535                 540

Val Val Thr His Phe Gly Asn His Glu Asp Asp Leu Asp Arg Lys Leu
545                 550                 555                 560

Gln Ala Ile Ala Val Ser Lys Leu Leu Lys Ser Ser Asn Gln Val
                565                 570                 575

Ile Phe Leu Gly Tyr Ile Thr Ser Ala Pro Gly Ser Arg Asp Tyr Leu
                580                 585                 590

Gln Leu Thr Glu His Gly Asn Val Lys Asp Ile Asp Ser Thr Asp His
            595                 600                 605

Asp Arg Trp Cys Glu Tyr Ile Met Tyr Arg Gly Leu Ile Arg Leu Gly
        610                 615                 620

Tyr Ala Arg Ile Ser His Ala Glu Leu Ser Asp Ser Glu Ile Gln Met
625                 630                 635                 640

Ala Lys Phe Arg Ile Pro Asp Asp Pro Thr Asn Tyr Arg Asp Asn Gln
                645                 650                 655

Lys Val Val Ile Asp His Arg Glu Val Ser Glu Lys Ile His Phe Asn
                660                 665                 670

Pro Arg Phe Gly Ser Tyr Lys Glu Gly His Asn Tyr Glu Asn Asn His
            675                 680                 685

His Phe His Met Asn Thr Pro Lys Tyr Phe Leu
        690                 695

<210> SEQ ID NO 3
<211> LENGTH: 287
<212> TYPE: DNA
<213> ORGANISM: Homo sapiens

<400> SEQUENCE: 3
gatcacgtgc tgtcgatatc cttcacattg ccatgttcag tgagctgtag ataatctctg      60
gagccaggtg ctgaagtgat atatcccaga aatatcactt gattagagct acttttcagt    120
agttttgaaa cagcaatagc ctgcagtttc ctgtcgaggt catcttcgtg gttcccaaag    180
tgtgtcacga caaaatccac cagcttgccc gaaatgttaa cggtcaatgt gatggctggt    240
gcgatcttgc tgtgttggcc aggctggtct caacgtgcag atagatc                  287

<210> SEQ ID NO 4
<211> LENGTH: 699
<212> TYPE: PRT
<213> ORGANISM: Homo sapiens

<400> SEQUENCE: 4

Met Thr Ser Leu Trp Arg Glu Ile Leu Leu Glu Ser Leu Leu Gly Cys
1               5                   10                  15

Val Ser Trp Ser Leu Tyr His Asp Leu Gly Pro Met Ile Tyr Tyr Phe
            20                  25                  30

Pro Leu Gln Thr Leu Glu Leu Thr Gly Leu Glu Gly Phe Ser Ile Ala
        35                  40                  45

Phe Leu Ser Pro Ile Phe Leu Thr Ile Thr Pro Phe Trp Lys Leu Val
    50                  55                  60

Asn Lys Lys Trp Met Leu Thr Leu Leu Arg Ile Ile Thr Ile Gly Ser
65              70                  75                  80

Ile Ala Ser Phe Gln Ala Pro Asn Ala Lys Leu Arg Leu Met Val Leu

-continued

```
                85                  90                  95
Ala Leu Gly Val Ser Ser Ser Leu Ile Val Gln Ala Val Thr Trp Trp
            100                 105                 110
Ser Gly Ser His Leu Gln Arg Tyr Leu Arg Ile Trp Gly Phe Ile Leu
            115                 120                 125
Gly Gln Ile Val Leu Val Val Leu Arg Ile Trp Tyr Thr Ser Leu Asn
            130                 135                 140
Pro Ile Trp Ser Tyr Gln Met Ser Asn Lys Val Ile Leu Thr Leu Ser
145                 150                 155                 160
Ala Ile Ala Thr Leu Asp Arg Ile Gly Thr Asp Gly Asp Cys Ser Lys
                165                 170                 175
Pro Glu Glu Lys Lys Thr Gly Glu Val Ala Thr Gly Met Ala Ser Arg
            180                 185                 190
Pro Asn Trp Leu Leu Ala Gly Ala Ala Phe Gly Ser Leu Val Phe Leu
            195                 200                 205
Thr His Trp Val Phe Gly Glu Val Ser Leu Val Ser Arg Trp Ala Val
            210                 215                 220
Ser Gly His Pro His Pro Gly Pro Asp Pro Asn Pro Phe Gly Gly Ala
225                 230                 235                 240
Val Leu Leu Cys Leu Ala Ser Gly Leu Met Leu Pro Ser Cys Leu Trp
                245                 250                 255
Phe Arg Gly Thr Gly Leu Ile Trp Trp Val Thr Gly Thr Ala Ser Ala
            260                 265                 270
Ala Gly Leu Leu Tyr Leu His Thr Trp Ala Ala Val Ser Gly Cys
            275                 280                 285
Val Phe Ala Ile Phe Thr Ala Ser Met Trp Pro Gln Thr Leu Gly His
            290                 295                 300
Leu Ile Asn Ser Gly Thr Asn Pro Gly Lys Thr Met Thr Ile Ala Met
305                 310                 315                 320
Ile Phe Tyr Leu Leu Glu Ile Phe Phe Cys Ala Trp Cys Thr Ala Phe
                325                 330                 335
Lys Phe Val Pro Gly Gly Val Tyr Ala Arg Glu Arg Ser Asp Val Leu
            340                 345                 350
Leu Gly Thr Met Met Leu Ile Ile Gly Leu Asn Met Leu Phe Gly Pro
            355                 360                 365
Lys Lys Asn Leu Asp Leu Leu Gln Thr Lys Asn Ser Ser Lys Val
370                 375                 380
Leu Phe Arg Lys Ser Glu Lys Tyr Met Lys Leu Phe Leu Trp Leu Leu
385                 390                 395                 400
Val Gly Val Gly Leu Leu Gly Leu Gly Leu Arg His Lys Ala Tyr Glu
            405                 410                 415
Arg Lys Leu Gly Lys Val Ala Pro Thr Lys Glu Val Ser Ala Ala Ile
            420                 425                 430
Trp Pro Phe Arg Phe Gly Tyr Asp Asn Glu Gly Trp Ser Ser Leu Glu
            435                 440                 445
Arg Ser Ala His Leu Leu Asn Glu Thr Gly Ala Asp Phe Ile Thr Ile
            450                 455                 460
Leu Glu Ser Asp Ala Ser Lys Pro Tyr Met Gly Asn Asn Asp Leu Thr
465                 470                 475                 480
Met Trp Leu Gly Glu Lys Leu Gly Phe Tyr Thr Asp Phe Gly Pro Ser
                485                 490                 495
Thr Arg Tyr His Thr Trp Gly Ile Met Ala Leu Ser Arg Tyr Pro Ile
            500                 505                 510
```

```
Val Lys Ser Glu His His Leu Leu Pro Ser Pro Glu Gly Glu Ile Ala
            515                 520                 525

Pro Ala Ile Thr Leu Thr Val Asn Ile Ser Gly Lys Leu Val Asp Phe
        530                 535                 540

Val Val Thr His Phe Gly Asn His Glu Asp Asp Leu Asp Arg Lys Leu
545                 550                 555                 560

Gln Ala Ile Ala Val Ser Lys Leu Leu Lys Ser Ser Asn Gln Val
                565                 570                 575

Ile Phe Leu Gly Tyr Ile Thr Ser Ala Pro Gly Ser Arg Asp Tyr Leu
                580                 585                 590

Gln Leu Thr Glu His Gly Asn Val Lys Asp Ile Asp Ser Thr Asp His
            595                 600                 605

Asp Arg Trp Cys Glu Tyr Ile Met Tyr Arg Gly Leu Ile Arg Leu Gly
        610                 615                 620

Tyr Ala Arg Ile Ser His Ala Glu Leu Ser Asp Ser Glu Ile Gln Met
625                 630                 635                 640

Ala Lys Phe Arg Ile Pro Asp Asp Pro Thr Asn Tyr Arg Asp Asn Gln
                645                 650                 655

Lys Val Val Ile Asp His Arg Glu Val Ser Glu Lys Ile His Phe Asn
                660                 665                 670

Pro Arg Phe Gly Ser Tyr Lys Glu Gly His Asn Tyr Glu Asn Asn His
            675                 680                 685

Asn Phe His Met Asn Thr Pro Lys Tyr Phe Leu
        690                 695

<210> SEQ ID NO 5
<211> LENGTH: 675
<212> TYPE: PRT
<213> ORGANISM: Yeast

<400> SEQUENCE: 5

Gly Phe Leu Phe Trp Ser Asn Val Thr Ser Leu Leu Cys Ser Ile Trp
1               5                   10                  15

His Phe Pro Leu Trp Tyr Met Gly Ile Ser Gly Tyr Glu Ala Ala Ile
                20                  25                  30

Leu Gly Tyr Leu Gly Pro Ile Phe Leu Tyr Leu Pro Phe Val Ser Glu
            35                  40                  45

Ala Phe Thr Gln Tyr Gly Val Leu Gly Gly Ile Ala Ile Gly
        50                  55                  60

Ala Tyr Ile Val Gln Met Pro Glu Leu Arg Leu Ile Ser Val Ala Val
65                  70                  75                  80

Gly Thr Ser Ile Thr Val Ala Thr Phe Val Gln Asn Leu Arg Tyr Ile
                85                  90                  95

Thr Asn Ala Glu Thr Ser Phe Ser Phe Ala Leu Thr Trp Leu Leu Gly
                100                 105                 110

Leu Val Ala Ser Val Ile Leu Lys Met Gly Phe Tyr Thr Asn Asn Pro
            115                 120                 125

Thr Trp Val Ile Leu Asp Glu Arg Asn Gly Gly Tyr Asn Lys Thr Ala
        130                 135                 140

Leu Val Leu Thr Val Leu Phe Gly Met Leu Ser Pro Tyr Val Asn Ser
145                 150                 155                 160

Ile Asn Phe Glu Gly Lys Arg Asn Ala Gln Ala Lys Ser Ala Ser Leu
                165                 170                 175

Ile Gly Lys Leu Phe Leu Ala Val Gly Phe Gly Ser Leu Leu Phe Gly
```

-continued

```
            180                 185                 190
Ile His Gln Leu Leu Thr Asp Ser Ser Thr Thr Ile Tyr Trp Ala Trp
            195                 200                 205
Glu Gly Tyr Asn Glu Ser His Gly Pro Leu Pro Trp Pro Trp Gly Ala
            210                 215                 220
Leu Thr Cys Thr Val Met Leu Phe Ala Ser Leu Ser Ser Val Lys Phe
225                 230                 235                 240
Met Gly Lys Pro Leu Val Pro Cys Leu Leu Leu Ile Ser Thr Ala
                245                 250                 255
Val Leu Ser Ala Arg Ser Ile Thr Gln Trp Pro Lys Tyr Ile Phe Gly
            260                 265                 270
Gly Leu Leu Tyr Ala Ile Ala Met Leu Trp Leu Val Pro Ser Tyr Phe
            275                 280                 285
Ser Ala Leu Gly Gln Val Gln Asn Ile Trp Val Tyr Val Leu Ser Phe
            290                 295                 300
Ser Val Tyr Ile Ile Phe Val Leu Ala His Val Trp Val Val Ala Tyr
305                 310                 315                 320
Ala Phe Val Pro Met Gly Trp Val Leu Arg Glu Lys Ile Glu Thr Val
                325                 330                 335
Leu Ala Phe Ser Ser Thr Phe Ile Ile Ile Gly Ala Leu Thr Cys Lys
                340                 345                 350
Asn Leu Asn Ile Gln Leu Val Thr Met Gly Lys Lys Phe Ile Tyr
            355                 360                 365
Val Phe Phe Phe Ala Val Ala Leu Leu Ser Leu Thr Ala Arg Phe Val
370                 375                 380
Tyr Asp Ile Arg Pro Thr Gly Ile Pro Gln Pro Tyr His Pro Asp Ser
385                 390                 395                 400
Gln Leu Ile Thr Ala Gly Ile Trp Thr Ile His Phe Gly Leu Asp Asn
            405                 410                 415
Asp Met Trp Ala Ser Glu Asp Arg Met Ile Asn Leu Ile Lys Asp Met
                420                 425                 430
Glu Leu Asp Val Val Gly Leu Leu Glu Thr Asp Thr Gln Arg Ile Thr
            435                 440                 445
Met Gly Asn Arg Asp Leu Thr Ser Lys Leu Ala His Asp Leu Asn Met
450                 455                 460
Tyr Ala Asp Phe Gly Pro Gly Pro Asn Lys His Thr Trp Gly Cys Val
465                 470                 475                 480
Leu Leu Ser Lys Phe Pro Ile Val Asn Ser Thr His Leu Leu Pro
                485                 490                 495
Ser Pro Val Gly Glu Leu Ala Pro Ala Ile His Ala Thr Leu Gln Thr
            500                 505                 510
Tyr Asn Asp Thr Leu Val Asp Val Phe Val Phe His Ser Gly Gln Glu
            515                 520                 525
Glu Asp Glu Glu Asp Arg Arg Leu Gln Ser Asn Tyr Met Ala Lys Leu
            530                 535                 540
Met Gly Asn Thr Thr Arg Pro Ala Ile Leu Leu Ser Tyr Leu Val Val
545                 550                 555                 560
Asp Pro Gly Glu Gly Asn Tyr Asn Thr Tyr Val Ser Glu Thr Ser Gly
                565                 570                 575
Met His Asp Ile Asp Pro Ser Asp Asp Asp Arg Trp Cys Glu Tyr Ile
            580                 585                 590
Leu Tyr Arg Gly Leu Arg Arg Thr Gly Tyr Ala Arg Val Ala Arg Gly
            595                 600                 605
```

Thr Ile Thr Asp Thr Glu Leu Gln Val Gly Lys Phe Gln Val Leu Ser
    610                 615                 620

Glu Gln Ala Leu Val Glu His Ser Asp Ser Met Tyr Glu Tyr Gly His
625                 630                 635                 640

Met Ser Glu Pro Glu Tyr Glu Asp Met Lys Phe Pro Asp Lys Phe Leu
            645                 650                 655

Gly Glu Gly Glu Arg Gly His Phe Tyr His Val Phe Asp Glu Pro Arg
            660                 665                 670

Tyr Tyr Leu
        675

<210> SEQ ID NO 6
<211> LENGTH: 24
<212> TYPE: DNA
<213> ORGANISM: Artificial Sequence
<220> FEATURE:
<223> OTHER INFORMATION: FLAG sequence

<400> SEQUENCE: 6
gattacaagg atgacgacga taag                                          24

<210> SEQ ID NO 7
<211> LENGTH: 14
<212> TYPE: DNA
<213> ORGANISM: Artificial Sequence
<220> FEATURE:
<223> OTHER INFORMATION: Primer

<400> SEQUENCE: 7
ttttgatcaa gctt                                                     14

<210> SEQ ID NO 8
<211> LENGTH: 42
<212> TYPE: DNA
<213> ORGANISM: Artificial Sequence
<220> FEATURE:
<223> OTHER INFORMATION: Adaptor

<400> SEQUENCE: 8
ctaatacgac tcactatagg gctcgagcgg ccgcccgggc ag                      42

<210> SEQ ID NO 9
<211> LENGTH: 12
<212> TYPE: DNA
<213> ORGANISM: Artificial Sequence
<220> FEATURE:
<223> OTHER INFORMATION: Adaptor

<400> SEQUENCE: 9
ggcccgtcct ag                                                       12

<210> SEQ ID NO 10
<211> LENGTH: 40
<212> TYPE: DNA
<213> ORGANISM: Artificial Sequence
<220> FEATURE:
<223> OTHER INFORMATION: Adaptor

<400> SEQUENCE: 10
gtaatacgac tcactatagg gcagcgtggt cgcggccgag                         40

<210> SEQ ID NO 11
<211> LENGTH: 10

```
<212> TYPE: DNA
<213> ORGANISM: Artificial Sequence
<220> FEATURE:
<223> OTHER INFORMATION: Adaptor

<400> SEQUENCE: 11
cggctcctag                                                              10

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
ctaatacgac tcactatagg gc                                                22

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
tcgagcggcc gcccgggcag ga                                                22

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
agcgtggtcg cggccgagga                                                   20

<210> SEQ ID NO 15
<211> LENGTH: 9
<212> TYPE: PRT
<213> ORGANISM: Homo sapiens

<400> SEQUENCE: 15

Gly Leu Glu Gly Phe Ser Ile Ala Phe
  1               5

<210> SEQ ID NO 16
<211> LENGTH: 9
<212> TYPE: PRT
<213> ORGANISM: Homo sapiens

<400> SEQUENCE: 16

Asp Ser Glu Ile Gln Met Ala Lys Phe
  1               5

<210> SEQ ID NO 17
<211> LENGTH: 9
<212> TYPE: PRT
<213> ORGANISM: Homo sapiens

<400> SEQUENCE: 17

Tyr Thr Asp Phe Gly Pro Ser Thr Arg
  1               5
```

```
<210> SEQ ID NO 18
<211> LENGTH: 9
<212> TYPE: PRT
<213> ORGANISM: Homo sapiens

<400> SEQUENCE: 18

Asn Leu Asp Leu Leu Leu Gln Thr Lys
 1               5

<210> SEQ ID NO 19
<211> LENGTH: 9
<212> TYPE: PRT
<213> ORGANISM: Homo sapiens

<400> SEQUENCE: 19

Thr Ser Ala Pro Gly Ser Arg Asp Tyr
 1               5

<210> SEQ ID NO 20
<211> LENGTH: 9
<212> TYPE: PRT
<213> ORGANISM: Homo sapiens

<400> SEQUENCE: 20

Lys Ser Glu His His Leu Leu Pro Ser
 1               5

<210> SEQ ID NO 21
<211> LENGTH: 9
<212> TYPE: PRT
<213> ORGANISM: Homo sapiens

<400> SEQUENCE: 21

Gly Pro Asp Pro Asn Pro Phe Gly Gly
 1               5

<210> SEQ ID NO 22
<211> LENGTH: 9
<212> TYPE: PRT
<213> ORGANISM: Homo sapiens

<400> SEQUENCE: 22

Tyr His Asp Leu Gly Pro Met Ile Tyr
 1               5

<210> SEQ ID NO 23
<211> LENGTH: 9
<212> TYPE: PRT
<213> ORGANISM: Homo sapiens

<400> SEQUENCE: 23

Asp Ile Asp Ser Thr Asp His Asp Arg
 1               5

<210> SEQ ID NO 24
<211> LENGTH: 9
<212> TYPE: PRT
<213> ORGANISM: Homo sapiens

<400> SEQUENCE: 24

Leu Val Asp Phe Val Val Thr His Phe
 1               5

<210> SEQ ID NO 25
<211> LENGTH: 9
```

```
<212> TYPE: PRT
<213> ORGANISM: Homo sapiens

<400> SEQUENCE: 25

Phe Gly Glu Val Ser Leu Val Ser Arg
 1               5

<210> SEQ ID NO 26
<211> LENGTH: 9
<212> TYPE: PRT
<213> ORGANISM: Homo sapiens

<400> SEQUENCE: 26

Thr Leu Glu Leu Thr Gly Leu Glu Gly
 1               5

<210> SEQ ID NO 27
<211> LENGTH: 9
<212> TYPE: PRT
<213> ORGANISM: Homo sapiens

<400> SEQUENCE: 27

Leu Met Leu Pro Ser Cys Leu Trp Phe
 1               5

<210> SEQ ID NO 28
<211> LENGTH: 9
<212> TYPE: PRT
<213> ORGANISM: Homo sapiens

<400> SEQUENCE: 28

Thr Ala Ser Ala Ala Gly Leu Leu Tyr
 1               5

<210> SEQ ID NO 29
<211> LENGTH: 9
<212> TYPE: PRT
<213> ORGANISM: Homo sapiens

<400> SEQUENCE: 29

Val Leu Val Val Leu Arg Ile Trp Tyr
 1               5

<210> SEQ ID NO 30
<211> LENGTH: 9
<212> TYPE: PRT
<213> ORGANISM: Homo sapiens

<400> SEQUENCE: 30

Ala Ile Trp Pro Phe Arg Phe Gly Tyr
 1               5

<210> SEQ ID NO 31
<211> LENGTH: 9
<212> TYPE: PRT
<213> ORGANISM: Homo sapiens

<400> SEQUENCE: 31

Asp Leu Gly Pro Met Ile Tyr Tyr Phe
 1               5

<210> SEQ ID NO 32
<211> LENGTH: 9
<212> TYPE: PRT
<213> ORGANISM: Homo sapiens
```

```
<400> SEQUENCE: 32

Trp Cys Glu Tyr Ile Met Tyr Arg Gly
 1               5

<210> SEQ ID NO 33
<211> LENGTH: 9
<212> TYPE: PRT
<213> ORGANISM: Homo sapiens

<400> SEQUENCE: 33

Glu Ser Asp Ala Ser Lys Pro Tyr Met
 1               5

<210> SEQ ID NO 34
<211> LENGTH: 9
<212> TYPE: PRT
<213> ORGANISM: Homo sapiens

<400> SEQUENCE: 34

Lys Ser Glu Lys Tyr Met Lys Leu Phe
 1               5

<210> SEQ ID NO 35
<211> LENGTH: 9
<212> TYPE: PRT
<213> ORGANISM: Homo sapiens

<400> SEQUENCE: 35

Thr Met Thr Ile Ala Met Ile Phe Tyr
 1               5

<210> SEQ ID NO 36
<211> LENGTH: 9
<212> TYPE: PRT
<213> ORGANISM: Homo sapiens

<400> SEQUENCE: 36

Lys Thr Met Thr Ile Ala Met Ile Phe
 1               5

<210> SEQ ID NO 37
<211> LENGTH: 9
<212> TYPE: PRT
<213> ORGANISM: Homo sapiens

<400> SEQUENCE: 37

Ile Pro Asp Asp Pro Thr Asn Tyr Arg
 1               5

<210> SEQ ID NO 38
<211> LENGTH: 9
<212> TYPE: PRT
<213> ORGANISM: Homo sapiens

<400> SEQUENCE: 38

Ala Ile Ala Val Ser Lys Leu Leu Lys
 1               5

<210> SEQ ID NO 39
<211> LENGTH: 9
<212> TYPE: PRT
<213> ORGANISM: Homo sapiens

<400> SEQUENCE: 39
```

```
Lys Ala Tyr Glu Arg Lys Leu Gly Lys
1               5
```

<210> SEQ ID NO 40
<211> LENGTH: 9
<212> TYPE: PRT
<213> ORGANISM: Homo sapiens

<400> SEQUENCE: 40

```
Phe Leu Thr Ile Thr Pro Phe Trp Lys
1               5
```

<210> SEQ ID NO 41
<211> LENGTH: 9
<212> TYPE: PRT
<213> ORGANISM: Homo sapiens

<400> SEQUENCE: 41

```
Leu Leu Glu Ser Leu Leu Gly Cys Val
1               5
```

<210> SEQ ID NO 42
<211> LENGTH: 9
<212> TYPE: PRT
<213> ORGANISM: Homo sapiens

<400> SEQUENCE: 42

```
Leu Leu Glu Ile Phe Phe Cys Ala Trp
1               5
```

<210> SEQ ID NO 43
<211> LENGTH: 9
<212> TYPE: PRT
<213> ORGANISM: Homo sapiens

<400> SEQUENCE: 43

```
Asn His Glu Asp Asp Leu Asp Arg Lys
1               5
```

<210> SEQ ID NO 44
<211> LENGTH: 9
<212> TYPE: PRT
<213> ORGANISM: Homo sapiens

<400> SEQUENCE: 44

```
His Ala Glu Leu Ser Asp Ser Glu Ile
1               5
```

<210> SEQ ID NO 45
<211> LENGTH: 9
<212> TYPE: PRT
<213> ORGANISM: Homo sapiens

<400> SEQUENCE: 45

```
Leu Ser Ala Ile Ala Thr Leu Asp Arg
1               5
```

<210> SEQ ID NO 46
<211> LENGTH: 9
<212> TYPE: PRT
<213> ORGANISM: Homo sapiens

<400> SEQUENCE: 46

```
Thr Ser Leu Asn Pro Ile Trp Ser Tyr
```

```
1               5

<210> SEQ ID NO 47
<211> LENGTH: 9
<212> TYPE: PRT
<213> ORGANISM: Homo sapiens

<400> SEQUENCE: 47

Arg Ser Asp Val Leu Leu Gly Thr Met
1               5

<210> SEQ ID NO 48
<211> LENGTH: 9
<212> TYPE: PRT
<213> ORGANISM: Homo sapiens

<400> SEQUENCE: 48

Trp Ser Gly Ser His Leu Gln Arg Tyr
1               5

<210> SEQ ID NO 49
<211> LENGTH: 9
<212> TYPE: PRT
<213> ORGANISM: Homo sapiens

<400> SEQUENCE: 49

Leu Ser Asp Ser Glu Ile Gln Met Ala
1               5

<210> SEQ ID NO 50
<211> LENGTH: 9
<212> TYPE: PRT
<213> ORGANISM: Homo sapiens

<400> SEQUENCE: 50

Ser Asn Gln Val Ile Phe Leu Gly Tyr
1               5

<210> SEQ ID NO 51
<211> LENGTH: 9
<212> TYPE: PRT
<213> ORGANISM: Homo sapiens

<400> SEQUENCE: 51

Leu Ile Ile Gly Leu Asn Met Leu Phe
1               5

<210> SEQ ID NO 52
<211> LENGTH: 9
<212> TYPE: PRT
<213> ORGANISM: Homo sapiens

<400> SEQUENCE: 52

Phe Leu Ser Pro Ile Phe Leu Thr Ile
1               5

<210> SEQ ID NO 53
<211> LENGTH: 9
<212> TYPE: PRT
<213> ORGANISM: Homo sapiens

<400> SEQUENCE: 53

Ser Ala Ala Ile Trp Pro Phe Arg Phe
1               5
```

```
<210> SEQ ID NO 54
<211> LENGTH: 9
<212> TYPE: PRT
<213> ORGANISM: Homo sapiens

<400> SEQUENCE: 54

Arg Ile Pro Asp Asp Pro Thr Asn Tyr
1               5

<210> SEQ ID NO 55
<211> LENGTH: 9
<212> TYPE: PRT
<213> ORGANISM: Homo sapiens

<400> SEQUENCE: 55

Gly Leu Gly Leu Arg His Lys Ala Tyr
1               5

<210> SEQ ID NO 56
<211> LENGTH: 9
<212> TYPE: PRT
<213> ORGANISM: Homo sapiens

<400> SEQUENCE: 56

Trp Leu Gly Glu Lys Leu Gly Phe Tyr
1               5

<210> SEQ ID NO 57
<211> LENGTH: 9
<212> TYPE: PRT
<213> ORGANISM: Homo sapiens

<400> SEQUENCE: 57

Tyr Ile Met Tyr Arg Gly Leu Ile Arg
1               5

<210> SEQ ID NO 58
<211> LENGTH: 9
<212> TYPE: PRT
<213> ORGANISM: Homo sapiens

<400> SEQUENCE: 58

Ile Thr Ile Gly Ser Ile Ala Ser Phe
1               5

<210> SEQ ID NO 59
<211> LENGTH: 9
<212> TYPE: PRT
<213> ORGANISM: Homo sapiens

<400> SEQUENCE: 59

Gly Ala Ala Phe Gly Ser Leu Val Phe
1               5

<210> SEQ ID NO 60
<211> LENGTH: 9
<212> TYPE: PRT
<213> ORGANISM: Homo sapiens

<400> SEQUENCE: 60

Leu Thr Glu His Gly Asn Val Lys Asp
1               5

<210> SEQ ID NO 61
```

```
<211> LENGTH: 9
<212> TYPE: PRT
<213> ORGANISM: Homo sapiens

<400> SEQUENCE: 61

Glu Gly Glu Ile Ala Pro Ala Ile Thr
1               5

<210> SEQ ID NO 62
<211> LENGTH: 9
<212> TYPE: PRT
<213> ORGANISM: Homo sapiens

<400> SEQUENCE: 62

Ser Pro Glu Gly Glu Ile Ala Pro Ala
1               5

<210> SEQ ID NO 63
<211> LENGTH: 9
<212> TYPE: PRT
<213> ORGANISM: Homo sapiens

<400> SEQUENCE: 63

Lys Leu Gln Ala Ile Ala Val Ser Lys
1               5

<210> SEQ ID NO 64
<211> LENGTH: 9
<212> TYPE: PRT
<213> ORGANISM: Homo sapiens

<400> SEQUENCE: 64

Thr Ile Leu Glu Ser Asp Ala Ser Lys
1               5

<210> SEQ ID NO 65
<211> LENGTH: 10
<212> TYPE: PRT
<213> ORGANISM: Homo sapiens

<400> SEQUENCE: 65

Leu Ser Asp Ser Glu Ile Gln Met Ala Lys
1               5                   10

<210> SEQ ID NO 66
<211> LENGTH: 10
<212> TYPE: PRT
<213> ORGANISM: Homo sapiens

<400> SEQUENCE: 66

Ser Thr Asp His Asp Arg Trp Cys Glu Tyr
1               5                   10

<210> SEQ ID NO 67
<211> LENGTH: 10
<212> TYPE: PRT
<213> ORGANISM: Homo sapiens

<400> SEQUENCE: 67

Tyr Thr Asp Phe Gly Pro Ser Thr Arg Tyr
1               5                   10

<210> SEQ ID NO 68
<211> LENGTH: 10
<212> TYPE: PRT
```

<213> ORGANISM: Homo sapiens

<400> SEQUENCE: 68

Ile Leu Glu Ser Asp Ala Ser Lys Pro Tyr
1               5                   10

<210> SEQ ID NO 69
<211> LENGTH: 10
<212> TYPE: PRT
<213> ORGANISM: Homo sapiens

<400> SEQUENCE: 69

Asp Ser Glu Ile Gln Met Ala Lys Phe Arg
1               5                   10

<210> SEQ ID NO 70
<211> LENGTH: 10
<212> TYPE: PRT
<213> ORGANISM: Homo sapiens

<400> SEQUENCE: 70

Asp Asn Glu Gly Trp Ser Ser Leu Glu Arg
1               5                   10

<210> SEQ ID NO 71
<211> LENGTH: 10
<212> TYPE: PRT
<213> ORGANISM: Homo sapiens

<400> SEQUENCE: 71

Val Ile Asp His Arg Glu Val Ser Glu Lys
1               5                   10

<210> SEQ ID NO 72
<211> LENGTH: 10
<212> TYPE: PRT
<213> ORGANISM: Homo sapiens

<400> SEQUENCE: 72

Thr Leu Glu Leu Thr Gly Leu Glu Gly Phe
1               5                   10

<210> SEQ ID NO 73
<211> LENGTH: 10
<212> TYPE: PRT
<213> ORGANISM: Homo sapiens

<400> SEQUENCE: 73

Tyr His Asp Leu Gly Pro Met Ile Tyr Tyr
1               5                   10

<210> SEQ ID NO 74
<211> LENGTH: 10
<212> TYPE: PRT
<213> ORGANISM: Homo sapiens

<400> SEQUENCE: 74

Gly Thr Ala Ser Ala Ala Gly Leu Leu Tyr
1               5                   10

<210> SEQ ID NO 75
<211> LENGTH: 10
<212> TYPE: PRT
<213> ORGANISM: Homo sapiens

```
<400> SEQUENCE: 75

Lys Thr Met Thr Ile Ala Met Ile Phe Tyr
1               5                   10

<210> SEQ ID NO 76
<211> LENGTH: 10
<212> TYPE: PRT
<213> ORGANISM: Homo sapiens

<400> SEQUENCE: 76

Ser Ser Asn Gln Val Ile Phe Leu Gly Tyr
1               5                   10

<210> SEQ ID NO 77
<211> LENGTH: 10
<212> TYPE: PRT
<213> ORGANISM: Homo sapiens

<400> SEQUENCE: 77

Asp Gly Asp Cys Ser Lys Pro Glu Glu Lys
1               5                   10

<210> SEQ ID NO 78
<211> LENGTH: 10
<212> TYPE: PRT
<213> ORGANISM: Homo sapiens

<400> SEQUENCE: 78

Ala Ala Ile Trp Pro Phe Arg Phe Gly Tyr
1               5                   10

<210> SEQ ID NO 79
<211> LENGTH: 10
<212> TYPE: PRT
<213> ORGANISM: Homo sapiens

<400> SEQUENCE: 79

Ile Val Leu Val Val Leu Arg Ile Trp Tyr
1               5                   10

<210> SEQ ID NO 80
<211> LENGTH: 10
<212> TYPE: PRT
<213> ORGANISM: Homo sapiens

<400> SEQUENCE: 80

Gly Ala Asp Phe Ile Thr Ile Leu Glu Ser
1               5                   10

<210> SEQ ID NO 81
<211> LENGTH: 10
<212> TYPE: PRT
<213> ORGANISM: Homo sapiens

<400> SEQUENCE: 81

His Arg Glu Val Ser Glu Lys Ile His Phe
1               5                   10

<210> SEQ ID NO 82
<211> LENGTH: 10
<212> TYPE: PRT
<213> ORGANISM: Homo sapiens

<400> SEQUENCE: 82
```

```
<210> SEQ ID NO 83
<211> LENGTH: 10
<212> TYPE: PRT
<213> ORGANISM: Homo sapiens

<400> SEQUENCE: 83

Leu Thr Glu His Gly Asn Val Lys Asp Ile
1               5                   10

<210> SEQ ID NO 83
<211> LENGTH: 10
<212> TYPE: PRT
<213> ORGANISM: Homo sapiens

<400> SEQUENCE: 83

Gly Leu Glu Gly Phe Ser Ile Ala Phe Leu
1               5                   10

<210> SEQ ID NO 84
<211> LENGTH: 10
<212> TYPE: PRT
<213> ORGANISM: Homo sapiens

<400> SEQUENCE: 84

Leu Leu Glu Ile Phe Phe Cys Ala Trp Cys
1               5                   10

<210> SEQ ID NO 85
<211> LENGTH: 10
<212> TYPE: PRT
<213> ORGANISM: Homo sapiens

<400> SEQUENCE: 85

Glu Ser Asp Ala Ser Lys Pro Tyr Met Gly
1               5                   10

<210> SEQ ID NO 86
<211> LENGTH: 10
<212> TYPE: PRT
<213> ORGANISM: Homo sapiens

<400> SEQUENCE: 86

Val Ser Glu Lys Ile His Phe Asn Pro Arg
1               5                   10

<210> SEQ ID NO 87
<211> LENGTH: 10
<212> TYPE: PRT
<213> ORGANISM: Homo sapiens

<400> SEQUENCE: 87

Tyr Thr Ser Leu Asn Pro Ile Trp Ser Tyr
1               5                   10

<210> SEQ ID NO 88
<211> LENGTH: 10
<212> TYPE: PRT
<213> ORGANISM: Homo sapiens

<400> SEQUENCE: 88

Gly Thr Asn Pro Gly Lys Thr Met Thr Ile
1               5                   10

<210> SEQ ID NO 89
<211> LENGTH: 10
<212> TYPE: PRT
<213> ORGANISM: Homo sapiens

<400> SEQUENCE: 89

Ile Thr Ser Ala Pro Gly Ser Arg Asp Tyr
1               5                   10
```

<210> SEQ ID NO 90
<211> LENGTH: 10
<212> TYPE: PRT
<213> ORGANISM: Homo sapiens

<400> SEQUENCE: 90

Gly Pro Asp Pro Asn Pro Phe Gly Gly Ala
1               5                   10

<210> SEQ ID NO 91
<211> LENGTH: 10
<212> TYPE: PRT
<213> ORGANISM: Homo sapiens

<400> SEQUENCE: 91

Glu Gly Glu Ile Ala Pro Ala Ile Thr Leu
1               5                   10

<210> SEQ ID NO 92
<211> LENGTH: 10
<212> TYPE: PRT
<213> ORGANISM: Homo sapiens

<400> SEQUENCE: 92

Thr Gly Glu Val Ala Thr Gly Met Ala Ser
1               5                   10

<210> SEQ ID NO 93
<211> LENGTH: 10
<212> TYPE: PRT
<213> ORGANISM: Homo sapiens

<400> SEQUENCE: 93

Leu Asn Glu Thr Gly Ala Asp Phe Ile Thr
1               5                   10

<210> SEQ ID NO 94
<211> LENGTH: 10
<212> TYPE: PRT
<213> ORGANISM: Homo sapiens

<400> SEQUENCE: 94

Ile Thr Pro Phe Trp Lys Leu Val Asn Lys
1               5                   10

<210> SEQ ID NO 95
<211> LENGTH: 10
<212> TYPE: PRT
<213> ORGANISM: Homo sapiens

<400> SEQUENCE: 95

Met Ala Leu Ser Arg Tyr Pro Ile Val Lys
1               5                   10

<210> SEQ ID NO 96
<211> LENGTH: 10
<212> TYPE: PRT
<213> ORGANISM: Homo sapiens

<400> SEQUENCE: 96

Gln Ala Ile Ala Val Ser Lys Leu Leu Lys
1               5                   10

```
<210> SEQ ID NO 97
<211> LENGTH: 10
<212> TYPE: PRT
<213> ORGANISM: Homo sapiens

<400> SEQUENCE: 97

Ile Thr Ile Leu Glu Ser Asp Ala Ser Lys
 1               5                  10

<210> SEQ ID NO 98
<211> LENGTH: 10
<212> TYPE: PRT
<213> ORGANISM: Homo sapiens

<400> SEQUENCE: 98

Leu Leu Glu Ser Leu Leu Gly Cys Val Ser
 1               5                  10

<210> SEQ ID NO 99
<211> LENGTH: 10
<212> TYPE: PRT
<213> ORGANISM: Homo sapiens

<400> SEQUENCE: 99

His Ala Glu Leu Ser Asp Ser Glu Ile Gln
 1               5                  10

<210> SEQ ID NO 100
<211> LENGTH: 10
<212> TYPE: PRT
<213> ORGANISM: Homo sapiens

<400> SEQUENCE: 100

Trp Cys Glu Tyr Ile Met Tyr Arg Gly Leu
 1               5                  10

<210> SEQ ID NO 101
<211> LENGTH: 10
<212> TYPE: PRT
<213> ORGANISM: Homo sapiens

<400> SEQUENCE: 101

Val Ser Ala Ala Ile Trp Pro Phe Arg Phe
 1               5                  10

<210> SEQ ID NO 102
<211> LENGTH: 10
<212> TYPE: PRT
<213> ORGANISM: Homo sapiens

<400> SEQUENCE: 102

Arg Ser Asp Val Leu Leu Gly Thr Met Met
 1               5                  10

<210> SEQ ID NO 103
<211> LENGTH: 10
<212> TYPE: PRT
<213> ORGANISM: Homo sapiens

<400> SEQUENCE: 103

Lys Ser Glu Lys Tyr Met Lys Leu Phe Leu
 1               5                  10

<210> SEQ ID NO 104
<211> LENGTH: 10
```

<212> TYPE: PRT
<213> ORGANISM: Homo sapiens

<400> SEQUENCE: 104

Phe Cys Ala Trp Cys Thr Ala Phe Lys Phe
1               5                   10

<210> SEQ ID NO 105
<211> LENGTH: 10
<212> TYPE: PRT
<213> ORGANISM: Homo sapiens

<400> SEQUENCE: 105

Leu Val Asp Phe Val Val Thr His Phe Gly
1               5                   10

<210> SEQ ID NO 106
<211> LENGTH: 10
<212> TYPE: PRT
<213> ORGANISM: Homo sapiens

<400> SEQUENCE: 106

Thr Leu Ser Ala Ile Ala Thr Leu Asp Arg
1               5                   10

<210> SEQ ID NO 107
<211> LENGTH: 10
<212> TYPE: PRT
<213> ORGANISM: Homo sapiens

<400> SEQUENCE: 107

Ile Thr Leu Thr Val Asn Ile Ser Gly Lys
1               5                   10

<210> SEQ ID NO 108
<211> LENGTH: 10
<212> TYPE: PRT
<213> ORGANISM: Homo sapiens

<400> SEQUENCE: 108

Met Ile Phe Tyr Leu Leu Glu Ile Phe Phe
1               5                   10

<210> SEQ ID NO 109
<211> LENGTH: 10
<212> TYPE: PRT
<213> ORGANISM: Homo sapiens

<400> SEQUENCE: 109

Leu Leu Gly Cys Val Ser Trp Ser Leu Tyr
1               5                   10

<210> SEQ ID NO 110
<211> LENGTH: 10
<212> TYPE: PRT
<213> ORGANISM: Homo sapiens

<400> SEQUENCE: 110

Asn Leu Asp Leu Leu Gln Thr Lys Asn
1               5                   10

<210> SEQ ID NO 111
<211> LENGTH: 10
<212> TYPE: PRT
<213> ORGANISM: Homo sapiens

```
<400> SEQUENCE: 111

Thr Ile Thr Pro Phe Trp Lys Leu Val Asn
 1               5                  10

<210> SEQ ID NO 112
<211> LENGTH: 10
<212> TYPE: PRT
<213> ORGANISM: Homo sapiens

<400> SEQUENCE: 112

Glu Ile Ala Pro Ala Ile Thr Leu Thr Val
 1               5                  10

<210> SEQ ID NO 113
<211> LENGTH: 10
<212> TYPE: PRT
<213> ORGANISM: Homo sapiens

<400> SEQUENCE: 113

Lys Val Leu Phe Arg Lys Ser Glu Lys Tyr
 1               5                  10

<210> SEQ ID NO 114
<211> LENGTH: 10
<212> TYPE: PRT
<213> ORGANISM: Homo sapiens

<400> SEQUENCE: 114

Met Leu Ile Ile Gly Leu Asn Met Leu Phe
 1               5                  10

<210> SEQ ID NO 115
<211> LENGTH: 9
<212> TYPE: PRT
<213> ORGANISM: Homo sapiens

<400> SEQUENCE: 115

Tyr Leu Leu Glu Ile Phe Phe Cys Ala
 1               5

<210> SEQ ID NO 116
<211> LENGTH: 9
<212> TYPE: PRT
<213> ORGANISM: Homo sapiens

<400> SEQUENCE: 116

Lys Leu Val Asn Lys Lys Trp Met Leu
 1               5

<210> SEQ ID NO 117
<211> LENGTH: 9
<212> TYPE: PRT
<213> ORGANISM: Homo sapiens

<400> SEQUENCE: 117

Ser Leu Val Phe Leu Thr His Trp Val
 1               5

<210> SEQ ID NO 118
<211> LENGTH: 9
<212> TYPE: PRT
<213> ORGANISM: Homo sapiens

<400> SEQUENCE: 118
```

```
Phe Ile Leu Gly Gln Ile Val Leu Val
1               5

<210> SEQ ID NO 119
<211> LENGTH: 9
<212> TYPE: PRT
<213> ORGANISM: Homo sapiens

<400> SEQUENCE: 119

Tyr Leu His Thr Trp Ala Ala Ala Val
1               5

<210> SEQ ID NO 120
<211> LENGTH: 9
<212> TYPE: PRT
<213> ORGANISM: Homo sapiens

<400> SEQUENCE: 120

Ile Leu Leu Glu Ser Leu Leu Gly Cys
1               5

<210> SEQ ID NO 121
<211> LENGTH: 9
<212> TYPE: PRT
<213> ORGANISM: Homo sapiens

<400> SEQUENCE: 121

Leu Leu Gly Cys Val Ser Trp Ser Leu
1               5

<210> SEQ ID NO 122
<211> LENGTH: 9
<212> TYPE: PRT
<213> ORGANISM: Homo sapiens

<400> SEQUENCE: 122

Arg Leu Met Val Leu Ala Leu Gly Val
1               5

<210> SEQ ID NO 123
<211> LENGTH: 9
<212> TYPE: PRT
<213> ORGANISM: Homo sapiens

<400> SEQUENCE: 123

Trp Val Phe Gly Glu Val Ser Leu Val
1               5

<210> SEQ ID NO 124
<211> LENGTH: 9
<212> TYPE: PRT
<213> ORGANISM: Homo sapiens

<400> SEQUENCE: 124

Leu Leu Tyr Leu His Thr Trp Ala Ala
1               5

<210> SEQ ID NO 125
<211> LENGTH: 9
<212> TYPE: PRT
<213> ORGANISM: Homo sapiens

<400> SEQUENCE: 125

Ile Met Tyr Arg Gly Leu Ile Arg Leu
```

```
<210> SEQ ID NO 126
<211> LENGTH: 9
<212> TYPE: PRT
<213> ORGANISM: Homo sapiens

<400> SEQUENCE: 126

Cys Leu Trp Phe Arg Gly Thr Gly Leu
 1               5

<210> SEQ ID NO 127
<211> LENGTH: 9
<212> TYPE: PRT
<213> ORGANISM: Homo sapiens

<400> SEQUENCE: 127

Tyr Met Lys Leu Phe Leu Trp Leu Leu
 1               5

<210> SEQ ID NO 128
<211> LENGTH: 9
<212> TYPE: PRT
<213> ORGANISM: Homo sapiens

<400> SEQUENCE: 128

Val Leu Leu Gly Thr Met Met Leu Ile
 1               5

<210> SEQ ID NO 129
<211> LENGTH: 9
<212> TYPE: PRT
<213> ORGANISM: Homo sapiens

<400> SEQUENCE: 129

Met Leu Phe Gly Pro Lys Lys Asn Leu
 1               5

<210> SEQ ID NO 130
<211> LENGTH: 9
<212> TYPE: PRT
<213> ORGANISM: Homo sapiens

<400> SEQUENCE: 130

Val Leu Leu Cys Leu Ala Ser Gly Leu
 1               5

<210> SEQ ID NO 131
<211> LENGTH: 9
<212> TYPE: PRT
<213> ORGANISM: Homo sapiens

<400> SEQUENCE: 131

Ile Leu Gly Gln Ile Val Leu Val Val
 1               5

<210> SEQ ID NO 132
<211> LENGTH: 9
<212> TYPE: PRT
<213> ORGANISM: Homo sapiens

<400> SEQUENCE: 132

Trp Leu Leu Val Gly Val Gly Leu Leu
 1               5
```

<210> SEQ ID NO 133
<211> LENGTH: 9
<212> TYPE: PRT
<213> ORGANISM: Homo sapiens

<400> SEQUENCE: 133

Leu Val Val Leu Arg Ile Trp Tyr Thr
1               5

<210> SEQ ID NO 134
<211> LENGTH: 9
<212> TYPE: PRT
<213> ORGANISM: Homo sapiens

<400> SEQUENCE: 134

Gly Leu Leu Tyr Leu His Thr Trp Ala
1               5

<210> SEQ ID NO 135
<211> LENGTH: 9
<212> TYPE: PRT
<213> ORGANISM: Homo sapiens

<400> SEQUENCE: 135

Phe Leu Ser Pro Ile Phe Leu Thr Ile
1               5

<210> SEQ ID NO 136
<211> LENGTH: 9
<212> TYPE: PRT
<213> ORGANISM: Homo sapiens

<400> SEQUENCE: 136

Gly Met Ala Ser Arg Pro Asn Trp Leu
1               5

<210> SEQ ID NO 137
<211> LENGTH: 9
<212> TYPE: PRT
<213> ORGANISM: Homo sapiens

<400> SEQUENCE: 137

Met Leu Ile Ile Gly Leu Asn Met Leu
1               5

<210> SEQ ID NO 138
<211> LENGTH: 9
<212> TYPE: PRT
<213> ORGANISM: Homo sapiens

<400> SEQUENCE: 138

Thr Ile Thr Pro Phe Trp Lys Leu Val
1               5

<210> SEQ ID NO 139
<211> LENGTH: 9
<212> TYPE: PRT
<213> ORGANISM: Homo sapiens

<400> SEQUENCE: 139

Arg Gly Thr Gly Leu Ile Trp Trp Val
1               5

<210> SEQ ID NO 140

```
<211> LENGTH: 9
<212> TYPE: PRT
<213> ORGANISM: Homo sapiens

<400> SEQUENCE: 140

Met Thr Ile Ala Met Ile Phe Tyr Leu
1               5

<210> SEQ ID NO 141
<211> LENGTH: 9
<212> TYPE: PRT
<213> ORGANISM: Homo sapiens

<400> SEQUENCE: 141

Trp Met Leu Thr Leu Leu Arg Ile Ile
1               5

<210> SEQ ID NO 142
<211> LENGTH: 9
<212> TYPE: PRT
<213> ORGANISM: Homo sapiens

<400> SEQUENCE: 142

Met Met Leu Ile Ile Gly Leu Asn Met
1               5

<210> SEQ ID NO 143
<211> LENGTH: 9
<212> TYPE: PRT
<213> ORGANISM: Homo sapiens

<400> SEQUENCE: 143

Val Ser Leu Val Ser Arg Trp Ala Val
1               5

<210> SEQ ID NO 144
<211> LENGTH: 9
<212> TYPE: PRT
<213> ORGANISM: Homo sapiens

<400> SEQUENCE: 144

Met Ile Tyr Tyr Phe Pro Leu Gln Thr
1               5

<210> SEQ ID NO 145
<211> LENGTH: 9
<212> TYPE: PRT
<213> ORGANISM: Homo sapiens

<400> SEQUENCE: 145

Tyr Leu Arg Ile Trp Gly Phe Ile Leu
1               5

<210> SEQ ID NO 146
<211> LENGTH: 9
<212> TYPE: PRT
<213> ORGANISM: Homo sapiens

<400> SEQUENCE: 146

Ala Met Ile Phe Tyr Leu Leu Glu Ile
1               5

<210> SEQ ID NO 147
<211> LENGTH: 9
<212> TYPE: PRT
```

```
<213> ORGANISM: Homo sapiens

<400> SEQUENCE: 147

Gly Leu Ile Trp Trp Val Thr Gly Thr
1               5

<210> SEQ ID NO 148
<211> LENGTH: 9
<212> TYPE: PRT
<213> ORGANISM: Homo sapiens

<400> SEQUENCE: 148

Leu Leu Gly Thr Met Met Leu Ile Ile
1               5

<210> SEQ ID NO 149
<211> LENGTH: 9
<212> TYPE: PRT
<213> ORGANISM: Homo sapiens

<400> SEQUENCE: 149

Tyr Met Gly Asn Asn Asp Leu Thr Met
1               5

<210> SEQ ID NO 150
<211> LENGTH: 9
<212> TYPE: PRT
<213> ORGANISM: Homo sapiens

<400> SEQUENCE: 150

Tyr Gln Met Ser Asn Lys Val Ile Leu
1               5

<210> SEQ ID NO 151
<211> LENGTH: 9
<212> TYPE: PRT
<213> ORGANISM: Homo sapiens

<400> SEQUENCE: 151

Ala Ala Phe Gly Ser Leu Val Phe Leu
1               5

<210> SEQ ID NO 152
<211> LENGTH: 9
<212> TYPE: PRT
<213> ORGANISM: Homo sapiens

<400> SEQUENCE: 152

Lys Leu Arg Leu Met Val Leu Ala Leu
1               5

<210> SEQ ID NO 153
<211> LENGTH: 9
<212> TYPE: PRT
<213> ORGANISM: Homo sapiens

<400> SEQUENCE: 153

Ile Met Ala Leu Ser Arg Tyr Pro Ile
1               5

<210> SEQ ID NO 154
<211> LENGTH: 9
<212> TYPE: PRT
<213> ORGANISM: Homo sapiens
```

```
<400> SEQUENCE: 154

Ile Leu Thr Leu Ser Ala Ile Ala Thr
1               5

<210> SEQ ID NO 155
<211> LENGTH: 9
<212> TYPE: PRT
<213> ORGANISM: Homo sapiens

<400> SEQUENCE: 155

Gln Met Ser Asn Lys Val Ile Leu Thr
1               5

<210> SEQ ID NO 156
<211> LENGTH: 9
<212> TYPE: PRT
<213> ORGANISM: Homo sapiens

<400> SEQUENCE: 156

Ala Val Ser Gly Cys Val Phe Ala Ile
1               5

<210> SEQ ID NO 157
<211> LENGTH: 9
<212> TYPE: PRT
<213> ORGANISM: Homo sapiens

<400> SEQUENCE: 157

Leu Gln Thr Lys Asn Ser Ser Lys Val
1               5

<210> SEQ ID NO 158
<211> LENGTH: 9
<212> TYPE: PRT
<213> ORGANISM: Homo sapiens

<400> SEQUENCE: 158

Ala Leu Gly Val Ser Ser Ser Leu Ile
1               5

<210> SEQ ID NO 159
<211> LENGTH: 9
<212> TYPE: PRT
<213> ORGANISM: Homo sapiens

<400> SEQUENCE: 159

Ile Ala Phe Leu Ser Pro Ile Phe Leu
1               5

<210> SEQ ID NO 160
<211> LENGTH: 9
<212> TYPE: PRT
<213> ORGANISM: Homo sapiens

<400> SEQUENCE: 160

Lys Leu Val Asp Phe Val Val Thr His
1               5

<210> SEQ ID NO 161
<211> LENGTH: 9
<212> TYPE: PRT
<213> ORGANISM: Homo sapiens

<400> SEQUENCE: 161
```

```
Leu Glu Gly Phe Ser Ile Ala Phe Leu
  1               5

<210> SEQ ID NO 162
<211> LENGTH: 9
<212> TYPE: PRT
<213> ORGANISM: Homo sapiens

<400> SEQUENCE: 162

Leu Gln Ala Ile Ala Val Ser Lys Leu
  1               5

<210> SEQ ID NO 163
<211> LENGTH: 9
<212> TYPE: PRT
<213> ORGANISM: Homo sapiens

<400> SEQUENCE: 163

Leu Gln Thr Leu Glu Leu Thr Gly Leu
  1               5

<210> SEQ ID NO 164
<211> LENGTH: 9
<212> TYPE: PRT
<213> ORGANISM: Homo sapiens

<400> SEQUENCE: 164

Lys Val Ile Leu Thr Leu Ser Ala Ile
  1               5

<210> SEQ ID NO 165
<211> LENGTH: 10
<212> TYPE: PRT
<213> ORGANISM: Homo sapiens

<400> SEQUENCE: 165

Trp Leu Gly Glu Lys Leu Gly Phe Tyr Thr
  1               5                  10

<210> SEQ ID NO 166
<211> LENGTH: 10
<212> TYPE: PRT
<213> ORGANISM: Homo sapiens

<400> SEQUENCE: 166

Lys Leu Phe Leu Trp Leu Leu Val Gly Val
  1               5                  10

<210> SEQ ID NO 167
<211> LENGTH: 10
<212> TYPE: PRT
<213> ORGANISM: Homo sapiens

<400> SEQUENCE: 167

Phe Leu Thr Ile Thr Pro Phe Trp Lys Leu
  1               5                  10

<210> SEQ ID NO 168
<211> LENGTH: 10
<212> TYPE: PRT
<213> ORGANISM: Homo sapiens

<400> SEQUENCE: 168

Val Leu Val Val Leu Arg Ile Trp Tyr Thr
  1               5                  10
```

<210> SEQ ID NO 169
<211> LENGTH: 10
<212> TYPE: PRT
<213> ORGANISM: Homo sapiens

<400> SEQUENCE: 169

Thr Met Thr Ile Ala Met Ile Phe Tyr Leu
1               5                   10

<210> SEQ ID NO 170
<211> LENGTH: 10
<212> TYPE: PRT
<213> ORGANISM: Homo sapiens

<400> SEQUENCE: 170

Lys Leu Leu Lys Ser Ser Ser Asn Gln Val
1               5                   10

<210> SEQ ID NO 171
<211> LENGTH: 10
<212> TYPE: PRT
<213> ORGANISM: Homo sapiens

<400> SEQUENCE: 171

Phe Leu Trp Leu Leu Val Gly Val Gly Leu
1               5                   10

<210> SEQ ID NO 172
<211> LENGTH: 10
<212> TYPE: PRT
<213> ORGANISM: Homo sapiens

<400> SEQUENCE: 172

Ser Leu Leu Gly Cys Val Ser Trp Ser Leu
1               5                   10

<210> SEQ ID NO 173
<211> LENGTH: 10
<212> TYPE: PRT
<213> ORGANISM: Homo sapiens

<400> SEQUENCE: 173

Ile Leu Leu Glu Ser Leu Leu Gly Cys Val
1               5                   10

<210> SEQ ID NO 174
<211> LENGTH: 10
<212> TYPE: PRT
<213> ORGANISM: Homo sapiens

<400> SEQUENCE: 174

Met Met Leu Ile Ile Gly Leu Asn Met Leu
1               5                   10

<210> SEQ ID NO 175
<211> LENGTH: 10
<212> TYPE: PRT
<213> ORGANISM: Homo sapiens

<400> SEQUENCE: 175

Leu Leu Asn Glu Thr Gly Ala Asp Phe Ile
1               5                   10

```
<210> SEQ ID NO 176
<211> LENGTH: 10
<212> TYPE: PRT
<213> ORGANISM: Homo sapiens

<400> SEQUENCE: 176

Lys Leu Gln Ala Ile Ala Val Ser Lys Leu
1               5                   10

<210> SEQ ID NO 177
<211> LENGTH: 10
<212> TYPE: PRT
<213> ORGANISM: Homo sapiens

<400> SEQUENCE: 177

Val Leu Phe Arg Lys Ser Glu Lys Tyr Met
1               5                   10

<210> SEQ ID NO 178
<211> LENGTH: 10
<212> TYPE: PRT
<213> ORGANISM: Homo sapiens

<400> SEQUENCE: 178

Phe Ile Leu Gly Gln Ile Val Leu Val Val
1               5                   10

<210> SEQ ID NO 179
<211> LENGTH: 10
<212> TYPE: PRT
<213> ORGANISM: Homo sapiens

<400> SEQUENCE: 179

Gly Leu Leu Tyr Leu His Thr Trp Ala Ala
1               5                   10

<210> SEQ ID NO 180
<211> LENGTH: 10
<212> TYPE: PRT
<213> ORGANISM: Homo sapiens

<400> SEQUENCE: 180

Phe Leu Ser Pro Ile Phe Leu Thr Ile Thr
1               5                   10

<210> SEQ ID NO 181
<211> LENGTH: 10
<212> TYPE: PRT
<213> ORGANISM: Homo sapiens

<400> SEQUENCE: 181

Leu Leu Gln Thr Lys Asn Ser Ser Lys Val
1               5                   10

<210> SEQ ID NO 182
<211> LENGTH: 10
<212> TYPE: PRT
<213> ORGANISM: Homo sapiens

<400> SEQUENCE: 182

Gly Met Ala Ser Arg Pro Asn Trp Leu Leu
1               5                   10

<210> SEQ ID NO 183
<211> LENGTH: 10
```

<212> TYPE: PRT
<213> ORGANISM: Homo sapiens

<400> SEQUENCE: 183

Tyr Ile Met Tyr Arg Gly Leu Ile Arg Leu
1               5                   10

<210> SEQ ID NO 184
<211> LENGTH: 10
<212> TYPE: PRT
<213> ORGANISM: Homo sapiens

<400> SEQUENCE: 184

Cys Ala Trp Cys Thr Ala Phe Lys Phe Val
1               5                   10

<210> SEQ ID NO 185
<211> LENGTH: 10
<212> TYPE: PRT
<213> ORGANISM: Homo sapiens

<400> SEQUENCE: 185

Leu Leu Val Gly Val Gly Leu Leu Gly Leu
1               5                   10

<210> SEQ ID NO 186
<211> LENGTH: 10
<212> TYPE: PRT
<213> ORGANISM: Homo sapiens

<400> SEQUENCE: 186

Ile Leu Thr Leu Ser Ala Ile Ala Thr Leu
1               5                   10

<210> SEQ ID NO 187
<211> LENGTH: 10
<212> TYPE: PRT
<213> ORGANISM: Homo sapiens

<400> SEQUENCE: 187

Phe Leu Thr His Trp Val Phe Gly Glu Val
1               5                   10

<210> SEQ ID NO 188
<211> LENGTH: 10
<212> TYPE: PRT
<213> ORGANISM: Homo sapiens

<400> SEQUENCE: 188

Val Leu Leu Gly Thr Met Met Leu Ile Ile
1               5                   10

<210> SEQ ID NO 189
<211> LENGTH: 10
<212> TYPE: PRT
<213> ORGANISM: Homo sapiens

<400> SEQUENCE: 189

Asn Ile Ser Gly Lys Leu Val Asp Phe Val
1               5                   10

<210> SEQ ID NO 190
<211> LENGTH: 10
<212> TYPE: PRT
<213> ORGANISM: Homo sapiens -continued

```
<400> SEQUENCE: 190

Asn Met Leu Phe Gly Pro Lys Lys Asn Leu
1               5                   10

<210> SEQ ID NO 191
<211> LENGTH: 10
<212> TYPE: PRT
<213> ORGANISM: Homo sapiens

<400> SEQUENCE: 191

Ile Met Ala Leu Ser Arg Tyr Pro Ile Val
1               5                   10

<210> SEQ ID NO 192
<211> LENGTH: 10
<212> TYPE: PRT
<213> ORGANISM: Homo sapiens

<400> SEQUENCE: 192

Leu Leu Tyr Leu His Thr Trp Ala Ala Ala
1               5                   10

<210> SEQ ID NO 193
<211> LENGTH: 10
<212> TYPE: PRT
<213> ORGANISM: Homo sapiens

<400> SEQUENCE: 193

Lys Leu Val Asn Lys Lys Trp Met Leu Thr
1               5                   10

<210> SEQ ID NO 194
<211> LENGTH: 10
<212> TYPE: PRT
<213> ORGANISM: Homo sapiens

<400> SEQUENCE: 194

Tyr Leu Gln Leu Thr Glu His Gly Asn Val
1               5                   10

<210> SEQ ID NO 195
<211> LENGTH: 10
<212> TYPE: PRT
<213> ORGANISM: Homo sapiens

<400> SEQUENCE: 195

Met Leu Thr Leu Leu Arg Ile Ile Thr Ile
1               5                   10

<210> SEQ ID NO 196
<211> LENGTH: 10
<212> TYPE: PRT
<213> ORGANISM: Homo sapiens

<400> SEQUENCE: 196

Ser Met Trp Pro Gln Thr Leu Gly His Leu
1               5                   10

<210> SEQ ID NO 197
<211> LENGTH: 10
<212> TYPE: PRT
<213> ORGANISM: Homo sapiens

<400> SEQUENCE: 197
```

Trp Met Leu Thr Leu Leu Arg Ile Ile Thr
1               5                   10

<210> SEQ ID NO 198
<211> LENGTH: 10
<212> TYPE: PRT
<213> ORGANISM: Homo sapiens

<400> SEQUENCE: 198

Tyr Leu Leu Glu Ile Phe Phe Cys Ala Trp
1               5                   10

<210> SEQ ID NO 199
<211> LENGTH: 10
<212> TYPE: PRT
<213> ORGANISM: Homo sapiens

<400> SEQUENCE: 199

Met Ile Tyr Tyr Phe Pro Leu Gln Thr Leu
1               5                   10

<210> SEQ ID NO 200
<211> LENGTH: 10
<212> TYPE: PRT
<213> ORGANISM: Homo sapiens

<400> SEQUENCE: 200

Leu Leu Cys Leu Ala Ser Gly Leu Met Leu
1               5                   10

<210> SEQ ID NO 201
<211> LENGTH: 10
<212> TYPE: PRT
<213> ORGANISM: Homo sapiens

<400> SEQUENCE: 201

Val Leu Ala Leu Gly Val Ser Ser Ser Leu
1               5                   10

<210> SEQ ID NO 202
<211> LENGTH: 10
<212> TYPE: PRT
<213> ORGANISM: Homo sapiens

<400> SEQUENCE: 202

Gln Met Ser Asn Lys Val Ile Leu Thr Leu
1               5                   10

<210> SEQ ID NO 203
<211> LENGTH: 10
<212> TYPE: PRT
<213> ORGANISM: Homo sapiens

<400> SEQUENCE: 203

Ile Leu Gly Gln Ile Val Leu Val Val Leu
1               5                   10

<210> SEQ ID NO 204
<211> LENGTH: 10
<212> TYPE: PRT
<213> ORGANISM: Homo sapiens

<400> SEQUENCE: 204

Ser Leu Tyr His Asp Leu Gly Pro Met Ile

```
                1               5                   10
```

<210> SEQ ID NO 205
<211> LENGTH: 10
<212> TYPE: PRT
<213> ORGANISM: Homo sapiens

<400> SEQUENCE: 205

```
Tyr Gln Met Ser Asn Lys Val Ile Leu Thr
1               5                   10
```

<210> SEQ ID NO 206
<211> LENGTH: 10
<212> TYPE: PRT
<213> ORGANISM: Homo sapiens

<400> SEQUENCE: 206

```
Ala Leu Gly Val Ser Ser Leu Ile Val
1               5                   10
```

<210> SEQ ID NO 207
<211> LENGTH: 10
<212> TYPE: PRT
<213> ORGANISM: Homo sapiens

<400> SEQUENCE: 207

```
Arg Ile Trp Tyr Thr Ser Leu Asn Pro Ile
1               5                   10
```

<210> SEQ ID NO 208
<211> LENGTH: 10
<212> TYPE: PRT
<213> ORGANISM: Homo sapiens

<400> SEQUENCE: 208

```
Gly Val Tyr Ala Arg Glu Arg Ser Asp Val
1               5                   10
```

<210> SEQ ID NO 209
<211> LENGTH: 10
<212> TYPE: PRT
<213> ORGANISM: Homo sapiens

<400> SEQUENCE: 209

```
Val Val Leu Arg Ile Trp Tyr Thr Ser Leu
1               5                   10
```

<210> SEQ ID NO 210
<211> LENGTH: 10
<212> TYPE: PRT
<213> ORGANISM: Homo sapiens

<400> SEQUENCE: 210

```
Gly Leu Glu Gly Phe Ser Ile Ala Phe Leu
1               5                   10
```

<210> SEQ ID NO 211
<211> LENGTH: 10
<212> TYPE: PRT
<213> ORGANISM: Homo sapiens

<400> SEQUENCE: 211

```
Ser Ile Ala Phe Leu Ser Pro Ile Phe Leu
1               5                   10
```

-continued

```
<210> SEQ ID NO 212
<211> LENGTH: 10
<212> TYPE: PRT
<213> ORGANISM: Homo sapiens

<400> SEQUENCE: 212

Gly Leu Ile Arg Leu Gly Tyr Ala Arg Ile
1               5                   10

<210> SEQ ID NO 213
<211> LENGTH: 10
<212> TYPE: PRT
<213> ORGANISM: Homo sapiens

<400> SEQUENCE: 213

Tyr Met Lys Leu Phe Leu Trp Leu Leu Val
1               5                   10

<210> SEQ ID NO 214
<211> LENGTH: 10
<212> TYPE: PRT
<213> ORGANISM: Homo sapiens

<400> SEQUENCE: 214

Thr Met Met Leu Ile Ile Gly Leu Asn Met
1               5                   10

<210> SEQ ID NO 215
<211> LENGTH: 9
<212> TYPE: PRT
<213> ORGANISM: Homo sapiens

<400> SEQUENCE: 215

Ala Leu Ser Arg Tyr Pro Ile Val Lys
1               5

<210> SEQ ID NO 216
<211> LENGTH: 9
<212> TYPE: PRT
<213> ORGANISM: Homo sapiens

<400> SEQUENCE: 216

Lys Leu Gly Lys Val Ala Pro Thr Lys
1               5

<210> SEQ ID NO 217
<211> LENGTH: 9
<212> TYPE: PRT
<213> ORGANISM: Homo sapiens

<400> SEQUENCE: 217

Lys Leu Gln Ala Ile Ala Val Ser Lys
1               5

<210> SEQ ID NO 218
<211> LENGTH: 9
<212> TYPE: PRT
<213> ORGANISM: Homo sapiens

<400> SEQUENCE: 218

Phe Leu Thr Ile Thr Pro Phe Trp Lys
1               5

<210> SEQ ID NO 219
```

```
<211> LENGTH: 9
<212> TYPE: PRT
<213> ORGANISM: Homo sapiens

<400> SEQUENCE: 219

Gly Leu Ile Arg Leu Gly Tyr Ala Arg
1               5

<210> SEQ ID NO 220
<211> LENGTH: 9
<212> TYPE: PRT
<213> ORGANISM: Homo sapiens

<400> SEQUENCE: 220

Gly Leu Asn Met Leu Phe Gly Pro Lys
1               5

<210> SEQ ID NO 221
<211> LENGTH: 9
<212> TYPE: PRT
<213> ORGANISM: Homo sapiens

<400> SEQUENCE: 221

Gly Leu Glu Gly Phe Ser Ile Ala Phe
1               5

<210> SEQ ID NO 222
<211> LENGTH: 9
<212> TYPE: PRT
<213> ORGANISM: Homo sapiens

<400> SEQUENCE: 222

Gly Leu Arg His Lys Ala Tyr Glu Arg
1               5

<210> SEQ ID NO 223
<211> LENGTH: 9
<212> TYPE: PRT
<213> ORGANISM: Homo sapiens

<400> SEQUENCE: 223

Asn Leu Asp Leu Leu Gln Thr Lys
1               5

<210> SEQ ID NO 224
<211> LENGTH: 9
<212> TYPE: PRT
<213> ORGANISM: Homo sapiens

<400> SEQUENCE: 224

Thr Leu Thr Val Asn Ile Ser Gly Lys
1               5

<210> SEQ ID NO 225
<211> LENGTH: 9
<212> TYPE: PRT
<213> ORGANISM: Homo sapiens

<400> SEQUENCE: 225

Gln Leu Thr Glu His Gly Asn Val Lys
1               5

<210> SEQ ID NO 226
<211> LENGTH: 9
<212> TYPE: PRT
```

<213> ORGANISM: Homo sapiens

<400> SEQUENCE: 226

Ala Ile Trp Pro Phe Arg Phe Gly Tyr
1               5

<210> SEQ ID NO 227
<211> LENGTH: 9
<212> TYPE: PRT
<213> ORGANISM: Homo sapiens

<400> SEQUENCE: 227

Val Leu Phe Arg Lys Ser Glu Lys Tyr
1               5

<210> SEQ ID NO 228
<211> LENGTH: 9
<212> TYPE: PRT
<213> ORGANISM: Homo sapiens

<400> SEQUENCE: 228

Leu Leu Gln Thr Lys Asn Ser Ser Lys
1               5

<210> SEQ ID NO 229
<211> LENGTH: 9
<212> TYPE: PRT
<213> ORGANISM: Homo sapiens

<400> SEQUENCE: 229

Met Leu Pro Ser Cys Leu Trp Phe Arg
1               5

<210> SEQ ID NO 230
<211> LENGTH: 9
<212> TYPE: PRT
<213> ORGANISM: Homo sapiens

<400> SEQUENCE: 230

Thr Met Thr Ile Ala Met Ile Phe Tyr
1               5

<210> SEQ ID NO 231
<211> LENGTH: 9
<212> TYPE: PRT
<213> ORGANISM: Homo sapiens

<400> SEQUENCE: 231

Val Leu Val Val Leu Arg Ile Trp Tyr
1               5

<210> SEQ ID NO 232
<211> LENGTH: 9
<212> TYPE: PRT
<213> ORGANISM: Homo sapiens

<400> SEQUENCE: 232

Lys Leu Arg Leu Met Val Leu Ala Leu
1               5

<210> SEQ ID NO 233
<211> LENGTH: 9
<212> TYPE: PRT
<213> ORGANISM: Homo sapiens -continued

```
<400> SEQUENCE: 233

Lys Ala Tyr Glu Arg Lys Leu Gly Lys
1               5

<210> SEQ ID NO 234
<211> LENGTH: 9
<212> TYPE: PRT
<213> ORGANISM: Homo sapiens

<400> SEQUENCE: 234

Ile Met Tyr Arg Gly Leu Ile Arg Leu
1               5

<210> SEQ ID NO 235
<211> LENGTH: 9
<212> TYPE: PRT
<213> ORGANISM: Homo sapiens

<400> SEQUENCE: 235

Leu Met Leu Pro Ser Cys Leu Trp Phe
1               5

<210> SEQ ID NO 236
<211> LENGTH: 9
<212> TYPE: PRT
<213> ORGANISM: Homo sapiens

<400> SEQUENCE: 236

Lys Val Leu Phe Arg Lys Ser Glu Lys
1               5

<210> SEQ ID NO 237
<211> LENGTH: 9
<212> TYPE: PRT
<213> ORGANISM: Homo sapiens

<400> SEQUENCE: 237

Tyr Met Lys Leu Phe Leu Trp Leu Leu
1               5

<210> SEQ ID NO 238
<211> LENGTH: 9
<212> TYPE: PRT
<213> ORGANISM: Homo sapiens

<400> SEQUENCE: 238

Ala Met Ile Phe Tyr Leu Leu Glu Ile
1               5

<210> SEQ ID NO 239
<211> LENGTH: 9
<212> TYPE: PRT
<213> ORGANISM: Homo sapiens

<400> SEQUENCE: 239

Lys Leu Val Asp Phe Val Val Thr His
1               5

<210> SEQ ID NO 240
<211> LENGTH: 9
<212> TYPE: PRT
<213> ORGANISM: Homo sapiens

<400> SEQUENCE: 240
```

```
Asp Leu Thr Met Trp Leu Gly Glu Lys
1               5
```

<210> SEQ ID NO 241
<211> LENGTH: 9
<212> TYPE: PRT
<213> ORGANISM: Homo sapiens

<400> SEQUENCE: 241

```
Lys Leu Val Asn Lys Lys Trp Met Leu
1               5
```

<210> SEQ ID NO 242
<211> LENGTH: 9
<212> TYPE: PRT
<213> ORGANISM: Homo sapiens

<400> SEQUENCE: 242

```
Phe Leu Ser Pro Ile Phe Leu Thr Ile
1               5
```

<210> SEQ ID NO 243
<211> LENGTH: 9
<212> TYPE: PRT
<213> ORGANISM: Homo sapiens

<400> SEQUENCE: 243

```
Tyr Leu Leu Glu Ile Phe Phe Cys Ala
1               5
```

<210> SEQ ID NO 244
<211> LENGTH: 9
<212> TYPE: PRT
<213> ORGANISM: Homo sapiens

<400> SEQUENCE: 244

```
Gly Leu Gly Leu Arg His Lys Ala Tyr
1               5
```

<210> SEQ ID NO 245
<211> LENGTH: 9
<212> TYPE: PRT
<213> ORGANISM: Homo sapiens

<400> SEQUENCE: 245

```
Phe Val Pro Gly Gly Val Tyr Ala Arg
1               5
```

<210> SEQ ID NO 246
<211> LENGTH: 9
<212> TYPE: PRT
<213> ORGANISM: Homo sapiens

<400> SEQUENCE: 246

```
Tyr Leu Arg Ile Trp Gly Phe Ile Leu
1               5
```

<210> SEQ ID NO 247
<211> LENGTH: 9
<212> TYPE: PRT
<213> ORGANISM: Homo sapiens

<400> SEQUENCE: 247

```
Thr Ile Leu Glu Ser Asp Ala Ser Lys
1               5
```

<210> SEQ ID NO 248
<211> LENGTH: 9
<212> TYPE: PRT
<213> ORGANISM: Homo sapiens

<400> SEQUENCE: 248

Asp Leu Gly Pro Met Ile Tyr Tyr Phe
1               5

<210> SEQ ID NO 249
<211> LENGTH: 9
<212> TYPE: PRT
<213> ORGANISM: Homo sapiens

<400> SEQUENCE: 249

Val Leu Leu Gly Thr Met Met Leu Ile
1               5

<210> SEQ ID NO 250
<211> LENGTH: 9
<212> TYPE: PRT
<213> ORGANISM: Homo sapiens

<400> SEQUENCE: 250

Gly Leu Ile Trp Trp Val Thr Gly Thr
1               5

<210> SEQ ID NO 251
<211> LENGTH: 9
<212> TYPE: PRT
<213> ORGANISM: Homo sapiens

<400> SEQUENCE: 251

Ala Ile Ala Val Ser Lys Leu Leu Lys
1               5

<210> SEQ ID NO 252
<211> LENGTH: 9
<212> TYPE: PRT
<213> ORGANISM: Homo sapiens

<400> SEQUENCE: 252

Met Leu Phe Gly Pro Lys Lys Asn Leu
1               5

<210> SEQ ID NO 253
<211> LENGTH: 9
<212> TYPE: PRT
<213> ORGANISM: Homo sapiens

<400> SEQUENCE: 253

Leu Leu Tyr Leu His Thr Trp Ala Ala
1               5

<210> SEQ ID NO 254
<211> LENGTH: 9
<212> TYPE: PRT
<213> ORGANISM: Homo sapiens

<400> SEQUENCE: 254

Leu Leu Asn Glu Thr Gly Ala Asp Phe
1               5

```
<210> SEQ ID NO 255
<211> LENGTH: 9
<212> TYPE: PRT
<213> ORGANISM: Homo sapiens

<400> SEQUENCE: 255

Leu Val Phe Leu Thr His Trp Val Phe
1               5

<210> SEQ ID NO 256
<211> LENGTH: 9
<212> TYPE: PRT
<213> ORGANISM: Homo sapiens

<400> SEQUENCE: 256

Leu Leu Gly Leu Gly Leu Arg His Lys
1               5

<210> SEQ ID NO 257
<211> LENGTH: 9
<212> TYPE: PRT
<213> ORGANISM: Homo sapiens

<400> SEQUENCE: 257

Ser Met Trp Pro Gln Thr Leu Gly His
1               5

<210> SEQ ID NO 258
<211> LENGTH: 9
<212> TYPE: PRT
<213> ORGANISM: Homo sapiens

<400> SEQUENCE: 258

Cys Leu Trp Phe Arg Gly Thr Gly Leu
1               5

<210> SEQ ID NO 259
<211> LENGTH: 9
<212> TYPE: PRT
<213> ORGANISM: Homo sapiens

<400> SEQUENCE: 259

His Met Asn Thr Pro Lys Tyr Phe Leu
1               5

<210> SEQ ID NO 260
<211> LENGTH: 9
<212> TYPE: PRT
<213> ORGANISM: Homo sapiens

<400> SEQUENCE: 260

Gly Leu Leu Gly Leu Gly Leu Arg His
1               5

<210> SEQ ID NO 261
<211> LENGTH: 9
<212> TYPE: PRT
<213> ORGANISM: Homo sapiens

<400> SEQUENCE: 261

Trp Leu Gly Glu Lys Leu Gly Phe Tyr
1               5

<210> SEQ ID NO 262
<211> LENGTH: 9
```

```
<212> TYPE: PRT
<213> ORGANISM: Homo sapiens

<400> SEQUENCE: 262

Leu Leu Gly Cys Val Ser Trp Ser Leu
 1               5

<210> SEQ ID NO 263
<211> LENGTH: 9
<212> TYPE: PRT
<213> ORGANISM: Homo sapiens

<400> SEQUENCE: 263

Lys Leu Phe Leu Trp Leu Leu Val Gly
 1               5

<210> SEQ ID NO 264
<211> LENGTH: 9
<212> TYPE: PRT
<213> ORGANISM: Homo sapiens

<400> SEQUENCE: 264

Gly Met Ala Ser Arg Pro Asn Trp Leu
 1               5

<210> SEQ ID NO 265
<211> LENGTH: 10
<212> TYPE: PRT
<213> ORGANISM: Homo sapiens

<400> SEQUENCE: 265

Gly Leu Asn Met Leu Phe Gly Pro Lys Lys
 1               5                  10

<210> SEQ ID NO 266
<211> LENGTH: 10
<212> TYPE: PRT
<213> ORGANISM: Homo sapiens

<400> SEQUENCE: 266

Gly Leu Arg His Lys Ala Tyr Glu Arg Lys
 1               5                  10

<210> SEQ ID NO 267
<211> LENGTH: 10
<212> TYPE: PRT
<213> ORGANISM: Homo sapiens

<400> SEQUENCE: 267

Lys Leu Val Asp Phe Val Val Thr His Phe
 1               5                  10

<210> SEQ ID NO 268
<211> LENGTH: 10
<212> TYPE: PRT
<213> ORGANISM: Homo sapiens

<400> SEQUENCE: 268

Leu Met Leu Pro Ser Cys Leu Trp Phe Arg
 1               5                  10

<210> SEQ ID NO 269
<211> LENGTH: 10
<212> TYPE: PRT
<213> ORGANISM: Homo sapiens
```

<400> SEQUENCE: 269

Leu Leu Leu Gln Thr Lys Asn Ser Ser Lys
1               5                   10

<210> SEQ ID NO 270
<211> LENGTH: 10
<212> TYPE: PRT
<213> ORGANISM: Homo sapiens

<400> SEQUENCE: 270

Gly Leu Leu Gly Leu Gly Leu Arg His Lys
1               5                   10

<210> SEQ ID NO 271
<211> LENGTH: 10
<212> TYPE: PRT
<213> ORGANISM: Homo sapiens

<400> SEQUENCE: 271

Thr Met Trp Leu Gly Glu Lys Leu Gly Phe
1               5                   10

<210> SEQ ID NO 272
<211> LENGTH: 10
<212> TYPE: PRT
<213> ORGANISM: Homo sapiens

<400> SEQUENCE: 272

Gly Leu Met Leu Pro Ser Cys Leu Trp Phe
1               5                   10

<210> SEQ ID NO 273
<211> LENGTH: 10
<212> TYPE: PRT
<213> ORGANISM: Homo sapiens

<400> SEQUENCE: 273

Ser Leu Val Phe Leu Thr His Trp Val Phe
1               5                   10

<210> SEQ ID NO 274
<211> LENGTH: 10
<212> TYPE: PRT
<213> ORGANISM: Homo sapiens

<400> SEQUENCE: 274

Gly Met Ala Ser Arg Pro Asn Trp Leu Leu
1               5                   10

<210> SEQ ID NO 275
<211> LENGTH: 10
<212> TYPE: PRT
<213> ORGANISM: Homo sapiens

<400> SEQUENCE: 275

Phe Leu Thr Ile Thr Pro Phe Trp Lys Leu
1               5                   10

<210> SEQ ID NO 276
<211> LENGTH: 10
<212> TYPE: PRT
<213> ORGANISM: Homo sapiens

<400> SEQUENCE: 276

Thr Leu Ser Ala Ile Ala Thr Leu Asp Arg
1               5                   10

<210> SEQ ID NO 277
<211> LENGTH: 10
<212> TYPE: PRT
<213> ORGANISM: Homo sapiens

<400> SEQUENCE: 277

Ser Leu Leu Gly Cys Val Ser Trp Ser Leu
1               5                   10

<210> SEQ ID NO 278
<211> LENGTH: 10
<212> TYPE: PRT
<213> ORGANISM: Homo sapiens

<400> SEQUENCE: 278

Val Ile Asp His Arg Glu Val Ser Glu Lys
1               5                   10

<210> SEQ ID NO 279
<211> LENGTH: 10
<212> TYPE: PRT
<213> ORGANISM: Homo sapiens

<400> SEQUENCE: 279

Met Leu Ile Ile Gly Leu Asn Met Leu Phe
1               5                   10

<210> SEQ ID NO 280
<211> LENGTH: 10
<212> TYPE: PRT
<213> ORGANISM: Homo sapiens

<400> SEQUENCE: 280

Lys Leu Gln Ala Ile Ala Val Ser Lys Leu
1               5                   10

<210> SEQ ID NO 281
<211> LENGTH: 10
<212> TYPE: PRT
<213> ORGANISM: Homo sapiens

<400> SEQUENCE: 281

Lys Leu Phe Leu Trp Leu Leu Val Gly Val
1               5                   10

<210> SEQ ID NO 282
<211> LENGTH: 10
<212> TYPE: PRT
<213> ORGANISM: Homo sapiens

<400> SEQUENCE: 282

Phe Leu Trp Leu Leu Val Gly Val Gly Leu
1               5                   10

<210> SEQ ID NO 283
<211> LENGTH: 10
<212> TYPE: PRT
<213> ORGANISM: Homo sapiens

<400> SEQUENCE: 283

Ala Met Ile Phe Tyr Leu Leu Glu Ile Phe

-continued

```
1               5                   10

<210> SEQ ID NO 284
<211> LENGTH: 10
<212> TYPE: PRT
<213> ORGANISM: Homo sapiens

<400> SEQUENCE: 284

Val Leu Leu Gly Thr Met Met Leu Ile Ile
1               5                   10

<210> SEQ ID NO 285
<211> LENGTH: 10
<212> TYPE: PRT
<213> ORGANISM: Homo sapiens

<400> SEQUENCE: 285

Tyr Leu Leu Glu Ile Phe Phe Cys Ala Trp
1               5                   10

<210> SEQ ID NO 286
<211> LENGTH: 10
<212> TYPE: PRT
<213> ORGANISM: Homo sapiens

<400> SEQUENCE: 286

Leu Leu Val Gly Val Gly Leu Leu Gly Leu
1               5                   10

<210> SEQ ID NO 287
<211> LENGTH: 10
<212> TYPE: PRT
<213> ORGANISM: Homo sapiens

<400> SEQUENCE: 287

Gly Leu Glu Gly Phe Ser Ile Ala Phe Leu
1               5                   10

<210> SEQ ID NO 288
<211> LENGTH: 10
<212> TYPE: PRT
<213> ORGANISM: Homo sapiens

<400> SEQUENCE: 288

Leu Leu Gly Cys Val Ser Trp Ser Leu Tyr
1               5                   10

<210> SEQ ID NO 289
<211> LENGTH: 10
<212> TYPE: PRT
<213> ORGANISM: Homo sapiens

<400> SEQUENCE: 289

Ser Leu Tyr His Asp Leu Gly Pro Met Ile
1               5                   10

<210> SEQ ID NO 290
<211> LENGTH: 10
<212> TYPE: PRT
<213> ORGANISM: Homo sapiens

<400> SEQUENCE: 290

His Leu Leu Asn Glu Thr Gly Ala Asp Phe
1               5                   10
```

```
<210> SEQ ID NO 291
<211> LENGTH: 10
<212> TYPE: PRT
<213> ORGANISM: Homo sapiens

<400> SEQUENCE: 291

His Thr Trp Gly Ile Met Ala Leu Ser Arg
 1               5                  10

<210> SEQ ID NO 292
<211> LENGTH: 10
<212> TYPE: PRT
<213> ORGANISM: Homo sapiens

<400> SEQUENCE: 292

Thr Leu Glu Leu Thr Gly Leu Glu Gly Phe
 1               5                  10

<210> SEQ ID NO 293
<211> LENGTH: 10
<212> TYPE: PRT
<213> ORGANISM: Homo sapiens

<400> SEQUENCE: 293

Thr Pro Phe Trp Lys Leu Val Asn Lys Lys
 1               5                  10

<210> SEQ ID NO 294
<211> LENGTH: 10
<212> TYPE: PRT
<213> ORGANISM: Homo sapiens

<400> SEQUENCE: 294

Gln Met Ser Asn Lys Val Ile Leu Thr Leu
 1               5                  10

<210> SEQ ID NO 295
<211> LENGTH: 10
<212> TYPE: PRT
<213> ORGANISM: Homo sapiens

<400> SEQUENCE: 295

Gly Leu Ile Arg Leu Gly Tyr Ala Arg Ile
 1               5                  10

<210> SEQ ID NO 296
<211> LENGTH: 10
<212> TYPE: PRT
<213> ORGANISM: Homo sapiens

<400> SEQUENCE: 296

Thr Met Thr Ile Ala Met Ile Phe Tyr Leu
 1               5                  10

<210> SEQ ID NO 297
<211> LENGTH: 10
<212> TYPE: PRT
<213> ORGANISM: Homo sapiens

<400> SEQUENCE: 297

Ser Leu Asn Pro Ile Trp Ser Tyr Gln Met
 1               5                  10

<210> SEQ ID NO 298
```

```
<211> LENGTH: 10
<212> TYPE: PRT
<213> ORGANISM: Homo sapiens

<400> SEQUENCE: 298

Gly Leu Leu Tyr Leu His Thr Trp Ala Ala
1               5                   10

<210> SEQ ID NO 299
<211> LENGTH: 10
<212> TYPE: PRT
<213> ORGANISM: Homo sapiens

<400> SEQUENCE: 299

Lys Thr Met Thr Ile Ala Met Ile Phe Tyr
1               5                   10

<210> SEQ ID NO 300
<211> LENGTH: 10
<212> TYPE: PRT
<213> ORGANISM: Homo sapiens

<400> SEQUENCE: 300

Ile Thr Leu Thr Val Asn Ile Ser Gly Lys
1               5                   10

<210> SEQ ID NO 301
<211> LENGTH: 10
<212> TYPE: PRT
<213> ORGANISM: Homo sapiens

<400> SEQUENCE: 301

Ser Met Trp Pro Gln Thr Leu Gly His Leu
1               5                   10

<210> SEQ ID NO 302
<211> LENGTH: 10
<212> TYPE: PRT
<213> ORGANISM: Homo sapiens

<400> SEQUENCE: 302

Arg Ile Gly Thr Asp Gly Asp Cys Ser Lys
1               5                   10

<210> SEQ ID NO 303
<211> LENGTH: 10
<212> TYPE: PRT
<213> ORGANISM: Homo sapiens

<400> SEQUENCE: 303

Ile Leu Glu Ser Asp Ala Ser Lys Pro Tyr
1               5                   10

<210> SEQ ID NO 304
<211> LENGTH: 10
<212> TYPE: PRT
<213> ORGANISM: Homo sapiens

<400> SEQUENCE: 304

Met Ile Phe Tyr Leu Leu Glu Ile Phe Phe
1               5                   10

<210> SEQ ID NO 305
<211> LENGTH: 10
<212> TYPE: PRT
```

<213> ORGANISM: Homo sapiens

<400> SEQUENCE: 305

Leu Ile Asn Ser Gly Thr Asn Pro Gly Lys
1               5                   10

<210> SEQ ID NO 306
<211> LENGTH: 10
<212> TYPE: PRT
<213> ORGANISM: Homo sapiens

<400> SEQUENCE: 306

Lys Val Leu Phe Arg Lys Ser Glu Lys Tyr
1               5                   10

<210> SEQ ID NO 307
<211> LENGTH: 10
<212> TYPE: PRT
<213> ORGANISM: Homo sapiens

<400> SEQUENCE: 307

Met Ala Leu Ser Arg Tyr Pro Ile Val Lys
1               5                   10

<210> SEQ ID NO 308
<211> LENGTH: 10
<212> TYPE: PRT
<213> ORGANISM: Homo sapiens

<400> SEQUENCE: 308

Met Leu Thr Leu Leu Arg Ile Ile Thr Ile
1               5                   10

<210> SEQ ID NO 309
<211> LENGTH: 10
<212> TYPE: PRT
<213> ORGANISM: Homo sapiens

<400> SEQUENCE: 309

Pro Ile Trp Ser Tyr Gln Met Ser Asn Lys
1               5                   10

<210> SEQ ID NO 310
<211> LENGTH: 10
<212> TYPE: PRT
<213> ORGANISM: Homo sapiens

<400> SEQUENCE: 310

Ile Thr Pro Phe Trp Lys Leu Val Asn Lys
1               5                   10

<210> SEQ ID NO 311
<211> LENGTH: 10
<212> TYPE: PRT
<213> ORGANISM: Homo sapiens

<400> SEQUENCE: 311

Ile Thr Ile Leu Glu Ser Asp Ala Ser Lys
1               5                   10

<210> SEQ ID NO 312
<211> LENGTH: 10
<212> TYPE: PRT
<213> ORGANISM: Homo sapiens

```
<400> SEQUENCE: 312

Ile Leu Gly Gln Ile Val Leu Val Val Leu
 1               5                  10

<210> SEQ ID NO 313
<211> LENGTH: 10
<212> TYPE: PRT
<213> ORGANISM: Homo sapiens

<400> SEQUENCE: 313

Ala Val Ser Gly Cys Val Phe Ala Ile Phe
 1               5                  10

<210> SEQ ID NO 314
<211> LENGTH: 10
<212> TYPE: PRT
<213> ORGANISM: Homo sapiens

<400> SEQUENCE: 314

Tyr Thr Ser Leu Asn Pro Ile Trp Ser Tyr
 1               5                  10

<210> SEQ ID NO 315
<211> LENGTH: 9
<212> TYPE: PRT
<213> ORGANISM: Homo sapiens

<400> SEQUENCE: 315

Lys Val Leu Phe Arg Lys Ser Glu Lys
 1               5

<210> SEQ ID NO 316
<211> LENGTH: 9
<212> TYPE: PRT
<213> ORGANISM: Homo sapiens

<400> SEQUENCE: 316

Lys Ala Tyr Glu Arg Lys Leu Gly Lys
 1               5

<210> SEQ ID NO 317
<211> LENGTH: 9
<212> TYPE: PRT
<213> ORGANISM: Homo sapiens

<400> SEQUENCE: 317

Phe Leu Thr Ile Thr Pro Phe Trp Lys
 1               5

<210> SEQ ID NO 318
<211> LENGTH: 9
<212> TYPE: PRT
<213> ORGANISM: Homo sapiens

<400> SEQUENCE: 318

Lys Leu Gly Lys Val Ala Pro Thr Lys
 1               5

<210> SEQ ID NO 319
<211> LENGTH: 9
<212> TYPE: PRT
<213> ORGANISM: Homo sapiens

<400> SEQUENCE: 319
```

```
Gly Leu Asn Met Leu Phe Gly Pro Lys
  1               5

<210> SEQ ID NO 320
<211> LENGTH: 9
<212> TYPE: PRT
<213> ORGANISM: Homo sapiens

<400> SEQUENCE: 320

Lys Leu Gln Ala Ile Ala Val Ser Lys
  1               5

<210> SEQ ID NO 321
<211> LENGTH: 9
<212> TYPE: PRT
<213> ORGANISM: Homo sapiens

<400> SEQUENCE: 321

Ala Leu Ser Arg Tyr Pro Ile Val Lys
  1               5

<210> SEQ ID NO 322
<211> LENGTH: 9
<212> TYPE: PRT
<213> ORGANISM: Homo sapiens

<400> SEQUENCE: 322

Ala Ile Ala Val Ser Lys Leu Leu Lys
  1               5

<210> SEQ ID NO 323
<211> LENGTH: 9
<212> TYPE: PRT
<213> ORGANISM: Homo sapiens

<400> SEQUENCE: 323

Phe Val Pro Gly Gly Val Tyr Ala Arg
  1               5

<210> SEQ ID NO 324
<211> LENGTH: 9
<212> TYPE: PRT
<213> ORGANISM: Homo sapiens

<400> SEQUENCE: 324

Gly Leu Ile Arg Leu Gly Tyr Ala Arg
  1               5

<210> SEQ ID NO 325
<211> LENGTH: 9
<212> TYPE: PRT
<213> ORGANISM: Homo sapiens

<400> SEQUENCE: 325

Thr Ile Leu Glu Ser Asp Ala Ser Lys
  1               5

<210> SEQ ID NO 326
<211> LENGTH: 9
<212> TYPE: PRT
<213> ORGANISM: Homo sapiens

<400> SEQUENCE: 326

Gly Gln Ile Val Leu Val Val Leu Arg
  1               5
```

<210> SEQ ID NO 327
<211> LENGTH: 9
<212> TYPE: PRT
<213> ORGANISM: Homo sapiens

<400> SEQUENCE: 327

Gly Leu Arg His Lys Ala Tyr Glu Arg
1               5

<210> SEQ ID NO 328
<211> LENGTH: 9
<212> TYPE: PRT
<213> ORGANISM: Homo sapiens

<400> SEQUENCE: 328

Asn Leu Asp Leu Leu Leu Gln Thr Lys
1               5

<210> SEQ ID NO 329
<211> LENGTH: 9
<212> TYPE: PRT
<213> ORGANISM: Homo sapiens

<400> SEQUENCE: 329

Thr Leu Thr Val Asn Ile Ser Gly Lys
1               5

<210> SEQ ID NO 330
<211> LENGTH: 9
<212> TYPE: PRT
<213> ORGANISM: Homo sapiens

<400> SEQUENCE: 330

Leu Leu Gln Thr Lys Asn Ser Ser Lys
1               5

<210> SEQ ID NO 331
<211> LENGTH: 9
<212> TYPE: PRT
<213> ORGANISM: Homo sapiens

<400> SEQUENCE: 331

Thr Pro Phe Trp Lys Leu Val Asn Lys
1               5

<210> SEQ ID NO 332
<211> LENGTH: 9
<212> TYPE: PRT
<213> ORGANISM: Homo sapiens

<400> SEQUENCE: 332

Gln Leu Thr Glu His Gly Asn Val Lys
1               5

<210> SEQ ID NO 333
<211> LENGTH: 9
<212> TYPE: PRT
<213> ORGANISM: Homo sapiens

<400> SEQUENCE: 333

Tyr Ile Met Tyr Arg Gly Leu Ile Arg
1               5

```
<210> SEQ ID NO 334
<211> LENGTH: 9
<212> TYPE: PRT
<213> ORGANISM: Homo sapiens

<400> SEQUENCE: 334

Phe Cys Ala Trp Cys Thr Ala Phe Lys
1               5

<210> SEQ ID NO 335
<211> LENGTH: 9
<212> TYPE: PRT
<213> ORGANISM: Homo sapiens

<400> SEQUENCE: 335

Tyr Thr Asp Phe Gly Pro Ser Thr Arg
1               5

<210> SEQ ID NO 336
<211> LENGTH: 9
<212> TYPE: PRT
<213> ORGANISM: Homo sapiens

<400> SEQUENCE: 336

Met Leu Pro Ser Cys Leu Trp Phe Arg
1               5

<210> SEQ ID NO 337
<211> LENGTH: 9
<212> TYPE: PRT
<213> ORGANISM: Homo sapiens

<400> SEQUENCE: 337

Lys Thr Met Thr Ile Ala Met Ile Phe
1               5

<210> SEQ ID NO 338
<211> LENGTH: 9
<212> TYPE: PRT
<213> ORGANISM: Homo sapiens

<400> SEQUENCE: 338

Gly Val Gly Leu Leu Gly Leu Gly Leu
1               5

<210> SEQ ID NO 339
<211> LENGTH: 9
<212> TYPE: PRT
<213> ORGANISM: Homo sapiens

<400> SEQUENCE: 339

Asn Gln Lys Val Val Ile Asp His Arg
1               5

<210> SEQ ID NO 340
<211> LENGTH: 9
<212> TYPE: PRT
<213> ORGANISM: Homo sapiens

<400> SEQUENCE: 340

Asp Leu Thr Met Trp Leu Gly Glu Lys
1               5

<210> SEQ ID NO 341
<211> LENGTH: 9
```

```
<212> TYPE: PRT
<213> ORGANISM: Homo sapiens

<400> SEQUENCE: 341

Gly Thr Met Met Leu Ile Ile Gly Leu
1               5

<210> SEQ ID NO 342
<211> LENGTH: 9
<212> TYPE: PRT
<213> ORGANISM: Homo sapiens

<400> SEQUENCE: 342

Glu Val Ala Thr Gly Met Ala Ser Arg
1               5

<210> SEQ ID NO 343
<211> LENGTH: 9
<212> TYPE: PRT
<213> ORGANISM: Homo sapiens

<400> SEQUENCE: 343

Pro Thr Asn Tyr Arg Asp Asn Gln Lys
1               5

<210> SEQ ID NO 344
<211> LENGTH: 9
<212> TYPE: PRT
<213> ORGANISM: Homo sapiens

<400> SEQUENCE: 344

Lys Val Ile Leu Thr Leu Ser Ala Ile
1               5

<210> SEQ ID NO 345
<211> LENGTH: 9
<212> TYPE: PRT
<213> ORGANISM: Homo sapiens

<400> SEQUENCE: 345

Tyr Ile Thr Ser Ala Pro Gly Ser Arg
1               5

<210> SEQ ID NO 346
<211> LENGTH: 9
<212> TYPE: PRT
<213> ORGANISM: Homo sapiens

<400> SEQUENCE: 346

Leu Asn Met Leu Phe Gly Pro Lys Lys
1               5

<210> SEQ ID NO 347
<211> LENGTH: 9
<212> TYPE: PRT
<213> ORGANISM: Homo sapiens

<400> SEQUENCE: 347

Leu Val Phe Leu Thr His Trp Val Phe
1               5

<210> SEQ ID NO 348
<211> LENGTH: 9
<212> TYPE: PRT
<213> ORGANISM: Homo sapiens
```

```
<400> SEQUENCE: 348

Asn Ser Ser Lys Val Leu Phe Arg Lys
1               5

<210> SEQ ID NO 349
<211> LENGTH: 9
<212> TYPE: PRT
<213> ORGANISM: Homo sapiens

<400> SEQUENCE: 349

Gly Asp Cys Ser Lys Pro Glu Glu Lys
1               5

<210> SEQ ID NO 350
<211> LENGTH: 9
<212> TYPE: PRT
<213> ORGANISM: Homo sapiens

<400> SEQUENCE: 350

Ala Val Ser Gly Cys Val Phe Ala Ile
1               5

<210> SEQ ID NO 351
<211> LENGTH: 9
<212> TYPE: PRT
<213> ORGANISM: Homo sapiens

<400> SEQUENCE: 351

Phe Gln Ala Pro Asn Ala Lys Leu Arg
1               5

<210> SEQ ID NO 352
<211> LENGTH: 9
<212> TYPE: PRT
<213> ORGANISM: Homo sapiens

<400> SEQUENCE: 352

Asp Cys Ser Lys Pro Glu Glu Lys Lys
1               5

<210> SEQ ID NO 353
<211> LENGTH: 9
<212> TYPE: PRT
<213> ORGANISM: Homo sapiens

<400> SEQUENCE: 353

Gly Asn His Glu Asp Asp Leu Asp Arg
1               5

<210> SEQ ID NO 354
<211> LENGTH: 9
<212> TYPE: PRT
<213> ORGANISM: Homo sapiens

<400> SEQUENCE: 354

Lys Lys Trp Met Leu Thr Leu Leu Arg
1               5

<210> SEQ ID NO 355
<211> LENGTH: 9
<212> TYPE: PRT
<213> ORGANISM: Homo sapiens

<400> SEQUENCE: 355
```

```
Lys Asn Ser Ser Lys Val Leu Phe Arg
 1               5
```

<210> SEQ ID NO 356
<211> LENGTH: 9
<212> TYPE: PRT
<213> ORGANISM: Homo sapiens

<400> SEQUENCE: 356

```
Arg Leu Met Val Leu Ala Leu Gly Val
 1               5
```

<210> SEQ ID NO 357
<211> LENGTH: 9
<212> TYPE: PRT
<213> ORGANISM: Homo sapiens

<400> SEQUENCE: 357

```
Lys Tyr Met Lys Leu Phe Leu Trp Leu
 1               5
```

<210> SEQ ID NO 358
<211> LENGTH: 9
<212> TYPE: PRT
<213> ORGANISM: Homo sapiens

<400> SEQUENCE: 358

```
Met Thr Ile Ala Met Ile Phe Tyr Leu
 1               5
```

<210> SEQ ID NO 359
<211> LENGTH: 9
<212> TYPE: PRT
<213> ORGANISM: Homo sapiens

<400> SEQUENCE: 359

```
His His Phe His Met Asn Thr Pro Lys
 1               5
```

<210> SEQ ID NO 360
<211> LENGTH: 9
<212> TYPE: PRT
<213> ORGANISM: Homo sapiens

<400> SEQUENCE: 360

```
Phe Arg Lys Ser Glu Lys Tyr Met Lys
 1               5
```

<210> SEQ ID NO 361
<211> LENGTH: 9
<212> TYPE: PRT
<213> ORGANISM: Homo sapiens

<400> SEQUENCE: 361

```
Phe Asn Pro Arg Phe Gly Ser Tyr Lys
 1               5
```

<210> SEQ ID NO 362
<211> LENGTH: 9
<212> TYPE: PRT
<213> ORGANISM: Homo sapiens

<400> SEQUENCE: 362

```
Leu Leu Gly Leu Gly Leu Arg His Lys
```

```
                1               5
```

<210> SEQ ID NO 363
<211> LENGTH: 9
<212> TYPE: PRT
<213> ORGANISM: Homo sapiens

<400> SEQUENCE: 363

```
Leu Val Gly Val Gly Leu Leu Gly Leu
 1               5
```

<210> SEQ ID NO 364
<211> LENGTH: 9
<212> TYPE: PRT
<213> ORGANISM: Homo sapiens

<400> SEQUENCE: 364

```
Ile Asn Ser Gly Thr Asn Pro Gly Lys
 1               5
```

<210> SEQ ID NO 365
<211> LENGTH: 10
<212> TYPE: PRT
<213> ORGANISM: Homo sapiens

<400> SEQUENCE: 365

```
Ile Thr Ile Leu Glu Ser Asp Ala Ser Lys
 1               5                  10
```

<210> SEQ ID NO 366
<211> LENGTH: 10
<212> TYPE: PRT
<213> ORGANISM: Homo sapiens

<400> SEQUENCE: 366

```
Ile Thr Leu Thr Val Asn Ile Ser Gly Lys
 1               5                  10
```

<210> SEQ ID NO 367
<211> LENGTH: 10
<212> TYPE: PRT
<213> ORGANISM: Homo sapiens

<400> SEQUENCE: 367

```
Gly Leu Arg His Lys Ala Tyr Glu Arg Lys
 1               5                  10
```

<210> SEQ ID NO 368
<211> LENGTH: 10
<212> TYPE: PRT
<213> ORGANISM: Homo sapiens

<400> SEQUENCE: 368

```
Gly Leu Asn Met Leu Phe Gly Pro Lys Lys
 1               5                  10
```

<210> SEQ ID NO 369
<211> LENGTH: 10
<212> TYPE: PRT
<213> ORGANISM: Homo sapiens

<400> SEQUENCE: 369

```
Gly Val Gly Leu Leu Gly Leu Gly Leu Arg
 1               5                  10
```

```
<210> SEQ ID NO 370
<211> LENGTH: 10
<212> TYPE: PRT
<213> ORGANISM: Homo sapiens

<400> SEQUENCE: 370

Arg Ile Gly Thr Asp Gly Asp Cys Ser Lys
 1               5                  10

<210> SEQ ID NO 371
<211> LENGTH: 10
<212> TYPE: PRT
<213> ORGANISM: Homo sapiens

<400> SEQUENCE: 371

Ile Thr Pro Phe Trp Lys Leu Val Asn Lys
 1               5                  10

<210> SEQ ID NO 372
<211> LENGTH: 10
<212> TYPE: PRT
<213> ORGANISM: Homo sapiens

<400> SEQUENCE: 372

Ile Phe Leu Thr Ile Thr Pro Phe Trp Lys
 1               5                  10

<210> SEQ ID NO 373
<211> LENGTH: 10
<212> TYPE: PRT
<213> ORGANISM: Homo sapiens

<400> SEQUENCE: 373

Leu Gln Leu Thr Glu His Gly Asn Val Lys
 1               5                  10

<210> SEQ ID NO 374
<211> LENGTH: 10
<212> TYPE: PRT
<213> ORGANISM: Homo sapiens

<400> SEQUENCE: 374

His Thr Trp Gly Ile Met Ala Leu Ser Arg
 1               5                  10

<210> SEQ ID NO 375
<211> LENGTH: 10
<212> TYPE: PRT
<213> ORGANISM: Homo sapiens

<400> SEQUENCE: 375

Leu Leu Leu Gln Thr Lys Asn Ser Ser Lys
 1               5                  10

<210> SEQ ID NO 376
<211> LENGTH: 10
<212> TYPE: PRT
<213> ORGANISM: Homo sapiens

<400> SEQUENCE: 376

Gln Ala Ile Ala Val Ser Lys Leu Leu Lys
 1               5                  10

<210> SEQ ID NO 377
```

```
<211> LENGTH: 10
<212> TYPE: PRT
<213> ORGANISM: Homo sapiens

<400> SEQUENCE: 377

Met Ala Leu Ser Arg Tyr Pro Ile Val Lys
 1               5                  10

<210> SEQ ID NO 378
<211> LENGTH: 10
<212> TYPE: PRT
<213> ORGANISM: Homo sapiens

<400> SEQUENCE: 378

Leu Ile Asn Ser Gly Thr Asn Pro Gly Lys
 1               5                  10

<210> SEQ ID NO 379
<211> LENGTH: 10
<212> TYPE: PRT
<213> ORGANISM: Homo sapiens

<400> SEQUENCE: 379

Thr Pro Phe Trp Lys Leu Val Asn Lys Lys
 1               5                  10

<210> SEQ ID NO 380
<211> LENGTH: 10
<212> TYPE: PRT
<213> ORGANISM: Homo sapiens

<400> SEQUENCE: 380

Val Ile Asp His Arg Glu Val Ser Glu Lys
 1               5                  10

<210> SEQ ID NO 381
<211> LENGTH: 10
<212> TYPE: PRT
<213> ORGANISM: Homo sapiens

<400> SEQUENCE: 381

Leu Phe Arg Lys Ser Glu Lys Tyr Met Lys
 1               5                  10

<210> SEQ ID NO 382
<211> LENGTH: 10
<212> TYPE: PRT
<213> ORGANISM: Homo sapiens

<400> SEQUENCE: 382

Lys Asn Ser Ser Lys Val Leu Phe Arg Lys
 1               5                  10

<210> SEQ ID NO 383
<211> LENGTH: 10
<212> TYPE: PRT
<213> ORGANISM: Homo sapiens

<400> SEQUENCE: 383

Lys Phe Val Pro Gly Gly Val Tyr Ala Arg
 1               5                  10

<210> SEQ ID NO 384
<211> LENGTH: 10
<212> TYPE: PRT
```

<213> ORGANISM: Homo sapiens

<400> SEQUENCE: 384

Gly Tyr Ile Thr Ser Ala Pro Gly Ser Arg
1               5                   10

<210> SEQ ID NO 385
<211> LENGTH: 10
<212> TYPE: PRT
<213> ORGANISM: Homo sapiens

<400> SEQUENCE: 385

Leu Met Leu Pro Ser Cys Leu Trp Phe Arg
1               5                   10

<210> SEQ ID NO 386
<211> LENGTH: 10
<212> TYPE: PRT
<213> ORGANISM: Homo sapiens

<400> SEQUENCE: 386

Arg Ile Pro Asp Asp Pro Thr Asn Tyr Arg
1               5                   10

<210> SEQ ID NO 387
<211> LENGTH: 10
<212> TYPE: PRT
<213> ORGANISM: Homo sapiens

<400> SEQUENCE: 387

His Phe Asn Pro Arg Phe Gly Ser Tyr Lys
1               5                   10

<210> SEQ ID NO 388
<211> LENGTH: 10
<212> TYPE: PRT
<213> ORGANISM: Homo sapiens

<400> SEQUENCE: 388

Phe Phe Cys Ala Trp Cys Thr Ala Phe Lys
1               5                   10

<210> SEQ ID NO 389
<211> LENGTH: 10
<212> TYPE: PRT
<213> ORGANISM: Homo sapiens

<400> SEQUENCE: 389

Ile Ala Ser Phe Gln Ala Pro Asn Ala Lys
1               5                   10

<210> SEQ ID NO 390
<211> LENGTH: 10
<212> TYPE: PRT
<213> ORGANISM: Homo sapiens

<400> SEQUENCE: 390

Lys Asn Leu Asp Leu Leu Leu Gln Thr Lys
1               5                   10

<210> SEQ ID NO 391
<211> LENGTH: 10
<212> TYPE: PRT
<213> ORGANISM: Homo sapiens

```
<400> SEQUENCE: 391

Gly Leu Leu Gly Leu Gly Leu Arg His Lys
 1               5                  10

<210> SEQ ID NO 392
<211> LENGTH: 10
<212> TYPE: PRT
<213> ORGANISM: Homo sapiens

<400> SEQUENCE: 392

Thr Leu Ser Ala Ile Ala Thr Leu Asp Arg
 1               5                  10

<210> SEQ ID NO 393
<211> LENGTH: 10
<212> TYPE: PRT
<213> ORGANISM: Homo sapiens

<400> SEQUENCE: 393

Gly Asn His Glu Asp Leu Asp Arg Lys
 1               5                  10

<210> SEQ ID NO 394
<211> LENGTH: 10
<212> TYPE: PRT
<213> ORGANISM: Homo sapiens

<400> SEQUENCE: 394

Gly Val Tyr Ala Arg Glu Arg Ser Asp Val
 1               5                  10

<210> SEQ ID NO 395
<211> LENGTH: 10
<212> TYPE: PRT
<213> ORGANISM: Homo sapiens

<400> SEQUENCE: 395

Glu Val Ser Ala Ala Ile Trp Pro Phe Arg
 1               5                  10

<210> SEQ ID NO 396
<211> LENGTH: 10
<212> TYPE: PRT
<213> ORGANISM: Homo sapiens

<400> SEQUENCE: 396

Lys Thr Met Thr Ile Ala Met Ile Phe Tyr
 1               5                  10

<210> SEQ ID NO 397
<211> LENGTH: 10
<212> TYPE: PRT
<213> ORGANISM: Homo sapiens

<400> SEQUENCE: 397

Arg Lys Leu Gln Ala Ile Ala Val Ser Lys
 1               5                  10

<210> SEQ ID NO 398
<211> LENGTH: 10
<212> TYPE: PRT
<213> ORGANISM: Homo sapiens

<400> SEQUENCE: 398
```

Arg Lys Leu Gly Lys Val Ala Pro Thr Lys
1               5                   10

<210> SEQ ID NO 399
<211> LENGTH: 10
<212> TYPE: PRT
<213> ORGANISM: Homo sapiens

<400> SEQUENCE: 399

Lys Val Leu Phe Arg Lys Ser Glu Lys Tyr
1               5                   10

<210> SEQ ID NO 400
<211> LENGTH: 10
<212> TYPE: PRT
<213> ORGANISM: Homo sapiens

<400> SEQUENCE: 400

Lys Val Ile Leu Thr Leu Ser Ala Ile Ala
1               5                   10

<210> SEQ ID NO 401
<211> LENGTH: 10
<212> TYPE: PRT
<213> ORGANISM: Homo sapiens

<400> SEQUENCE: 401

Pro Ile Trp Ser Tyr Gln Met Ser Asn Lys
1               5                   10

<210> SEQ ID NO 402
<211> LENGTH: 10
<212> TYPE: PRT
<213> ORGANISM: Homo sapiens

<400> SEQUENCE: 402

Phe Tyr Thr Asp Phe Gly Pro Ser Thr Arg
1               5                   10

<210> SEQ ID NO 403
<211> LENGTH: 10
<212> TYPE: PRT
<213> ORGANISM: Homo sapiens

<400> SEQUENCE: 403

Glu Tyr Ile Met Tyr Arg Gly Leu Ile Arg
1               5                   10

<210> SEQ ID NO 404
<211> LENGTH: 10
<212> TYPE: PRT
<213> ORGANISM: Homo sapiens

<400> SEQUENCE: 404

Gly Asp Cys Ser Lys Pro Glu Glu Lys Lys
1               5                   10

<210> SEQ ID NO 405
<211> LENGTH: 10
<212> TYPE: PRT
<213> ORGANISM: Homo sapiens

<400> SEQUENCE: 405

Gly Thr Ala Ser Ala Ala Gly Leu Leu Tyr
1               5                   10

<210> SEQ ID NO 406
<211> LENGTH: 10
<212> TYPE: PRT
<213> ORGANISM: Homo sapiens

<400> SEQUENCE: 406

Lys Val Ala Pro Thr Lys Glu Val Ser Ala
 1               5                  10

<210> SEQ ID NO 407
<211> LENGTH: 10
<212> TYPE: PRT
<213> ORGANISM: Homo sapiens

<400> SEQUENCE: 407

Ile Val Leu Val Val Leu Arg Ile Trp Tyr
 1               5                  10

<210> SEQ ID NO 408
<211> LENGTH: 10
<212> TYPE: PRT
<213> ORGANISM: Homo sapiens

<400> SEQUENCE: 408

Asp Pro Thr Asn Tyr Arg Asp Asn Gln Lys
 1               5                  10

<210> SEQ ID NO 409
<211> LENGTH: 10
<212> TYPE: PRT
<213> ORGANISM: Homo sapiens

<400> SEQUENCE: 409

Gly Val Ser Ser Ser Leu Ile Val Gln Ala
 1               5                  10

<210> SEQ ID NO 410
<211> LENGTH: 10
<212> TYPE: PRT
<213> ORGANISM: Homo sapiens

<400> SEQUENCE: 410

Gly Thr Asn Pro Gly Lys Thr Met Thr Ile
 1               5                  10

<210> SEQ ID NO 411
<211> LENGTH: 10
<212> TYPE: PRT
<213> ORGANISM: Homo sapiens

<400> SEQUENCE: 411

Gly Gln Ile Val Leu Val Leu Arg Ile
 1               5                  10

<210> SEQ ID NO 412
<211> LENGTH: 10
<212> TYPE: PRT
<213> ORGANISM: Homo sapiens

<400> SEQUENCE: 412

Arg Tyr Leu Arg Ile Trp Gly Phe Ile Leu
 1               5                  10

<210> SEQ ID NO 413
<211> LENGTH: 10
<212> TYPE: PRT
<213> ORGANISM: Homo sapiens

<400> SEQUENCE: 413

Gly Glu Val Ala Thr Gly Met Ala Ser Arg
 1               5                  10

<210> SEQ ID NO 414
<211> LENGTH: 10
<212> TYPE: PRT
<213> ORGANISM: Homo sapiens

<400> SEQUENCE: 414

Gly Leu Met Leu Pro Ser Cys Leu Trp Phe
 1               5                  10

<210> SEQ ID NO 415
<211> LENGTH: 9
<212> TYPE: PRT
<213> ORGANISM: Homo sapiens

<400> SEQUENCE: 415

Lys Tyr Met Lys Leu Phe Leu Trp Leu
 1               5

<210> SEQ ID NO 416
<211> LENGTH: 9
<212> TYPE: PRT
<213> ORGANISM: Homo sapiens

<400> SEQUENCE: 416

Ile Tyr Tyr Phe Pro Leu Gln Thr Leu
 1               5

<210> SEQ ID NO 417
<211> LENGTH: 9
<212> TYPE: PRT
<213> ORGANISM: Homo sapiens

<400> SEQUENCE: 417

Arg Tyr Leu Arg Ile Trp Gly Phe Ile
 1               5

<210> SEQ ID NO 418
<211> LENGTH: 9
<212> TYPE: PRT
<213> ORGANISM: Homo sapiens

<400> SEQUENCE: 418

Ser Tyr Gln Met Ser Asn Lys Val Ile
 1               5

<210> SEQ ID NO 419
<211> LENGTH: 9
<212> TYPE: PRT
<213> ORGANISM: Homo sapiens

<400> SEQUENCE: 419

Glu Tyr Ile Met Tyr Arg Gly Leu Ile
 1               5

<210> SEQ ID NO 420
<211> LENGTH: 9

```
<212> TYPE: PRT
<213> ORGANISM: Homo sapiens

<400> SEQUENCE: 420

Leu Tyr His Asp Leu Gly Pro Met Ile
1               5

<210> SEQ ID NO 421
<211> LENGTH: 9
<212> TYPE: PRT
<213> ORGANISM: Homo sapiens

<400> SEQUENCE: 421

Tyr Phe Pro Leu Gln Thr Leu Glu Leu
1               5

<210> SEQ ID NO 422
<211> LENGTH: 9
<212> TYPE: PRT
<213> ORGANISM: Homo sapiens

<400> SEQUENCE: 422

Ser Phe Gln Ala Pro Asn Ala Lys Leu
1               5

<210> SEQ ID NO 423
<211> LENGTH: 9
<212> TYPE: PRT
<213> ORGANISM: Homo sapiens

<400> SEQUENCE: 423

Gly Phe Ile Leu Gly Gln Ile Val Leu
1               5

<210> SEQ ID NO 424
<211> LENGTH: 9
<212> TYPE: PRT
<213> ORGANISM: Homo sapiens

<400> SEQUENCE: 424

His Phe Gly Asn His Glu Asp Asp Leu
1               5

<210> SEQ ID NO 425
<211> LENGTH: 9
<212> TYPE: PRT
<213> ORGANISM: Homo sapiens

<400> SEQUENCE: 425

Lys Leu Val Asn Lys Lys Trp Met Leu
1               5

<210> SEQ ID NO 426
<211> LENGTH: 9
<212> TYPE: PRT
<213> ORGANISM: Homo sapiens

<400> SEQUENCE: 426

Ile Phe Tyr Leu Leu Glu Ile Phe Phe
1               5

<210> SEQ ID NO 427
<211> LENGTH: 9
<212> TYPE: PRT
<213> ORGANISM: Homo sapiens
```

```
<400> SEQUENCE: 427

Phe Phe Cys Ala Trp Cys Thr Ala Phe
1               5

<210> SEQ ID NO 428
<211> LENGTH: 9
<212> TYPE: PRT
<213> ORGANISM: Homo sapiens

<400> SEQUENCE: 428

Arg Tyr His Thr Trp Gly Ile Met Ala
1               5

<210> SEQ ID NO 429
<211> LENGTH: 9
<212> TYPE: PRT
<213> ORGANISM: Homo sapiens

<400> SEQUENCE: 429

Lys Pro Tyr Met Gly Asn Asn Asp Leu
1               5

<210> SEQ ID NO 430
<211> LENGTH: 9
<212> TYPE: PRT
<213> ORGANISM: Homo sapiens

<400> SEQUENCE: 430

Leu Thr Val Asn Ile Ser Gly Lys Leu
1               5

<210> SEQ ID NO 431
<211> LENGTH: 9
<212> TYPE: PRT
<213> ORGANISM: Homo sapiens

<400> SEQUENCE: 431

Gly Asn Asn Asp Leu Thr Met Trp Leu
1               5

<210> SEQ ID NO 432
<211> LENGTH: 9
<212> TYPE: PRT
<213> ORGANISM: Homo sapiens

<400> SEQUENCE: 432

Lys Thr Met Thr Ile Ala Met Ile Phe
1               5

<210> SEQ ID NO 433
<211> LENGTH: 9
<212> TYPE: PRT
<213> ORGANISM: Homo sapiens

<400> SEQUENCE: 433

Leu Ala Leu Gly Val Ser Ser Ser Leu
1               5

<210> SEQ ID NO 434
<211> LENGTH: 9
<212> TYPE: PRT
<213> ORGANISM: Homo sapiens

<400> SEQUENCE: 434
```

Met Ser Asn Lys Val Ile Leu Thr Leu
1               5

<210> SEQ ID NO 435
<211> LENGTH: 9
<212> TYPE: PRT
<213> ORGANISM: Homo sapiens

<400> SEQUENCE: 435

Leu Trp Leu Leu Val Gly Val Gly Leu
1               5

<210> SEQ ID NO 436
<211> LENGTH: 9
<212> TYPE: PRT
<213> ORGANISM: Homo sapiens

<400> SEQUENCE: 436

Gln Ala Ile Ala Val Ser Lys Leu Leu
1               5

<210> SEQ ID NO 437
<211> LENGTH: 9
<212> TYPE: PRT
<213> ORGANISM: Homo sapiens

<400> SEQUENCE: 437

Leu Gly Gln Ile Val Leu Val Val Leu
1               5

<210> SEQ ID NO 438
<211> LENGTH: 9
<212> TYPE: PRT
<213> ORGANISM: Homo sapiens

<400> SEQUENCE: 438

Ala Tyr Glu Arg Lys Leu Gly Lys Val
1               5

<210> SEQ ID NO 439
<211> LENGTH: 9
<212> TYPE: PRT
<213> ORGANISM: Homo sapiens

<400> SEQUENCE: 439

Lys Leu Arg Leu Met Val Leu Ala Leu
1               5

<210> SEQ ID NO 440
<211> LENGTH: 9
<212> TYPE: PRT
<213> ORGANISM: Homo sapiens

<400> SEQUENCE: 440

Leu Thr Ile Thr Pro Phe Trp Lys Leu
1               5

<210> SEQ ID NO 441
<211> LENGTH: 9
<212> TYPE: PRT
<213> ORGANISM: Homo sapiens

<400> SEQUENCE: 441

Leu Thr Met Trp Leu Gly Glu Lys Leu

```
<210> SEQ ID NO 442
<211> LENGTH: 9
<212> TYPE: PRT
<213> ORGANISM: Homo sapiens

<400> SEQUENCE: 442

Leu Tyr Leu His Thr Trp Ala Ala Ala
1               5

<210> SEQ ID NO 443
<211> LENGTH: 9
<212> TYPE: PRT
<213> ORGANISM: Homo sapiens

<400> SEQUENCE: 443

Gly Tyr Ile Thr Ser Ala Pro Gly Ser
1               5

<210> SEQ ID NO 444
<211> LENGTH: 9
<212> TYPE: PRT
<213> ORGANISM: Homo sapiens

<400> SEQUENCE: 444

Phe Tyr Leu Leu Glu Ile Phe Phe Cys
1               5

<210> SEQ ID NO 445
<211> LENGTH: 9
<212> TYPE: PRT
<213> ORGANISM: Homo sapiens

<400> SEQUENCE: 445

Ser Gly Leu Met Leu Pro Ser Cys Leu
1               5

<210> SEQ ID NO 446
<211> LENGTH: 9
<212> TYPE: PRT
<213> ORGANISM: Homo sapiens

<400> SEQUENCE: 446

Ser Ser Leu Glu Arg Ser Ala His Leu
1               5

<210> SEQ ID NO 447
<211> LENGTH: 9
<212> TYPE: PRT
<213> ORGANISM: Homo sapiens

<400> SEQUENCE: 447

Met Leu Ile Ile Gly Leu Asn Met Leu
1               5

<210> SEQ ID NO 448
<211> LENGTH: 9
<212> TYPE: PRT
<213> ORGANISM: Homo sapiens

<400> SEQUENCE: 448

Val Leu Leu Cys Leu Ala Ser Gly Leu
1               5
```

<210> SEQ ID NO 449
<211> LENGTH: 9
<212> TYPE: PRT
<213> ORGANISM: Homo sapiens

<400> SEQUENCE: 449

Gly Thr Met Met Leu Ile Ile Gly Leu
1               5

<210> SEQ ID NO 450
<211> LENGTH: 9
<212> TYPE: PRT
<213> ORGANISM: Homo sapiens

<400> SEQUENCE: 450

Thr Ile Ala Met Ile Phe Tyr Leu Leu
1               5

<210> SEQ ID NO 451
<211> LENGTH: 9
<212> TYPE: PRT
<213> ORGANISM: Homo sapiens

<400> SEQUENCE: 451

Gln Ala Pro Asn Ala Lys Leu Arg Leu
1               5

<210> SEQ ID NO 452
<211> LENGTH: 9
<212> TYPE: PRT
<213> ORGANISM: Homo sapiens

<400> SEQUENCE: 452

Lys Ser Glu Lys Tyr Met Lys Leu Phe
1               5

<210> SEQ ID NO 453
<211> LENGTH: 9
<212> TYPE: PRT
<213> ORGANISM: Homo sapiens

<400> SEQUENCE: 453

Ser Ala Pro Gly Ser Arg Asp Tyr Leu
1               5

<210> SEQ ID NO 454
<211> LENGTH: 9
<212> TYPE: PRT
<213> ORGANISM: Homo sapiens

<400> SEQUENCE: 454

Leu Cys Leu Ala Ser Gly Leu Met Leu
1               5

<210> SEQ ID NO 455
<211> LENGTH: 9
<212> TYPE: PRT
<213> ORGANISM: Homo sapiens

<400> SEQUENCE: 455

Tyr Gln Met Ser Asn Lys Val Ile Leu
1               5

<210> SEQ ID NO 456

```
<211> LENGTH: 9
<212> TYPE: PRT
<213> ORGANISM: Homo sapiens

<400> SEQUENCE: 456

Gly Pro Met Ile Tyr Tyr Phe Pro Leu
1               5

<210> SEQ ID NO 457
<211> LENGTH: 9
<212> TYPE: PRT
<213> ORGANISM: Homo sapiens

<400> SEQUENCE: 457

Met Trp Pro Gln Thr Leu Gly His Leu
1               5

<210> SEQ ID NO 458
<211> LENGTH: 9
<212> TYPE: PRT
<213> ORGANISM: Homo sapiens

<400> SEQUENCE: 458

Phe Gly Pro Lys Lys Asn Leu Asp Leu
1               5

<210> SEQ ID NO 459
<211> LENGTH: 9
<212> TYPE: PRT
<213> ORGANISM: Homo sapiens

<400> SEQUENCE: 459

Leu Thr Leu Ser Ala Ile Ala Thr Leu
1               5

<210> SEQ ID NO 460
<211> LENGTH: 9
<212> TYPE: PRT
<213> ORGANISM: Homo sapiens

<400> SEQUENCE: 460

Asp Val Leu Leu Gly Thr Met Met Leu
1               5

<210> SEQ ID NO 461
<211> LENGTH: 9
<212> TYPE: PRT
<213> ORGANISM: Homo sapiens

<400> SEQUENCE: 461

Phe Tyr Thr Asp Phe Gly Pro Ser Thr
1               5

<210> SEQ ID NO 462
<211> LENGTH: 9
<212> TYPE: PRT
<213> ORGANISM: Homo sapiens

<400> SEQUENCE: 462

His Met Asn Thr Pro Lys Tyr Phe Leu
1               5

<210> SEQ ID NO 463
<211> LENGTH: 9
<212> TYPE: PRT
```

<213> ORGANISM: Homo sapiens

<400> SEQUENCE: 463

His Trp Val Phe Gly Glu Val Ser Leu
1               5

<210> SEQ ID NO 464
<211> LENGTH: 9
<212> TYPE: PRT
<213> ORGANISM: Homo sapiens

<400> SEQUENCE: 464

Trp Tyr Thr Ser Leu Asn Pro Ile Trp
1               5

<210> SEQ ID NO 465
<211> LENGTH: 10
<212> TYPE: PRT
<213> ORGANISM: Homo sapiens

<400> SEQUENCE: 465

Lys Tyr Met Lys Leu Phe Leu Trp Leu Leu
1               5                   10

<210> SEQ ID NO 466
<211> LENGTH: 10
<212> TYPE: PRT
<213> ORGANISM: Homo sapiens

<400> SEQUENCE: 466

Arg Tyr Leu Arg Ile Trp Gly Phe Ile Leu
1               5                   10

<210> SEQ ID NO 467
<211> LENGTH: 10
<212> TYPE: PRT
<213> ORGANISM: Homo sapiens

<400> SEQUENCE: 467

Arg Tyr His Thr Trp Gly Ile Met Ala Leu
1               5                   10

<210> SEQ ID NO 468
<211> LENGTH: 10
<212> TYPE: PRT
<213> ORGANISM: Homo sapiens

<400> SEQUENCE: 468

Ser Tyr Gln Met Ser Asn Lys Val Ile Leu
1               5                   10

<210> SEQ ID NO 469
<211> LENGTH: 10
<212> TYPE: PRT
<213> ORGANISM: Homo sapiens

<400> SEQUENCE: 469

Tyr Tyr Phe Pro Leu Gln Thr Leu Glu Leu
1               5                   10

<210> SEQ ID NO 470
<211> LENGTH: 10
<212> TYPE: PRT
<213> ORGANISM: Homo sapiens

```
<400> SEQUENCE: 470

Gly Tyr Ala Arg Ile Ser His Ala Glu Leu
1               5                   10

<210> SEQ ID NO 471
<211> LENGTH: 10
<212> TYPE: PRT
<213> ORGANISM: Homo sapiens

<400> SEQUENCE: 471

Val Tyr Ala Arg Glu Arg Ser Asp Val Leu
1               5                   10

<210> SEQ ID NO 472
<211> LENGTH: 10
<212> TYPE: PRT
<213> ORGANISM: Homo sapiens

<400> SEQUENCE: 472

Gly Tyr Asp Asn Glu Gly Trp Ser Ser Leu
1               5                   10

<210> SEQ ID NO 473
<211> LENGTH: 10
<212> TYPE: PRT
<213> ORGANISM: Homo sapiens

<400> SEQUENCE: 473

Asn Tyr Arg Asp Asn Gln Lys Val Val Ile
1               5                   10

<210> SEQ ID NO 474
<211> LENGTH: 10
<212> TYPE: PRT
<213> ORGANISM: Homo sapiens

<400> SEQUENCE: 474

Asn Tyr Glu Asn Asn His His Phe His Met
1               5                   10

<210> SEQ ID NO 475
<211> LENGTH: 10
<212> TYPE: PRT
<213> ORGANISM: Homo sapiens

<400> SEQUENCE: 475

Leu Phe Gly Pro Lys Lys Asn Leu Asp Leu
1               5                   10

<210> SEQ ID NO 476
<211> LENGTH: 10
<212> TYPE: PRT
<213> ORGANISM: Homo sapiens

<400> SEQUENCE: 476

Lys Leu Gln Ala Ile Ala Val Ser Lys Leu
1               5                   10

<210> SEQ ID NO 477
<211> LENGTH: 10
<212> TYPE: PRT
<213> ORGANISM: Homo sapiens

<400> SEQUENCE: 477
```

```
Phe Tyr Leu Leu Glu Ile Phe Phe Cys Ala
1               5                   10
```

<210> SEQ ID NO 478
<211> LENGTH: 10
<212> TYPE: PRT
<213> ORGANISM: Homo sapiens

<400> SEQUENCE: 478

```
Ala Phe Leu Ser Pro Ile Phe Leu Thr Ile
1               5                   10
```

<210> SEQ ID NO 479
<211> LENGTH: 10
<212> TYPE: PRT
<213> ORGANISM: Homo sapiens

<400> SEQUENCE: 479

```
Lys Ser Glu Lys Tyr Met Lys Leu Phe Leu
1               5                   10
```

<210> SEQ ID NO 480
<211> LENGTH: 10
<212> TYPE: PRT
<213> ORGANISM: Homo sapiens

<400> SEQUENCE: 480

```
Met Thr Ile Ala Met Ile Phe Tyr Leu Leu
1               5                   10
```

<210> SEQ ID NO 481
<211> LENGTH: 10
<212> TYPE: PRT
<213> ORGANISM: Homo sapiens

<400> SEQUENCE: 481

```
Lys Leu Val Asp Phe Val Val Thr His Phe
1               5                   10
```

<210> SEQ ID NO 482
<211> LENGTH: 10
<212> TYPE: PRT
<213> ORGANISM: Homo sapiens

<400> SEQUENCE: 482

```
His Phe His Met Asn Thr Pro Lys Tyr Phe
1               5                   10
```

<210> SEQ ID NO 483
<211> LENGTH: 10
<212> TYPE: PRT
<213> ORGANISM: Homo sapiens

<400> SEQUENCE: 483

```
Ile Phe Phe Cys Ala Trp Cys Thr Ala Phe
1               5                   10
```

<210> SEQ ID NO 484
<211> LENGTH: 10
<212> TYPE: PRT
<213> ORGANISM: Homo sapiens

<400> SEQUENCE: 484

```
Ala Tyr Glu Arg Lys Leu Gly Lys Val Ala
1               5                   10
```

```
<210> SEQ ID NO 485
<211> LENGTH: 10
<212> TYPE: PRT
<213> ORGANISM: Homo sapiens

<400> SEQUENCE: 485

Ser Leu Leu Gly Cys Val Ser Trp Ser Leu
 1               5                  10

<210> SEQ ID NO 486
<211> LENGTH: 10
<212> TYPE: PRT
<213> ORGANISM: Homo sapiens

<400> SEQUENCE: 486

Lys Ser Ser Ser Asn Gln Val Ile Phe Leu
 1               5                  10

<210> SEQ ID NO 487
<211> LENGTH: 10
<212> TYPE: PRT
<213> ORGANISM: Homo sapiens

<400> SEQUENCE: 487

Asp Tyr Leu Gln Leu Thr Glu His Gly Asn
 1               5                  10

<210> SEQ ID NO 488
<211> LENGTH: 10
<212> TYPE: PRT
<213> ORGANISM: Homo sapiens

<400> SEQUENCE: 488

Leu Tyr Leu His Thr Trp Ala Ala Ala Val
 1               5                  10

<210> SEQ ID NO 489
<211> LENGTH: 10
<212> TYPE: PRT
<213> ORGANISM: Homo sapiens

<400> SEQUENCE: 489

Val Gly Val Gly Leu Leu Gly Leu Gly Leu
 1               5                  10

<210> SEQ ID NO 490
<211> LENGTH: 10
<212> TYPE: PRT
<213> ORGANISM: Homo sapiens

<400> SEQUENCE: 490

Ser Ser Leu Glu Arg Ser Ala His Leu Leu
 1               5                  10

<210> SEQ ID NO 491
<211> LENGTH: 10
<212> TYPE: PRT
<213> ORGANISM: Homo sapiens

<400> SEQUENCE: 491

Met Gly Asn Asn Asp Leu Thr Met Trp Leu
 1               5                  10
```

```
<210> SEQ ID NO 492
<211> LENGTH: 10
<212> TYPE: PRT
<213> ORGANISM: Homo sapiens

<400> SEQUENCE: 492

Thr Gly Met Ala Ser Arg Pro Asn Trp Leu
 1               5                  10

<210> SEQ ID NO 493
<211> LENGTH: 10
<212> TYPE: PRT
<213> ORGANISM: Homo sapiens

<400> SEQUENCE: 493

Asp Pro Asn Pro Phe Gly Gly Ala Val Leu
 1               5                  10

<210> SEQ ID NO 494
<211> LENGTH: 10
<212> TYPE: PRT
<213> ORGANISM: Homo sapiens

<400> SEQUENCE: 494

Ala Val Leu Leu Cys Leu Ala Ser Gly Leu
 1               5                  10

<210> SEQ ID NO 495
<211> LENGTH: 10
<212> TYPE: PRT
<213> ORGANISM: Homo sapiens

<400> SEQUENCE: 495

Met Met Leu Ile Ile Gly Leu Asn Met Leu
 1               5                  10

<210> SEQ ID NO 496
<211> LENGTH: 10
<212> TYPE: PRT
<213> ORGANISM: Homo sapiens

<400> SEQUENCE: 496

Met Tyr Arg Gly Leu Ile Arg Leu Gly Tyr
 1               5                  10

<210> SEQ ID NO 497
<211> LENGTH: 10
<212> TYPE: PRT
<213> ORGANISM: Homo sapiens

<400> SEQUENCE: 497

Ser Tyr Lys Glu Gly His Asn Tyr Glu Asn
 1               5                  10

<210> SEQ ID NO 498
<211> LENGTH: 10
<212> TYPE: PRT
<213> ORGANISM: Homo sapiens

<400> SEQUENCE: 498

Thr Leu Thr Val Asn Ile Ser Gly Lys Leu
 1               5                  10

<210> SEQ ID NO 499
<211> LENGTH: 10
```

<212> TYPE: PRT
<213> ORGANISM: Homo sapiens

<400> SEQUENCE: 499

Tyr Ile Met Tyr Arg Gly Leu Ile Arg Leu
1               5                   10

<210> SEQ ID NO 500
<211> LENGTH: 10
<212> TYPE: PRT
<213> ORGANISM: Homo sapiens

<400> SEQUENCE: 500

Trp Cys Glu Tyr Ile Met Tyr Arg Gly Leu
1               5                   10

<210> SEQ ID NO 501
<211> LENGTH: 10
<212> TYPE: PRT
<213> ORGANISM: Homo sapiens

<400> SEQUENCE: 501

Asn Met Leu Phe Gly Pro Lys Lys Asn Leu
1               5                   10

<210> SEQ ID NO 502
<211> LENGTH: 10
<212> TYPE: PRT
<213> ORGANISM: Homo sapiens

<400> SEQUENCE: 502

Tyr Pro Ile Val Lys Ser Glu His His Leu
1               5                   10

<210> SEQ ID NO 503
<211> LENGTH: 10
<212> TYPE: PRT
<213> ORGANISM: Homo sapiens

<400> SEQUENCE: 503

Leu Val Asn Lys Lys Trp Met Leu Thr Leu
1               5                   10

<210> SEQ ID NO 504
<211> LENGTH: 10
<212> TYPE: PRT
<213> ORGANISM: Homo sapiens

<400> SEQUENCE: 504

Leu Tyr His Asp Leu Gly Pro Met Ile Tyr
1               5                   10

<210> SEQ ID NO 505
<211> LENGTH: 10
<212> TYPE: PRT
<213> ORGANISM: Homo sapiens

<400> SEQUENCE: 505

Leu Leu Val Gly Val Gly Leu Leu Gly Leu
1               5                   10

<210> SEQ ID NO 506
<211> LENGTH: 10
<212> TYPE: PRT
<213> ORGANISM: Homo sapiens

```
<400> SEQUENCE: 506

Leu Trp Leu Leu Val Gly Val Gly Leu Leu
1               5                   10

<210> SEQ ID NO 507
<211> LENGTH: 10
<212> TYPE: PRT
<213> ORGANISM: Homo sapiens

<400> SEQUENCE: 507

Val Val Leu Arg Ile Trp Tyr Thr Ser Leu
1               5                   10

<210> SEQ ID NO 508
<211> LENGTH: 10
<212> TYPE: PRT
<213> ORGANISM: Homo sapiens

<400> SEQUENCE: 508

Phe Gly Pro Lys Lys Asn Leu Asp Leu Leu
1               5                   10

<210> SEQ ID NO 509
<211> LENGTH: 10
<212> TYPE: PRT
<213> ORGANISM: Homo sapiens

<400> SEQUENCE: 509

Glu Gly Glu Ile Ala Pro Ala Ile Thr Leu
1               5                   10

<210> SEQ ID NO 510
<211> LENGTH: 10
<212> TYPE: PRT
<213> ORGANISM: Homo sapiens

<400> SEQUENCE: 510

Leu Gly Pro Met Ile Tyr Tyr Phe Pro Leu
1               5                   10

<210> SEQ ID NO 511
<211> LENGTH: 10
<212> TYPE: PRT
<213> ORGANISM: Homo sapiens

<400> SEQUENCE: 511

Ser Cys Leu Trp Phe Arg Gly Thr Gly Leu
1               5                   10

<210> SEQ ID NO 512
<211> LENGTH: 10
<212> TYPE: PRT
<213> ORGANISM: Homo sapiens

<400> SEQUENCE: 512

Gly Leu Glu Gly Phe Ser Ile Ala Phe Leu
1               5                   10

<210> SEQ ID NO 513
<211> LENGTH: 10
<212> TYPE: PRT
<213> ORGANISM: Homo sapiens

<400> SEQUENCE: 513
```

Leu Trp Arg Glu Ile Leu Leu Glu Ser Leu
1               5                   10

<210> SEQ ID NO 514
<211> LENGTH: 10
<212> TYPE: PRT
<213> ORGANISM: Homo sapiens

<400> SEQUENCE: 514

Ile Leu Gly Gln Ile Val Leu Val Val Leu
1               5                   10

<210> SEQ ID NO 515
<211> LENGTH: 9
<212> TYPE: PRT
<213> ORGANISM: Homo sapiens

<400> SEQUENCE: 515

Gly Pro Met Ile Tyr Tyr Phe Pro Leu
1               5

<210> SEQ ID NO 516
<211> LENGTH: 9
<212> TYPE: PRT
<213> ORGANISM: Homo sapiens

<400> SEQUENCE: 516

Tyr Ala Arg Glu Arg Ser Asp Val Leu
1               5

<210> SEQ ID NO 517
<211> LENGTH: 9
<212> TYPE: PRT
<213> ORGANISM: Homo sapiens

<400> SEQUENCE: 517

Tyr Ala Arg Ile Ser His Ala Glu Leu
1               5

<210> SEQ ID NO 518
<211> LENGTH: 9
<212> TYPE: PRT
<213> ORGANISM: Homo sapiens

<400> SEQUENCE: 518

Gly Pro Lys Lys Asn Leu Asp Leu Leu
1               5

<210> SEQ ID NO 519
<211> LENGTH: 9
<212> TYPE: PRT
<213> ORGANISM: Homo sapiens

<400> SEQUENCE: 519

Asn Pro Phe Gly Gly Ala Val Leu Leu
1               5

<210> SEQ ID NO 520
<211> LENGTH: 9
<212> TYPE: PRT
<213> ORGANISM: Homo sapiens

<400> SEQUENCE: 520

Lys Pro Tyr Met Gly Asn Asn Asp Leu

```
                  1               5

<210> SEQ ID NO 521
<211> LENGTH: 9
<212> TYPE: PRT
<213> ORGANISM: Homo sapiens

<400> SEQUENCE: 521

Ala Pro Asn Ala Lys Leu Arg Leu Met
  1               5

<210> SEQ ID NO 522
<211> LENGTH: 9
<212> TYPE: PRT
<213> ORGANISM: Homo sapiens

<400> SEQUENCE: 522

Lys Leu Arg Leu Met Val Leu Ala Leu
  1               5

<210> SEQ ID NO 523
<211> LENGTH: 9
<212> TYPE: PRT
<213> ORGANISM: Homo sapiens

<400> SEQUENCE: 523

Tyr Leu Arg Ile Trp Gly Phe Ile Leu
  1               5

<210> SEQ ID NO 524
<211> LENGTH: 9
<212> TYPE: PRT
<213> ORGANISM: Homo sapiens

<400> SEQUENCE: 524

Val Leu Arg Ile Trp Tyr Thr Ser Leu
  1               5

<210> SEQ ID NO 525
<211> LENGTH: 9
<212> TYPE: PRT
<213> ORGANISM: Homo sapiens

<400> SEQUENCE: 525

Ala Ala Phe Gly Ser Leu Val Phe Leu
  1               5

<210> SEQ ID NO 526
<211> LENGTH: 9
<212> TYPE: PRT
<213> ORGANISM: Homo sapiens

<400> SEQUENCE: 526

Gly Val Gly Leu Leu Gly Leu Gly Leu
  1               5

<210> SEQ ID NO 527
<211> LENGTH: 9
<212> TYPE: PRT
<213> ORGANISM: Homo sapiens

<400> SEQUENCE: 527

Asp Val Leu Leu Gly Thr Met Met Leu
  1               5
```

```
<210> SEQ ID NO 528
<211> LENGTH: 9
<212> TYPE: PRT
<213> ORGANISM: Homo sapiens

<400> SEQUENCE: 528

Leu Val Gly Val Gly Leu Leu Gly Leu
1               5

<210> SEQ ID NO 529
<211> LENGTH: 9
<212> TYPE: PRT
<213> ORGANISM: Homo sapiens

<400> SEQUENCE: 529

Ile Val Lys Ser Glu His His Leu Leu
1               5

<210> SEQ ID NO 530
<211> LENGTH: 9
<212> TYPE: PRT
<213> ORGANISM: Homo sapiens

<400> SEQUENCE: 530

Met Ala Ser Arg Pro Asn Trp Leu Leu
1               5

<210> SEQ ID NO 531
<211> LENGTH: 9
<212> TYPE: PRT
<213> ORGANISM: Homo sapiens

<400> SEQUENCE: 531

Ser Ala Pro Gly Ser Arg Asp Tyr Leu
1               5

<210> SEQ ID NO 532
<211> LENGTH: 9
<212> TYPE: PRT
<213> ORGANISM: Homo sapiens

<400> SEQUENCE: 532

Ala Ser Ala Ala Gly Leu Leu Tyr Leu
1               5

<210> SEQ ID NO 533
<211> LENGTH: 9
<212> TYPE: PRT
<213> ORGANISM: Homo sapiens

<400> SEQUENCE: 533

Gln Ala Pro Asn Ala Lys Leu Arg Leu
1               5

<210> SEQ ID NO 534
<211> LENGTH: 9
<212> TYPE: PRT
<213> ORGANISM: Homo sapiens

<400> SEQUENCE: 534

Leu Ala Gly Ala Ala Phe Gly Ser Leu
1               5

<210> SEQ ID NO 535
```

```
<211> LENGTH: 9
<212> TYPE: PRT
<213> ORGANISM: Homo sapiens

<400> SEQUENCE: 535

Ile Ala Phe Leu Ser Pro Ile Phe Leu
 1               5

<210> SEQ ID NO 536
<211> LENGTH: 9
<212> TYPE: PRT
<213> ORGANISM: Homo sapiens

<400> SEQUENCE: 536

Gln Ala Ile Ala Val Ser Lys Leu Leu
 1               5

<210> SEQ ID NO 537
<211> LENGTH: 9
<212> TYPE: PRT
<213> ORGANISM: Homo sapiens

<400> SEQUENCE: 537

Gly Thr Met Met Leu Ile Ile Gly Leu
 1               5

<210> SEQ ID NO 538
<211> LENGTH: 9
<212> TYPE: PRT
<213> ORGANISM: Homo sapiens

<400> SEQUENCE: 538

Thr Ala Ser Met Trp Pro Gln Thr Leu
 1               5

<210> SEQ ID NO 539
<211> LENGTH: 9
<212> TYPE: PRT
<213> ORGANISM: Homo sapiens

<400> SEQUENCE: 539

Tyr Gln Met Ser Asn Lys Val Ile Leu
 1               5

<210> SEQ ID NO 540
<211> LENGTH: 9
<212> TYPE: PRT
<213> ORGANISM: Homo sapiens

<400> SEQUENCE: 540

Leu Thr Met Trp Leu Gly Glu Lys Leu
 1               5

<210> SEQ ID NO 541
<211> LENGTH: 9
<212> TYPE: PRT
<213> ORGANISM: Homo sapiens

<400> SEQUENCE: 541

Leu Ala Leu Gly Val Ser Ser Ser Leu
 1               5

<210> SEQ ID NO 542
<211> LENGTH: 9
<212> TYPE: PRT
```

<213> ORGANISM: Homo sapiens

<400> SEQUENCE: 542

Asn Ala Lys Leu Arg Leu Met Val Leu
1               5

<210> SEQ ID NO 543
<211> LENGTH: 9
<212> TYPE: PRT
<213> ORGANISM: Homo sapiens

<400> SEQUENCE: 543

Trp Pro Gln Thr Leu Gly His Leu Ile
1               5

<210> SEQ ID NO 544
<211> LENGTH: 9
<212> TYPE: PRT
<213> ORGANISM: Homo sapiens

<400> SEQUENCE: 544

Leu Thr Ile Thr Pro Phe Trp Lys Leu
1               5

<210> SEQ ID NO 545
<211> LENGTH: 9
<212> TYPE: PRT
<213> ORGANISM: Homo sapiens

<400> SEQUENCE: 545

His Met Asn Thr Pro Lys Tyr Phe Leu
1               5

<210> SEQ ID NO 546
<211> LENGTH: 9
<212> TYPE: PRT
<213> ORGANISM: Homo sapiens

<400> SEQUENCE: 546

Met Thr Ser Leu Trp Arg Glu Ile Leu
1               5

<210> SEQ ID NO 547
<211> LENGTH: 9
<212> TYPE: PRT
<213> ORGANISM: Homo sapiens

<400> SEQUENCE: 547

Met Leu Phe Gly Pro Lys Lys Asn Leu
1               5

<210> SEQ ID NO 548
<211> LENGTH: 9
<212> TYPE: PRT
<213> ORGANISM: Homo sapiens

<400> SEQUENCE: 548

Ala Val Ser Gly Cys Val Phe Ala Ile
1               5

<210> SEQ ID NO 549
<211> LENGTH: 9
<212> TYPE: PRT
<213> ORGANISM: Homo sapiens -continued

<400> SEQUENCE: 549

Ala Pro Thr Lys Glu Val Ser Ala Ala
1               5

<210> SEQ ID NO 550
<211> LENGTH: 9
<212> TYPE: PRT
<213> ORGANISM: Homo sapiens

<400> SEQUENCE: 550

Val Asn Lys Lys Trp Met Leu Thr Leu
1               5

<210> SEQ ID NO 551
<211> LENGTH: 9
<212> TYPE: PRT
<213> ORGANISM: Homo sapiens

<400> SEQUENCE: 551

Tyr Met Lys Leu Phe Leu Trp Leu Leu
1               5

<210> SEQ ID NO 552
<211> LENGTH: 9
<212> TYPE: PRT
<213> ORGANISM: Homo sapiens

<400> SEQUENCE: 552

Cys Leu Trp Phe Arg Gly Thr Gly Leu
1               5

<210> SEQ ID NO 553
<211> LENGTH: 9
<212> TYPE: PRT
<213> ORGANISM: Homo sapiens

<400> SEQUENCE: 553

Thr Ser Leu Trp Arg Glu Ile Leu Leu
1               5

<210> SEQ ID NO 554
<211> LENGTH: 9
<212> TYPE: PRT
<213> ORGANISM: Homo sapiens

<400> SEQUENCE: 554

Phe Gly Pro Lys Lys Asn Leu Asp Leu
1               5

<210> SEQ ID NO 555
<211> LENGTH: 9
<212> TYPE: PRT
<213> ORGANISM: Homo sapiens

<400> SEQUENCE: 555

Ser Ser Ser Asn Gln Val Ile Phe Leu
1               5

<210> SEQ ID NO 556
<211> LENGTH: 9
<212> TYPE: PRT
<213> ORGANISM: Homo sapiens

<400> SEQUENCE: 556

Met Ser Asn Lys Val Ile Leu Thr Leu
1               5

<210> SEQ ID NO 557
<211> LENGTH: 9
<212> TYPE: PRT
<213> ORGANISM: Homo sapiens

<400> SEQUENCE: 557

Val Thr Trp Trp Ser Gly Ser His Leu
1               5

<210> SEQ ID NO 558
<211> LENGTH: 9
<212> TYPE: PRT
<213> ORGANISM: Homo sapiens

<400> SEQUENCE: 558

Met Leu Ile Ile Gly Leu Asn Met Leu
1               5

<210> SEQ ID NO 559
<211> LENGTH: 9
<212> TYPE: PRT
<213> ORGANISM: Homo sapiens

<400> SEQUENCE: 559

Leu Ile Arg Leu Gly Tyr Ala Arg Ile
1               5

<210> SEQ ID NO 560
<211> LENGTH: 9
<212> TYPE: PRT
<213> ORGANISM: Homo sapiens

<400> SEQUENCE: 560

Phe Gly Gly Ala Val Leu Leu Cys Leu
1               5

<210> SEQ ID NO 561
<211> LENGTH: 9
<212> TYPE: PRT
<213> ORGANISM: Homo sapiens

<400> SEQUENCE: 561

Leu Gln Thr Leu Glu Leu Thr Gly Leu
1               5

<210> SEQ ID NO 562
<211> LENGTH: 9
<212> TYPE: PRT
<213> ORGANISM: Homo sapiens

<400> SEQUENCE: 562

Leu Gly Gln Ile Val Leu Val Val Leu
1               5

<210> SEQ ID NO 563
<211> LENGTH: 9
<212> TYPE: PRT
<213> ORGANISM: Homo sapiens

<400> SEQUENCE: 563

Gly Thr Ala Ser Ala Ala Gly Leu Leu
1               5

<210> SEQ ID NO 564
<211> LENGTH: 9
<212> TYPE: PRT
<213> ORGANISM: Homo sapiens

<400> SEQUENCE: 564

Met Thr Ile Ala Met Ile Phe Tyr Leu
1               5

<210> SEQ ID NO 565
<211> LENGTH: 10
<212> TYPE: PRT
<213> ORGANISM: Homo sapiens

<400> SEQUENCE: 565

Ala Pro Gly Ser Arg Asp Tyr Leu Gln Leu
1               5                   10

<210> SEQ ID NO 566
<211> LENGTH: 10
<212> TYPE: PRT
<213> ORGANISM: Homo sapiens

<400> SEQUENCE: 566

Tyr Ala Arg Glu Arg Ser Asp Val Leu Leu
1               5                   10

<210> SEQ ID NO 567
<211> LENGTH: 10
<212> TYPE: PRT
<213> ORGANISM: Homo sapiens

<400> SEQUENCE: 567

Tyr Pro Ile Val Lys Ser Glu His His Leu
1               5                   10

<210> SEQ ID NO 568
<211> LENGTH: 10
<212> TYPE: PRT
<213> ORGANISM: Homo sapiens

<400> SEQUENCE: 568

Gly Pro Lys Lys Asn Leu Asp Leu Leu Leu
1               5                   10

<210> SEQ ID NO 569
<211> LENGTH: 10
<212> TYPE: PRT
<213> ORGANISM: Homo sapiens

<400> SEQUENCE: 569

Asp Pro Asn Pro Phe Gly Gly Ala Val Leu
1               5                   10

<210> SEQ ID NO 570
<211> LENGTH: 10
<212> TYPE: PRT
<213> ORGANISM: Homo sapiens

<400> SEQUENCE: 570

Ala Val Thr Trp Trp Ser Gly Ser His Leu
1               5                   10

```
<210> SEQ ID NO 571
<211> LENGTH: 10
<212> TYPE: PRT
<213> ORGANISM: Homo sapiens

<400> SEQUENCE: 571

Ala Val Leu Leu Cys Leu Ala Ser Gly Leu
 1               5                  10

<210> SEQ ID NO 572
<211> LENGTH: 10
<212> TYPE: PRT
<213> ORGANISM: Homo sapiens

<400> SEQUENCE: 572

Ala Pro Ala Ile Thr Leu Thr Val Asn Ile
 1               5                  10

<210> SEQ ID NO 573
<211> LENGTH: 10
<212> TYPE: PRT
<213> ORGANISM: Homo sapiens

<400> SEQUENCE: 573

Ala Pro Thr Lys Glu Val Ser Ala Ala Ile
 1               5                  10

<210> SEQ ID NO 574
<211> LENGTH: 10
<212> TYPE: PRT
<213> ORGANISM: Homo sapiens

<400> SEQUENCE: 574

Val Val Leu Arg Ile Trp Tyr Thr Ser Leu
 1               5                  10

<210> SEQ ID NO 575
<211> LENGTH: 10
<212> TYPE: PRT
<213> ORGANISM: Homo sapiens

<400> SEQUENCE: 575

Asn Pro Gly Lys Thr Met Thr Ile Ala Met
 1               5                  10

<210> SEQ ID NO 576
<211> LENGTH: 10
<212> TYPE: PRT
<213> ORGANISM: Homo sapiens

<400> SEQUENCE: 576

Cys Val Ser Trp Ser Leu Tyr His Asp Leu
 1               5                  10

<210> SEQ ID NO 577
<211> LENGTH: 10
<212> TYPE: PRT
<213> ORGANISM: Homo sapiens

<400> SEQUENCE: 577

Leu Val Asn Lys Lys Trp Met Leu Thr Leu
 1               5                  10

<210> SEQ ID NO 578
<211> LENGTH: 10
```

<212> TYPE: PRT
<213> ORGANISM: Homo sapiens

<400> SEQUENCE: 578

Ala Pro Asn Ala Lys Leu Arg Leu Met Val
1               5                   10

<210> SEQ ID NO 579
<211> LENGTH: 10
<212> TYPE: PRT
<213> ORGANISM: Homo sapiens

<400> SEQUENCE: 579

Ala Ser Phe Gln Ala Pro Asn Ala Lys Leu
1               5                   10

<210> SEQ ID NO 580
<211> LENGTH: 10
<212> TYPE: PRT
<213> ORGANISM: Homo sapiens

<400> SEQUENCE: 580

Thr Gly Met Ala Ser Arg Pro Asn Trp Leu
1               5                   10

<210> SEQ ID NO 581
<211> LENGTH: 10
<212> TYPE: PRT
<213> ORGANISM: Homo sapiens

<400> SEQUENCE: 581

Ala Ser Gly Leu Met Leu Pro Ser Cys Leu
1               5                   10

<210> SEQ ID NO 582
<211> LENGTH: 10
<212> TYPE: PRT
<213> ORGANISM: Homo sapiens

<400> SEQUENCE: 582

Thr Ala Ser Ala Ala Gly Leu Leu Tyr Leu
1               5                   10

<210> SEQ ID NO 583
<211> LENGTH: 10
<212> TYPE: PRT
<213> ORGANISM: Homo sapiens

<400> SEQUENCE: 583

Gly Ala Ala Phe Gly Ser Leu Val Phe Leu
1               5                   10

<210> SEQ ID NO 584
<211> LENGTH: 10
<212> TYPE: PRT
<213> ORGANISM: Homo sapiens

<400> SEQUENCE: 584

Tyr Ile Met Tyr Arg Gly Leu Ile Arg Leu
1               5                   10

<210> SEQ ID NO 585
<211> LENGTH: 10
<212> TYPE: PRT
<213> ORGANISM: Homo sapiens

<400> SEQUENCE: 585

Ser Thr Arg Tyr His Thr Trp Gly Ile Met
1               5                   10

<210> SEQ ID NO 586
<211> LENGTH: 10
<212> TYPE: PRT
<213> ORGANISM: Homo sapiens

<400> SEQUENCE: 586

Gly Met Ala Ser Arg Pro Asn Trp Leu Leu
1               5                   10

<210> SEQ ID NO 587
<211> LENGTH: 10
<212> TYPE: PRT
<213> ORGANISM: Homo sapiens

<400> SEQUENCE: 587

Asn Met Leu Phe Gly Pro Lys Lys Asn Leu
1               5                   10

<210> SEQ ID NO 588
<211> LENGTH: 10
<212> TYPE: PRT
<213> ORGANISM: Homo sapiens

<400> SEQUENCE: 588

Met Ile Tyr Tyr Phe Pro Leu Gln Thr Leu
1               5                   10

<210> SEQ ID NO 589
<211> LENGTH: 10
<212> TYPE: PRT
<213> ORGANISM: Homo sapiens

<400> SEQUENCE: 589

Thr Ser Ala Pro Gly Ser Arg Asp Tyr Leu
1               5                   10

<210> SEQ ID NO 590
<211> LENGTH: 10
<212> TYPE: PRT
<213> ORGANISM: Homo sapiens

<400> SEQUENCE: 590

Phe Leu Thr Ile Thr Pro Phe Trp Lys Leu
1               5                   10

<210> SEQ ID NO 591
<211> LENGTH: 10
<212> TYPE: PRT
<213> ORGANISM: Homo sapiens

<400> SEQUENCE: 591

Cys Val Phe Ala Ile Phe Thr Ala Ser Met
1               5                   10

<210> SEQ ID NO 592
<211> LENGTH: 10
<212> TYPE: PRT
<213> ORGANISM: Homo sapiens

<400> SEQUENCE: 592

```
Leu Gln Ala Ile Ala Val Ser Lys Leu Leu
 1               5                  10
```

<210> SEQ ID NO 593
<211> LENGTH: 10
<212> TYPE: PRT
<213> ORGANISM: Homo sapiens

<400> SEQUENCE: 593

```
Leu Gly Thr Met Met Leu Ile Ile Gly Leu
 1               5                  10
```

<210> SEQ ID NO 594
<211> LENGTH: 10
<212> TYPE: PRT
<213> ORGANISM: Homo sapiens

<400> SEQUENCE: 594

```
Leu Trp Arg Glu Ile Leu Leu Glu Ser Leu
 1               5                  10
```

<210> SEQ ID NO 595
<211> LENGTH: 10
<212> TYPE: PRT
<213> ORGANISM: Homo sapiens

<400> SEQUENCE: 595

```
Met Thr Ser Leu Trp Arg Glu Ile Leu Leu
 1               5                  10
```

<210> SEQ ID NO 596
<211> LENGTH: 10
<212> TYPE: PRT
<213> ORGANISM: Homo sapiens

<400> SEQUENCE: 596

```
Phe Gln Ala Pro Asn Ala Lys Leu Arg Leu
 1               5                  10
```

<210> SEQ ID NO 597
<211> LENGTH: 10
<212> TYPE: PRT
<213> ORGANISM: Homo sapiens

<400> SEQUENCE: 597

```
Ser Cys Leu Trp Phe Arg Gly Thr Gly Leu
 1               5                  10
```

<210> SEQ ID NO 598
<211> LENGTH: 10
<212> TYPE: PRT
<213> ORGANISM: Homo sapiens

<400> SEQUENCE: 598

```
Leu Leu Cys Leu Ala Ser Gly Leu Met Leu
 1               5                  10
```

<210> SEQ ID NO 599
<211> LENGTH: 10
<212> TYPE: PRT
<213> ORGANISM: Homo sapiens

<400> SEQUENCE: 599

```
Lys Ser Ser Ser Asn Gln Val Ile Phe Leu
 1               5                  10
```

```
  1               5                  10
```

<210> SEQ ID NO 600
<211> LENGTH: 10
<212> TYPE: PRT
<213> ORGANISM: Homo sapiens

<400> SEQUENCE: 600

```
Leu Leu Val Gly Val Gly Leu Leu Gly Leu
 1               5                  10
```

<210> SEQ ID NO 601
<211> LENGTH: 10
<212> TYPE: PRT
<213> ORGANISM: Homo sapiens

<400> SEQUENCE: 601

```
Phe Thr Ala Ser Met Trp Pro Gln Thr Leu
 1               5                  10
```

<210> SEQ ID NO 602
<211> LENGTH: 10
<212> TYPE: PRT
<213> ORGANISM: Homo sapiens

<400> SEQUENCE: 602

```
Phe Leu Trp Leu Leu Val Gly Val Gly Leu
 1               5                  10
```

<210> SEQ ID NO 603
<211> LENGTH: 10
<212> TYPE: PRT
<213> ORGANISM: Homo sapiens

<400> SEQUENCE: 603

```
Ile Leu Gly Gln Ile Val Leu Val Val Leu
 1               5                  10
```

<210> SEQ ID NO 604
<211> LENGTH: 10
<212> TYPE: PRT
<213> ORGANISM: Homo sapiens

<400> SEQUENCE: 604

```
Val Thr Gly Thr Ala Ser Ala Ala Gly Leu
 1               5                  10
```

<210> SEQ ID NO 605
<211> LENGTH: 10
<212> TYPE: PRT
<213> ORGANISM: Homo sapiens

<400> SEQUENCE: 605

```
Ser Leu Leu Gly Cys Val Ser Trp Ser Leu
 1               5                  10
```

<210> SEQ ID NO 606
<211> LENGTH: 10
<212> TYPE: PRT
<213> ORGANISM: Homo sapiens

<400> SEQUENCE: 606

```
Thr Leu Thr Val Asn Ile Ser Gly Lys Leu
 1               5                  10
```

```
<210> SEQ ID NO 607
<211> LENGTH: 10
<212> TYPE: PRT
<213> ORGANISM: Homo sapiens

<400> SEQUENCE: 607

Leu Gln Thr Lys Asn Ser Ser Lys Val Leu
 1               5                  10

<210> SEQ ID NO 608
<211> LENGTH: 10
<212> TYPE: PRT
<213> ORGANISM: Homo sapiens

<400> SEQUENCE: 608

Gln Met Ser Asn Lys Val Ile Leu Thr Leu
 1               5                  10

<210> SEQ ID NO 609
<211> LENGTH: 10
<212> TYPE: PRT
<213> ORGANISM: Homo sapiens

<400> SEQUENCE: 609

Trp Gly Phe Ile Leu Gly Gln Ile Val Leu
 1               5                  10

<210> SEQ ID NO 610
<211> LENGTH: 10
<212> TYPE: PRT
<213> ORGANISM: Homo sapiens

<400> SEQUENCE: 610

Ser Ile Ala Phe Leu Ser Pro Ile Phe Leu
 1               5                  10

<210> SEQ ID NO 611
<211> LENGTH: 10
<212> TYPE: PRT
<213> ORGANISM: Homo sapiens

<400> SEQUENCE: 611

Phe Gly Pro Lys Lys Asn Leu Asp Leu Leu
 1               5                  10

<210> SEQ ID NO 612
<211> LENGTH: 10
<212> TYPE: PRT
<213> ORGANISM: Homo sapiens

<400> SEQUENCE: 612

Met Gly Asn Asn Asp Leu Thr Met Trp Leu
 1               5                  10

<210> SEQ ID NO 613
<211> LENGTH: 10
<212> TYPE: PRT
<213> ORGANISM: Homo sapiens

<400> SEQUENCE: 613

Trp Ser Gly Ser His Leu Gln Arg Tyr Leu
 1               5                  10

<210> SEQ ID NO 614
```

```
<211> LENGTH: 10
<212> TYPE: PRT
<213> ORGANISM: Homo sapiens

<400> SEQUENCE: 614

Thr Met Thr Ile Ala Met Ile Phe Tyr Leu
1               5                   10

<210> SEQ ID NO 615
<211> LENGTH: 9
<212> TYPE: PRT
<213> ORGANISM: Homo sapiens

<400> SEQUENCE: 615

Gly Pro Lys Lys Asn Leu Asp Leu Leu
1               5

<210> SEQ ID NO 616
<211> LENGTH: 9
<212> TYPE: PRT
<213> ORGANISM: Homo sapiens

<400> SEQUENCE: 616

Ala Pro Asn Ala Lys Leu Arg Leu Met
1               5

<210> SEQ ID NO 617
<211> LENGTH: 9
<212> TYPE: PRT
<213> ORGANISM: Homo sapiens

<400> SEQUENCE: 617

Lys Pro Tyr Met Gly Asn Asn Asp Leu
1               5

<210> SEQ ID NO 618
<211> LENGTH: 9
<212> TYPE: PRT
<213> ORGANISM: Homo sapiens

<400> SEQUENCE: 618

His Pro Gly Pro Asp Pro Asn Pro Phe
1               5

<210> SEQ ID NO 619
<211> LENGTH: 9
<212> TYPE: PRT
<213> ORGANISM: Homo sapiens

<400> SEQUENCE: 619

Gly Pro Met Ile Tyr Tyr Phe Pro Leu
1               5

<210> SEQ ID NO 620
<211> LENGTH: 9
<212> TYPE: PRT
<213> ORGANISM: Homo sapiens

<400> SEQUENCE: 620

Asn Pro Phe Gly Gly Ala Val Leu Leu
1               5

<210> SEQ ID NO 621
<211> LENGTH: 9
<212> TYPE: PRT
```

-continued

<213> ORGANISM: Homo sapiens

<400> SEQUENCE: 621

Tyr Ala Arg Glu Arg Ser Asp Val Leu
1               5

<210> SEQ ID NO 622
<211> LENGTH: 9
<212> TYPE: PRT
<213> ORGANISM: Homo sapiens

<400> SEQUENCE: 622

Gly Ser Tyr Lys Glu Gly His Asn Tyr
1               5

<210> SEQ ID NO 623
<211> LENGTH: 9
<212> TYPE: PRT
<213> ORGANISM: Homo sapiens

<400> SEQUENCE: 623

Arg Ile Pro Asp Asp Pro Thr Asn Tyr
1               5

<210> SEQ ID NO 624
<211> LENGTH: 9
<212> TYPE: PRT
<213> ORGANISM: Homo sapiens

<400> SEQUENCE: 624

Trp Ser Gly Ser His Leu Gln Arg Tyr
1               5

<210> SEQ ID NO 625
<211> LENGTH: 9
<212> TYPE: PRT
<213> ORGANISM: Homo sapiens

<400> SEQUENCE: 625

Ser Ser Leu Glu Arg Ser Ala His Leu
1               5

<210> SEQ ID NO 626
<211> LENGTH: 9
<212> TYPE: PRT
<213> ORGANISM: Homo sapiens

<400> SEQUENCE: 626

Gly Pro Ser Thr Arg Tyr His Thr Trp
1               5

<210> SEQ ID NO 627
<211> LENGTH: 9
<212> TYPE: PRT
<213> ORGANISM: Homo sapiens

<400> SEQUENCE: 627

Thr Ser Ala Pro Gly Ser Arg Asp Tyr
1               5

<210> SEQ ID NO 628
<211> LENGTH: 9
<212> TYPE: PRT
<213> ORGANISM: Homo sapiens

```
<400> SEQUENCE: 628

Thr Ser Leu Asn Pro Ile Trp Ser Tyr
1               5

<210> SEQ ID NO 629
<211> LENGTH: 9
<212> TYPE: PRT
<213> ORGANISM: Homo sapiens

<400> SEQUENCE: 629

Lys Ser Ser Ser Asn Gln Val Ile Phe
1               5

<210> SEQ ID NO 630
<211> LENGTH: 9
<212> TYPE: PRT
<213> ORGANISM: Homo sapiens

<400> SEQUENCE: 630

Asn Ala Lys Leu Arg Leu Met Val Leu
1               5

<210> SEQ ID NO 631
<211> LENGTH: 9
<212> TYPE: PRT
<213> ORGANISM: Homo sapiens

<400> SEQUENCE: 631

Tyr Ala Arg Ile Ser His Ala Glu Leu
1               5

<210> SEQ ID NO 632
<211> LENGTH: 9
<212> TYPE: PRT
<213> ORGANISM: Homo sapiens

<400> SEQUENCE: 632

Trp Pro Gln Thr Leu Gly His Leu Ile
1               5

<210> SEQ ID NO 633
<211> LENGTH: 9
<212> TYPE: PRT
<213> ORGANISM: Homo sapiens

<400> SEQUENCE: 633

Lys Thr Gly Glu Val Ala Thr Gly Met
1               5

<210> SEQ ID NO 634
<211> LENGTH: 9
<212> TYPE: PRT
<213> ORGANISM: Homo sapiens

<400> SEQUENCE: 634

Lys Leu Arg Leu Met Val Leu Ala Leu
1               5

<210> SEQ ID NO 635
<211> LENGTH: 9
<212> TYPE: PRT
<213> ORGANISM: Homo sapiens

<400> SEQUENCE: 635
```

Arg Ser Asp Val Leu Leu Gly Thr Met
1               5

<210> SEQ ID NO 636
<211> LENGTH: 9
<212> TYPE: PRT
<213> ORGANISM: Homo sapiens

<400> SEQUENCE: 636

Thr Ala Ser Ala Ala Gly Leu Leu Tyr
1               5

<210> SEQ ID NO 637
<211> LENGTH: 9
<212> TYPE: PRT
<213> ORGANISM: Homo sapiens

<400> SEQUENCE: 637

Val Ser Trp Ser Leu Tyr His Asp Leu
1               5

<210> SEQ ID NO 638
<211> LENGTH: 9
<212> TYPE: PRT
<213> ORGANISM: Homo sapiens

<400> SEQUENCE: 638

Thr Ser Leu Trp Arg Glu Ile Leu Leu
1               5

<210> SEQ ID NO 639
<211> LENGTH: 9
<212> TYPE: PRT
<213> ORGANISM: Homo sapiens

<400> SEQUENCE: 639

Ala Ser Ala Ala Gly Leu Leu Tyr Leu
1               5

<210> SEQ ID NO 640
<211> LENGTH: 9
<212> TYPE: PRT
<213> ORGANISM: Homo sapiens

<400> SEQUENCE: 640

Ser Ser Ser Asn Gln Val Ile Phe Leu
1               5

<210> SEQ ID NO 641
<211> LENGTH: 9
<212> TYPE: PRT
<213> ORGANISM: Homo sapiens

<400> SEQUENCE: 641

Val Ser Gly Cys Val Phe Ala Ile Phe
1               5

<210> SEQ ID NO 642
<211> LENGTH: 9
<212> TYPE: PRT
<213> ORGANISM: Homo sapiens

<400> SEQUENCE: 642

Met Ser Asn Lys Val Ile Leu Thr Leu
1               5

```
<210> SEQ ID NO 643
<211> LENGTH: 9
<212> TYPE: PRT
<213> ORGANISM: Homo sapiens

<400> SEQUENCE: 643

Ile Val Lys Ser Glu His His Leu Leu
1               5

<210> SEQ ID NO 644
<211> LENGTH: 9
<212> TYPE: PRT
<213> ORGANISM: Homo sapiens

<400> SEQUENCE: 644

Arg Pro Asn Trp Leu Leu Ala Gly Ala
1               5

<210> SEQ ID NO 645
<211> LENGTH: 9
<212> TYPE: PRT
<213> ORGANISM: Homo sapiens

<400> SEQUENCE: 645

Glu Leu Ser Asp Ser Glu Ile Gln Met
1               5

<210> SEQ ID NO 646
<211> LENGTH: 9
<212> TYPE: PRT
<213> ORGANISM: Homo sapiens

<400> SEQUENCE: 646

Asp Pro Asn Pro Phe Gly Gly Ala Val
1               5

<210> SEQ ID NO 647
<211> LENGTH: 9
<212> TYPE: PRT
<213> ORGANISM: Homo sapiens

<400> SEQUENCE: 647

Trp Leu Gly Glu Lys Leu Gly Phe Tyr
1               5

<210> SEQ ID NO 648
<211> LENGTH: 9
<212> TYPE: PRT
<213> ORGANISM: Homo sapiens

<400> SEQUENCE: 648

Leu Ala Gly Ala Ala Phe Gly Ser Leu
1               5

<210> SEQ ID NO 649
<211> LENGTH: 9
<212> TYPE: PRT
<213> ORGANISM: Homo sapiens

<400> SEQUENCE: 649

Leu Ala Leu Gly Val Ser Ser Ser Leu
1               5
```

<210> SEQ ID NO 650
<211> LENGTH: 9
<212> TYPE: PRT
<213> ORGANISM: Homo sapiens

<400> SEQUENCE: 650

Cys Ala Trp Cys Thr Ala Phe Lys Phe
 1               5

<210> SEQ ID NO 651
<211> LENGTH: 9
<212> TYPE: PRT
<213> ORGANISM: Homo sapiens

<400> SEQUENCE: 651

Leu Pro Ser Pro Glu Gly Glu Ile Ala
 1               5

<210> SEQ ID NO 652
<211> LENGTH: 9
<212> TYPE: PRT
<213> ORGANISM: Homo sapiens

<400> SEQUENCE: 652

Ala Pro Thr Lys Glu Val Ser Ala Ala
 1               5

<210> SEQ ID NO 653
<211> LENGTH: 9
<212> TYPE: PRT
<213> ORGANISM: Homo sapiens

<400> SEQUENCE: 653

Tyr Leu Arg Ile Trp Gly Phe Ile Leu
 1               5

<210> SEQ ID NO 654
<211> LENGTH: 9
<212> TYPE: PRT
<213> ORGANISM: Homo sapiens

<400> SEQUENCE: 654

Glu Ser Asp Ala Ser Lys Pro Tyr Met
 1               5

<210> SEQ ID NO 655
<211> LENGTH: 9
<212> TYPE: PRT
<213> ORGANISM: Homo sapiens

<400> SEQUENCE: 655

Val Asn Lys Lys Trp Met Leu Thr Leu
 1               5

<210> SEQ ID NO 656
<211> LENGTH: 9
<212> TYPE: PRT
<213> ORGANISM: Homo sapiens

<400> SEQUENCE: 656

Gln Ala Pro Asn Ala Lys Leu Arg Leu
 1               5

<210> SEQ ID NO 657
<211> LENGTH: 9

<212> TYPE: PRT
<213> ORGANISM: Homo sapiens

<400> SEQUENCE: 657

Tyr Met Lys Leu Phe Leu Trp Leu Leu
1               5

<210> SEQ ID NO 658
<211> LENGTH: 9
<212> TYPE: PRT
<213> ORGANISM: Homo sapiens

<400> SEQUENCE: 658

Gln Ala Ile Ala Val Ser Lys Leu Leu
1               5

<210> SEQ ID NO 659
<211> LENGTH: 9
<212> TYPE: PRT
<213> ORGANISM: Homo sapiens

<400> SEQUENCE: 659

Gly Ser Arg Asp Tyr Leu Gln Leu Thr
1               5

<210> SEQ ID NO 660
<211> LENGTH: 9
<212> TYPE: PRT
<213> ORGANISM: Homo sapiens

<400> SEQUENCE: 660

Gln Thr Lys Asn Ser Ser Lys Val Leu
1               5

<210> SEQ ID NO 661
<211> LENGTH: 9
<212> TYPE: PRT
<213> ORGANISM: Homo sapiens

<400> SEQUENCE: 661

Lys Ser Glu Lys Tyr Met Lys Leu Phe
1               5

<210> SEQ ID NO 662
<211> LENGTH: 9
<212> TYPE: PRT
<213> ORGANISM: Homo sapiens

<400> SEQUENCE: 662

Thr Ala Ser Met Trp Pro Gln Thr Leu
1               5

<210> SEQ ID NO 663
<211> LENGTH: 9
<212> TYPE: PRT
<213> ORGANISM: Homo sapiens

<400> SEQUENCE: 663

Val Leu Arg Ile Trp Tyr Thr Ser Leu
1               5

<210> SEQ ID NO 664
<211> LENGTH: 9
<212> TYPE: PRT
<213> ORGANISM: Homo sapiens

<400> SEQUENCE: 664

Gly Ala Ala Phe Gly Ser Leu Val Phe
1               5

<210> SEQ ID NO 665
<211> LENGTH: 10
<212> TYPE: PRT
<213> ORGANISM: Homo sapiens

<400> SEQUENCE: 665

Gly Pro Lys Lys Asn Leu Asp Leu Leu Leu
1               5                   10

<210> SEQ ID NO 666
<211> LENGTH: 10
<212> TYPE: PRT
<213> ORGANISM: Homo sapiens

<400> SEQUENCE: 666

Asn Pro Gly Lys Thr Met Thr Ile Ala Met
1               5                   10

<210> SEQ ID NO 667
<211> LENGTH: 10
<212> TYPE: PRT
<213> ORGANISM: Homo sapiens

<400> SEQUENCE: 667

Ala Pro Gly Ser Arg Asp Tyr Leu Gln Leu
1               5                   10

<210> SEQ ID NO 668
<211> LENGTH: 10
<212> TYPE: PRT
<213> ORGANISM: Homo sapiens

<400> SEQUENCE: 668

Asp Pro Asn Pro Phe Gly Gly Ala Val Leu
1               5                   10

<210> SEQ ID NO 669
<211> LENGTH: 10
<212> TYPE: PRT
<213> ORGANISM: Homo sapiens

<400> SEQUENCE: 669

Tyr Pro Ile Val Lys Ser Glu His His Leu
1               5                   10

<210> SEQ ID NO 670
<211> LENGTH: 10
<212> TYPE: PRT
<213> ORGANISM: Homo sapiens

<400> SEQUENCE: 670

Ser Pro Ile Phe Leu Thr Ile Thr Pro Phe
1               5                   10

<210> SEQ ID NO 671
<211> LENGTH: 10
<212> TYPE: PRT
<213> ORGANISM: Homo sapiens

<400> SEQUENCE: 671

Tyr Ala Arg Glu Arg Ser Asp Val Leu Leu
1               5                   10

<210> SEQ ID NO 672
<211> LENGTH: 10
<212> TYPE: PRT
<213> ORGANISM: Homo sapiens

<400> SEQUENCE: 672

Trp Ser Leu Tyr His Asp Leu Gly Pro Met
1               5                   10

<210> SEQ ID NO 673
<211> LENGTH: 10
<212> TYPE: PRT
<213> ORGANISM: Homo sapiens

<400> SEQUENCE: 673

Asn Ser Gly Thr Asn Pro Gly Lys Thr Met
1               5                   10

<210> SEQ ID NO 674
<211> LENGTH: 10
<212> TYPE: PRT
<213> ORGANISM: Homo sapiens

<400> SEQUENCE: 674

Ser Ser Leu Glu Arg Ser Ala His Leu Leu
1               5                   10

<210> SEQ ID NO 675
<211> LENGTH: 10
<212> TYPE: PRT
<213> ORGANISM: Homo sapiens

<400> SEQUENCE: 675

Ser Ser Asn Gln Val Ile Phe Leu Gly Tyr
1               5                   10

<210> SEQ ID NO 676
<211> LENGTH: 10
<212> TYPE: PRT
<213> ORGANISM: Homo sapiens

<400> SEQUENCE: 676

Lys Ser Ser Ser Asn Gln Val Ile Phe Leu
1               5                   10

<210> SEQ ID NO 677
<211> LENGTH: 10
<212> TYPE: PRT
<213> ORGANISM: Homo sapiens

<400> SEQUENCE: 677

Ala Pro Ala Ile Thr Leu Thr Val Asn Ile
1               5                   10

<210> SEQ ID NO 678
<211> LENGTH: 10
<212> TYPE: PRT
<213> ORGANISM: Homo sapiens

<400> SEQUENCE: 678

Ala Pro Thr Lys Glu Val Ser Ala Ala Ile

```
1               5                   10
```

<210> SEQ ID NO 679
<211> LENGTH: 10
<212> TYPE: PRT
<213> ORGANISM: Homo sapiens

<400> SEQUENCE: 679

```
Ala Ala Ile Trp Pro Phe Arg Phe Gly Tyr
 1               5                  10
```

<210> SEQ ID NO 680
<211> LENGTH: 10
<212> TYPE: PRT
<213> ORGANISM: Homo sapiens

<400> SEQUENCE: 680

```
Ser Thr Arg Tyr His Thr Trp Gly Ile Met
 1               5                  10
```

<210> SEQ ID NO 681
<211> LENGTH: 10
<212> TYPE: PRT
<213> ORGANISM: Homo sapiens

<400> SEQUENCE: 681

```
Arg Ser Asp Val Leu Leu Gly Thr Met Met
 1               5                  10
```

<210> SEQ ID NO 682
<211> LENGTH: 10
<212> TYPE: PRT
<213> ORGANISM: Homo sapiens

<400> SEQUENCE: 682

```
Gln Ala Pro Asn Ala Lys Leu Arg Leu Met
 1               5                  10
```

<210> SEQ ID NO 683
<211> LENGTH: 10
<212> TYPE: PRT
<213> ORGANISM: Homo sapiens

<400> SEQUENCE: 683

```
Val Ser Ala Ala Ile Trp Pro Phe Arg Phe
 1               5                  10
```

<210> SEQ ID NO 684
<211> LENGTH: 10
<212> TYPE: PRT
<213> ORGANISM: Homo sapiens

<400> SEQUENCE: 684

```
Phe Ser Ile Ala Phe Leu Ser Pro Ile Phe
 1               5                  10
```

<210> SEQ ID NO 685
<211> LENGTH: 10
<212> TYPE: PRT
<213> ORGANISM: Homo sapiens

<400> SEQUENCE: 685

```
Ala Ser Gly Leu Met Leu Pro Ser Cys Leu
 1               5                  10
```

```
<210> SEQ ID NO 686
<211> LENGTH: 10
<212> TYPE: PRT
<213> ORGANISM: Homo sapiens

<400> SEQUENCE: 686

Thr Ser Ala Pro Gly Ser Arg Asp Tyr Leu
1               5                   10

<210> SEQ ID NO 687
<211> LENGTH: 10
<212> TYPE: PRT
<213> ORGANISM: Homo sapiens

<400> SEQUENCE: 687

Trp Ser Ser Leu Glu Arg Ser Ala His Leu
1               5                   10

<210> SEQ ID NO 688
<211> LENGTH: 10
<212> TYPE: PRT
<213> ORGANISM: Homo sapiens

<400> SEQUENCE: 688

Trp Ser Gly Ser His Leu Gln Arg Tyr Leu
1               5                   10

<210> SEQ ID NO 689
<211> LENGTH: 10
<212> TYPE: PRT
<213> ORGANISM: Homo sapiens

<400> SEQUENCE: 689

Ala Ser Phe Gln Ala Pro Asn Ala Lys Leu
1               5                   10

<210> SEQ ID NO 690
<211> LENGTH: 10
<212> TYPE: PRT
<213> ORGANISM: Homo sapiens

<400> SEQUENCE: 690

Lys Pro Glu Glu Lys Lys Thr Gly Glu Val
1               5                   10

<210> SEQ ID NO 691
<211> LENGTH: 10
<212> TYPE: PRT
<213> ORGANISM: Homo sapiens

<400> SEQUENCE: 691

Lys Val Leu Phe Arg Lys Ser Glu Lys Tyr
1               5                   10

<210> SEQ ID NO 692
<211> LENGTH: 10
<212> TYPE: PRT
<213> ORGANISM: Homo sapiens

<400> SEQUENCE: 692

Lys Pro Tyr Met Gly Asn Asn Asp Leu Thr
1               5                   10

<210> SEQ ID NO 693
```

```
<211> LENGTH: 10
<212> TYPE: PRT
<213> ORGANISM: Homo sapiens

<400> SEQUENCE: 693

Lys Thr Met Thr Ile Ala Met Ile Phe Tyr
1               5                   10

<210> SEQ ID NO 694
<211> LENGTH: 10
<212> TYPE: PRT
<213> ORGANISM: Homo sapiens

<400> SEQUENCE: 694

Lys Leu Val Asp Phe Val Val Thr His Phe
1               5                   10

<210> SEQ ID NO 695
<211> LENGTH: 10
<212> TYPE: PRT
<213> ORGANISM: Homo sapiens

<400> SEQUENCE: 695

Ala Pro Asn Ala Lys Leu Arg Leu Met Val
1               5                   10

<210> SEQ ID NO 696
<211> LENGTH: 10
<212> TYPE: PRT
<213> ORGANISM: Homo sapiens

<400> SEQUENCE: 696

Arg Pro Asn Trp Leu Leu Ala Gly Ala Ala
1               5                   10

<210> SEQ ID NO 697
<211> LENGTH: 10
<212> TYPE: PRT
<213> ORGANISM: Homo sapiens

<400> SEQUENCE: 697

Trp Ala Ala Ala Val Ser Gly Cys Val Phe
1               5                   10

<210> SEQ ID NO 698
<211> LENGTH: 10
<212> TYPE: PRT
<213> ORGANISM: Homo sapiens

<400> SEQUENCE: 698

Leu Gln Arg Tyr Leu Arg Ile Trp Gly Phe
1               5                   10

<210> SEQ ID NO 699
<211> LENGTH: 10
<212> TYPE: PRT
<213> ORGANISM: Homo sapiens

<400> SEQUENCE: 699

Gln Thr Lys Asn Ser Ser Lys Val Leu Phe
1               5                   10

<210> SEQ ID NO 700
<211> LENGTH: 10
<212> TYPE: PRT
```

<213> ORGANISM: Homo sapiens

<400> SEQUENCE: 700

Gly Ala Ala Phe Gly Ser Leu Val Phe Leu
1               5                   10

<210> SEQ ID NO 701
<211> LENGTH: 10
<212> TYPE: PRT
<213> ORGANISM: Homo sapiens

<400> SEQUENCE: 701

Lys Ser Glu Lys Tyr Met Lys Leu Phe Leu
1               5                   10

<210> SEQ ID NO 702
<211> LENGTH: 10
<212> TYPE: PRT
<213> ORGANISM: Homo sapiens

<400> SEQUENCE: 702

Val Asn Lys Lys Trp Met Leu Thr Leu Leu
1               5                   10

<210> SEQ ID NO 703
<211> LENGTH: 10
<212> TYPE: PRT
<213> ORGANISM: Homo sapiens

<400> SEQUENCE: 703

Thr Ala Ser Ala Ala Gly Leu Leu Tyr Leu
1               5                   10

<210> SEQ ID NO 704
<211> LENGTH: 10
<212> TYPE: PRT
<213> ORGANISM: Homo sapiens

<400> SEQUENCE: 704

Phe Gly Ser Tyr Lys Glu Gly His Asn Tyr
1               5                   10

<210> SEQ ID NO 705
<211> LENGTH: 10
<212> TYPE: PRT
<213> ORGANISM: Homo sapiens

<400> SEQUENCE: 705

Ser Ser Leu Ile Val Gln Ala Val Thr Trp
1               5                   10

<210> SEQ ID NO 706
<211> LENGTH: 10
<212> TYPE: PRT
<213> ORGANISM: Homo sapiens

<400> SEQUENCE: 706

Ser Pro Glu Gly Glu Ile Ala Pro Ala Ile
1               5                   10

<210> SEQ ID NO 707
<211> LENGTH: 10
<212> TYPE: PRT
<213> ORGANISM: Homo sapiens

```
<400> SEQUENCE: 707

Lys Ala Tyr Glu Arg Lys Leu Gly Lys Val
 1               5                  10

<210> SEQ ID NO 708
<211> LENGTH: 10
<212> TYPE: PRT
<213> ORGANISM: Homo sapiens

<400> SEQUENCE: 708

Ile Val Leu Val Val Leu Arg Ile Trp Tyr
 1               5                  10

<210> SEQ ID NO 709
<211> LENGTH: 10
<212> TYPE: PRT
<213> ORGANISM: Homo sapiens

<400> SEQUENCE: 709

Asn Pro Phe Gly Gly Ala Val Leu Leu Cys
 1               5                  10

<210> SEQ ID NO 710
<211> LENGTH: 10
<212> TYPE: PRT
<213> ORGANISM: Homo sapiens

<400> SEQUENCE: 710

Thr Met Met Leu Ile Ile Gly Leu Asn Met
 1               5                  10

<210> SEQ ID NO 711
<211> LENGTH: 10
<212> TYPE: PRT
<213> ORGANISM: Homo sapiens

<400> SEQUENCE: 711

Gly Ser His Leu Gln Arg Tyr Leu Arg Ile
 1               5                  10

<210> SEQ ID NO 712
<211> LENGTH: 10
<212> TYPE: PRT
<213> ORGANISM: Homo sapiens

<400> SEQUENCE: 712

Trp Pro Gln Thr Leu Gly His Leu Ile Asn
 1               5                  10

<210> SEQ ID NO 713
<211> LENGTH: 10
<212> TYPE: PRT
<213> ORGANISM: Homo sapiens

<400> SEQUENCE: 713

Leu Gly Leu Gly Leu Arg His Lys Ala Tyr
 1               5                  10

<210> SEQ ID NO 714
<211> LENGTH: 10
<212> TYPE: PRT
<213> ORGANISM: Homo sapiens

<400> SEQUENCE: 714
```

```
Ile Thr Ser Ala Pro Gly Ser Arg Asp Tyr
1               5                  10
```

<210> SEQ ID NO 715
<211> LENGTH: 23
<212> TYPE: PRT
<213> ORGANISM: Homo sapiens

<400> SEQUENCE: 715

```
Met Thr Ser Leu Trp Arg Glu Ile Leu Leu Glu Ser Leu Leu Gly Cys
1               5                  10                  15

Val Ser Trp Ser Leu Tyr His
            20
```

<210> SEQ ID NO 716
<211> LENGTH: 23
<212> TYPE: PRT
<213> ORGANISM: Homo sapiens

<400> SEQUENCE: 716

```
Leu Glu Gly Phe Ser Ile Ala Phe Leu Ser Pro Ile Phe Leu Thr Ile
1               5                  10                  15

Thr Pro Phe Trp Lys Leu Val
            20
```

<210> SEQ ID NO 717
<211> LENGTH: 23
<212> TYPE: PRT
<213> ORGANISM: Homo sapiens

<400> SEQUENCE: 717

```
Met Val Leu Ala Leu Gly Val Ser Ser Ser Leu Ile Val Gln Ala Val
1               5                  10                  15

Thr Trp Trp Ser Gly Ser His
            20
```

<210> SEQ ID NO 718
<211> LENGTH: 23
<212> TYPE: PRT
<213> ORGANISM: Homo sapiens

<400> SEQUENCE: 718

```
Tyr Leu Arg Ile Trp Gly Phe Ile Leu Gly Gln Ile Val Leu Val Val
1               5                  10                  15

Leu Arg Ile Trp Tyr Thr Ser
            20
```

<210> SEQ ID NO 719
<211> LENGTH: 23
<212> TYPE: PRT
<213> ORGANISM: Homo sapiens

<400> SEQUENCE: 719

```
Met Ala Ser Arg Pro Asn Trp Leu Leu Ala Gly Ala Ala Phe Gly Ser
1               5                  10                  15

Leu Val Phe Leu Thr His Trp
            20
```

<210> SEQ ID NO 720
<211> LENGTH: 23
<212> TYPE: PRT
<213> ORGANISM: Homo sapiens

```
<400> SEQUENCE: 720

Gly Gly Ala Val Leu Leu Cys Leu Ala Ser Gly Leu Met Leu Pro Ser
1               5                   10                  15

Cys Leu Trp Phe Arg Gly Thr
            20

<210> SEQ ID NO 721
<211> LENGTH: 23
<212> TYPE: PRT
<213> ORGANISM: Homo sapiens

<400> SEQUENCE: 721

Thr Ala Ser Ala Ala Gly Leu Leu Tyr Leu His Thr Trp Ala Ala
1               5                   10                  15

Val Ser Gly Cys Val Phe Ala
            20

<210> SEQ ID NO 722
<211> LENGTH: 23
<212> TYPE: PRT
<213> ORGANISM: Homo sapiens

<400> SEQUENCE: 722

Ile Ala Met Ile Phe Tyr Leu Leu Glu Ile Phe Phe Cys Ala Trp Cys
1               5                   10                  15

Thr Ala Phe Lys Phe Val Pro
            20

<210> SEQ ID NO 723
<211> LENGTH: 19
<212> TYPE: PRT
<213> ORGANISM: Homo sapiens

<400> SEQUENCE: 723

Asp Val Leu Leu Gly Thr Met Met Leu Ile Ile Gly Leu Asn Met Leu
1               5                   10                  15

Phe Gly Pro

<210> SEQ ID NO 724
<211> LENGTH: 22
<212> TYPE: PRT
<213> ORGANISM: Homo sapiens

<400> SEQUENCE: 724

Glu Lys Tyr Met Lys Leu Phe Leu Trp Leu Leu Val Gly Val Gly Leu
1               5                   10                  15

Leu Gly Leu Gly Leu Arg
            20

<210> SEQ ID NO 725
<211> LENGTH: 4
<212> TYPE: PRT
<213> ORGANISM: Homo sapiens

<400> SEQUENCE: 725

Asn Ser Ser Lys
1

<210> SEQ ID NO 726
<211> LENGTH: 4
<212> TYPE: PRT
<213> ORGANISM: Homo sapiens
```

<400> SEQUENCE: 726

Asn Glu Thr Gly
1

<210> SEQ ID NO 727
<211> LENGTH: 4
<212> TYPE: PRT
<213> ORGANISM: Homo sapiens

<400> SEQUENCE: 727

Asn Ile Ser Gly
1

<210> SEQ ID NO 728
<211> LENGTH: 4
<212> TYPE: PRT
<213> ORGANISM: Homo sapiens

<400> SEQUENCE: 728

Thr Gly Leu Glu
1

<210> SEQ ID NO 729
<211> LENGTH: 4
<212> TYPE: PRT
<213> ORGANISM: Homo sapiens

<400> SEQUENCE: 729

Thr Asp Gly Asp
1

<210> SEQ ID NO 730
<211> LENGTH: 4
<212> TYPE: PRT
<213> ORGANISM: Homo sapiens

<400> SEQUENCE: 730

Ser Lys Pro Glu
1

<210> SEQ ID NO 731
<211> LENGTH: 4
<212> TYPE: PRT
<213> ORGANISM: Homo sapiens

<400> SEQUENCE: 731

Ser Ser Leu Glu
1

<210> SEQ ID NO 732
<211> LENGTH: 4
<212> TYPE: PRT
<213> ORGANISM: Homo sapiens

<400> SEQUENCE: 732

Thr Gly Ala Asp
1

<210> SEQ ID NO 733
<211> LENGTH: 4
<212> TYPE: PRT
<213> ORGANISM: Homo sapiens

<400> SEQUENCE: 733

Thr Ile Leu Glu
1

<210> SEQ ID NO 734
<211> LENGTH: 4
<212> TYPE: PRT
<213> ORGANISM: Homo sapiens

<400> SEQUENCE: 734

Thr Asp His Asp
1

<210> SEQ ID NO 735
<211> LENGTH: 4
<212> TYPE: PRT
<213> ORGANISM: Homo sapiens

<400> SEQUENCE: 735

Ser His Ala Glu
1

<210> SEQ ID NO 736
<211> LENGTH: 4
<212> TYPE: PRT
<213> ORGANISM: Homo sapiens

<400> SEQUENCE: 736

Ser Asp Ser Glu
1

<210> SEQ ID NO 737
<211> LENGTH: 4
<212> TYPE: PRT
<213> ORGANISM: Homo sapiens

<400> SEQUENCE: 737

Ser Tyr Lys Glu
1

<210> SEQ ID NO 738
<211> LENGTH: 8
<212> TYPE: PRT
<213> ORGANISM: Homo sapiens

<400> SEQUENCE: 738

Arg Trp Cys Glu Tyr Ile Met Tyr
1               5

<210> SEQ ID NO 739
<211> LENGTH: 9
<212> TYPE: PRT
<213> ORGANISM: Homo sapiens

<400> SEQUENCE: 739

Arg Ile Pro Asp Asp Pro Thr Asn Tyr
1               5

<210> SEQ ID NO 740
<211> LENGTH: 6
<212> TYPE: PRT
<213> ORGANISM: Homo sapiens

<400> SEQUENCE: 740

Gly Ser Ile Ala Ser Phe

```
<210> SEQ ID NO 741
<211> LENGTH: 6
<212> TYPE: PRT
<213> ORGANISM: Homo sapiens

<400> SEQUENCE: 741

Gly Val Ser Ser Ser Leu
1               5

<210> SEQ ID NO 742
<211> LENGTH: 6
<212> TYPE: PRT
<213> ORGANISM: Homo sapiens

<400> SEQUENCE: 742

Gly Ala Ala Phe Gly Ser
1               5

<210> SEQ ID NO 743
<211> LENGTH: 6
<212> TYPE: PRT
<213> ORGANISM: Homo sapiens

<400> SEQUENCE: 743

Gly Thr Ala Ser Ala Ala
1               5

<210> SEQ ID NO 744
<211> LENGTH: 6
<212> TYPE: PRT
<213> ORGANISM: Homo Sapiens

<400> SEQUENCE: 744

Gly Cys Val Phe Ala Ile
1               5

<210> SEQ ID NO 745
<211> LENGTH: 6
<212> TYPE: PRT
<213> ORGANISM: Homo Sapiens

<400> SEQUENCE: 745

Gly Thr Asn Pro Gly Lys
1               5

<210> SEQ ID NO 746
<211> LENGTH: 6
<212> TYPE: PRT
<213> ORGANISM: Homo Sapiens

<400> SEQUENCE: 746

Gly Gly Val Tyr Ala Arg
1               5
```

125P5C8: TISSUE SPECIFIC PROTEIN HIGHLY EXPRESSED IN VARIOUS CANCERS

CROSS-REFERENCE TO RELATED APPLICATIONS

This application is a division of U.S. patent application Ser. No. 09/809,638 filed Mar. 14, 2001, which is now U.S. Pat. No. 7,271,240. The contents of this document are incorporated herein by reference in its entirety.

Reference to Sequence Listing Submitted Via EFS-Web

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 511582003510Seqlist.txt | Apr. 16, 2008 | 120,323 bytes |

FIELD OF THE INVENTION

The invention described herein relates to a novel gene and its encoded protein, termed 125P5C8, and to diagnostic and therapeutic methods and compositions useful in the management of various cancers that express 125P5C8.

BACKGROUND OF THE INVENTION

Cancer is the second leading cause of human death next to coronary disease. Worldwide, millions of people die from cancer every year. In the United States alone, cancer causes the death of well over a half-million people annually, with some 1.4 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Worldwide, prostate cancer is the fourth most prevalent cancer in men. In North America and Northern Europe, it is by far the most common cancer in males and is the second leading cause of cancer death in men. In the United States alone, well over 40,000 men die annually of this disease—second only to lung cancer. Despite the magnitude of these Figures, there is still no effective treatment for metastatic prostate cancer. Surgical prostatectomy, radiation therapy, hormone ablation therapy, surgical castration and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the diagnosis and management of this disease. Although the serum prostate specific antigen (PSA) assay has been a very useful tool, however its specificity and general utility is widely regarded as lacking in several important respects.

Progress in identifying additional specific markers for prostate cancer has been improved by the generation of prostate cancer xenografts that can recapitulate different stages of the disease in mice. The LAPC (Los Angeles Prostate Cancer) xenografts are prostate cancer xenografts that have survived passage in severe combined immune deficient (SCID) mice and have exhibited the capacity to mimic the transition from androgen dependence to androgen independence (Klein et al., 1997, Nat. Med. 3:402). More recently identified prostate cancer markers include PCTA-1 (Su et al., 1996, Proc. Natl. Acad. Sci. USA 93: 7252), prostate-specific membrane (PSM) antigen (Pinto et al., Clin Cancer Res Sep. 2, 1996 (9): 1445-51), STEAP (Hubert, et al., Proc Natl Acad Sci USA. Dec. 7, 1999; 96(25): 14523-8) and prostate stem cell antigen (PSCA) (Reiter et al., 1998, Proc. Natl. Acad. Sci. USA 95: 1735).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

SUMMARY OF THE INVENTION

The present invention relates to a novel gene, designated 125P5C8, that is over-expressed in multiple cancers listed in Table I. Northern blot expression analysis of 125P5C8 gene expression in normal tissues shows a restricted expression pattern in adult tissues. The nucleotide (FIG. 2) and amino acid (FIG. 2 and FIG. 3) sequences of 125P5C8 are provided. The tissue-related profile of 125P5C8 in normal adult tissues, combined with the over-expression observed in prostate and other tumors, shows that 125P5C8 is aberrantly over-expressed in at least some cancers, and thus serves as a useful diagnostic and/or therapeutic target for cancers of the tissues such as those listed in Table I.

The invention provides polynucleotides corresponding or complementary to all or part of the 125P5C8 genes, mRNAs, and/or coding sequences, preferably in isolated form, including polynucleotides encoding 125P5C8-related proteins and fragments of 4, 5, 6, 7, 8, 9, 10, 11, 12, 13, 14, 15, 16, 17, 18, 19, 20, 21, 22, 23, 24, 25, or more than 25 contiguous amino acids; at least 30, 35, 40, 45, 50, 55, 60, 65, 70, 80, 85, 90, 95, 100 or more than 100 contiguous amino acids of a 125P5C8-related protein, as well as the peptides/proteins themselves; DNA, RNA, DNA/RNA hybrids, and related molecules, polynucleotides or oligonucleotides complementary or having at least a 90% homology to the 125P5C8 genes or mRNA sequences or parts thereof, and polynucleotides or oligonucleotides that hybridize to the 125P5C8 genes, mRNAs, or to 125P5C8-encoding polynucleotides. Also provided are means for isolating cDNAs and the genes encoding 125P5C8. Recombinant DNA molecules containing 125P5C8 polynucleotides, cells transformed or transduced with such molecules, and host-vector systems for the expression of 125P5C8 gene products are also provided. The invention further provides antibodies that bind to 125P5C8 proteins and polypeptide fragments thereof, including polyclonal and monoclonal antibodies, murine and other mammalian antibodies, chimeric antibodies, humanized and fully human antibodies, and antibodies labeled with a detectable marker.

The invention further provides methods for detecting the presence and status of 125P5C8 polynucleotides and proteins in various biological samples, as well as methods for identifying cells that express 125P5C8. A typical embodiment of this invention provides methods for monitoring 125P5C8 gene products in a tissue or hematology sample having or suspected of having some form of growth dysregulation such as cancer.

The invention further provides various immunogenic or therapeutic compositions and strategies for treating cancers that express 125P5C8 such as prostate cancers, including therapies aimed at inhibiting the transcription, translation, processing or function of 125P5C8 as well as cancer vaccines.

BRIEF DESCRIPTION OF THE FIGURES

FIG. 1. 125P5C8 SSH sequence (SEQ ID NO:3). The SSH experiment was performed with cDNA digested with DPN II. The 125P5C8 sequence contains 287 bp.

FIGS. 2A-B. The cDNA (SEQ ID NO:1) and amino acid sequence SEQ ID NO:2) of 125P5C8.

FIG. 3. The amino acid sequence (SEQ ID NO:2) encoded by the open reading frame of the nucleic acid sequence set forth in FIGS. 2A-B.

FIGS. 4A-B. Alignment of 125P5C8 (SEQ ID NO:2) with AK025164 (SEQ ID NO:4) (FIG. 4A) and the yeast protein YCR017 (SEQ ID NO:5) (FIG. 4B) using the BLAST function (NCBI).

FIG. 5. High expression of 125P5C8 in prostate tissues. RT-PCR analysis shows high expression in the prostate cancer xenografts, normal prostate, prostate cancer, and to a lower extent in kidney, colon and bladder cancer specimens. Results are shown for 26 cycles (upper panel) and 30 cycles (lower panel). Lanes represent: VP1: Liver, kidney, lung; VP2: Stomach, spleen, pancreas; XeP: Xenograft pool: LAPC4AD, LAPC4AI, LAPC9AD, LAPC9AI; N.Pr.: Normal prostate pool; PrCa: Prostate cancer pool; BlCa: Bladder cancer pool; KiCa: Kidney cancer pool; CoCa: Colon cancer pool; LuCa: Lung cancer patient.

(FIG. 6A) 1. Heart; 2. Brain; 3. Placenta; 4. Lung; 5. Liver; 6. Skeletal Muscle; 7. Kidney; 8. Pancreas; (FIG. 6B) 1. Spleen; 2. Thymus; 3. Prostate; 4. Testis; 5. Ovary; 6. Small Intestine; 7. Colon; 8. Leukocytes; (FIG. 6C) 1. Normal Prostate; 2. LAPC-4 AD; 3. LAPC-4 AI; 4. LAPC-9 AD; 5. LAPC-9 AI.

FIG. 8. Expression of 125P5C8 in kidney cancer patient tissues. RNA was extracted from normal kidney, normal adjacent to tumor, and tumor tissues. Northern blots with 10 μg of total RNA were probed with the 125P5C8 SSH fragment. Size standards in kilobases are on the side. Results show down-regulation of 125P5C8 in kidney tumor tissues. Lanes represent: Patient 1—papillary cell, grade 1; Patient 2—papillary adenocarcinoma, nuclear, grade 3; Patient 3—clear cell, Fuhrman grade 2 of 4; Patient 4—clear cell, grade III; Patient 5—clear cell, grade II/IV; Patient 6—clear cell, grade 3; Patient 7—clear cell, grade III/IV; Patient 8—chromophobe cell type, grade IV ; Patient 9—metastasis to chest wall. NK=Normal kidney; N=Normal adjacent tissue; T=Tumor.

DETAILED DESCRIPTION OF THE INVENTION

Figure 6C:
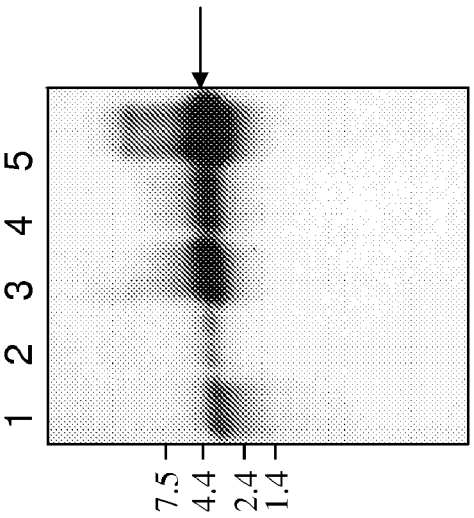
FIG. 6A-C. Expression of 125P5C8 in normal tissues (FIGS. 6A-B) and in prostate cancer xenografts (FIG. 6C). Two multiple tissue northern blots (Clontech) and a LAPC xenograft blot with 2 μg of mRNA/lane were probed with the 125P5C8 SSH fragment. Size standards in kilobases (kb) are indicated on the side. The results show high expression of a 3 kb transcript in normal prostate and prostate cancer xenografts LAPC4AI and LAPC9AI. Lower expression was detected in normal kidney and colon. Lanes represent.

Outline of Sections
I.) Definitions
II.) Properties of 125P5C8.
III.) 125P5C8 Polynucleotides
    III.A.) Uses of 125P5C8 Polynucleotides
        III.A.1.) Monitoring of Genetic Abnormalities
        III.A.2.) Antisense Embodiments
        III.A.3.) Primers and Primer Pairs
        III.A.4.) Isolation of 125P5C8-Encoding Nucleic Acid Molecules
        III.A.5.) Recombinant Nucleic Acid Molecules and Host-Vector Systems
IV.) 125P5C8-related Proteins
    IV.A.) Motif-bearing Protein Embodiments
    IV.B.) Expression of 125P5C8-related Proteins
    IV.C.) Modifications of 125P5C8-related Proteins
    IV.D.) Uses of 125P5C8-related Proteins
V.) 125P5C8 Antibodies
VI.) 125P5C8 Transgenic Animals
VII.) Methods for the Detection of 125P5C8
VIII.) Methods for Monitoring the Status of 125P5C8-related Genes and Their Products
IX.) Identification of Molecules That Interact With 125P5C8
X.) Therapeutic Methods and Compositions
    X.A.) 125P5C8 as a Target for Antibody-Based Therapy
    X.B.) Anti-Cancer Vaccines
XI.) Inhibition of 125P5C8 Protein Function
    XI.A.) Inhibition of 125P5C8 With Intracellular Antibodies
    XII.B.) Inhibition of 125P5C8 with Recombinant Proteins
    XI.C.) Inhibition of 125P5C8 Transcription or Translation
    XI.D.) General Considerations for Therapeutic Strategies
XII.) KITS I.) Definitions:

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

"Altering the native glycosylation pattern" is intended for purposes herein to mean deleting one or more carbohydrate moieties found in native sequence 125P5C8 (either by removing the underlying glycosylation site or by deleting the glycosylation by chemical and/or enzymatic means), and/or adding one or more glycosylation sites that are not present in the native sequence 125P5C8. In addition, the phrase includes qualitative changes in the glycosylation of the native proteins, involving a change in the nature and proportions of the various carbohydrate moieties present.

The term "analog" refers to a molecule which is structurally similar or shares similar or corresponding attributes with another molecule (e.g. a 125P5C8-related protein). For example an analog of the 125P5C8 protein can be specifically bound by an antibody or T cell that specifically binds to 125P5C8.

The term "antibody" is used in the broadest sense. Therefore an "antibody" can be naturally occurring or man-made such as monoclonal antibodies produced by conventional hybridoma technology. Anti-125P5C8 antibodies comprise monoclonal and polyclonal antibodies as well as fragments containing the antigen-binding domain and/or one or more complementarity determining regions of these antibodies.

As used herein, an "antibody fragment" is defined as at least a portion of the variable region of the immunoglobulin molecule that binds to its target, i.e., the antigen-binding region. In one embodiment it specifically covers single anti-125P5C8 antibodies and clones thereof (including agonist, antagonist and neutralizing antibodies) and anti-125P5C8 antibody compositions with polyepitopic specificity.

The term "codon optimized sequences" refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

The term "cytotoxic agent" as used herein refers to a substance that inhibits or prevents the function of cells and/or causes destruction of cells. The term is intended to include radioactive isotopes chemotherapeutic agents, and toxins such as small molecule toxins or enzymatically active toxins of bacterial, fungal, plant or animal origin, including fragments and/or variants thereof. Examples of cytotoxic agents include, but are not limited to maytansinoids, ytrium, bismuth ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha-sarcin, gelonin, mitogellin, retstrictocin, phenomycin, enomycin, curicin, crotin, calicheamicin, sapaonaria officinalis inhibitor, and glucocorticoid and other chemotherapeutic agents, as well as radioisotopes such as $At^{211}$, $I^{131, I125}$, $Y^{90}$, $Re^{186}$, $Re^{188}$, $Sm^{153}$, $Bi^{212}$, $P^{32}$ and radioactive isotopes of Lu. Antibodies may also be conjugated to an anti-cancer pro-drug activating enzyme capable of converting the pro-drug to its active form.

The term "homolog" refers to a molecule which exhibits homology to another molecule, by for example, having sequences of chemical residues that are the same or similar at corresponding positions.

As used herein, the terms "hybridize", "hybridizing", "hybridizes" and the like, used in the context of polynucleotides, are meant to refer to conventional hybridization conditions, preferably such as hybridization in 50% formamide/6×SSC/0.1% SDS/100 μg/ml ssDNA, in which temperatures for hybridization are above 37 degrees C. and temperatures for washing in 0.1×SSC/0.1% SDS are above 55 degrees C.

As used herein, a polynucleotide is said to be "isolated" when it is substantially separated from contaminant polynucleotides that correspond or are complementary to genes other than the 125P5C8 gene or that encode polypeptides other than 125P5C8 gene product or fragments thereof. A skilled artisan can readily employ nucleic acid isolation procedures to obtain an isolated 125P5C8 polynucleotide.

As used herein, a protein is said to be "isolated" when physical, mechanical or chemical methods are employed to remove the 125P5C8 protein from cellular constituents that are normally associated with the protein. A skilled artisan can readily employ standard purification methods to obtain an isolated 125P5C8 protein. Alternatively, an isolated protein can be prepared by chemical means.

The term "mammal" as used herein refers to any organism classified as a mammal, including mice, rats, rabbits, dogs, cats, cows, horses and humans. In one embodiment of the invention, the mammal is a mouse. In another embodiment of the invention, the mammal is a human.

As used herein, the terms "metastatic prostate cancer" and "metastatic disease" mean prostate cancers that have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is a preferred treatment modality. Patients with metastatic prostate cancer eventually develop an androgen-refractory state within 12 to 18 months of treatment initiation. Approximately half of these androgen-refractory patients die within 6 months after developing that status. The most common site for prostate cancer metastasis is bone. Prostate cancer bone metastases are often osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

The term "monoclonal antibody" as used herein refers to an antibody obtained from a population of substantially homogeneous antibodies, i.e., the antibodies comprising the population are identical except for possible naturally occurring mutations that are present in minor amounts.

As used herein "motif" as in biological motif of an 125P5C8-related protein, refers to any pattern of amino acids forming part of the primary sequence of a protein, that is associated with a particular function (e.g. protein-protein interaction, protein-DNA interaction, etc) or modification (e.g. that is phosphorylated, glycosylated or amidated), or localization (e.g. secretory sequence, nuclear localization sequence, etc.) or a sequence that is correlated with being immunogenic, either humorally or cellularly. A motif can be either contiguous or capable of being aligned to certain positions that are generally correlated with a certain function or property.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA and/or RNA. In the art, this term if often used interchangeably with "oligonucleotide". A polynucleotide can comprise a nucleotide sequence disclosed herein wherein thymidine (T) (as shown for example in SEQ ID NO: 1) can also be uracil (U); this definition pertains to the differences between the chemical structures of DNA and RNA, in particular the observation that one of the four major bases in RNA is uracil (U) instead of thymidine (T).

As used herein, the term "polypeptide" means a polymer of at least about 4, 5, 6, 7, or 8 amino acids. Throughout the specification, standard three letter or single letter designations for amino acids are used. In the art, this term is often used interchangeably with "peptide" or "protein".

As used herein, a "recombinant" DNA or RNA molecule is a DNA or RNA molecule that has been subjected to molecular manipulation in vitro.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured nucleic acid sequences to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, are identified by, but not limited to, those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. "Moderately stringent conditions" are described by, but not limited to, those in Sambrook et al., Molecular Cloning: A Laboratory Manual, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

A "transgenic animal" (e.g., a mouse or rat) is an animal having cells that contain a transgene, which transgene was introduced into the animal or an ancestor of the animal at a prenatal, e.g., an embryonic stage. A "transgene" is a DNA that is integrated into the genome of a cell from which a transgenic animal develops.

The term "variant" refers to a molecule that exhibits a variation from a described type or norm, such as a protein that has one or more different amino acid residues in the corresponding position(s) of a specifically described protein (e.g. the 125P5C8 protein shown in FIG. 2). An analog is an example of a variant protein.

As used herein, the 125P5C8-related gene and 125P5C8-related protein includes the 125P5C8 genes and proteins specifically described herein, as well as structurally and/or functionally similar variants or analog of the foregoing. 125P5C8 peptide analogs generally share at least about 50%, 60%, 70%, 80%, 90% or more amino acid homology (using BLAST criteria). 125P5C8 nucleotide analogs preferably share 50%, 60%, 70%, 80%, 90% or more nucleic acid homology (using BLAST criteria). In some embodiments, however, lower homology is preferred so as to select preferred residues in view of species-specific codon preferences and/or optimal peptide epitopes tailored to a particular target population, as is appreciated by those skilled in the art.

The 125P5C8-related proteins of the invention include those specifically identified herein, as well as allelic variants, conservative substitution variants, analogs and homologs that can be isolated/generated and characterized without undue experimentation following the methods outlined herein or readily available in the art. Fusion proteins that combine parts of different 125P5C8 proteins or fragments thereof, as well as fusion proteins of a 125P5C8 protein and a heterologous polypeptide are also included. Such 125P5C8 proteins are collectively referred to as the 125P5C8-related proteins, the proteins of the invention, or 125P5C8. As used herein, the term "125P5C8-related protein" refers to a polypeptide fragment or an 125P5C8 protein sequence of 4, 5, 6, 7, 8, 9, 10, 11, 12, 13, 14, 15, 16, 17, 18, 19, 20, 21, 22, 23, 24, 25, or more than 25 amino acids; or, at least 30, 35, 40, 45, 50, 55, 60, 65, 70, 80, 85, 90, 95, 100 or more than 100 amino acids.

II.) Properties of 125P5C8.

As disclosed herein, 125P5C8 exhibits specific properties that are analogous to those found in a family of molecules whose polynucleotides, polypeptides, reactive cytotoxic T cells (CTL), reactive helper T cells (HTL) and anti-polypeptide antibodies are used in well known diagnostic assays that examine conditions associated with dysregulated cell growth such as cancer, in particular prostate cancer (see, e.g., both its highly specific pattern of tissue expression as well as its overexpression in prostate cancers as described for example in Example 4). The best-known member of this class is PSA, the archetypal marker that has been used by medical practitioners for years to identify and monitor the presence of prostate cancer (see, e.g., Merrill et al., J. Urol. 163(2): 503-5120 (2000); Polascik et al., J. Urol. Aug; 162(2):293-306 (1999) and Fortier et al., J. Nat. Cancer Inst. 91(19): 1635-1640(1999)). A variety of other diagnostic markers are also used in this context including p53 and K-ras (see, e.g., Tulchinsky et al., Int J Mol Med Jul. 4, 1999 (1):99-102 and Minimoto et al., Cancer Detect Prev 2000;24(1):1-12). Therefore, this disclosure of the 125P5C8 polynucleotides and polypeptides (as well as the 125P5C8 polynucleotide probes and anti-125P5C8 antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the 125P5C8 polynucleotides, polypeptides, reactive T cells and antibodies are analogous to those methods from well-established diagnostic assays which employ, e.g., PSA polynucleotides, polypeptides, reactive T cells and antibodies. For example, just as PSA polynucleotides are used as probes (for example in Northern analysis, see, e.g., Sharief et al., Biochem. Mol. Biol. Int. 33(3):567-74(1994)) and primers (for example in PCR analysis, see, e.g., Okegawa et al., J. Urol. 163(4): 1189-1190 (2000)) to observe the presence and/or the level of PSA mRNAs in methods of monitoring PSA overexpression or the metastasis of prostate cancers, the 125P5C8 polynucleotides described herein can be utilized in the same way to detect 125P5C8 overexpression or the metastasis of prostate and other cancers expressing this gene. Alternatively, just as PSA polypeptides are used to generate antibodies specific for PSA which can then be used to observe the presence and/or the level of PSA proteins in methods to monitor PSA protein overexpression (see, e.g., Stephan et al., Urology 55(4):560-3 (2000)) or the metastasis of prostate cells (see, e.g., Alanen et al., Pathol. Res. Pract. 192(3):233-7 (1996)), the 125P5C8 polypeptides described herein can be utilized to generate antibodies for use in detecting 125P5C8 overexpression or the metastasis of prostate cells and cells of other cancers expressing this gene.

Specifically, because metastases involves the movement of cancer cells from an organ of origin (such as the lung or prostate gland etc.) to a different area of the body (such as a lymph node), assays which examine a biological sample for the presence of cells expressing 125P5C8 polynucleotides and/or polypeptides can be used to provide evidence of metastasis. For example, when a biological sample from tissue that does not normally contain 125P5C8-expressing cells (lymph node) is found to contain 125P5C8-expressing cells such as the 125P5C8 expression seen in LAPC4 and LAPC9, xenografts isolated from lymph node and bone metastasis, respectively, this finding is indicative of metastasis.

Alternatively 125P5C8 polynucleotides and/or polypeptides can be used to provide evidence of cancer, for example, when cells in a biological sample that do not normally express 125P5C8 or express 125P5C8 at a different level are found to express 125P5C8 or have an increased expression of 125P5C8 (see, e.g., the 125P5C8 expression in kidney, lung and colon cancer cells and in patient samples etc. shown in FIGS. 5-9). In such assays, artisans may further wish to generate supplementary evidence of metastasis by testing the biological sample for the presence of a second tissue restricted marker (in addition to 125P5C8) such as PSA, PSCA etc. (see, e.g., Alanen et al., Pathol. Res. Pract. 192(3): 233-237 (1996)).

Just as PSA polynucleotide fragments and polynucleotide variants are employed by skilled artisans for use in methods of monitoring PSA, 125P5C8 polynucleotide fragments and polynucleotide variants are used in an analogous manner. In particular, typical PSA polynucleotides used in methods of monitoring PSA are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see, e.g., Caetano-Anolles, G. Biotechniques 25(3): 472-476, 478-480 (1998); Robertson et al., Methods Mol. Biol. 98:121-154 (1998)). An additional illustration of the use of such fragments is provided in Example 4, where a 125P5C8 polynucleotide fragment is used as a probe to show the expression of 125P5C8 RNAs in cancer cells. In addition, variant polynucleotide sequences are typically used as primers and probes for the corresponding mRNAs in PCR and Northern analyses (see, e.g., Sawai et al., Fetal Diagn. Ther. Nov.-Dec. 11, 1996 (6):407-13 and Current Protocols In Molecular Biology, Volume 2, Unit 2, Frederick M. Ausubul et al. eds., 1995)). Polynucleotide fragments and variants are useful in this context where they are capable of binding to a target polynucleotide sequence (e.g. the 125P5C8 polynucleotide shown in SEQ ID NO: 1) under conditions of high stringency.

Furthermore, PSA polypeptides which contain an epitope that can be recognized by an antibody or T cell that specifically binds to that epitope are used in methods of monitoring PSA. 125P5C8 polypeptide fragments and polypeptide analogs or variants can also be used in an analogous manner. This practice of using polypeptide fragments or polypeptide variants to generate antibodies (such as anti-PSA antibodies or T cells) is typical in the art with a wide variety of systems such as fusion proteins being used by practitioners (see, e.g., Current Protocols In Molecular Biology, Volume 2, Unit 16, Frederick M. Ausubul et al. eds., 1995). In this context, each epitope(s) functions to provide the architecture with which an antibody or T cell is reactive. Typically, skilled artisans create a variety of different polypeptide fragments that can be used in order to generate immune responses specific for different portions of a polypeptide of interest (see, e.g., U.S. Pat. No. 5,840,501 and U.S. Pat. No. 5,939,533). For example it may be preferable to utilize a polypeptide comprising one of the 125P5C8 biological motifs discussed herein or available in the art. Polypeptide fragments, variants or analogs are typically useful in this context as long as they comprise an epitope capable of generating an antibody or T cell specific for a target polypeptide sequence (e.g. the 125P5C8 polypeptide shown in SEQ ID NO: 2).

As shown herein, the 125P5C8 polynucleotides and polypeptides (as well as the 125P5C8 polynucleotide probes and anti-125P5C8 antibodies or T cells used to identify the presence of these molecules) exhibit specific properties that make them useful in diagnosing cancers of the prostate. Diagnostic assays that measure the presence of 125P5C8 gene products, in order to evaluate the presence or onset of a disease condition described herein, such as prostate cancer, are used to identify patients for preventive measures or further monitoring, as has been done so successfully with PSA. Moreover, these materials satisfy a need in the art for molecules having similar or complementary characteristics to PSA in situations where, for example, a definite diagnosis of metastasis of prostatic origin cannot be made on the basis of a test for PSA alone (see, e.g., Alanen et al., Pathol. Res. Pract. 192(3): 233-237 (1996)), and consequently, materials such as 125P5C8 polynucleotides and polypeptides (as well as the 125P5C8 polynucleotide probes and anti-125P5C8 antibodies used to identify the presence of these molecules) must be employed to confirm metastases of prostatic origin.

Finally, in addition to their use in diagnostic assays, the 125P5C8 polynucleotides disclosed herein have a number of other specific utilities such as their use in the identification of oncogenetic associated chromosomal abnormalities in the chromosomal region to which the 125P5C8 gene maps (see Example 3 below). Moreover, in addition to their use in diagnostic assays, the 125P5C8-related proteins and polynucleotides disclosed herein have other utilities such as their use in the forensic analysis of tissues of unknown origin (see, e.g., Takahama K Forensic Sci Int Jun. 28, 1996; 80(1-2): 63-9).

Additionally, 125P5C8-related proteins or polynucleotides of the invention can be used to treat a pathologic condition characterized by the over-expression of 125P5C8. For example, the amino acid or nucleic acid sequence of FIG. 2, or fragments thereof, can be used to generate an immune response to the 125P5C8 antigen. Antibodies or other molecules that react with 125P5C8 can be used to modulate the function of this molecule, and thereby provide a therapeutic benefit.

III.) 125P5C8 Polynucleotides

One aspect of the invention provides polynucleotides corresponding or complementary to all or part of an 125P5C8 gene, mRNA, and/or coding sequence, preferably in isolated form, including polynucleotides encoding an 125P5C8-related protein and fragments thereof, DNA, RNA, DNA/RNA hybrid, and related molecules, polynucleotides or oligonucleotides complementary to an 125P5C8 gene or mRNA sequence or a part thereof, and polynucleotides or oligonucleotides that hybridize to an 125P5C8 gene, mRNA, or to an 125P5C8 encoding polynucleotide (collectively, "125P5C8 polynucleotides"). In all instances when referred to in this section, T can also be U in FIG. 2.

Embodiments of a 125P5C8 polynucleotide include: a 125P5C8 polynucleotide having the sequence shown in FIG. 2, the nucleotide sequence of 125P5C8 as shown in FIG. 2, wherein T is U; at least 10 contiguous nucleotides of a polynucleotide having the sequence as shown in FIG. 2; or, at least 10 contiguous nucleotides of a polynucleotide having the sequence as shown in FIG. 2 where T is U. Further 125P5C8 nucleotides comprise, where T can be U:

(a) a polynucleotide having the sequence as shown in FIG. 2 (SEQ ID NO: 1), from nucleotide residue number 1 through nucleotide residue number 2103; or, (b) a polynucleotide having the sequence as shown in FIG. 2 (SEQ ID NO: 1), from nucleotide residue number 1 through nucleotide residue number 2100; or, (c) a polynucleotide having the sequence as shown in FIG. 2 (SEQ ID NO: 1), from nucleotide residue number 1 through nucleotide residue number 2097; or (d) a polynucleotide of at least 10 bases of FIG. 2 (SEQ ID NO: 1) that comprises the base at position 339;

(e) a polynucleotide of at least 10 bases of FIG. 2 (SEQ ID NO: 1) that comprises the base at position 1119;

(f) a polynucleotide of at least 10 bases of FIG. 2 (SEQ ID NO: 1) that comprises the base at position 2065;

(g) a polynucleotide that selectively hybridizes under stringent conditions to a polynucleotide of (a)-(f).

As used herein, a range is understood to specifically disclose all whole unit positions thereof. Moreover, a peptide that is encoded by any of the foregoing is also within the scope of the invention. An alternative embodiment comprises a polynucleotide of the invention with a proviso that the nucleic acid does not include one or more of the specified positions or ranges.

Also within the scope of the invention is a nucleotide, as well as any peptide encoded thereby, that starts at any of the following positions and ends at a higher position or range: 1, 1-338, 339, 340-1118, 1119, 1120-2064, 2065, 2066-2097, 2100, and 2103; wherein a range as used in this section is understood to specifically disclose all whole unit positions thereof.

Another embodiment of the invention comprises a polynucleotide that encodes a 125P5C8-related protein whose sequence is encoded by the cDNA contained in the plasmid deposited with American Type Culture Collection (ATCC) as Accession No. PTA-3137 on Mar. 1, 2001. Another embodiment comprises a polynucleotide that hybridizes under stringent hybridization conditions, to the human 125P5C8 cDNA shown in FIG. 2 or to a polynucleotide fragment thereof.

Typical embodiments of the invention disclosed herein include 125P5C8 polynucleotides that encode specific portions of the 125P5C8 mRNA sequence (and those which are complementary to such sequences) such as those that encode the protein and fragments thereof, for example of 4, 5, 6, 7, 8, 9, 10, 11, 12, 13, 14, 15 or more contiguous amino acids.

For example, representative embodiments of the invention disclosed herein include: polynucleotides and their encoded peptides themselves encoding about amino acid 1 to about amino acid 10 of the 125P5C8 protein shown in FIG. 2 or FIG. 3, polynucleotides encoding about amino acid 10 to about amino acid 20 of the 125P5C8 protein shown in FIG. 2 or FIG. 3, polynucleotides encoding about amino acid 20 to about amino acid 30 of the 125P5C8 protein shown in FIG. 2 or FIG. 3, polynucleotides encoding about amino acid 30 to about amino acid 40 of the 125P5C8 protein shown in FIG. 2 or FIG. 3, polynucleotides encoding about amino acid 40 to about amino acid 50 of the 125P5C8 protein shown in FIG. 2 or FIG. 3, polynucleotides encoding about amino acid 50 to about amino acid 60 of the 125P5C8 protein shown in FIG. 2 or FIG. 3, polynucleotides encoding about amino acid 60 to about amino acid 70 of the 125P5C8 protein shown in FIG. 2 or FIG. 3, polynucleotides encoding about amino acid 70 to about amino acid 80 of the 125P5C8 protein shown in FIG. 2 or FIG. 3, polynucleotides encoding about amino acid 80 to about amino acid 90 of the 125P5C8 protein shown in FIG. 2 or FIG. 3, polynucleotides encoding about amino acid 90 to about amino acid 100 of the 125P5C8 protein shown in FIG. 2 or FIG. 3, in increments of about 10 amino acids, ending at the carboxyl terminal amino acid set forth in FIG. 2 or FIG. 3. Accordingly polynucleotides encoding portions of the amino acid sequence (of about 10 amino acids), of amino acids 100 through the carboxyl terminal amino acid of the 125P5C8 protein are embodiments of the invention. Wherein it is understood that each particular amino acid position discloses that position plus or minus five amino acid residues.

Polynucleotides encoding relatively long portions of the 125P5C8 protein are also within the scope of the invention. For example, polynucleotides encoding from about amino acid 1 (or 20 or 30 or 40 etc.) to about amino acid 20, (or 30, or 40 or 50 etc.) of the 125P5C8 protein shown in FIG. 2 can be generated by a variety of techniques well known in the art. These polynucleotide fragments can include any portion of the 125P5C8 sequence as shown in FIG. 2.

Additional illustrative embodiments of the invention disclosed herein include 125P5C8 polynucleotide fragments encoding one or more of the biological motifs contained within the 125P5C8 protein sequence, including one or more of the motif-bearing subsequences of the 125P5C8 protein set forth in Tables V-XIX. In another embodiment, typical polynucleotide fragments of the invention encode one or more of the regions of 125P5C8 that exhibit homology to a known molecule. In another embodiment of the invention, typical polynucleotide fragments can encode one or more of the 125P5C8 N-glycosylation sites, cAMP and cGMP-dependent protein kinase phosphorylation sites, casein kinase II phosphorylation sites or N-myristoylation site and amidation sites.

III.A.) Uses of 125P5C8 Polynucleotides

III.A.1.) Monitoring of Genetic Abnormalities

The polynucleotides of the preceding paragraphs have a number of different specific uses. The human 125P5C8 gene maps to the chromosomal location set forth in Example 3). For example, because the 125P5C8 gene maps to this chromosome, polynucleotides that encode different regions of the 125P5C8 protein are used to characterize cytogenetic abnormalities of this chromosomal locale, such as abnormalities that are identified as being associated with various cancers. In certain genes, a variety of chromosomal abnormalities including rearrangements have been identified as frequent cytogenetic abnormalities in a number of different cancers (see e.g. Krajinovic et al., Mutat. Res. 382(3-4): 81-83 (1998); Johansson et al., Blood 86(10): 3905-3914 (1995) and Finger et al., P.N.A.S. 85(23): 9158-9162 (1988)). Thus, polynucleotides encoding specific regions of the 125P5C8 protein provide new tools that can be used to delineate, with greater precision than previously possible, cytogenetic abnormalities in the chromosomal region that encodes 125P5C8 that may contribute to the malignant phenotype. In this context, these polynucleotides satisfy a need in the art for expanding the sensitivity of chromosomal screening in order to identify more subtle and less common chromosomal abnormalities (see e.g. Evans et al., Am. J. Obstet. Gynecol 171(4): 1055-1057 (1994)).

Furthermore, as 125P5C8 was shown to be highly expressed in prostate and other cancers, 125P5C8 polynucleotides are used in methods assessing the status of 125P5C8 gene products in normal versus cancerous tissues. Typically, polynucleotides that encode specific regions of the 125P5C8 protein are used to assess the presence of perturbations (such as deletions, insertions, point mutations, or alterations resulting in a loss of an antigen etc.) in specific regions of the 125P5C8 gene, such as such regions containing one or more motifs. Exemplary assays include both RT-PCR assays as well as single-strand conformation polymorphism (SSCP) analysis (see, e.g., Marrogi et al., J. Cutan. Pathol. 26(8): 369-378 (1999), both of which utilize polynucleotides encoding specific regions of a protein to examine these regions within the protein.

III.A.2.) Antisense Embodiments

Other specifically contemplated nucleic acid related embodiments of the invention disclosed herein are genomic DNA, cDNAs, ribozymes, and antisense molecules, as well as nucleic acid molecules based on an alternative backbone, or including alternative bases, whether derived from natural sources or synthesized, and include molecules capable of inhibiting the RNA or protein expression of 125P5C8. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the 125P5C8 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 125P5C8. See for example, Jack Cohen, Oligodeoxynucleotides, Antisense Inhibitors of Gene Expression, CRC Press, 1989; and Synthesis 1:1-5 (1988). The 125P5C8 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention can be prepared by treatment of the corresponding O-oligos with 3H-1,2-benzodithiol-3-one-1,1-dioxide, which is a sulfur transfer reagent. See Iyer, R. P. et al, J. Org. Chem. 55:4693-4698 (1990); and Iyer, R. P. et al., J. Am. Chem. Soc. 112: 1253-1254 (1990). Additional 125P5C8 antisense oligonucleotides of the present invention include morpholino antisense oligonucleotides known in the art (see, e.g., Partridge et al., 1996, Antisense & Nucleic Acid Drug Development 6: 169-175).

The 125P5C8 antisense oligonucleotides of the present invention typically can be RNA or DNA that is complementary to and stably hybridizes with the first 100 5' codons or last 100 3' codons of the 125P5C8 genomic sequence or the corresponding mRNA. Absolute complementarity is not required, although high degrees of complementarity are preferred. Use of an oligonucleotide complementary to this region allows for the selective hybridization to 125P5C8 mRNA and not to mRNA specifying other regulatory subunits of protein kinase. In one embodiment, 125P5C8 antisense oligonucleotides of the present invention are 15 to 30-mer fragments of the antisense DNA molecule that have a sequence that hybridizes to 125P5C8 mRNA. Optionally, 125P5C8 antisense oligonucleotide is a 30-mer oligonucleotide that is complementary to a region in the first 10 5' codons or last 10 3' codons of 125P5C8. Alternatively, the antisense molecules are modified to employ ribozymes in the inhibition of 125P5C8 expression, see, e.g., L. A. Couture & D. T. Stinchcomb; *Trends Genet* 12: 510-515 (1996).

III.A.3.) Primers and Primer Pairs

Further specific embodiments of this nucleotides of the invention include primers and primer pairs, which allow the specific amplification of polynucleotides of the invention or of any specific parts thereof, and probes that selectively or specifically hybridize to nucleic acid molecules of the invention or to any part thereof. Probes can be labeled with a detectable marker, such as, for example, a radioisotope, fluorescent compound, bioluminescent compound, a chemiluminescent compound, metal chelator or enzyme. Such probes and primers are used to detect the presence of a 125P5C8 polynucleotide in a sample and as a means for detecting a cell expressing a 125P5C8 protein.

Examples of such probes include polypeptides comprising all or part of the human 125P5C8 cDNA sequences shown in FIG. 2. Examples of primer pairs capable of specifically amplifying 125P5C8 mRNAs are also described in the Examples. As will be understood by the skilled artisan, a great many different primers and probes can be prepared based on the sequences provided herein and used effectively to amplify and/or detect a 125P5C8 mRNA.

The 125P5C8 polynucleotides of the invention are useful for a variety of purposes, including but not limited to their use as probes and primers for the amplification and/or detection of the 125P5C8 gene(s), mRNA(s), or fragments thereof; as reagents for the diagnosis and/or prognosis of prostate cancer and other cancers; as coding sequences capable of directing the expression of 125P5C8 polypeptides; as tools for modulating or inhibiting the expression of the 125P5C8 gene(s) and/or translation of the 125P5C8 transcript(s); and as therapeutic agents.

III.A.4.) Isolation of 125P5C8-Encoding Nucleic Acid Molecules

The 125P5C8 cDNA sequences described herein enable the isolation of other polynucleotides encoding 125P5C8 gene product(s), as well as the isolation of polynucleotides encoding 125P5C8 gene product homologs, alternatively spliced isoforms, allelic variants, and mutant forms of the 125P5C8 gene product as well as polynucleotides that encode analogs of 125P5C8-related proteins. Various molecular cloning methods that can be employed to isolate full length cDNAs encoding an 125P5C8 gene are well known (see, for example, Sambrook, J. et al., Molecular Cloning: A Laboratory Manual, 2d edition, Cold Spring Harbor Press, New York, 1989; Current Protocols in Molecular Biology. Ausubel et al., Eds., Wiley and Sons, 1995). For example, lambda phage cloning methodologies can be conveniently employed, using commercially available cloning systems (e.g., Lambda ZAP Express, Stratagene). Phage clones containing 125P5C8 gene cDNAs can be identified by probing with a labeled 125P5C8 cDNA or a fragment thereof. For example, in one embodiment, the 125P5C8 cDNA (FIG. 2) or a portion thereof can be synthesized and used as a probe to retrieve overlapping and full-length cDNAs corresponding to a 125P5C8 gene. The 125P5C8 gene itself can be isolated by screening genomic DNA libraries, bacterial artificial chromosome libraries (BACs), yeast artificial chromosome libraries (YACs), and the like, with 125P5C8 DNA probes or primers.

III.A.5.) Recombinant Nucleic Acid Molecules and Host-Vector Systems

The invention also provides recombinant DNA or RNA molecules containing an 125P5C8 polynucleotide, fragment, analog or homologue thereof, including but not limited to phages, plasmids, phagemids, cosmids, YACs, BACs, as well as various viral and non-viral vectors well known in the art, and cells transformed or transfected with such recombinant DNA or RNA molecules. Methods for generating such molecules are well known (see, for example, Sambrook et al, 1989, supra).

The invention further provides a host-vector system comprising a recombinant DNA molecule containing a 125P5C8 polynucleotide, fragment, analog or homologue thereof within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as DU145 and TsuPr1, other transfectable or transducible prostate cancer cell lines, primary cells (PrEC), as well as a number of mammalian cells routinely used for the expression of recombinant proteins (e.g., COS, CHO, 293, 293T cells). More particularly, a polynucleotide comprising the coding sequence of 125P5C8 or a fragment, analog or homolog thereof can be used to generate 125P5C8 proteins or fragments thereof using any number of host-vector systems routinely used and widely known in the art.

A wide range of host-vector systems suitable for the expression of 125P5C8 proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRatkneo (Muller et al., 1991, MCB 11:1785). Using these expression vectors, 125P5C8 can be expressed in several prostate cancer and non-prostate cell lines, including for example 293, 293T, rat-1, NIH 3T3 and TsuPr1. The host-vector systems of the invention are useful for the production of a 125P5C8 protein or fragment thereof. Such host-vector systems can be employed to study the functional properties of 125P5C8 and 125P5C8 mutations or analogs.

Recombinant human 125P5C8 protein or an analog or homolog or fragment thereof can be produced by mammalian cells transfected with a construct encoding a 125P5C8-related nucleotide. For example, 293T cells can be transfected with an expression plasmid encoding 125P5C8 or fragment, analog or homolog thereof, the 125P5C8 or related protein is expressed in the 293T cells, and the recombinant 125P5C8 protein is isolated using standard purification methods (e.g., affinity purification using anti-125P5C8 antibodies). In another embodiment, a 125P5C8 coding sequence is subcloned into the retroviral vector pSRαMSVtkneo and used to infect various mammalian cell lines, such as NIH 3T3, TsuPr1, 293 and rat-1 in order to establish 125P5C8 expressing cell lines. Various other expression systems well known in the art can also be employed. Expression constructs encoding a leader peptide joined in frame to the 125P5C8 coding sequence can be used for the generation of a secreted form of recombinant 125P5C8 protein.

As discussed herein, redundancy in the genetic code permits variation in 125P5C8 gene sequences. In particular, it is known in the art that specific host species often have specific codon preferences, and thus one can adapt the disclosed sequence as preferred for a desired host. For example, preferred analog codon sequences typically have rare codons (i.e., codons having a usage frequency of less than about 20% in known sequences of the desired host) replaced with higher frequency codons. Codon preferences for a specific species are calculated, for example, by utilizing codon usage tables available on the INTERNET such as: http://www.dna.affrc.go.jp/~nakamura/codon.html.

Additional sequence modifications are known to enhance protein expression in a cellular host. These include elimination of sequences encoding spurious polyadenylation signals, exon/intron splice site signals, transposon-like repeats, and/or other such well-characterized sequences that are deleterious to gene expression. The GC content of the sequence is adjusted to levels average for a given cellular host, as calculated by reference to known genes expressed in the host cell. Where possible, the sequence is modified to avoid predicted hairpin secondary mRNA structures. Other useful modifications include the addition of a translational initiation consensus sequence at the start of the open reading frame, as described in Kozak, *Mol. Cell Biol.*, 9:5073-5080 (1989). Skilled artisans understand that the general rule that eukaryotic ribosomes initiate translation exclusively at the 5' proximal AUG codon is abrogated only under rare conditions (see, e.g., Kozak PNAS 92(7): 2662-2666, (1995) and Kozak NAR 15(20): 8125-8148 (1987)).

IV.) 125P5C8-Related Proteins

Another aspect of the present invention provides 125P5C8-related proteins. Specific embodiments of 125P5C8 proteins comprise a polypeptide having all or part of the amino acid sequence of human 125P5C8 as shown in FIG. 2. Alternatively, embodiments of 125P5C8 proteins comprise variant, homolog or analog polypeptides that have alterations in the amino acid sequence of 125P5C8 shown in FIG. 2.

In general, naturally occurring allelic variants of human 125P5C8 share a high degree of structural identity and homology (e.g., 90% or more homology). Typically, allelic variants of the 125P5C8 protein contain conservative amino acid substitutions within the 125P5C8 sequences described herein or contain a substitution of an amino acid from a corresponding position in a homologue of 125P5C8. One class of 125P5C8 allelic variants are proteins that share a high degree of homology with at least a small region of a particular 125P5C8 amino acid sequence, but further contain a radical departure from the sequence, such as a non-conservative substitution, truncation, insertion or frame shift. In comparisons of protein sequences, the terms, similarity, identity, and homology each have a distinct meaning as appreciated in the field of genetics. Moreover, orthology and paralogy can be important concepts describing the relationship of members of a given protein family in one organism to the members of the same family in other organisms.

Amino acid abbreviations are provided in Table II. Conservative amino acid substitutions can frequently be made in a protein without altering either the conformation or the function of the protein. Proteins of the invention can comprise 1, 2, 3, 4, 5, 6, 7, 8, 9, 10, 11, 12, 13, 14, 15 conservative substitutions. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III herein; pages 13-15 "Biochemistry" $2^{nd}$ ED. Lubert Stryer ed (Stanford University); Henikoff et al., PNAS 1992 Vol 89 10915-10919; Lei et al., J Biol Chem May 19, 1995; 270(20):11882-6).

Embodiments of the invention disclosed herein include a wide variety of art-accepted variants or analogs of 125P5C8 proteins such as polypeptides having amino acid insertions, deletions and substitutions. 125P5C8 variants can be made using methods known in the art such as site-directed mutagenesis, alanine scanning, and PCR mutagenesis. Site-directed mutagenesis (Carter et al., *Nucl. Acids Res.*, 13:4331 (1986); Zoller et al., *Nucl. Acids Res.*, 10:6487 (1987)), cassette mutagenesis (Wells et al., Gene, 34:315 (1985)), restriction selection mutagenesis (Wells et al., *Philos. Trans. R. Soc. London SerA*, 317:415 (1986)) or other known techniques can be performed on the cloned DNA to produce the 125P5C8 variant DNA.

Scanning amino acid analysis can also be employed to identify one or more amino acids along a contiguous sequence that is involved in a specific biological activity such as a protein-protein interaction. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, *The Proteins*, (W.H. Freeman & Co., N.Y.); Chothia, J. Mol. Biol., 150:1 (1976)). If alanine substitution does not yield adequate amounts of variant, an isosteric amino acid can be used.

As defined herein, 125P5C8 variants, analogs or homologs, have the distinguishing attribute of having at least one epitope that is "cross reactive" with a 125P5C8 protein having the amino acid sequence of SEQ ID NO: 2. As used in this sentence, "cross reactive" means that an antibody or T cell that specifically binds to an 125P5C8 variant also specifically binds to the 125P5C8 protein having the amino acid sequence of SEQ ID NO: 2. A polypeptide ceases to be a variant of the protein shown in SEQ ID NO: 2 when it no longer contains any epitope capable of being recognized by an antibody or T cell that specifically binds to the 125P5C8 protein. Those skilled in the art understand that antibodies that recognize proteins bind to epitopes of varying size, and a grouping of the order of about four or five amino acids, contiguous or not, is regarded as a typical number of amino acids in a minimal epitope. See, e.g., Nair et al., J. Immunol 2000 165(12): 6949-6955; Hebbes et al., Mol Immunol (1989) 26(9):865-73; Schwartz et al., J Immunol (1985) 135 (4):2598-608.

Another class of 125P5C8-related protein variants share 70%, 75%, 80%, 85% or 90% or more similarity with the amino acid sequence of SEQ ID NO: 2 or a fragment thereof. Another specific class of 125P5C8 protein variants or analogs comprise one or more of the 125P5C8 biological motifs described herein or presently known in the art. Thus, encompassed by the present invention are analogs of 125P5C8 fragments (nucleic or amino acid) that have altered functional (e.g. immunogenic) properties relative to the starting fragment. It is to be appreciated that motifs now or which become part of the art are to be applied to the nucleic or amino acid sequences of FIG. 2.

As discussed herein, embodiments of the claimed invention include polypeptides containing less than the 532 amino acid sequence of the 125P5C8 protein shown in FIG. 2. For example, representative embodiments of the invention comprise peptides/proteins having any 4, 5, 6, 7, 8, 9, 10, 11, 12, 13, 14, 15 or more contiguous amino acids of the 125P5C8 protein shown in FIG. 2 (SEQ ID NO: 2).

Moreover, representative embodiments of the invention disclosed herein include polypeptides consisting of about amino acid 1 to about amino acid 10 of the 125P5C8 protein shown in FIG. 2 or FIG. 3, polypeptides consisting of about amino acid 10 to about amino acid 20 of the 125P5C8 protein shown in FIG. 2 or FIG. 3, polypeptides consisting of about amino acid 20 to about amino acid 30 of the 125P5C8 protein shown in FIG. 2 or FIG. 3, polypeptides consisting of about amino acid 30 to about amino acid 40 of the 125P5C8 protein shown in FIG. 2 or FIG. 3, polypeptides consisting of about amino acid 40 to about amino acid 50 of the 125P5C8 protein shown in FIG. 2 or FIG. 3, polypeptides consisting of about amino acid 50 to about amino acid 60 of the 125P5C8 protein shown in FIG. 2 or FIG. 3, polypeptides consisting of about amino acid 60 to about amino acid 70 of the 125P5C8 protein shown in FIG. 2 or FIG. 3, polypeptides consisting of about amino acid 70 to about amino acid 80 of the 125P5C8 protein shown in FIG. 2 or FIG. 3, polypeptides consisting of about amino acid 80 to about amino acid 90 of the 125P5C8 protein shown in FIG. 2 or FIG. 3, polypeptides consisting of about amino acid 90 to about amino acid 100 of the 125P5C8 protein shown in FIG. 2 or FIG. 3, etc. throughout the entirety of the 125P5C8 amino acid sequence. Moreover, polypeptides consisting of about amino acid 1 (or 20 or 30 or 40 etc.) to about amino acid 20, (or 130, or 140 or 150 etc.) of the 125P5C8 protein shown in FIG. 2 are embodiments of the invention. It is to be appreciated that the starting and stopping positions in this paragraph refer to the specified position as well as that position plus or minus 5 residues.

125P5C8-related proteins are generated using standard peptide synthesis technology or using chemical cleavage methods well known in the art. Alternatively, recombinant methods can be used to generate nucleic acid molecules that encode a 125P5C8-related protein. In one embodiment, nucleic acid molecules provide a means to generate defined fragments of the 125P5C8 protein (or variants, homologs or analogs thereof).

IV.A.) Motif-Bearing Protein Embodiments

Additional illustrative embodiments of the invention disclosed herein include 125P5C8 polypeptides comprising the amino acid residues of one or more of the biological motifs contained within the 125P5C8 polypeptide sequence set forth in FIG. 2 or FIG. 3. Various motifs are known in the art, and a protein can be evaluated for the presence of such motifs by a number of publicly available sites (see, e.g.: http://pfam.wustl.edu/; http://searchlauncher.bcm.tmc.edu/seq-search/struc-predict.html http://psort.ims.u-tokyo.ac.jp/; http://www.cbs.dtu.dk/; http//www.ebi.ac.uk/interpro/scan.html; http://www.expasy.ch/tools/scnpsit1.html; Epimatrix™ and Epimer™, Brown University, http://www.brown.edu/Research/TB-HIV_Lab/epimatrix/epimatrix.html; and BIMAS, http://bimas.dcrt.nih.gov/.). Motif bearing subsequences of the 125P5C8 protein are set forth and identified in Table XIX.

Table XX sets forth several frequently occurring motifs based on pfam searches (http://pfam.wustl.edu/). The columns of Table XX list (1) motif name abbreviation, (2) percent identity found amongst the different member of the motif family, (3) motif name or description and (4) most common function; location information is included if the motif is relevant for location.

Polypeptides comprising one or more of the 125P5C8 motifs discussed above are useful in elucidating the specific characteristics of a malignant phenotype in view of the observation that the 125P5C8 motifs discussed above are associated with growth dysregulation and because 125P5C8 is overexpressed in certain cancers (See, e.g., Table I). Casein kinase II, cAMP and camp-dependent protein kinase, and Protein Kinase C, for example, are enzymes known to be associated with the development of the malignant phenotype (see e.g. Chen et al., Lab Invest., 78(2): 165-174 (1998); Gaiddon et al., Endocrinology 136(10): 4331-4338 (1995); hall et al., Nucleic Acids Research 24(6): 1119-1126 (1996); Peterziel et al., Oncogene 18(46): 6322-6329 (1999) and O'Brian, Oncol. Rep. 5(2): 305-309 (1998)). Moreover, both glycosylation and myristoylation are protein modifications also associated with cancer and cancer progression (see e.g. Dennis et al., Biochem. Biophys. Acta 1473(1):21-34 (1999); Raju et al., Exp. Cell Res. 235(1): 145-154 (1997)). Amidation is another protein modification also associated with cancer and cancer progression (see e.g. Treston et al., J. Natl. Cancer Inst. Monogr. (13): 169-175 (1992)).

In another embodiment, proteins of the invention comprise one or more of the immunoreactive epitopes identified in accordance with art-accepted methods, such as the peptides set forth in Tables V-XVIII. CTL epitopes can be determined using specific algorithms to identify peptides within an 125P5C8 protein that are capable of optimally binding to specified HLA alleles (e.g., Table IV (A) and Table IV (B); Epimatrix™ and Epimer™, Brown University, http://www.brow.edu/Research/TB-HIV_Lab/epimatirx/epimatrix.html; and BIMAS, http://bimas.dcrt.nih.gov/. Moreover, processes for identifying peptides that have sufficient binding affinity for HLA molecules and which are correlated with being immunogenic epitopes, are well known in the art, and are carried out without undue experimentation. In addition, processes for identifying peptides that are immunogenic epitopes, are well known in the art, and are carried out without undue experimentation either in vitro or in vivo.

Also known in the art are principles for creating analogs of such epitopes in order to modulate immunogenicity. For example, one begins with an epitope that bears a CTL or HTL motif (see, e.g., the HLA Class I motifs or Table IV (A) and the HTL motif of Table IV (B)). The epitope is analoged by substituting out an amino acid at one of the specified positions, and replacing it with another amino acid specified for that position.

A variety of references reflect the art regarding the identification and generation of epitopes in a protein of interest as well as analogs thereof. See, for example, WO 9733602 to Chesnut et al.; Sette, Immunogenetics 1999 50(3-4): 201-212; Sette et al., J. Immunol. 2001 166(2): 1389-1397; Sidney et al., Hum. Immunol. 1997 58(1): 12-20; Kondo et al., Immunogenetics 1997 45(4): 249-258; Sidney et al., J. Immunol. 1996 157(8): 3480-90; and Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)); Kast et al., 1994 152(8): 3904-12; Borras-Cuesta et al., Hum. Immunol. 2000 61(3): 266-278; Alexander et al., J. Immunol. 2000 164(3); 164(3): 1625-1633; Alexander et al., PMID: 7895164, UI: 95202582; O'Sullivan et al., J. Immunol. 1991 147(8):2663-2669; Alexander et al., Immunity 1994 1(9): 751-761 and Alexander et al., Immunol. Res. 1998 18(2): 79-92.

Related embodiments of the inventions include polypeptides comprising combinations of the different motifs set forth in Table XIX, and/or, one or more of the predicted CTL epitopes of Table V through Table XVIII, and/or, one or more of the T cell binding motifs known in the art. Preferred embodiments contain no insertions, deletions or substitutions either within the motifs or the intervening sequences of the polypeptides. In addition, embodiments which include a number of either N-terminal and/or C-terminal amino acid residues on either side of these motifs may be desirable (to, for example, include a greater portion of the polypeptide architecture in which the motif is located). Typically the number of N-terminal and/or C-terminal amino acid residues on either side of a motif is between about 1 to about 100 amino acid residues, preferably 5 to about 50 amino acid residues.

125P5C8-related proteins are embodied in many forms, preferably in isolated form. A purified 125P5C8 protein molecule will be substantially free of other proteins or molecules that impair the binding of 125P5C8 to antibody, T cell or other ligand. The nature and degree of isolation and purification will depend on the intended use. Embodiments of a 125P5C8-related proteins include purified 125P5C8-related proteins and functional, soluble 125P5C8-related proteins. In one embodiment, a functional, soluble 125P5C8 protein or fragment thereof retains the ability to be bound by antibody, T cell or other ligand.

The invention also provides 125P5C8 proteins comprising biologically active fragments of the 125P5C8 amino acid sequence shown in FIG. 2. Such proteins exhibit properties of the 125P5C8 protein, such as the ability to elicit the generation of antibodies that specifically bind an epitope associated with the 125P5C8 protein; to be bound by such antibodies; to elicit the activation of HTL or CTL; and/or, to be recognized by HTL or CTL.

125P5C8-related polypeptides that contain particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments that contain such structures are particularly useful in generating subunit-specific anti-125P5C8 antibodies, or T cells or in identifying cellular factors that bind to 125P5C8.

CTL epitopes can be determined using specific algorithms to identify peptides within an 125P5C8 protein that are capable of optimally binding to specified HLA alleles (e.g., Table IV (A) and Table IV (B); Epimatrix™ and Epimer™, Brown University (http://www.brown.edu/Research/TB-HIV_Lab/epimatrix/epimatrix.html); and BIMAS, http:/bimas.dcrt.nih.gov/). Illustrating this, peptide epitopes from 125P5C8 that are presented in the context of human MHC class I molecules HLA-A1, A2, A3, A11, A24, B7 and B35 were predicted (Tables V-XVIII). Specifically, the complete amino acid sequence of the 125P5C8 protein was entered into the HLA Peptide Motif Search algorithm found in the Bioinformatics and Molecular Analysis Section (BIMAS) web site listed above. The HLA peptide motif search algorithm was developed by Dr. Ken Parker based on binding of specific peptide sequences in the groove of HLA Class I molecules and specifically HLA-A2 (see, e.g., Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)). This algorithm allows location and ranking of 8-mer, 9-mer, and 10-mer peptides from a complete protein sequence for predicted binding to HLA-A2 as well as numerous other HLA Class I molecules. Many HLA class I binding peptides are 8-, 9-, 10 or 11-mers. For example, for class I HLA-A2, the epitopes preferably contain a leucine (L) or methionine (M) at position 2 and a valine (V) or leucine (L) at the C-terminus (see, e.g., Parker et al., J. Immunol. 149:3580-7 (1992)). Selected results of 125P5C8 predicted binding peptides are shown in Tables V-XVIII herein. In Tables V-XVIII, the top 50 ranking candidates, 9-mers and 10-mers, for each family member are shown along with their location, the amino acid sequence of each specific peptide, and an estimated binding score. The binding score corresponds to the estimated half-time of dissociation of complexes containing the peptide at 37° C. at pH 6.5. Peptides with the highest binding score are predicted to be the most tightly bound to HLA Class I on the cell surface for the greatest period of time and thus represent the best immunogenic targets for T-cell recognition.

Actual binding of peptides to an HLA allele can be evaluated by stabilization of HLA expression on the antigen-processing defective cell line T2 (see, e.g., Xue et al., Prostate 30:73-8 (1997) and Peshwa et al., Prostate 36:129-38 (1998)). Immunogenicity of specific peptides can be evaluated in vitro by stimulation of CD8+ cytotoxic T lymphocytes (CTL) in the presence of antigen presenting cells such as dendritic cells.

It is to be appreciated that every epitope predicted by the BIMAS site, Epimer™ and Epimatrix™ sites, or specified by the HLA class I or class I motifs available in the art or which become part of the art such as set forth in Table IV (A) and Table IV (B) are to be "applied" to the 125P5C8 protein. As used in this context "applied" means that the 125P5C8 protein is evaluated, e.g., visually or by computer-based patterns finding methods, as appreciated by those of skill in the relevant art. Every subsequence of the 125P5C8 of 8, 9, 10, or 11 amino acid residues that bears an HLA Class I motif, or a subsequence of 9 or more amino acid residues that bear an HLA Class II motif are within the scope of the invention.

IV.B.) Expression of 125P5C8-Related Proteins

In an embodiment described in the examples that follow, 125P5C8 can be conveniently expressed in cells (such as 293T cells) transfected with a commercially available expression vector such as a CMV-driven expression vector encoding 125P5C8 with a C-terminal 6XHis and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted 125P5C8 protein in transfected cells. The secreted HIS-tagged 125P5C8 in the culture media can be purified, e.g., using a nickel column using standard techniques.

IV.C.) Modifications of 125P5C8-Related Proteins

Modifications of 125P5C8-related proteins such as covalent modifications are included within the scope of this invention. One type of covalent modification includes reacting targeted amino acid residues of a 125P5C8 polypeptide with an organic derivatizing agent that is capable of reacting with selected side chains or the N- or C-terminal residues of the 125P5C8. Another type of covalent modification of the 125P5C8 polypeptide included within the scope of this invention comprises altering the native glycosylation pattern of a protein of the invention. Another type of covalent modification of 125P5C8 comprises linking the 125P5C8 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The 125P5C8-related proteins of the present invention can also be modified to form a chimeric molecule comprising 125P5C8 fused to another, heterologous polypeptide or amino acid sequence. Such a chimeric molecule can be synthesized chemically or recombinantly. A chimeric molecule can have a protein of the invention fused to another tumor-associated antigen or fragment thereof. Alternatively, a protein in accordance with the invention can comprise a fusion of fragments of the 125P5C8 sequence (amino or nucleic acid) such that a molecule is created that is not, through its length, directly homologous to the amino or nucleic acid sequences respectively of FIG. 2. Such a chimeric molecule can comprise multiples of the same subsequence of 125P5C8. A chimeric molecule can comprise a fusion of a 125P5C8-related protein with a polyhistidine epitope tag, which provides an epitope to which immobilized nickel can selectively bind, with cytokines or with growth factors. The epitope tag is generally placed at the amino- or carboxyl-terminus of the 125P5C8. In an alternative embodiment, the chimeric molecule can comprise a fusion of a 125P5C8-related protein with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a 125P5C8 polypeptide in place of at least one variable region within an Ig molecule. In a preferred embodiment, the immunoglobulin fusion includes the hinge, CH2 and CH3, or the hinge, CHI, CH2 and CH3 regions of an IgGI molecule. For the production of immunoglobulin fusions see, e.g., U.S. Pat. No. 5,428, 130 issued Jun. 27, 1995.

IV.D.) Uses of 125P5C8-Related Proteins

The proteins of the invention have a number of different specific uses. As 125P5C8 is highly expressed in prostate and other cancers, 125P5C8-related proteins are used in methods that assess the status of 125P5C8 gene products in normal versus cancerous tissues, thereby elucidating the malignant phenotype. Typically, polypeptides from specific regions of the 125P5C8 protein are used to assess the presence of perturbations (such as deletions, insertions, point mutations etc.) in those regions (such as regions containing one or more motifs). Exemplary assays utilize antibodies or T cells targeting 125P5C8-related proteins comprising the amino acid residues of one or more of the biological motifs contained within the 125P5C8 polypeptide sequence in order to evaluate the characteristics of this region in normal versus cancerous tissues or to elicit an immune response to the epitope. Alternatively, 125P5C8-related proteins that contain the amino acid residues of one or more of the biological motifs in the 125P5C8 protein are used to screen for factors that interact with that region of 125P5C8.

125P5C8 protein fragments/subsequences are particularly useful in generating and characterizing domain-specific antibodies (e.g., antibodies recognizing an extracellular or intracellular epitope of an 125P5C8 protein), for identifying agents or cellular factors that bind to 125P5C8 or a particular structural domain thereof, and in various therapeutic and diagnostic contexts, including but not limited to diagnostic assays, cancer vaccines and methods of preparing such vaccines.

Proteins encoded by the 125P5C8 genes, or by analogs, homologs or fragments thereof, have a variety of uses, including but not limited to generating antibodies and in methods for identifying ligands and other agents and cellular constituents that bind to an 125P5C8 gene product. Antibodies raised against an 125P5C8 protein or fragment thereof are useful in diagnostic and prognostic assays, and imaging methodologies in the management of human cancers characterized by expression of 125P5C8 protein, such as those listed in Table I. Such antibodies can be expressed intracellularly and used in methods of treating patients with such cancers. 125P5C8-related nucleic acids or proteins are also used in generating HTL or CTL responses.

Various immunological assays useful for the detection of 125P5C8 proteins are used, including but not limited to various types of radioimmunoassays, enzyme-linked immunosorbent assays (ELISA), enzyme-linked immunofluorescent assays (ELIFA), immunocytochemical methods, and the like. Antibodies can be labeled and used as immunological imaging reagents capable of detecting 125P5C8-expressing cells (e.g., in radioscintigraphic imaging methods). 125P5C8 proteins are also particularly useful in generating cancer vaccines, as further described herein.

V.) 125P5C8 Antibodies

Another aspect of the invention provides antibodies that bind to 125P5C8-related proteins. Preferred antibodies specifically bind to a 125P5C8-related protein and do not bind (or bind weakly) to peptides or proteins that are not 125P5C8-related proteins. For example, antibodies bind 125P5C8 can bind 125P5C8-related proteins such as the homologs or analogs thereof.

125P5C8 antibodies of the invention are particularly useful in prostate cancer diagnostic and prognostic assays, and imaging methodologies. Similarly, such antibodies are useful in the treatment, diagnosis, and/or prognosis of other cancers, to the extent 125P5C8 is also expressed or overexpressed in these other cancers. Moreover, intracellularly expressed antibodies (e.g., single chain antibodies) are therapeutically useful in treating cancers in which the expression of 125P5C8 is involved, such as advanced or metastatic prostate cancers.

The invention also provides various immunological assays useful for the detection and quantification of 125P5C8 and mutant 125P5C8-related proteins. Such assays can comprise one or more 125P5C8 antibodies capable of recognizing and binding a 125P5C8-related protein, as appropriate. These assays are performed within various immunological assay formats well known in the art, including but not limited to various types of radioimmunoassays, enzyme-linked immunosorbent assays (ELISA), enzyme-linked immunofluorescent assays (ELIFA), and the like.

Immunological non-antibody assays of the invention also comprise T cell immunogenicity assays (inhibitory or stimulatory) as well as major histocompatibility complex (MHC) binding assays.

In addition, immunological imaging methods capable of detecting prostate cancer and other cancers expressing 125P5C8 are also provided by the invention, including but not limited to radioscintigraphic imaging methods using labeled 125P5C8 antibodies. Such assays are clinically useful in the detection, monitoring, and prognosis of 125P5C8 expressing cancers such as prostate cancer.

125P5C8 antibodies are also used in methods for purifying a 125P5C8-related protein and for isolating 125P5C8 homologues and related molecules. For example, a method of purifying a 125P5C8-related protein comprises incubating an 125P5C8 antibody, which has been coupled to a solid matrix, with a lysate or other solution containing a 125P5C8-related protein under conditions that permit the 125P5C8 antibody to bind to the 125P5C8-related protein; washing the solid matrix to eliminate impurities; and eluting the 125P5C8-related protein from the coupled antibody. Other uses of the 125P5C8 antibodies of the invention include generating anti-idiotypic antibodies that mimic the 125P5C8 protein.

Various methods for the preparation of antibodies are well known in the art. For example, antibodies can be prepared by immunizing a suitable mammalian host using a 125P5C8-related protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of 125P5C8 can also be used, such as a 125P5C8 GST-fusion protein. In a particular embodiment, a GST fusion protein comprising all or most of the amino acid sequence of FIG. 2 or FIG. 3 is produced, then used as an immunogen to generate appropriate antibodies. In another embodiment, a 125P5C8-related protein is synthesized and used as an immunogen.

In addition, naked DNA immunization techniques known in the art are used (with or without purified 125P5C8-related protein or 125P5C8 expressing cells) to generate an immune response to the encoded immunogen (for review, see Donnelly et al., 1997, Ann. Rev. Immunol. 15: 617-648).

The amino acid sequence of 125P5C8 as shown in FIG. 2 or FIG. 3 can be analyzed to select specific regions of the 125P5C8 protein for generating antibodies. For example, hydrophobicity and hydrophilicity analyses of the 125P5C8 amino acid sequence are used to identify hydrophilic regions in the 125P5C8 structure. Regions of the 125P5C8 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Thus, each region identified by any of these programs or methods is within the scope of the present invention. Methods for the generation of 125P5C8 antibodies are further illustrated by way of the examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents such as those supplied by Pierce Chemical Co., Rockford, Ill., are effective. Administration of a 125P5C8 immunogen is often conducted by injection over a suitable time period and with use of a suitable adjuvant, as is understood in the art. During the immunization schedule, titers of antibodies can be taken to determine adequacy of antibody formation.

125P5C8 monoclonal antibodies can be produced by various means well known in the art. For example, immortalized cell lines that secrete a desired monoclonal antibody are prepared using the standard hybridoma technology of Kohler and Milstein or modifications that immortalize antibody-producing B cells, as is generally known. Immortalized cell lines that secrete the desired antibodies are screened by immunoassay in which the antigen is a 125P5C8-related protein. When the appropriate immortalized cell culture is identified, the cells can be expanded and antibodies produced either from in vitro cultures or from ascites fluid.

The antibodies or fragments of the invention can also be produced, by recombinant means. Regions that bind specifically to the desired regions of the 125P5C8 protein can also be produced in the context of chimeric or complementarity determining region (CDR) grafted antibodies of multiple species origin. Humanized or human 125P5C8 antibodies can also be produced, and are preferred for use in therapeutic contexts. Methods for humanizing murine and other non-human antibodies, by substituting one or more of the non-human antibody CDRs for corresponding human antibody sequences, are well known (see for example, Jones et al., 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296.

Methods for producing fully human monoclonal antibodies include phage display and transgenic methods (for review, see Vaughan et al., 1998, Nature Biotechnology 16: 535-539). Fully human 125P5C8 monoclonal antibodies can be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man, Clark, M. (Ed.), Nottingham Academic, pp 45-64 (1993); Burton and Barbas, Human Antibodies from combinatorial libraries. Id., pp 65-82). Fully human 125P5C8 monoclonal antibodies can also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607-614; U.S. Pat. No. 6,162,963 issued 19 Dec. 2000; U.S. Pat. No. 6,150,584 issued 12 Nov. 2000; and, U.S. Pat. No. 6,114,598 issued 5 Sep. 2000). This method avoids the in vitro manipulation required with phage display technology and efficiently produces high affinity authentic human antibodies.

Reactivity of 125P5C8 antibodies with an 125P5C8-related protein can be established by a number of well known means, including Western blot, immunoprecipitation, ELISA, and FACS analyses using, as appropriate, 125P5C8-related proteins, 125P5C8-expressing cells or extracts thereof. A 125P5C8 antibody or fragment thereof can be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more 125P5C8 epitopes are generated using methods generally known in the art. Homodimeric antibodies can also be generated by cross-linking techniques known in the art (e.g., Wolff et al., Cancer Res. 53: 2560-2565).

VI.) 125P5C8 Transgenic Animals

Nucleic acids that encode a 125P5C8-related protein can also be used to generate either transgenic animals or "knock out" animals which, in turn, are useful in the development and screening of therapeutically useful reagents. In accordance with established techniques, cDNA encoding 125P5C8 can be used to clone genomic DNA that encodes 125P5C8. The cloned genomic sequences can then be used to generate transgenic animals containing cells that express DNA that encode 125P5C8. Methods for generating transgenic animals, particularly animals such as mice or rats, have become conventional in the art and are described, for example, in U.S. Pat. No. 4,736,866 issued 12 Apr. 1988, and U.S. Pat. No. 4,870,009 issued 26 Sep. 1989. Typically, particular cells would be targeted for 125P5C8 transgene incorporation with tissue-specific enhancers.

Transgenic animals that include a copy of a transgene encoding 125P5C8 can be used to examine the effect of increased expression of DNA that encodes 125P5C8. Such animals can be used as tester animals for reagents thought to confer protection from, for example, pathological conditions associated with its overexpression. In accordance with this aspect of the invention, an animal is treated with a reagent and a reduced incidence of a pathological condition, compared to untreated animals that bear the transgene, would indicate a potential therapeutic intervention for the pathological condition.

Alternatively, non-human homologues of 125P5C8 can be used to construct a 125P5C8 "knock out" animal that has a defective or altered gene encoding 125P5C8 as a result of homologous recombination between the endogenous gene encoding 125P5C8 and altered genomic DNA encoding 125P5C8 introduced into an embryonic cell of the animal. For example, cDNA that encodes 125P5C8 can be used to clone genomic DNA encoding 125P5C8 in accordance with established techniques. A portion of the genomic DNA encoding 125P5C8 can be deleted or replaced with another gene, such as a gene encoding a selectable marker that can be used to monitor integration. Typically, several kilobases of unaltered flanking DNA (both at the 5' and 3' ends) are included in the vector (see, e.g., Thomas and Capecchi, Cell, 51:503 (1987) for a description of homologous recombination vectors). The vector is introduced into an embryonic stem cell line (e.g., by electroporation) and cells in which the introduced DNA has homologously recombined with the endogenous DNA are selected (see, e.g., Li et al., *Cell*, 69:915 (1992)). The selected cells are then injected into a blastocyst of an animal (e.g., a mouse or rat) to form aggregation chimeras (see, e.g., Bradley, in *Teratocarcinomas and Embryonic Stem Cells: A Practical Approach*, E. J. Robertson, ed. (IRL, Oxford, 1987), pp. 113-152). A chimeric embryo can then be implanted into a suitable pseudopregnant female foster animal, and the embryo brought to term to create a "knock out" animal. Progeny harboring the homologously recombined DNA in their germ cells can be identified by standard techniques and used to breed animals in which all cells of the animal contain the homologously recombined DNA. Knock out animals can be characterized, for example, for their ability to defend against certain pathological conditions or for their development of pathological conditions due to absence of the 125P5C8 polypeptide.

VII.) Methods for the Detection of 125P5C8

Another aspect of the present invention relates to methods for detecting 125P5C8 polynucleotides and 125P5C8-related proteins, as well as methods for identifying a cell that expresses 125P5C8. The expression profile of 125P5C8 makes it a diagnostic marker for metastasized disease. Accordingly, the status of 125P5C8 gene products provides information useful for predicting a variety of factors including susceptibility to advanced stage disease, rate of progression, and/or tumor aggressiveness. As discussed in detail herein, the status of 125P5C8 gene products in patient samples can be analyzed by a variety protocols that are well known in the art including immunohistochemical analysis, the variety of Northern blotting techniques including in situ hybridization, RT-PCR analysis (for example on laser capture micro-dissected samples), Western blot analysis and tissue array analysis.

More particularly, the invention provides assays for the detection of 125P5C8 polynucleotides in a biological sample, such as serum, bone, prostate, and other tissues, urine, semen, cell preparations, and the like. Detectable 125P5C8 polynucleotides include, for example, a 125P5C8 gene or fragment thereof, 125P5C8 mRNA, alternative splice variant 125P5C8 mRNAs, and recombinant DNA or RNA molecules that contain a 125P5C8 polynucleotide. A number of methods for amplifying and/or detecting the presence of 125P5C8 polynucleotides are well known in the art and can be employed in the practice of this aspect of the invention.

In one embodiment, a method for detecting an 125P5C8 mRNA in a biological sample comprises producing cDNA from the sample by reverse transcription using at least one primer; amplifying the cDNA so produced using an 125P5C8 polynucleotides as sense and antisense primers to amplify 125P5C8 cDNAs therein; and detecting the presence of the amplified 125P5C8 cDNA. Optionally, the sequence of the amplified 125P5C8 cDNA can be determined.

In another embodiment, a method of detecting a 125P5C8 gene in a biological sample comprises first isolating genomic DNA from the sample; amplifying the isolated genomic DNA using 125P5C8 polynucleotides as sense and antisense primers; and detecting the presence of the amplified 125P5C8 gene. Any number of appropriate sense and antisense probe combinations can be designed from the nucleotide sequence provided for the 125P5C8 (FIG. 2) and used for this purpose.

The invention also provides assays for detecting the presence of an 125P5C8 protein in a tissue or other biological sample such as serum, semen, bone, prostate, urine, cell preparations, and the like. Methods for detecting a 125P5C8-related protein are also well known and include, for example, immunoprecipitation, immunohistochemical analysis, Western blot analysis, molecular binding assays, ELISA, ELIFA and the like. For example, a method of detecting the presence of a 125P5C8-related protein in a biological sample comprises first contacting the sample with a 125P5C8 antibody, a 125P5C8-reactive fragment thereof, or a recombinant protein containing an antigen binding region of a 125P5C8 antibody; and then detecting the binding of 125P5C8-related protein in the sample.

Methods for identifying a cell that expresses 125P5C8 are also within the scope of the invention. In one embodiment, an assay for identifying a cell that expresses a 125P5C8 gene comprises detecting the presence of 125P5C8 mRNA in the cell. Methods for the detection of particular mRNAs in cells are well known and include, for example, hybridization assays using complementary DNA probes (such as in situ hybridization using labeled 125P5C8 riboprobes, Northern blot and related techniques) and various nucleic acid amplification assays (such as RT-PCR using complementary primers specific for 125P5C8, and other amplification type detection methods, such as, for example, branched DNA, SISBA, TMA and the like). Alternatively, an assay for identifying a cell that expresses a 125P5C8 gene comprises detecting the presence of 125P5C8-related protein in the cell or secreted by the cell. Various methods for the detection of proteins are well known in the art and are employed for the detection of 125P5C8-related proteins and cells that express 125P5C8-related proteins.

125P5C8 expression analysis is also useful as a tool for identifying and evaluating agents that modulate 125P5C8 gene expression. For example, 125P5C8 expression is significantly upregulated in prostate cancer, and is expressed in cancers of the tissues listed in Table I. Identification of a molecule or biological agent that inhibits 125P5C8 expression or over-expression in cancer cells is of therapeutic value. For example, such an agent can be identified by using a screen that quantifies 125P5C8 expression by RT-PCR, nucleic acid hybridization or antibody binding.

VIII.) Methods for Monitoring the Status of 125P5C8-Related Genes and Their Products Oncogenesis is known to be a multistep process where cellular growth becomes progressively dysregulated and cells progress from a normal physiological state to precancerous and then cancerous states (see, e.g., Alers et al., Lab Invest. 77(5): 437-438 (1997) and Isaacs et al., Cancer Surv. 23: 19-32 (1995)). In this context, examining a biological sample for evidence of dysregulated cell growth (such as aberrant 125P5C8 expression in cancers) allows for early detection of such aberrant physiology, before a pathologic state such as cancer has progressed to a stage that therapeutic options are more limited and or the prognosis is worse. In such examinations, the status of 125P5C8 in a biological sample of interest can be compared, for example, to the status of 125P5C8 in a corresponding normal sample (e.g. a sample from that individual or alternatively another individual that is not effected by a pathology). An alteration in the status of 125P5C8 in the biological sample (as compared to the normal sample) provides evidence of dysregulated cellular growth. In addition to using a biological sample that is not effected by a pathology as a normal sample, one can also use a predetermined normative value such as a predetermined normal level of mRNA expression (see, e.g., Grever et al., J. Comp. Neurol. Dec. 9, 1996; 376(2):306-14 and U.S. Pat. No. 5,837,501) to compare 125P5C8 status in a sample.

The term "status" in this context is used according to its art accepted meaning and refers to the condition or state of a gene and its products. Typically, skilled artisans use a number of parameters to evaluate the condition or state of a gene and its products. These include, but are not limited to the location of expressed gene products (including the location of 125P5C8 expressing cells) as well as the, level, and biological activity of expressed gene products (such as 125P5C8 mRNA polynucleotides and polypeptides). Typically, an alteration in the status of 125P5C8 comprises a change in the location of 125P5C8 and/or 125P5C8 expressing cells and/or an increase in 125P5C8 mRNA and/or protein expression.

125P5C8 status in a sample can be analyzed by a number of means well known in the art, including without limitation, immunohistochemical analysis, in situ hybridization, RT-PCR analysis on laser capture micro-dissected samples, Western blot analysis, and tissue array analysis. Typical protocols for evaluating the status of the 125P5C8 gene and gene products are found, for example in Ausubul et al. eds., 1995, Current Protocols In Molecular Biology, Units 2 (Northern Blotting), 4 (Southern Blotting), 15 (Immunoblotting) and 18 (PCR Analysis). Thus, the status of 125P5C8 in a biological sample is evaluated by various methods utilized by skilled artisans including, but not limited to genomic Southern analysis (to examine, for example perturbations in the 125P5C8 gene), Northern analysis and/or PCR analysis of 125P5C8 mRNA (to examine, for example alterations in the polynucleotide sequences or expression levels of 125P5C8 mRNAs), and, Western and/or immunohistochemical analysis (to examine, for example alterations in polypeptide sequences, alterations in polypeptide localization within a sample, alterations in expression levels of 125P5C8 proteins and/or associations of 125P5C8 proteins with polypeptide binding partners). Detectable 125P5C8 polynucleotides include, for example, a 125P5C8 gene or fragment thereof, 125P5C8 mRNA, alternative splice variants, 125P5C8 mRNAs, and recombinant DNA or RNA molecules containing a 125P5C8 polynucleotide.

The expression profile of 125P5C8 makes it a diagnostic marker for local and/or metastasized disease, and provides information on the growth or oncogenic potential of a biological sample. In particular, the status of 125P5C8 provides information useful for predicting susceptibility to particular disease stages, progression, and/or tumor aggressiveness. The invention provides methods and assays for determining 125P5C8 status and diagnosing cancers that express 125P5C8, such as cancers of the tissues listed in Table I. For example, because 125P5C8 mRNA is so highly expressed in prostate and other cancers relative to normal prostate tissue, assays that evaluate the levels of 125P5C8 mRNA transcripts or proteins in a biological sample can be used to diagnose a disease associated with 125P5C8 dysregulation, and can provide prognostic information useful in defining appropriate therapeutic options.

The expression status of 125P5C8 provides information including the presence, stage and location of dysplastic, precancerous and cancerous cells, predicting susceptibility to various stages of disease, and/or for gauging tumor aggressiveness. Moreover, the expression profile makes it useful as an imaging reagent for metastasized disease. Consequently, an aspect of the invention is directed to the various molecular prognostic and diagnostic methods for examining the status of 125P5C8 in biological samples such as those from individuals suffering from, or suspected of suffering from a pathology characterized by dysregulated cellular growth, such as cancer.

As described above, the status of 125P5C8 in a biological sample can be examined by a number of well-known procedures in the art. For example, the status of 125P5C8 in a biological sample taken from a specific location in the body can be examined by evaluating the sample for the presence or absence of 125P5C8 expressing cells (e.g. those that express 125P5C8 mRNAs or proteins). This examination can provide evidence of dysregulated cellular growth, for example, when 125P5C8-expressing cells are found in a biological sample that does not normally contain such cells (such as a lymph node), because such alterations in the status of 125P5C8 in a biological sample are often associated with dysregulated cellular growth. Specifically, one indicator of dysregulated cellular growth is the metastases of cancer cells from an organ of origin (such as the prostate) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see, e.g., Murphy et al., Prostate 42(4): 315-317 (2000); Su et al., Semin. Surg. Oncol. 18(1): 17-28 (2000) and Freeman et al., J Urol August 1995 154(2 Pt 1):474-8).

In one aspect, the invention provides methods for monitoring 125P5C8 gene products by determining the status of 125P5C8 gene products expressed by cells from an individual suspected of having a disease associated with dysregulated cell growth (such as hyperplasia or cancer) and then comparing the status so determined to the status of 125P5C8 gene products in a corresponding normal sample. The presence of aberrant 125P5C8 gene products in the test sample relative to the normal sample provides an indication of the presence of dysregulated cell growth within the cells of the individual.

In another aspect, the invention provides assays useful in determining the presence of cancer in an individual, comprising detecting a significant increase in 125P5C8 mRNA or protein expression in a test cell or tissue sample relative to expression levels in the corresponding normal cell or tissue. The presence of 125P5C8 mRNA can, for example, be evaluated in tissue samples including but not limited to those listed in Table I. The presence of significant 125P5C8 expression in any of these tissues is useful to indicate the emergence, presence and/or severity of a cancer, since the corresponding normal tissues do not express 125P5C8 mRNA or express it at lower levels.

In a related embodiment, 125P5C8 status is determined at the protein level rather than at the nucleic acid level. For example, such a method comprises determining the level of 125P5C8 protein expressed by cells in a test tissue sample and comparing the level so determined to the level of 125P5C8 expressed in a corresponding normal sample. In one embodiment, the presence of 125P5C8 protein is evaluated, for example, using immunohistochemical methods. 125P5C8 antibodies or binding partners capable of detecting 125P5C8 protein expression are used in a variety of assay formats well known in the art for this purpose.

In a further embodiment, one can evaluate the status 125P5C8 nucleotide and amino acid sequences in a biological sample in order to identify perturbations in the structure of these molecules. These perturbations can include insertions, deletions, substitutions and the like. Such evaluations are useful because perturbations in the nucleotide and amino acid sequences are observed in a large number of proteins associated with a growth dysregulated phenotype (see, e.g., Marrogi et al., 1999, J. Cutan. Pathol. 26(8):369-378). For example, a mutation in the sequence of 125P5C8 may be indicative of the presence or promotion of a tumor. Such assays therefore have diagnostic and predictive value where a mutation in 125P5C8 indicates a potential loss of function or increase in tumor growth.

A wide variety of assays for observing perturbations in nucleotide and amino acid sequences are well known in the art. For example, the size and structure of nucleic acid or amino acid sequences of 125P5C8 gene products are observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. No. 5,382,510 issued 7, Sep. 1999, and U.S. Pat. No. 5,952,170 issued 17 Jan. 1995).

Additionally, one can examine the methylation status of the 125P5C8 gene in a biological sample. Aberrant demethylation and/or hypermethylation of CpG islands in gene 5' regulatory regions frequently occurs in immortalized and transformed cells, and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985-1992 (1999)). In addition, this alteration is present in at least 70% of cases of high-grade prostatic intraepithelial neoplasia (PIN) (Brooks et al, Cancer Epidemiol. Biomarkers Prev., 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al., Int. J. Cancer 76(6): 903-908 (1998)). A variety of assays for examining methylation status of a gene are well known in the art. For example, one can utilize, in Southern hybridization approaches, methylation-sensitive restriction enzymes which cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubul et al. eds., 1995.

Gene amplification is an additional method for assessing the status of 125P5C8. Gene amplification is measured in a sample directly, for example, by conventional Southern blotting or Northern blotting to quantitate the transcription of mRNA (Thomas, 1980, Proc. Natl. Acad. Sci. USA, 77:5201-5205), dot blotting (DNA analysis), or in situ hybridization, using an appropriately labeled probe, based on the sequences provided herein. Alternatively, antibodies are employed that recognize specific duplexes, including DNA duplexes, RNA duplexes, and DNA-RNA hybrid duplexes or DNA-protein duplexes. The antibodies in turn are labeled and the assay carried out where the duplex is bound to a surface, so that upon the formation of duplex on the surface, the presence of antibody bound to the duplex can be detected.

Biopsied tissue or peripheral blood can be conveniently assayed for the presence of cancer cells using for example, Northern, dot blot or RT-PCR analysis to detect 125P5C8 expression. The presence of RT-PCR amplifiable 125P5C8 mRNA provides an indication of the presence of cancer. RT-PCR assays are well known in the art. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25:373-384; Ghossein et al., 1995, J. Clin. Oncol. 13:1195-2000; Heston et al., 1995, Clin. Chem. 41:1687-1688).

A further aspect of the invention is an assessment of the susceptibility that an individual has for developing cancer. In one embodiment, a method for predicting susceptibility to cancer comprises detecting 125P5C8 mRNA or 125P5C8 protein in a tissue sample, its presence indicating susceptibility to cancer, wherein the degree of 125P5C8 mRNA expression correlates to the degree of susceptibility. In a specific embodiment, the presence of 125P5C8 in prostate or other tissue is examined, with the presence of 125P5C8 in the sample providing an indication of prostate cancer susceptibility (or the emergence or existence of a prostate tumor). Similarly, one can evaluate the integrity 125P5C8 nucleotide and amino acid sequences in a biological sample, in order to identify perturbations in the structure of these molecules such as insertions, deletions, substitutions and the like. The presence of one or more perturbations in 125P5C8 gene products in the sample is an indication of cancer susceptibility (or the emergence or existence of a tumor).

The invention also comprises methods for gauging tumor aggressiveness. In one embodiment, a method for gauging aggressiveness of a tumor comprises determining the level of 125P5C8 mRNA or 125P5C8 protein expressed by tumor cells, comparing the level so determined to the level of 125P5C8 mRNA or 125P5C8 protein expressed in a corresponding normal tissue taken from the same individual or a normal tissue reference sample, wherein the degree of 125P5C8 mRNA or 125P5C8 protein expression in the tumor sample relative to the normal sample indicates the degree of aggressiveness. In a specific embodiment, aggressiveness of a tumor is evaluated by determining the extent to which 125P5C8 is expressed in the tumor cells, with higher expression levels indicating more aggressive tumors. Another embodiment is the evaluation of the integrity of 125P5C8 nucleotide and amino acid sequences in a biological sample, in order to identify perturbations in the structure of these molecules such as insertions, deletions, substitutions and the like. The presence of one or more perturbations indicates more aggressive tumors.

Another embodiment of the invention is directed to methods for observing the progression of a malignancy in an individual over time. In one embodiment, methods for observing the progression of a malignancy in an individual over time comprise determining the level of 125P5C8 mRNA or 125P5C8 protein expressed by cells in a sample of the tumor, comparing the level so determined to the level of 125P5C8 mRNA or 125P5C8 protein expressed in an equivalent tissue sample taken from the same individual at a different time, wherein the degree of 125P5C8 mRNA or 125P5C8 protein expression in the tumor sample over time provides information on the progression of the cancer. In a specific embodiment, the progression of a cancer is evaluated by determining 125P5C8 expression in the tumor cells over time, where increased expression over time indicates a progression of the cancer. Also, one can evaluate the integrity 125P5C8 nucleotide and amino acid sequences in a biological sample in order to identify perturbations in the structure of these molecules such as insertions, deletions, substitutions and the like, where the presence of one or more perturbations indicates a progression of the cancer.

The above diagnostic approaches can be combined with any one of a wide variety of prognostic and diagnostic protocols known in the art. For example, another embodiment of the invention is directed to methods for observing a coincidence between the expression of 125P5C8 gene and 125P5C8 gene products (or perturbations in 125P5C8 gene and 125P5C8 gene products) and a factor that is associated with malignancy, as a means for diagnosing and prognosticating the status of a tissue sample. A wide variety of factors associated with malignancy can be utilized, such as the expression of genes associated with malignancy (e.g. PSA, PSCA and PSM expression for prostate cancer etc.) as well as gross cytological observations (see, e.g., Bocking et al., 1984, Anal. Quant. Cytol. 6(2):74-88; Epstein, 1995, Hum. Pathol. 26(2):223-9; Thorson et al., 1998, Mod. Pathol. 11(6):543-51; Baisden et al., 1999, Am. J. Surg. Pathol. 23(8):918-24). Methods for observing a coincidence between the expression of 125P5C8 gene and 125P5C8 gene products (or perturbations in 125P5C8 gene and 125P5C8 gene products) and another factor that is associated with malignancy are useful, for example, because the presence of a set of specific factors that coincide with disease provides information crucial for diagnosing and prognosticating the status of a tissue sample.

In one embodiment, methods for observing a coincidence between the expression of 125P5C8 gene and 125P5C8 gene products (or perturbations in 125P5C8 gene and 125P5C8 gene products) and another factor associated with malignancy entails detecting the overexpression of 125P5C8 mRNA or protein in a tissue sample, detecting the overexpression of PSA mRNA or protein in a tissue sample (or PSCA or PSM expression), and observing a coincidence of 125P5C8 mRNA or protein and PSA mRNA or protein overexpression (or PSCA or PSM expression). In a specific embodiment, the expression of 125P5C8 and PSA mRNA in prostate tissue is examined, where the coincidence of 125P5C8 and PSA mRNA overexpression in the sample indicates the existence of prostate cancer, prostate cancer susceptibility or the emergence or status of a prostate tumor.

Methods for detecting and quantifying the expression of 125P5C8 mRNA or protein are described herein, and standard nucleic acid and protein detection and quantification technologies are well known in the art. Standard methods for the detection and quantification of 125P5C8 mRNA include in situ hybridization using labeled 125P5C8 riboprobes, Northern blot and related techniques using 125P5C8 polynucleotide probes, RT-PCR analysis using primers specific for 125P5C8, and other amplification type detection methods, such as, for example, branched DNA, SISBA, TMA and the like. In a specific embodiment, semi-quantitative RT-PCR is used to detect and quantify 125P5C8 mRNA expression. Any number of primers capable of amplifying 125P5C8 can be used for this purpose, including but not limited to the various primer sets specifically described herein. In a specific embodiment, polyclonal or monoclonal antibodies specifically reactive with the wild-type 125P5C8 protein can be used in an immunohistochemical assay of biopsied tissue.

IX.) Identification of Molecules that Interact with 125P5C8

The 125P5C8 protein and nucleic acid sequences disclosed herein allow a skilled artisan to identify proteins, small molecules and other agents that interact with 125P5C8, as well as pathways activated by 125P5C8 via any one of a variety of art accepted protocols. For example, one can utilize one of the so-called interaction trap systems (also referred to as the "two-hybrid assay"). In such systems, molecules interact and reconstitute a transcription factor which directs expression of a reporter gene, whereupon the expression of the reporter gene is assayed. Other systems identify protein-protein interactions in vivo through reconstitution of a eukaryotic transcriptional activator, see, e.g., U.S. Pat. No. 5,955,280 issued 21 Sep. 1999, U.S. Pat. No. 5,925,523 issued 20 Jul. 1999, U.S. Pat. No. 5,846,722 issued 8 Dec. 1998 and U.S. Pat. No. 6,004,746 issued 21 Dec. 1999. Algorithms are also available in the art for genome-based predictions of protein function (see, e.g., Marcotte, et al., Nature 402: 4 Nov. 1999, 83-86).

Alternatively one can screen peptide libraries to identify molecules that interact with 125P5C8 protein sequences. In such methods, peptides that bind to a molecule such as 125P5C8 are identified by screening libraries that encode a random or controlled collection of amino acids. Peptides encoded by the libraries are expressed as fusion proteins of bacteriophage coat proteins, the bacteriophage particles are then screened against the protein of interest.

Accordingly, peptides having a wide variety of uses, such as therapeutic, prognostic or diagnostic reagents, are thus identified without any prior information on the structure of the expected ligand or receptor molecule. Typical peptide libraries and screening methods that can be used to identify molecules that interact with 125P5C8 protein sequences are disclosed for example in U.S. Pat. No. 5,723,286 issued 3 Mar. 1998 and U.S. Pat. No. 5,733,731 issued Mar. 3, 1998.

Alternatively, cell lines that express 125P5C8 are used to identify protein-protein interactions mediated by 125P5C8. Such interactions can be examined using immunoprecipitation techniques (see, e.g., Hamilton B J, et al. Biochem. Biophys. Res. Commun. 1999, 261:646-51). 125P5C8 protein can be immunoprecipitated from 125P5C8-expressing cell lines using anti-125P5C8 antibodies. Alternatively, antibodies against His-tag can be used in a cell line engineered to express 125P5C8 (vectors mentioned above). The immunoprecipitated complex can be examined for protein association by procedures such as Western blotting, $^{35}$S-methionine labeling of proteins, protein microsequencing, silver staining and two-dimensional gel electrophoresis.

Small molecules and ligands that interact with 125P5C8 can be identified through related embodiments of such screening assays. For example, small molecules can be identified that interfere with protein function, including molecules that interfere with 125P5C8's ability to mediate phosphorylation and de-phosphorylation, interaction with DNA or RNA molecules as an indication of regulation of cell cycles, second messenger signaling or tumorigenesis. Similarly, small molecules that modulate ion channel, protein pump, or cell communication function of 125P5C8 are identified and used to treat patients that have a cancer that expresses the 125P5C8 antigen (see, e.g., Hille, B., Ionic Channels of Excitable Membranes $2^{nd}$ Ed., Sinauer Assoc., Sunderland, Mass., 1992). Moreover, ligands that regulate 125P5C8 function can be identified based on their ability to bind 125P5C8 and activate a reporter construct. Typical methods are discussed for example in U.S. Pat. No. 5,928,868 issued 27 Jul. 1999, and include methods for forming hybrid ligands in which at least one ligand is a small molecule. In an illustrative embodiment, cells engineered to express a fusion protein of 125P5C8 and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying both activators and inhibitors of 125P5C8.

An embodiment of this invention comprises a method of screening for a molecule that interacts with an 125P5C8 amino acid sequence shown in FIG. 2 and FIG. 3 (SEQ ID NO: 2), comprising the steps of contacting a population of molecules with the 125P5C8 amino acid sequence, allowing the population of molecules and the 125P5C8 amino acid sequence to interact under conditions that facilitate an interaction, determining the presence of a molecule that interacts with the 125P5C8 amino acid sequence, and then separating molecules that do not interact with the 125P5C8 amino acid sequence from molecules that do. In a specific embodiment, the method further comprises purifying a molecule that interacts with the 125P5C8 amino acid sequence. The identified molecule can be used to modulate a function performed by 125P5C8. In a preferred embodiment, the 125P5C8 amino acid sequence is contacted with a library of peptides.

X.) Therapeutic Methods and Compositions

The identification of 125P5C8 as a protein that is normally expressed in a restricted set of tissues, but which is also expressed in prostate and other cancers, opens a number of therapeutic approaches to the treatment of such cancers. As discussed herein, it is possible that 125P5C8 functions as a transcription factor involved in activating tumor-promoting genes or repressing genes that block tumorigenesis.

Accordingly, therapeutic approaches that inhibit the activity of the 125P5C8 protein are useful for patients suffering a cancer that expresses 125P5C8. These therapeutic approaches generally fall into two classes. One class comprises various methods for inhibiting the binding or association of the 125P5C8 protein with its binding partner or with others proteins. Another class comprises a variety of methods for inhibiting the transcription of the 125P5C8 gene or translation of 125P5C8 mRNA.

X.A.) 125P5C8 as a Target for Antibody-Based Therapy

125P5C8 is an attractive target for antibody-based therapeutic strategies. A number of antibody strategies are known in the art for targeting both extracellular and intracellular molecules (see, e.g., complement and ADCC mediated killing as well as the use of intrabodies). Because 125P5C8 is expressed by cancer cells of various lineages and not by corresponding normal cells, systemic administration of 125P5C8-immunoreactive compositions are prepared that exhibit excellent sensitivity without toxic, non-specific and/or non-target effects caused by binding of the immunoreactive composition to non-target organs and tissues. Antibodies specifically reactive with domains of 125P5C8 are useful to treat 125P5C8-expressing cancers systemically, either as conjugates with a toxin or therapeutic agent, or as naked antibodies capable of inhibiting cell proliferation or function.

125P5C8 antibodies can be introduced into a patient such that the antibody binds to 125P5C8 and modulates a function, such as an interaction with a binding partner, and consequently mediates destruction of the tumor cells and/or inhibits the growth of the tumor cells. Mechanisms by which such antibodies exert a therapeutic effect can include complement-mediated cytolysis, antibody-dependent cellular cytotoxicity, modulation of the physiological function of 125P5C8, inhibition of ligand binding or signal transduction pathways, modulation of tumor cell differentiation, alteration of tumor angiogenesis factor profiles, and/or apoptosis.

Those skilled in the art understand that antibodies can be used to specifically target and bind immunogenic molecules such as an immunogenic region of the 125P5C8 sequence shown in FIG. 2. In addition, skilled artisans understand that it is routine to conjugate antibodies to cytotoxic agents. When cytotoxic and/or therapeutic agents are delivered directly to cells, such as by conjugating them to antibodies specific for a molecule expressed by that cell (e.g. 125P5C8), the cytotoxic agent will exert its known biological effect (i.e. cytotoxicity) on those cells.

A wide variety of compositions and methods for using antibody-cytotoxic agent conjugates to kill cells are known in the art. In the context of cancers, typical methods entail administering to an animal having a tumor a biologically effective amount of a conjugate comprising a selected cytotoxic and/or therapeutic agent linked to a targeting agent (e.g. an anti-125P5C8 antibody) that binds to a marker (e.g. 125P5C8) expressed, accessible to binding or localized on the cell surfaces. A typical embodiment is a method of delivering a cytotoxic and/or therapeutic agent to a cell expressing 125P5C8, comprising conjugating the cytotoxic agent to an antibody that immunospecifically binds to a 125P5C8 epitope, and, exposing the cell to the antibody-agent conjugate. Another illustrative embodiment is a method of treating an individual suspected of suffering from metastasized cancer, comprising a step of administering parenterally to said individual a pharmaceutical composition comprising a therapeutically effective amount of an antibody conjugated to a cytotoxic and/or therapeutic agent.

Cancer immunotherapy using anti-125P5C8 antibodies can be done in accordance with various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186, Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11:117-127). Some therapeutic approaches involve conjugation of naked antibody to a toxin, such as the conjugation of $Y^{91}$ or $I^{131}$ to anti-CD20 antibodies (e.g., Zevalin™, IDEC Pharmaceuticals Corp. or Bexxar™, Coulter Pharmaceuticals), while others involve co-administration of antibodies and other therapeutic agents, such as Herceptin™ (trastuzumab) with paclitaxel (Genentech, Inc.). To treat prostate cancer, for example, 125P5C8 antibodies can be administered in conjunction with radiation, chemotherapy or hormone ablation.

Although 125P5C8 antibody therapy is useful for all stages of cancer, antibody therapy can be particularly appropriate in advanced or metastatic cancers. Treatment with the antibody therapy of the invention is indicated for patients who have received one or more rounds of chemotherapy. Alternatively, antibody therapy of the invention is combined with a chemotherapeutic or radiation regimen for patients who have not received chemotherapeutic treatment. Additionally, antibody therapy can enable the use of reduced dosages of concomitant chemotherapy, particularly for patients who do not tolerate the toxicity of the chemotherapeutic agent very well.

Cancer patients can be evaluated for the presence and level of 125P5C8 expression, preferably using immunohistochemical assessments of tumor tissue, quantitative 125P5C8 imaging, or other techniques that reliably indicate the presence and degree of 125P5C8 expression. Immunohistochemical analysis of tumor biopsies or surgical specimens is preferred for this purpose. Methods for immunohistochemical analysis of tumor tissues are well known in the art.

Anti-125P5C8 monoclonal antibodies that treat prostate and other cancers include those that initiate a potent immune response against the tumor or those that are directly cytotoxic. In this regard, anti-125P5C8 monoclonal antibodies (mAbs) can elicit tumor cell lysis by either complement-mediated or antibody-dependent cell cytotoxicity (ADCC) mechanisms, both of which require an intact Fc portion of the immunoglobulin molecule for interaction with effector cell Fc receptor sites on complement proteins. In addition, anti-125P5C8 mAbs that exert a direct biological effect on tumor growth are useful to treat cancers that express 125P5C8. Mechanisms by which directly cytotoxic mAbs act include: inhibition of cell growth, modulation of cellular differentiation, modulation of tumor angiogenesis factor profiles, and the induction of apoptosis. The mechanism(s) by which a particular anti-125P5C8 mAb exerts an anti-tumor effect is evaluated using any number of in vitro assays that evaluate cell death such as ADCC, ADMMC, complement-mediated cell lysis, and so forth, as is generally known in the art.

In some patients, the use of murine or other non-human monoclonal antibodies, or human/mouse chimeric mAbs can induce moderate to strong immune responses against the non-human antibody. This can result in clearance of the antibody from circulation and reduced efficacy. In the most severe cases, such an immune response can lead to the extensive formation of immune complexes which, potentially, can cause renal failure. Accordingly, preferred monoclonal antibodies used in the therapeutic methods of the invention are those that are either fully human or humanized and that bind specifically to the target 125P5C8 antigen with high affinity but exhibit low or no antigenicity in the patient.

Therapeutic methods of the invention contemplate the administration of single anti-125P5C8 mAbs as well as combinations, or cocktails, of different mAbs. Such mAb cocktails can have certain advantages inasmuch as they contain mAbs that target different epitopes, exploit different effector mechanisms or combine directly cytotoxic mAbs with mAbs that rely on immune effector functionality. Such mAbs in combination can exhibit synergistic therapeutic effects. In addition, anti-125P5C8 mAbs can be administered concomitantly with other therapeutic modalities, including but not limited to various chemotherapeutic agents, androgen-blockers, immune modulators (e.g., IL-2, GM-CSF), surgery or radiation. The anti-125P5C8 mAbs are administered in their "naked" or unconjugated form, or can have a therapeutic agent(s) conjugated to them.

Anti-125P5C8 antibody formulations are administered via any route capable of delivering the antibodies to a tumor cell. Routes of administration include, but are not limited to, intravenous, intraperitoneal, intramuscular, intratumor, intradermal, and the like. Treatment generally involves repeated administration of the anti-125P5C8 antibody preparation, via an acceptable route of administration such as intravenous injection (IV), typically at a dose in the range of about 0.1 to about 10 mg/kg body weight. In general, doses in the range of 10-500 mg mAB per week are effective and well tolerated.

Based on clinical experience with the Herceptin mAb in the treatment of metastatic breast cancer, an initial loading dose of approximately 4 mg/kg patient body weight IV, followed by weekly doses of about 2 mg/kg IV of the anti-125P5C8 mAb preparation represents an acceptable dosing regimen. Preferably, the initial loading dose is administered as a 90 minute or longer infusion. The periodic maintenance dose is administered as a 30 minute or longer infusion, provided the initial dose was well tolerated. As appreciated by those of skill in the art, various factors can influence the ideal dose regimen in a particular case. Such factors include, for example, the binding affinity and half life of the Ab or mAbs used, the degree of 125P5C8 expression in the patient, the extent of circulating shed 125P5C8 antigen, the desired steady-state antibody concentration level, frequency of treatment, and the influence of chemotherapeutic or other agents used in combination with the treatment method of the invention, as well as the health status of a particular patient.

Optionally, patients should be evaluated for the levels of 125P5C8 in a given sample (e.g. the levels of circulating 125P5C8 antigen and/or 125P5C8 expressing cells) in order to assist in the determination of the most effective dosing regimen, etc. Such evaluations are also used for monitoring purposes throughout therapy, and are useful to gauge therapeutic success in combination with the evaluation of other parameters (such as serum PSA levels in prostate cancer therapy).

X.B.) Anti-Cancer Vaccines

The invention further provides cancer vaccines comprising a 125P5C8-related protein or 125P5C8-related nucleic acid. In view of the expression of 125P5C8, cancer vaccines prevent and/or treat 125P5C8-expressing cancers without creating non-specific effects on non-target tissues. The use of a tumor antigen in a vaccine that generates humoral and/or cell-mediated immune responses as anti-cancer therapy is well known in the art and has been employed in prostate cancer using human PSMA and rodent PAP immunogens (Hodge et al., 1995, Int. J. Cancer 63:231-237; Fong et al., 1997, J. Immunol. 159:3113-3117).

Genetic immunization methods can be employed to generate prophylactic or therapeutic humoral and cellular immune responses directed against cancer cells expressing 125P5C8. Constructs comprising DNA encoding a 125P5C8-related protein/immunogen and appropriate regulatory sequences can be injected directly into muscle or skin of an individual, such that the cells of the muscle or skin take-up the construct and express the encoded 125P5C8 protein/immunogen. Alternatively, a vaccine comprises a 125P5C8-related protein. Expression of the 125P5C8-related protein immunogen results in the generation of prophylactic or therapeutic humoral and cellular immunity against cells that bear 125P5C8 protein. Various prophylactic and therapeutic genetic immunization techniques known in the art can be used (for review, see information and references published at Internet address www.genweb.com).

Such methods can be readily practiced by employing a 125P5C8-related protein, or an 125P5C8-encoding nucleic acid molecule and recombinant vectors capable of expressing and presenting the 125P5C8 immunogen (which typically comprises a number of antibody or T cell epitopes). Skilled artisans understand that a wide variety of vaccine systems for delivery of immunoreactive epitopes are known in the art (see, e.g., Heryln et al., Ann Med Febrary 1999 31(1):66-78; Maruyama et al., Cancer Immunol Immunother June 2000 49(3):123-32) Briefly, such methods of generating an immune response (e.g. humoral and/or cell-mediated) in a mammal, comprise the steps of: exposing the mammal's immune system to an immunoreactive epitope (e.g. an epitope present in the 125P5C8 protein shown in SEQ ID NO: 2 or analog or homolog thereof) so that the mammal generates an immune response that is specific for that epitope (e.g. generates antibodies that specifically recognize that epitope). In a preferred method, the 125P5C8 immunogen contains a biological motif.

CTL epitopes can be determined using specific algorithms to identify peptides within 125P5C8 protein that are capable of optimally binding to specified HLA alleles (e.g., Table IV (A) and Table IV (B); Epimer™ and Epimatrix™, Brown University (http://www.brown.edu/Research/TB-HIV_Lab/epimatrix/epimatrix.html); and, BIMAS, (http://bimas.dcrt.nih.gov/). In a preferred embodiment, the 125P5C8 immunogen contains one or more amino acid sequences identified using one of the pertinent analytical techniques well known in the art, such as the sequences shown in Tables V-XVIII or a peptide of 8, 9, 10 or 11 amino acids specified by an HLA Class I motif (e.g., Table IV (A)) and/or a peptide of at least 9 amino acids that comprises an HLA Class II motif (e.g., Table IV (B)). As is appreciated in the art, the HLA Class I binding grove is essentially closed ended so that peptides of only a particular size range can fit into the groove and be bound, generally HLA Class I epitopes are 8, 9, 10, or 11 amino acids long. In contrast, the HLA Class II binding groove is essentially open ended; therefore a of about 9 or more amino acids can be bound by an HLA Class II molecule. Due to the binding groove differences between HLA Class I and II, HLA Class I motifs are length specific, i.e., position two of a Class I motif is the second amino acid in an amino to carboxyl direction of the peptide. The amino acid positions in a Class II motif are relative only to each other, not the overall peptide, i.e., additional amino acids can be attached to the amino and/or carboxyl termini of a motif-bearing sequence. HLA Class II epitopes are often 9, 10, 11, 12, 13, 14, 15, 16, 17, 18, 19, 20, 21, 22, 23, 24, or 25 amino acids long, or longer than 25 amino acids.

A wide variety of methods for generating an immune response in a mammal are known in the art (for example as the first step in the generation of hybridomas). Methods of generating an immune response in a mammal comprise exposing the mammal's immune system to an immunogenic epitope on a protein (e.g. the 125P5C8 protein) so that an immune response is generated. A typical embodiment consists of a method for generating an immune response to 125P5C8 in a host, by contacting the host with a sufficient amount of at least one 125P5C8 B cell or cytotoxic T-cell epitope or analog thereof; and at least one periodic interval thereafter re-contacting the host with the 125P5C8 B cell or cytotoxic T-cell epitope or analog thereof. A specific embodiment consists of a method of generating an immune response against a 125P5C8-related protein or a man-made multiepitopic peptide comprising: administering 125P5C8 immunogen (e.g. the 125P5C8 protein or a peptide fragment thereof, an 125P5C8 fusion protein or analog etc.) in a vaccine preparation to a human or another mammal. Typically, such vaccine preparations further contain a suitable adjuvant (see, e.g., U.S. Pat. No. 6,146,635) or a universal helper epitope such as a PADRE™ peptide (Epimmune Inc., San Diego, Calif.; see, e.g., Alexander et al., J. Immunol. 2000 164(3); 164(3): 1625-1633; Alexander et al., Immunity 1994 1(9): 751-761 and Alexander et al., Immunol. Res. 1998 18(2): 79-92). An alternative method comprises generating an immune response in an individual against a 125P5C8 immunogen by: administering in vivo to muscle or skin of the individual's body a DNA molecule that comprises a DNA sequence that encodes an 125P5C8 immunogen, the DNA sequence operatively linked to regulatory sequences which control the expression of the DNA sequence; wherein the DNA molecule is taken up by cells, the DNA sequence is expressed in the cells and an immune response is generated against the immunogen (see, e.g., U.S. Pat. No. 5,962,428). The DNA can be dissociated from an infectious agent. Optionally a genetic vaccine facilitator such as anionic lipids; saponins; lectins; estrogenic compounds; hydroxylated lower alkyls; dimethyl sulfoxide; and urea is also administered.

Thus, viral gene delivery systems are used to deliver a 125P5C8-related nucleic acid molecule. Various viral gene delivery systems that can be used in the practice of the invention include, but are not limited to, vaccinia, fowlpox, canarypox, adenovirus, influenza, poliovirus, adeno-associated virus, lentivirus, and sindbis virus (Restifo, 1996, Curr. Opin. Immunol. 8:658-663). Non-viral delivery systems can also be employed by introducing naked DNA encoding a 125P5C8-related protein into the patient (e.g., intramuscularly or intradermally) to induce an anti-tumor response. In one embodiment, the full-length human 125P5C8 cDNA is employed. In another embodiment, 125P5C8 nucleic acid molecules encoding specific cytotoxic T lymphocyte (CTL) and/or antibody epitopes are employed.

Various ex vivo strategies can also be employed to generate an immune response. One approach involves the use of antigen presenting cells (APCs) such as dendritic cells to present 125P5C8 antigen to a patient's immune system. Dendritic cells express MHC class I and II molecules, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28:65-69; Murphy et al., 1996, Prostate 29:371-380). Thus, dendritic cells can be used to present 125P5C8 peptides to T cells in the context of MHC class I or II molecules. In one embodiment, autologous dendritic cells are pulsed with 125P5C8 peptides capable of binding to MHC class I and/or class II molecules. In another embodiment, dendritic cells are pulsed with the complete 125P5C8 protein. Yet another embodiment involves engineering the overexpression of the 125P5C8 gene in dendritic cells using various implementing vectors known in the art, such as adenovirus (Arthur et al., 1997, Cancer Gene Ther. 4:17-25), retrovirus (Henderson et al., 1996, Cancer Res. 56:3763-3770), lentivirus, adeno-associated virus, DNA transfection (Ribas et al., 1997, Cancer Res. 57:2865-2869), or tumor-derived RNA transfection (Ashley et al., 1997, J. Exp. Med. 186:1177-1182). Cells that express 125P5C8 can also be engineered to express immune modulators, such as GM-CSF, and used as immunizing agents.

Anti-idiotypic anti-125P5C8 antibodies can also be used in anti-cancer therapy as a vaccine for inducing an immune response to cells expressing a 125P5C8-related protein. In particular, the generation of anti-idiotypic antibodies is well known in the art; this methodology can readily be adapted to generate anti-idiotypic anti-125P5C8 antibodies that mimic an epitope on a 125P5C8-related protein (see, for example, Wagner et al., 1997, Hybridoma 16: 33-40; Foon et al., 1995, J. Clin. Invest. 96:334-342; Herlyn et al., 1996, Cancer Immunol. Immunother. 43:65-76). Such an anti-idiotypic antibody can be used in cancer vaccine strategies.

XI.) Inhibition of 125P5C8 Protein Function

The invention includes various methods and compositions for inhibiting the binding of 125P5C8 to its binding partner or its association with other protein(s) as well as methods for inhibiting 125P5C8 function.

XI.A.) Inhibition of 125P5C8 With Intracellular Antibodies

In one approach, a recombinant vector that encodes single chain antibodies that specifically bind to 125P5C8 are introduced into 125P5C8 expressing cells via gene transfer technologies. Accordingly, the encoded single chain anti-125P5C8 antibody is expressed intracellularly, binds to 125P5C8 protein, and thereby inhibits its function. Methods for engineering such intracellular single chain antibodies are well known. Such intracellular antibodies, also known as "intrabodies", are specifically targeted to a particular compartment within the cell, providing control over where the inhibitory activity of the treatment is focused. This technology has been successfully applied in the art (for review, see Richardson and Marasco, 1995, TIBTECH vol. 13). Intrabodies have been shown to virtually eliminate the expression of otherwise abundant cell surface receptors (see, e.g., Richardson et al., 1995, Proc. Natl. Acad. Sci. USA 92: 3137-3141; Beerli et al., 1994, J. Biol. Chem. 289: 23931-23936; Deshane et al., 1994, Gene Ther. 1: 332-337).

Single chain antibodies comprise the variable domains of the heavy and light chain joined by a flexible linker polypeptide, and are expressed as a single polypeptide. Optionally, single chain antibodies are expressed as a single chain variable region fragment joined to the light chain constant region. Well-known intracellular trafficking signals are engineered into recombinant polynucleotide vectors encoding such single chain antibodies in order to precisely target the intrabody to the desired intracellular compartment. For example, intrabodies targeted to the endoplasmic reticulum (ER) are engineered to incorporate a leader peptide and, optionally, a C-terminal ER retention signal, such as the KDEL amino acid motif. Intrabodies intended to exert activity in the nucleus are engineered to include a nuclear localization signal. Lipid moieties are joined to intrabodies in order to tether the intrabody to the cytosolic side of the plasma membrane. Intrabodies can also be targeted to exert function in the cytosol. For example, cytosolic intrabodies are used to sequester factors within the cytosol, thereby preventing them from being transported to their natural cellular destination.

In one embodiment, intrabodies are used to capture 125P5C8 in the nucleus, thereby preventing its activity within the nucleus. Nuclear targeting signals are engineered into such 125P5C8 intrabodies in order to achieve the desired targeting. Such 125P5C8 intrabodies are designed to bind specifically to a particular 125P5C8 domain. In another embodiment, cytosolic intrabodies that specifically bind to the 125P5C8 protein are used to prevent 125P5C8 from gaining access to the nucleus, thereby preventing it from exerting any biological activity within the nucleus (e.g., preventing 125P5C8 from forming transcription complexes with other factors).

In order to specifically direct the expression of such intrabodies to particular cells, the transcription of the intrabody is placed under the regulatory control of an appropriate tumor-specific promoter and/or enhancer. In order to target intrabody expression specifically to prostate, for example, the PSA promoter and/or promoter/enhancer can be utilized (See, for example, U.S. Pat. No. 5,919,652 issued 6 Jul. 1999).

XI.B.) Inhibition of 125P5C8 with Recombinant Proteins

In another approach, recombinant molecules bind to 125P5C8 and thereby inhibit 125P5C8 function. For example, these recombinant molecules prevent or inhibit 125P5C8 from accessing/binding to its binding partner(s) or associating with other protein(s). Such recombinant molecules can, for example, contain the reactive part(s) of a 125P5C8 specific antibody molecule. In a particular embodiment, the 125P5C8 binding domain of a 125P5C8 binding partner is engineered into a dimeric fusion protein, whereby the fusion protein comprises two 125P5C8 ligand binding domains linked to the Fc portion of a human IgG, such as human IgG1. Such IgG portion can contain, for example, the $C_H2$ and $C_H3$ domains and the hinge region, but not the $C_H1$ domain. Such dimeric fusion proteins are administered in soluble form to patients suffering from a cancer associated with the expression of 125P5C8, whereby the dimeric fusion protein specifically binds to 125P5C8 and blocks 125P5C8 interaction with a binding partner. Such dimeric fusion proteins are further combined into multimeric proteins using known antibody linking technologies.

XI.C.) Inhibition of 125P5C8 Transcription or Translation

The present invention also comprises various methods and compositions for inhibiting the transcription of the 125P5C8 gene. Similarly, the invention also provides methods and compositions for inhibiting the translation of 125P5C8 mRNA into protein.

In one approach, a method of inhibiting the transcription of the 125P5C8 gene comprises contacting the 125P5C8 gene with a 125P5C8 antisense polynucleotide. In another approach, a method of inhibiting 125P5C8 mRNA translation comprises contacting the 125P5C8 mRNA with an antisense polynucleotide. In another approach, a 125P5C8 specific ribozyme is used to cleave the 125P5C8 message, thereby inhibiting translation. Such antisense and ribozyme based methods can also be directed to the regulatory regions of the 125P5C8 gene, such as the 125P5C8 promoter and/or enhancer elements. Similarly, proteins capable of inhibiting a 125P5C8 gene transcription factor are used to inhibit 125P5C8 mRNA transcription. The various polynucleotides and compositions useful in the aforementioned methods have been described above. The use of antisense and ribozyme molecules to inhibit transcription and translation is well known in the art.

Other factors that inhibit the transcription of 125P5C8 by interfering with 125P5C8 transcriptional activation are also useful to treat cancers expressing 125P5C8. Similarly, factors that interfere with 125P5C8 processing are useful to treat cancers that express 125P5C8. Cancer treatment methods utilizing such factors are also within the scope of the invention.

XI.D.) General Considerations for Therapeutic Strategies

Gene transfer and gene therapy technologies can be used to deliver therapeutic polynucleotide molecules to tumor cells synthesizing 125P5C8 (i.e., antisense, ribozyme, polynucleotides encoding intrabodies and other 125P5C8 inhibitory molecules). A number of gene therapy approaches are known in the art. Recombinant vectors encoding 125P5C8 antisense polynucleotides, ribozymes, factors capable of interfering with 125P5C8 transcription, and so forth, can be delivered to target tumor cells using such gene therapy approaches.

The above therapeutic approaches can be combined with any one of a wide variety of surgical, chemotherapy or radiation therapy regimens. The therapeutic approaches of the invention can enable the use of reduced dosages of chemotherapy (or other therapies) and/or less frequent administration, an advantage for all patients and particularly for those that do not tolerate the toxicity of the chemotherapeutic agent well.

The anti-tumor activity of a particular composition (e.g., antisense, ribozyme, intrabody), or a combination of such compositions, can be evaluated using various in vitro and in vivo assay systems. In vitro assays that evaluate therapeutic activity include cell growth assays, soft agar assays and other assays indicative of tumor promoting activity, binding assays capable of determining the extent to which a therapeutic composition will inhibit the binding of 125P5C8 to a binding partner, etc.

In vivo, the effect of a 125P5C8 therapeutic composition can be evaluated in a suitable animal model. For example, xenogenic prostate cancer models can be used, wherein human prostate cancer explants or passaged xenograft tissues are introduced into immune compromised animals, such as nude or SCID mice (Klein et al., 1997, Nature Medicine 3: 402-408). For example, PCT Patent Application WO98/16628, Sawyers et al., published Apr. 23, 1998, describes various xenograft models of human prostate cancer capable of recapitulating the development of primary tumors, micrometastasis, and the formation of osteoblastic metastases characteristic of late stage disease. Efficacy can be predicted using assays that measure inhibition of tumor formation, tumor regression or metastasis, and the like.

In vivo assays that evaluate the promotion of apoptosis are useful in evaluating therapeutic compositions. In one embodiment, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods can be formulated into pharmaceutical compositions comprising a carrier suitable for the desired delivery method. Suitable carriers include any material that when combined with the therapeutic composition retains the anti-tumor function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed., 1980).

Therapeutic formulations can be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations can be lyophilized and stored as sterile powders, preferably under vacuum, and then reconstituted in bacteriostatic water (containing for example, benzyl alcohol preservative) or in sterile water prior to injection.

Dosages and administration protocols for the treatment of cancers using the foregoing methods will vary with the method and the target cancer, and will generally depend on a number of other factors appreciated in the art.

XII.) Kits

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. Such probe can be an antibody or polynucleotide specific for a 125P5C8-related protein or a 125P5C8 gene or message, respectively. Where the method utilizes nucleic acid hybridization to detect the target nucleic acid, the kit can also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label. The kit can include all or part of the amino acid sequence of FIG. 2 or analogs thereof, or a nucleic acid molecule that encodes such amino acid sequences.

The kit of the invention will typically comprise the container described above and one or more other containers comprising materials desirable from a commercial and user standpoint, including buffers, diluents, filters, needles, syringes, and package inserts with instructions for use.

A label can be present on the container to indicate that the composition is used for a specific therapy or non-therapeutic application, and can also indicate directions for either in vivo or in vitro use, such as those described above. Directions and or other information can also be included on an insert which is included with the kit.

PTA-3137 has been deposited under the requirements of the Budapest Treaty on Mar. 1, 2001, with the American Type Culture Collection (ATCC), 10801 University Blvd., Manassas, Va. 20110-2209 USA, and has been identified as ATCC Accession No. PTA-3137.

EXAMPLES

Various aspects of the invention are further described and illustrated by way of the several examples that follow, none of which are intended to limit the scope of the invention.

Example 1

SSH-Generated Isolation of a cDNA Fragment of the 125P5C8 Gene

The SSH cDNA fragment 125P5C8 (FIG. 1) was derived from a subtraction utilizing the xenografts LAPC9AD (14 days after castration) minus LAPC9AD (non-castrated mouse). The full-length cDNA clone 125P5C8-Pro-pCR2.1 (FIG. 2) was identified by assembling EST fragments homologous to 125P5C8 into a large contiguous sequence with an ORF and amplifying the ORF by PCR using prostate first strand cDNA.

The cDNA clone 125P5C8-Pro-pCR2.1 encodes a 699 amino acid ORF with 10 transmembrane domains predicted at the cell surface (PSORT). The 125P5C8 protein is similar to a GenBank protein AK025164 with one amino acid difference (FIG. 4A). This amino acid difference at amino acid position 689 may be significant since it is located in the long extracellular C-terminal region that may be involved in ligand binding, may affect the stability of the protein, or may be involved in the binding of the 125P5C8 protein to itself or other proteins. Protein AK025164 is novel, it was isolated from normal colon library, and has not been associated with any cancers. In addition, 125P5C8 is homologous to several yeast proteins, one of which is predicted to be localized to the cell surface and involved in sensitivity to certain drugs (FIG. 4B).

Materials and Methods

LAPC Xenografts and Human Tissues:

LAPC xenografts were obtained from Dr. Charles Sawyers (UCLA) and generated as described (Klein et al, 1997, Nature Med. 3: 402-408; Craft et al., 1999, Cancer Res. 59: 5030-5036). Androgen dependent and independent LAPC-4 xenografts LAPC-4 AD and AI, respectively) and LAPC-9 AD and AI xenografts were grown in male SCID mice and were passaged as small tissue chunks in recipient males. LAPC-4 and -9 AI xenografts were derived from LAPC-4 or -9 AD tumors, respectively. To generate the AI xenografts, male mice bearing AD tumors were castrated and maintained for 2-3 months. After the tumors re-grew, the tumors were harvested and passaged in castrated males or in female SCID mice.

Cell Lines:

Human cell lines (e.g., HeLa) were obtained from the ATCC and were maintained in DMEM with 5% fetal calf serum.

RNA Isolation:

Tumor tissue and cell lines were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.

```
DPNCDN (cDNA synthesis primer):
                                       (SEQ ID NO: 7)
5'TTTTGATCAAGCTT₃₀3'

Adaptor 1:
                                       (SEQ ID NO: 8)
5'CTAATACGACTCACTATAGGGCTCGAGCGGCCGCCCGGGCAG3'

(SEQ ID NO: 9)
3'GGCCCGTCCTAG5'

Adaptor 2:
                                       (SEQ ID NO: 10)
5'GTAATACGACTCACTATAGGGCAGCGTGGTCGCGGCCGAG3'

(SEQ ID NO: 11)
3'CGGCTCCTAG5'

PCR primer 1:
                                       (SEQ ID NO: 12)
5'CTAATACGACTCACTATAGGGC3'

Nested primer (NP)1:
                                       (SEQ ID NO: 13)
5'TCGAGCGGCCGCCCGGGCAGGA3'

Nested primer (NP)2:
                                       (SEQ ID NO: 14)
5'AGCGTGGTCGCGGCCGAGGA3'
```

Suppression Subtractive Hybridization:

Suppression Subtractive Hybridization (SSH) was used to identify cDNAs corresponding to genes that may be differentially expressed in prostate cancer. The SSH reaction utilized cDNA from two LAPC-9 AD xenografts. Specifically, to isolate genes that are involved in the progression of androgen dependent (AD) prostate cancer to androgen independent (AI) cancer, an experiment was conducted with the LAPC-9 AD xenograft in male SCID mice. Mice that harbored LAPC-9 AD xenografts were castrated when the tumors reached a size of 1 cm in diameter. The tumors regressed in size and temporarily stopped producing the androgen dependent protein PSA. Seven to fourteen days post-castration, PSA levels were detectable again in the blood of the mice. Eventually the tumors develop an AI phenotype and start growing again in the castrated males. Tumors were harvested at different time points after castration to identify genes that are turned on or off during the transition to androgen independence.

The gene 125P5C8 was derived from an LAPC-9 AD tumor (14 days post-castration) minus an LAPC-9 AD tumor (grown in intact male mouse) subtraction. The SSH DNA sequence of 278 bp (FIG. 1) was identified.

The cDNA derived from an LAPC-9 AD tumor (14 days post-castration) was used as the source of the "tester" cDNA, while the cDNA from the LAPC-9 AD tumor (grown in intact male mouse) was used as the source of the "driver" cDNA. Double stranded cDNAs corresponding to tester and driver cDNAs were synthesized from 2 μg of poly(A)⁺ RNA isolated from the relevant xenograft tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs at 37° C. Digested cDNA was extracted with phenol/chloroform (1:1) and ethanol precipitated.

Driver cDNA was generated by combining in a 1:1 ratio Dpn II digested cDNA from the relevant xenograft source (see above) with a mix of digested cDNAs derived from the human cell lines HeLa, 293, A431, Colo205, and mouse liver.

Tester cDNA was generated by diluting 1 μl of Dpn II digested cDNA from the relevant xenograft source (see above) (400 ng) in 5 μl of water. The diluted cDNA (2 μl, 160 ng) was then ligated to 2 μl of Adaptor 1 and Adaptor 2 (10 μM), in separate ligation reactions, in a total volume of 10 μl at 16° C. overnight, using 400 u of T4 DNA ligase (CLONTECH). Ligation was terminated with 1 μl of 0.2 M EDTA and heating at 72° C. for 5 min.

The first hybridization was performed by adding 1.5 μl (600 ng) of driver cDNA to each of two tubes containing 1.5 μl (20 ng) Adaptor 1- and Adaptor 2-ligated tester cDNA. In a final volume of 4 μl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 μl of fresh denatured driver cDNA and were allowed to hybridize overnight at 68° C. The second hybridization was then diluted in 200 μl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 μl of the diluted final hybridization mix was added to 1 μl of PCR primer 1 (10 μM), 0.5 μl dNTP mix (10 μM), 2.5 μl 10×reaction buffer (CLONTECH) and 0.5 μl 50×Advantage cDNA polymerase Mix (CLONTECH) in a final volume of 25 μl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 μl from the pooled and diluted primary PCR reaction was added to the same reaction mix as used for PCR 1, except that primers NP1 and NP2 (10 μM) were used instead of PCR primer 1. PCR 2 was performed using 10-12 cycles of 94° C. for 10 sec, 68° C. for 30 sec, and 72° C. for 1.5 minutes. The PCR products were analyzed using 2% agarose gel electrophoresis.

The PCR products were inserted into pCR2.1 using the T/A vector cloning kit (Invitrogen). Transformed *E. coli* were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis:

First strand cDNAs can be generated from 1 µg of mRNA with oligo (dT)12-18 priming using the Gibco-BRL Superscript Preamplification system. The manufacturer's protocol was used which included an incubation for 50 min at 42° C. with reverse transcriptase followed by RNAse H treatment at 37° C. for 20 min. After completing the reaction, the volume can be increased to 200 µl with water prior to normalization. First strand cDNAs from 16 different normal human tissues can be obtained from Clontech.

Normalization of the first strand cDNAs from multiple tissues was performed by using the primers 5'atatcgc-cgcgctcgtcgtcgacaa3' (SEQ ID NO: 15) and 5'agccacacg-cagctcattgtagaagg 3' (SEQ ID NO: 16) to amplify β-actin. First strand cDNA (5 µl) were amplified in a total volume of 50 µl containing 0.4 µM primers, 0.2 µM each dNTPs, 1×PCR buffer (Clontech, 10 mM Tris-HCL, 1.5 mM $MgCl_2$, 50 mM KCl, pH8.3) and 1X Klentaq DNA polymerase (Clontech). Five µl of the PCR reaction can be removed at 18, 20, and 22 cycles and used for agarose gel electrophoresis. PCR was performed using an MJ Research thermal cycler under the following conditions: Initial denaturation can be at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 b.p. β-actin bands from multiple tissues were compared by visual inspection. Dilution factors for the first strand cDNAs were calculated to result in equal β-actin band intensities in all tissues after 22 cycles of PCR. Three rounds of normalization can be required to achieve equal band intensities in all tissues after 22 cycles of PCR.

To determine expression levels of the 125P5C8 gene, 5 µl of normalized first strand cDNA were analyzed by PCR using 26, and 30 cycles of amplification. Semi-quantitative expression analysis can be achieved by comparing the PCR products at cycle numbers that give light band intensities.

In a typical RT-PCR Expression analysis shown in FIG. 5. RT-PCR expression analysis was performed on first strand cDNAs generated using pools of tissues from multiple samples. The cDNAs were subsequently normalized using beta-actin PCR. Expression of 125P5C8 was observed in prostate cancer xenografts, normal prostate tissue pools, prostate cancer tissue pools, colon cancer tissue pools, kidney cancer tissue pools, and bladder cancer tissue pools.

Example 2

Full Length Cloning of 125P5C8 and Homology Comparison to Known Sequences

To isolate genes that are involved in the progression of androgen dependent (AD) prostate cancer to androgen independent (AI) cancer, we conducted an experiment with the LAPC-4 AD xenograft in male SCID mice. Mice that harbored LAPC-9 AD xenografts were castrated when the tumors reached a size of 1 cm in diameter. The tumors regressed in size and temporarily stopped producing the androgen dependent protein PSA. Seven to fourteen days post-castration, PSA levels were detectable again in the blood of the mice. Eventually the tumors develop an AI phenotype and start growing again in the castrated males. Tumors were harvested at different time points after castration to identify genes that are turned on or off during the transition to androgen independence.

The gene 125P5C8 was derived from an LAPC-9 AD (14 days post-castration) minus LAPC-9 AD (no castration) subtraction. The SSH DNA sequence of 287 bp (FIG. 1) was designated 125P5C8. The full-length cDNA clone 125P5C8-Pro-pCR2.1 (FIG. 2) was identified by assembling EST fragments homologous to 125P5C8 into a large contiguous sequence with an ORF and amplifying the ORF by PCR using prostate first strand cDNA. The cDNA clone 125P5C8-Pro-pCR2.1 encodes a 699 amino acid ORF with 10 transmembrane domains predicted at the cell surface based on PSORT analysis (http://psort.nibb.ac.jp:8800/form.html).

The 125P5C8 protein is expected to be a cell surface protein based on topology algorithms. This can be confirmed by IHC, immunofluorescence, flow cytometry and cell fractionation techniques, using engineered cell lines, as well as non-engineered cell lines and primary tissues that express 125P5C8. When 125P5C8 is expressed at the cell surface, it is used as a target for diagnostic, preventative and therapeutic purposes.

The 125P5C8 protein is similar to GenBank protein AK025164 with one amino acid difference (FIG. 4A). This amino acid difference at amino acid position 689 may be significant since it is located in the long extracellular C-terminal region that may be involved in signal transduction, ligand binding, may affect the stability of the protein, or may be involved in the binding of the 125P5C8 protein to itself or other proteins. In addition, 125P5C8 is homologous to several yeast proteins, one of which is predicted to be localized to the cell surface and be involved in sensitivity to certain drugs (FIG. 4B).

At the protein level, 125P5C8 shows 33% identity and 49% homology to YCR017 (SPAC589), a 5-transmembrane containing yeast protein proposed to play a role in drug sensitivity. In addition, 125P5C8 has 23% identity and 20% homology to an ABC transporter (E81015) containing 13 transmembrane domains. Most of the homology to the ABC transporter was located between amino acids 80-330 of 125P5C8, and overlaps with one of the transporter motifs of the ABC protein. Based on protein motifs present in 125P5C8 as well as homology analysis, 125P5C8 can function as (1) a protein transporter or drug resistance gene, (2) an ion symporter or (3) ion channel.

The 125P5C8 cDNA was deposited on Mar. 1, 2001 with the American Type Culture Collection (ATCC; Manassas, Va.) as plasmid "*Escherichia coli* DH5A 125P5C8PRO", and has been assigned Accession No. PTA-3137.

Example 3

Chromosomal Mapping of the 125P5C8 Gene

The chromosomal localization of 125P5C8 was determined using the NCBI Human Genome web site (http://www.ncbi.nlm.nih.gov/genome/seq/page.cgi?F=HsBlast.html&&ORG=Hs). The mapping program placed 125P5C8 on chromosome 6q23, between D6S1040 and D6S457, a genomic region found to be rearranged in certain cancers.

Example 4

Expression Analysis of 125P5C8 in Normal Tissues, Cancer Cell Lines and Patient Samples Expression analysis by RT-PCR demonstrated that normal tissue expression of 125P5C8 is restricted predominantly to prostate and, to lower extent, it is detected in a pool of kidney, liver and lung (FIG. 5). Analysis of human cancer patient RNA pools showed expression in prostate, bladder kidney, as well as colon cancers (FIG. 5).

Figure 6B:
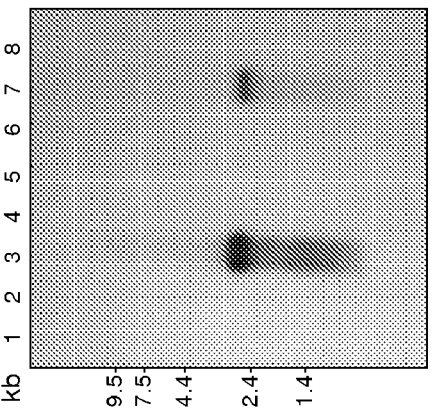
Figure 6A:
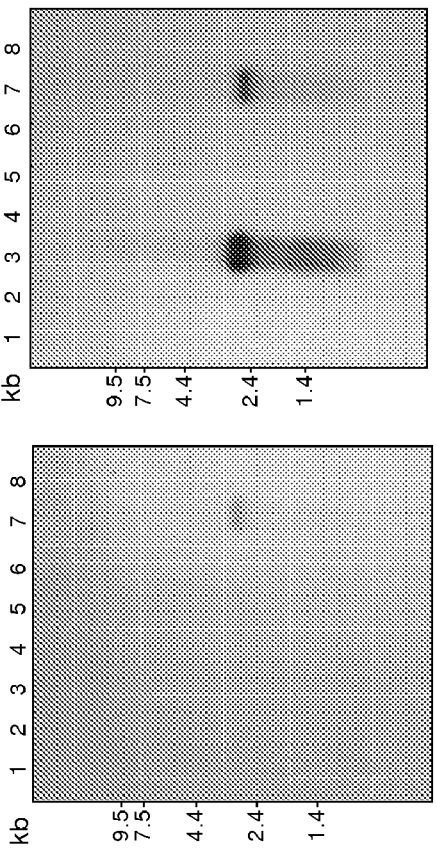

Extensive Northern blot analysis of 125P5C8 in 16 human normal tissues confirms the expression observed by RT-PCR (FIGS. 6A and 6B). A 3 kb transcript is detected in normal prostate and to lower extent in colon and kidney. 125P5C8 expression was also shown in prostate cancer xenografts (FIG. 6C). Expression is highest in LAPC4AI and LAPC9AI when compared to the androgen dependent counterparts suggesting a role in acquiring androgen independent tumor growth.

Figure 7:
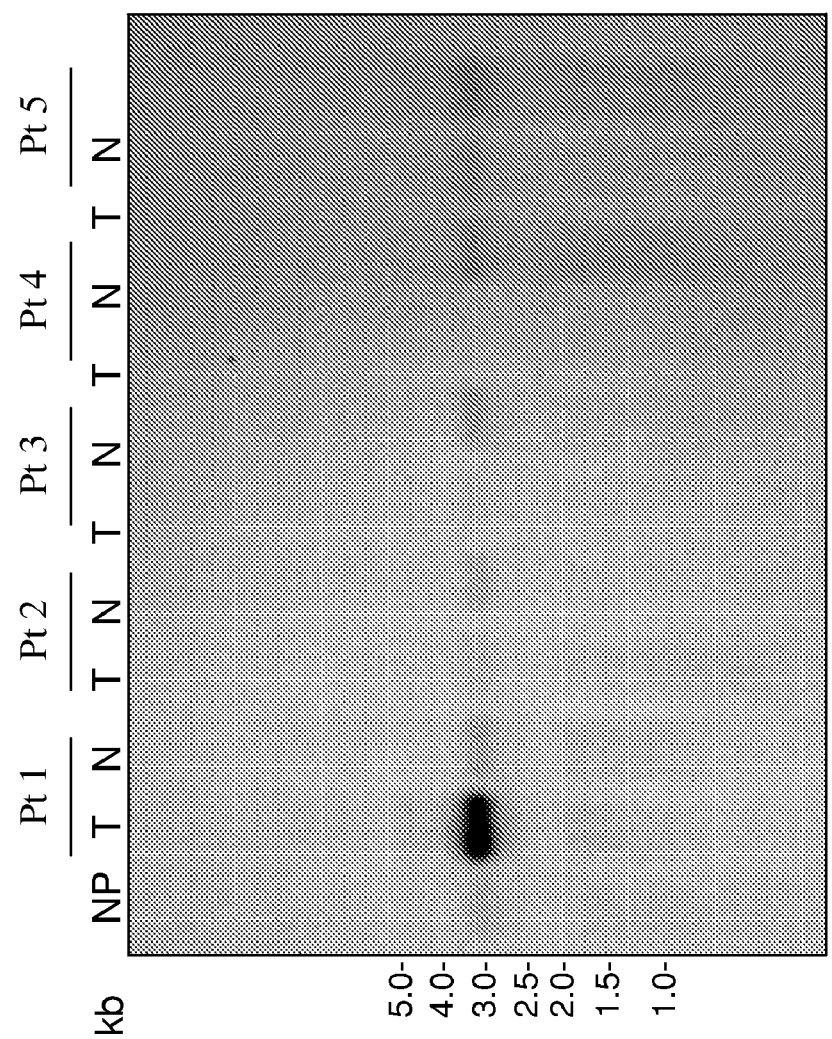
FIG. 7. Expression of 125P5C8 in prostate cancer patient tissues. RNA was extracted from normal prostate, normal adjacent to tumor, and tumor tissues. Northern blots with 10 μg of total RNA were probed with the 125P5C8 SSH fragment. Size standards in kilobases are on the side. Results show expression in tumor-normal pairs with overexpression in patient 1 tumor. Pt 1=Patient 1—Gleason 7; Pt 2=Patient 2—Gleason 7; Pt 3=Patient 3—Gleason 7; Pt 4=Patient 4—Gleason 8; Pt 5=Patient 5—Gleason 7; NP=Normal prostate; N=Normal adjacent tissue; T=Tumor.

Northern blot analysis shows that 125P5C8 is expressed in prostate tumor tissues derived from prostate cancer patients (FIG. 7). One of five tumor-normal prostate pairs shows overexpression in tumor. The expression of 125P5C8 in kidney cancer is down-regulated when compared to the normal and adjacent kidney tissues (FIG. 8).

Biological Relevance

The expression pattern of 125P5C8 is prostate-restricted. In normal tissues 125P5C8 is only expressed in prostate and at lower levels in kidney and colon. High expression is also seen in prostate cancer xenografts and in prostate cancer patient samples. Accordingly, the expression pattern of 125P5C8 indicates its utility in prostate cancer.

Therapeutic applications for 125P5C8 include use as a small molecule therapy and/or a vaccine (T cell or antibody) target. Diagnostic applications for 125P5C8 include use as a diagnostic marker for local and/or metastasized disease. 125P5C8 is expressed in the LAPC-4 and LAPC-9 xenografts that are derived from lymph node and bone metastasis of prostate cancer, respectively. The restricted expression of 125P5C8 in normal tissues makes it useful as a tumor target for diagnosis and therapy. 125P5C8 expression analysis provides information useful for predicting susceptibility to advanced stage disease, rate of progression, and/or tumor aggressiveness. 125P5C8 expression status in patient samples, tissue arrays and/or cell lines may be analyzed by: (i) immunohistochemical analysis; (ii) in situ hybridization; (iii) RT-PCR analysis on laser capture micro-dissected samples; (iv) Western blot analysis; and (v) Northern analysis.

Example 5

Generation of 125P5C8 Polyclonal Antibodies

Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. For example, 125P5C8, recombinant bacterial fusion proteins or peptides encoding various regions of the 125P5C8 sequence are used to immunize New Zealand White rabbits. Typically a peptide can be designed from a coding region of 125P5C8. The peptide can be conjugated to keyhole limpet hemocyanin (KLH) and used to immunize a rabbit. Alternatively the immunizing agent may include all or portions of the 125P5C8 protein, analogs or fusion proteins thereof. For example, the 125P5C8 amino acid sequence can be fused to any one of a variety of fusion protein partners that are well known in the art, such as maltose binding protein, LacZ, thioredoxin or an immunoglobulin constant region (see e.g. *Current Protocols In Molecular Biology*, Volume 2, Unit 16, Frederick M. Ausubul et al. eds., 1995; Linsley, P. S., Brady, W., Urnes, M., Grosmaire, L., Damle, N., and Ledbetter, L. (1991) *J. Exp. Med.* 174, 561-566). Other recombinant bacterial proteins include glutathione-S-transferase (GST), and HIS tagged fusion proteins of 125P5C8 that are purified from induced bacteria using the appropriate affinity matrix.

It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate).

In a typical protocol, rabbits are initially immunized subcutaneously with up to 200 μg, typically 5-50 μg, of fusion protein or peptide conjugated to KLH mixed in complete Freund's adjuvant. Rabbits are then injected subcutaneously every two weeks with up to 200 μg, typically 5-50 μg, of immunogen in incomplete Freund's adjuvant. Test bleeds are taken approximately 7-10 days following each immunization and used to monitor the titer of the antiserum by ELISA.

To test serum, such as rabbit serum, for reactivity with 125P5C8 proteins, the full-length 125P5C8 cDNA can be cloned into an expression vector such as one that provides a 6His tag at the carboxyl-terminus (pCDNA 3.1 myc-his, Invitrogen). After transfection of the constructs into 293T cells, cell lysates can be probed with anti-His antibody (Santa Cruz Biotechnologies, Santa Cruz, Calif.) and the anti-125P5C8 serum using Western blotting. Alternatively specificity of the antiserum is tested by Western blot and immunoprecipitation analyses using lysates of cells that express 125P5C8. Serum from rabbits immunized with GST or MBP fusion proteins is first semi-purified by removal of anti-GST or anti-MBP antibodies by passage over GST and MBP protein columns respectively. Sera from His-tagged protein and peptide immunized rabbits as well as depleted GST and MBP protein sera are purified by passage over an affinity column composed of the respective immunogen covalently coupled to Affigel matrix (BioRad).

Example 6

Generation of 125P5C8 Monoclonal Antibodies (MAbs)

In one embodiment, therapeutic MAbs to 125P5C8 will include those that react with extracellular epitopes of 125P5C8. Immunogens for generation of such MAbs are designed to encode or contain extracellular regions of the 125P5C8 protein predicted from protein topology algorithms. These immunogens include peptides, recombinant bacterial proteins, and mammalian expressed Tag5 proteins and human and murine IgG FC fusion proteins. The membrane topology of 125P5C8 is that of a 10 transmembrane protein (Table XIX) with the amino-terminus embedded in the membrane and the long carboxy terminus extracellular (Sosui topology prediction). Thus, extracellular regions useful to include in immunogen design are the carboxy terminus encoding amino acids 412-699 and inter-transmembrane sequences encoding amino acids 65-93, amino acids 143-188, amino acids 261-268, and amino acids 341-349. Alternatively, if the carboxy terminus is intracellular, extracellular regions useful to include in antigen design are amino acids 24-41, amino acids 117-119, amino acids 212-237, amino acids 292-317, and amino acids 369-389. To generate MAbs to 125P5C8, mice are first immunized intraperitoneally (IP) with up to 200 µg, typically 10-50 µg, of protein immunogen mixed in complete Freund's adjuvant. Mice are then subsequently immunized IP every 2-4 weeks with up to 200 µg, typically 10-50 µg, of antigen mixed in Freund's incomplete adjuvant. Alternatively, Ribi adjuvant is used immunizations. In addition, a DNA-based immunization protocol is employed in which a mammalian expression vector encoding 125P5C8 sequence is used to immunize mice by direct injection of the plasmid DNA. For example, pCDNA 3.1 encoding either the full length 125P5C8 cDNA or extracellular coding regions of 125P5C8 fused to the coding sequence of murine or human IgG are used. This protocol is used alone or in combination with protein immunogens. Test bleeds are taken 7-10 days following immunization to monitor titer and specificity of the immune response. Once appropriate reactivity and specificity is obtained as determined by ELISA, Western blotting, and immunoprecipitation analyses, fusion and hybridoma generation is then carried with established procedures well known in the art (Harlow and Lane, 1988).

In one embodiment for generating 125P5C8 monoclonal antibodies, a glutathione-S-transferase (GST) fusion protein encompassing the carboxy-terminal domain of 125P5C8 (amino acids 412-699) is expressed, purified, and used as immunogen. Balb C mice are initially immunized intraperitoneally with 25 µg of the GST-125P5C8 fusion protein mixed in complete Freund's adjuvant. Mice are subsequently immunized every two weeks with 25 µg of GST-125P5C8 protein mixed in Freund's incomplete adjuvant for a total of three immunizations. To determine titer of serum from immunized mice, ELISA is carried out using a 125P5C8-specific cleavage fragment of the immunogen in which GST is removed by site specific proteolysis. Reactivity and specificity of serum to full length 125P5C8 protein is monitored by Western blotting and flow cytometry using 293T cells transfected with an expression vector encoding the 125P5C8 cDNA (Example 7). Mice showing the strongest reactivity are rested for three weeks and given a final injection of 125P5C8 cleavage fragment in PBS and then sacrificed four days later. The spleens of the sacrificed mice are then harvested and fused to SPO/2 myeloma cells using standard procedures (Harlow and Lane, 1988). Supernatants from growth wells following HAT selection are screened by ELISA, Western blot, and flow cytometry to identify 125P5C8 specific antibody-producing clones.

The binding affinity of a 125P5C8 monoclonal antibody is determined using standard technologies. Affinity measurements quantify the strength of antibody to epitope binding and can be used to help define which 125P5C8 monoclonal antibodies are preferred for diagnostic or therapeutic use. The BIAcore system (Uppsala, Sweden) is a preferred method for determining binding affinity. The BIAcore system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Example 7

Production of Recombinant 125P5C8 in Bacterial and Mammalian Systems

Bacterial Constructs pGEX Constructs

To express 125P5C8 in bacterial cells, portions of 125P5C8 are fused to the Glutathione S-transferase (GST) gene by cloning into pGEX-6P-1 (Amersham Pharmacia Biotech, NJ). The constructs were made in order to generate recombinant 125P5C8 protein sequences with GST fused at the N-terminus and a six histidine epitope at the C-terminus. The six histidine epitope tag is generated by adding the histidine codons to the cloning primer at the 3' end of the open reading frame (ORF). A PreScission™ recognition site permits cleavage of the GST tag from 125P5C8-related protein. The ampicillin resistance gene and pBR322 origin permits selection and maintenance of the plasmid in *E. coli*. For example, cDNA encoding the following fragments of 125P5C8 protein were cloned into pGEX-6P-1: amino acids 1 to 141; amino acids 142 to 288; amino acids 142 to 188, amino acids 188 to 410; and amino acids 411 to 699, or any 8, 9, 10, 11, 12, 13, 14 or 15 contiguous amino acids from 125P5C8 or an analog thereof.

pMAL Constructs

To express 125P5C8 in bacterial cells, all or part of the 125P5C8 nucleic acid sequence are fused to the maltose-binding protein (MBP) gene by cloning into pMAL-c2X and pMAL-p2X (New England Biolabs, MA). The constructs are made to generate recombinant 125P5C8 protein sequences with MBP fused at the N-terminus and a six histidine epitope at the C-terminus. The six histidine epitope tag is generated by adding the histidine codons to the 3' cloning primer. A Factor Xa recognition site permits cleavage of the GST tag from 125P5C8. The pMAL-c2X and pMAL-p2X vectors are optimized to express the recombinant protein in the cytoplasm or periplasm respectively. Periplasm expression enhances folding of proteins with disulfide bonds. For example, cDNA encoding the following fragments of 125P5C8 protein are cloned into pMAL-c2X and pMAL-p2X: amino acids 1 to 141; amino acids 142 to 288; amino acids 142 to 188, amino acids 188 to 410; and amino acids 411 to 699, or any 8, 9, 10, 11, 12, 13, 14 or 15 contiguous amino acids from 125P5C8 or an analog thereof.

pCRII

To generate 125P5C8 sense and anti-sense riboprobes for RNA in situ investigations, a pCRII construct (Invitrogen, Carlsbad Calif.) is generated using cDNA sequence encoding amino acids 1 to 141, and 142 to 288. The pCRII vector has Sp6 and T7 promoters flanking the insert to drive the production of 125P5C8 RNA riboprobes which are used in RNA in situ hybridization experiments.

Mammalian Constructs

To express recombinant 125P5C8, the full or partial length 125P5C8 cDNA can be cloned into any one of a variety of expression vectors known in the art. The constructs can be transfected into any one of a wide variety of mammalian cells such as 293T cells. Transfected 293T cell lysates can be probed with the anti-125P5C8 polyclonal serum, described in Example 5 above, in a Western blot.

The 125P5C8 genes can also be subcloned into the retroviral expression vector pSRαMSVtkneo and used to establish 125P5C8-expressing cell lines as follows: The 125P5C8 coding sequence (from translation initiation ATG and Kozak translation start consensus sequence to the termination codons) is amplified by PCR using ds cDNA template from 125P5C8 cDNA. The PCR product is subcloned into pSRαMSVtkneo vector and transformed into DH5α competent cells. Colonies are picked to screen for clones with unique internal restriction sites on the cDNA. The positive clone is confirmed by sequencing of the cDNA insert. The retroviral vectors can thereafter be used for infection and generation of various cell lines using, for example, NIH 3T3, TsuPrl, 293 or rat-1 cells.

Additional illustrative mammalian and bacterial systems are discussed below.

pcDNA4/HisMax-TOPO Constructs

To express 125P5C8 in mammalian cells, the 125P5C8 ORF is cloned into pcDNA4/HisMax-TOPO Version A (cat# K864-20, Invitrogen, Carlsbad, Calif.). Protein expression is driven from the cytomegalovirus (CMV) promoter and the SP163 translational enhancer. The recombinant protein has Xpress™ and six histidine epitopes fused to the N-terminus to aid in detection and purification of the recombinant protein. The pcDNA4/HisMax-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in E. coli.

pcDNA3.1/MycHis Constructs

To express 125P5C8 in mammalian cells, the ORF with consensus Kozak translation initiation site was cloned into pcDNA3.1/MycHis_Version A (Invitrogen, Carlsbad, Calif.). Protein expression is driven from the cytomegalovirus (CMV) promoter. The recombinant protein has the myc epitope and six histidines fused to the C-terminus to aid in detection and purification of the recombinant protein. The pcDNA3.1/MycHis vector also contains the bovine growth hormone (BGH) polyadenylation signal and transcription termination sequence to enhance mRNA stability, along with the SV40 origin for episomal replication and simple vector rescue in cell lines expressing the large T antigen. The Neomycin resistance gene can be used, as it allows for selection of mammalian cells expressing the protein and the ampicillin resistance gene and ColE1 origin permits selection and maintenance of the plasmid in E. coli.

pcDNA3.1/V5His-TOPO Constructs

To express 125P5C8 in mammalian cells, the cDNA encoding the 125P5C8 ORF and Kozak consensus translation initiation sequence is cloned into pcDNA4/V5His-TOPO (cat# K4800-01, Invitrogen, Carlsbad, Calif.). Protein expression is driven from the cytomegalovirus (CMV) promoter. The recombinant protein has V5™ and six histidine epitopes fused at the C-terminus to aid in detection and purification of the recombinant protein. The pcDNA4/V5His-TOPO vector also contains the bovine growth hormone (BGH) polyadenylation signal and transcription termination sequence to enhance mRNA stability along with the SV40 origin for episomal replication and simple vector rescue in cell lines expressing the large T antigen. The Zeocin resistance gene allows for selection of mammalian cells expressing the protein and the ampicillin resistance gene and ColE1 origin permits selection and maintenance of the plasmid in E. coli.

pcDNA3.1CT-GFP-TOPO Construct

To express 125P5C8 in mammalian cells and to allow detection of the recombinant protein using fluorescence, the ORF with consensus Kozak translation initiation site is cloned into pcDNA3.1CT-GFP-TOPO (Invitrogen, CA). Protein expression is driven from the cytomegalovirus (CMV) promoter. The recombinant protein has the Green Fluorescent Protein (GFP) fused to the C-terminus facilitating non-invasive, in vivo detection and cell biology studies. The pcDNA3.1/MycHis vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells that express the protein, and the ampicillin resistance gene and ColE1 origin permits selection and maintenance of the plasmid in E. coli. An additional construct with a N-terminal GFP fusion is made in pcDNA3.1NT-GFP-TOPO spanning the entire length of the 125P5C8 protein.

pAPtag Constructs

The cDNA encoding 125P5C8 amino acids 142-188 and 411-699 are cloned into pAPtag-5 (GenHunter Corp. Nashville, Tenn.). This construct generates an alkaline phosphatase fusion at the C-terminus of the 125P5C8 protein while fusing the IgGK signal sequence to N-terminus. The resulting recombinant 125P5C8 protein is optimized for secretion into the media of transfected mammalian cells and can be used to identify proteins such as ligands or receptors that interact with the 125P5C8 protein. Protein expression is driven from the CMV promoter and the recombinant protein also contains myc and six histidines fused to the C-terminus of alkaline phosphatase to aid in detection and purification of the recombinant protein. The Zeosin resistance gene allows for selection of mammalian cells expressing the protein and the ampicillin resistance gene permits selection of the plasmid in E. coli.

ptag5 Constructs

The cDNA encoding for 125P5C8 amino acids 142-188 and 411-699 are cloned into pTag-5. This vector is similar to pAPtag but without the alkaline phosphatase fusion. This construct generates an immunoglobulin G1 Fc fusion at the C-terminus of the 125P5C8 protein while fusing the IgGK signal sequence to the N-terminus. The resulting recombinant 125P5C8 protein is optimized for secretion into the media of transfected mammalian cells, and can be used to identify proteins such as ligands or receptors that interact with the 125P5C8 protein. Protein expression is driven from the CMV promoter and the recombinant protein also contains myc and six histidines fused to the C-terminus to aid in detection and purification of the recombinant protein. The Zeocin resistance gene allows for selection of mammalian cells expressing the protein, and the ampicillin resistance gene permits selection of the plasmid in E. coli.

psecFc Constructs

The cDNA encoding for 125P5C8 amino acids 142-188 and 411-699 are cloned into psecFc. The psecFc vector was assembled by cloning immunoglobulin G1 Fc (hinge, CH2, CH3 regions) into pSecTag2 (Invitrogen, California). This construct generates an immunoglobulin G1 Fc fusion at the C-terminus of the 125P5C8 protein, while fusing the IgGK signal sequence to N-terminus. The resulting recombinant 125P5C8 protein is optimized for secretion into the media of transfected mammalian cells, and can be used to identify proteins such as ligands or receptors that interact with the 125P5C8 protein. Protein expression is driven from the CMV promoter. The Zeocin resistance gene allows for selection of mammalian cells that express the protein, and the ampicillin resistance gene permits selection of the plasmid in *E. coli*.

pSRαConstructs

To generate mammalian cell lines that express 125P5C8 constitutively, the ORF is cloned into pSRα constructs. Amphotropic and ecotropic retroviruses are generated by transfection of pSRα constructs into the 293T-10A1 packaging line or co-transfection of pSRα and a helper plasmid ((φ~) in the 293 cells, respectively. The retrovirus can be used to infect a variety of mammalian cell lines, resulting in the integration of the cloned gene, 125P5C8, into the host cell-lines. Protein expression is driven from a long terminal repeat (LTR). The Neomycin resistance gene allows for selection of mammalian cells that express the protein, and the ampicillin resistance gene and ColE1 origin permit selection and maintenance of the plasmid in *E. coli*.

An additional pSRα construct was made that fused the FLAG tag to the C-terminus to allow detection using anti-FLAG antibodies. The FLAG sequence 5' gat tac aag gat gac gac gat aag 3' (SEQ ID NO: 6) were added to cloning primer at the 3' end of the ORF.

Additional pSRα constructs are made to produce both N-terminal and C-terminal GFP and myc/6 HIS fusion proteins of the full-length 125P5C8 protein.

Example 8

Production of Recombinant 125P5C8 in a Baculovirus System

To generate a recombinant 125P5C8 protein in a baculovirus expression system, cDNA sequence encoding the 125P5C8 protein is cloned into the baculovirus transfer vector pBlueBac 4.5 (Invitrogen), which provides a His-tag at the N-terminus Specifically, pBlueBac-125P5C8 is co-transfected with helper plasmid pBac-N-Blue (Invitrogen) into SF9 (*Spodoptera frugiperda*) insect cells to generate recombinant baculovirus (see Invitrogen instruction manual for details). Baculovirus is then collected from cell supernatant and purified by plaque assay.

Recombinant 125P5C8 protein is then generated by infection of HighFive insect cells (Invitrogen) with the purified baculovirus. Recombinant 125P5C8 protein can be detected using anti-125P5C8 antibody. 125P5C8 protein can be purified and used in various cell-based assays or as immunogen to generate polyclonal and monoclonal antibodies specific for 125P5C8.

Example 9

Identification of Potential Signal Transduction Pathways

Transporters have been reported to interact with a variety of signaling molecules and regulate signaling pathways (J Neurochem. 2001; 76:217-223). Using immunoprecipitation and Western blotting techniques, we can identify proteins that associate with 125P5C8 and mediate signaling events. Several pathways known to play a role in cancer biology can be regulated by 125P5C8, including phospholipid pathways such as PI3K, AKT, etc, as well as mitogenic/survival cascades such as ERK, p38, etc (Cell Growth Differ. 2000,11: 279; J Biol Chem. 1999, 274:801; Oncogene. 2000, 19:3003.). Using Western blotting techniques, we can evaluate the role that 125P5C8 plays in the regulation of these pathways. Cells lacking 125P5C8 and cells expressing 125P5C8 are either left untreated or stimulated with cytokines, androgen and anti-integrin Ab. Cell lysates are analyzed using anti-phosphos-specific antibodies (Cell Signaling, Santa Cruz Biotechnology) in order to detect phosphorylation and regulation of ERK, p38, AKT, PI3K, PLC and other signaling molecules. When 125P5C8 plays a role in the regulation of signaling pathways, 125P5C8 is used as a target for diagnostic, preventative and therapeutic purposes.

To determine whether 125P5C8 directly or indirectly activates known signal transduction pathways in cells, luciferase (luc) based transcriptional reporter assays are carried out in cells expressing 125P5C8. These transcriptional reporters contain consensus-binding sites for known transcription factors that lie downstream of well-characterized signal transduction pathways. The reporters and examples of these associated transcription factors, signal transduction pathways, and activation stimuli are listed below.

1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress 125P5C8-mediated effects can be assayed in cells showing mRNA expression. Luciferase reporter plasmids can be introduced by lipid-mediated transfection (TFX-50, Promega). Luciferase activity, an indicator of relative transcriptional activity, is measured by incubation of cell extracts with luciferin substrate and luminescence of the reaction is monitored in a luminometer.

Signaling pathways activated by 125P5C8 are mapped and used for the identification and validation of therapeutic targets in the 125P5C8 pathway. When 125P5C8 is involved in cell signaling, it is used as a target for diagnostic, preventative and therapeutic purposes.

Example 10

Involvement of 125P5C8 in Tumor Progression

125P5C8 can contribute to the growth of cancer cells. The role of 125P5C8 in tumor growth is investigated in prostate, colon and kidney cell lines as well as NIH 3T3 cells engineered to stably express 125P5C8. Parental 125P5C8 negative cells and 125P5C8-expressing cells are evaluated for cell growth using a well-documented proliferation assay (Fraser S P, Grimes J A, Djamgoz M B. Prostate. 2000;44:61, Johnson D E, Ochieng J, Evans S L. Anticancer Drugs. 1996, 7:288).

To determine the role of 125P5C8 in the transformation process, we investigate its effect in colony forming assays. Parental NIH3T3 cells lacking 125P5C8 are compared to NHI-3T3-125P5C8 cells in a soft agar assay under stringent and more permissive conditions (Song Z. et al. Cancer Res. 2000;60:6730).

To determine the role of 125P5C8 in invasion and metastasis of cancer cells, we use a well-established Transwell Insert System assay (Becton Dickinson) (Cancer Res. 1999; 59:6010). Cells lacking 125P5C8 and cells expressing 125P5C8 are loaded with the fluorescent dye, calcein, and plated in the top well of the Transwell insert. Invasion is determined by fluorescence of cells in the lower chamber relative to the fluorescence of the entire cell population.

125P5C8 can also play a role in cell cycle and apoptosis. PC3-125P5C8 cells are compared to 125P5C8-negative PC3 for differences in cell cycle regulation using a well-established BrdU assay (Abdel-Malek Z A. J Cell Physiol. 1988, 136:247). In short, cells are grown under both optimal (full serum) and limiting (low serum) conditions are labeled with BrdU for 1 hour and stained with anti-BrdU Ab and propidium iodide. Cells are analyzed for entry into the G1, S, and G2M phases of the cell cycle. Alternatively, the effect of stress on apoptosis is evaluated in 125P5C8-negative cells and 125P5C8-expressing cells, including normal and tumor prostate, colon and lung cells. Engineered and parental cells treated with various chemotherapeutic agents and protein synthesis inhibitors are stained with annexin V-FITC. Cell death is measured by FACS analysis.

The effect of 125P5C8 on stress- and chemotherapeutic-induced cell death can be evaluated by FACS. 125P5C8-negative cells and 125P5C8-expressing cells are treated with various chemotherapeutic agents, such as etoposide, flutamide, etc, and protein synthesis inhibitors, such as cycloheximide. The cells are stained with annexin V-FITC and cell death is measured.

Furthermore, 125P5C8-expressing cells, such as normal and tumor prostate, colon and lung cells, are compared to 125P5C8-negative cells for differences in cell cycle regulation using a well-established BrdU assay (Abdel-Malek Z A. J Cell Physiol. 1988, 136:247). In short, cells grown under both optimal (full serum) and limiting (low serum) conditions are labeled with BrdU for 1 hour and stained with anti-BrdU Ab and propidium iodide. Cells are analyzed for entry into the G1, S, and G2M phases of the cell cycle.

When 125P5C8 plays a role in cell growth, transformation, invasion or apoptosis, it is used as a target for diagnostic, preventative and therapeutic purposes.

Example 11

Western Analysis of 125P5C8 Expression in Subcellular Fractions

The cellular location of 125P5C8 can be assessed using subcellular fractionation techniques widely used in cellular biology (Storrie B, et al. Methods Enzymol. 1990;182:203-25). Prostate or other cell lines can be separated into nuclear, cytosolic and membrane fractions. The expression of 125P5C8 in the different fractions can be tested using Western blotting techniques.

Alternatively, to determine the subcellular localization of 125P5C8, 293T cells can be transfected with an expression vector encoding HIS-tagged 125P5C8 (PCDNA 3.1 MYC/HIS, Invitrogen). The transfected cells can be harvested and subjected to a differential subcellular fractionation protocol as previously described (Pemberton, P. A. et al, 1997, J of Histochemistry and Cytochemistry, 45:1697-1706.) This protocol separates the cell into fractions enriched for nuclei, heavy membranes (lysosomes, peroxisomes, and mitochondria), light membranes (plasma membrane and endoplasmic reticulum), and soluble proteins.

Example 12

Protein Transporter Function

Using a modified rhodamine retention assay (Davies J et al. Science 2000, 290:2295; Leith C et al. Blood 1995, 86:2329) one can determine whether 125P5C8 functions as a protein transporter. Cell lines, such as prostate, colon and kidney cancer and normal cells, expressing or lacking 125P5C8 are loaded with Calcein AM (Molecular Probes). Cells are examined over time for dye transport using a fluorescent microscope or fluorometer. Quantitation is performed using a fluorometer (Hollo Z. et al. 1994. 1191:384). Information obtained from such experiments is used in determining whether 125P5C8 extrudes chemotherapeutic drugs, such as doxorubicin, paclitaxel, etoposide, etc, from tumor cells, thereby lowering drug content and reducing tumor responsiveness to treatment. Using this technique, we are able to identify substrates for 125P5C8, and determine which drugs may be more efficacious in treating individual patients. When 125P5C8 functions as a protein transporter, 125P5C8 is used as a target for preventative and therapeutic purposes as well as drug sensitivity/resistance.

The function of 125P5C8 as an ion channel is determined by FACS analysis and electrophysiology (Gergely L, Cook L, Agnello V. Clin Diagn Lab Immunol. 1997;4:70; Skryma R, et al. J Physiol. 2000, 527: 71). Using FACS analysis and commercially available indicators (Molecular Probes), the ability of parental cells and cells expressing 125P5C8 to transport calcium, sodium and potassium is compared. Prostate, colon and kidney normal and tumor cell lines are used in these studies. For example cells loaded with calcium responsive indicators such as Fluo4 and Fura red are incubated in the presence or absence of ions and analyzed by flow cytometry. Information derived from these experiments provides a mechanism by which cancer cells are regulated. This is particularly true in the case of calcium, as calcium channel inhibitors have been reported to induce the death of certain cancer cells, including prostate cancer cell lines (Batra S, Popper L D, Hartley-Asp B. Prostate. 1991,19: 299).

The 125P5C8 protein can function as a sodium symporter. In this case, 125P5C8 co-transports ions and/or proteins along with sodium. Several molecules have been identified to co-transport with Na+, the most common being iodide. The sodium/iodide co-transporter was shown to be over-expressed in breast cancer and to play a role in iodide uptake in thyroid cancer cells (Tazebay U et al. Nat. Med. 2000, 6:871; Filetti S et al. Eur. J. Endocrinol. 1999. 141: 443). In addition, the sodium/iodide symporter has been associated with radioiodine treatment modality in prostate and thyroid cancer (Spitzweg C et al. Cancer Res. 2000, 60:6526). In these studies $^{131}$I was (1) injected into tumor cells in vivo experiment or (2) used to bathe tumor cells in vitro. In either case, accumulation of $^{131}$I induced tumor cell death. The function of 125P5C8 as a co-transporter of iodide and sodium is studied using FACS analysis techniques as well as labeled $^{131}$I. This study is critical in light of the importance of Na+/I− transporter in therapy. When 125P5C8 is a sodium symporter, it is used as a target for diagnostic, preventative and therapeutic purposes.

Using electrophysiology, uninjected oocytes and oocytes injected with 125P5C8 cRNA are compared for ion channel activity. Patch/voltage clamp assays are performed on oocytes in the presence or absence of selected ions, including calcium, potassium, sodium, etc. Ion channel activators (such as cAMP/GMP, forskolin, TPA, etc) and inhibitors (such as calcicludine, conotoxin, TEA, tetrodotoxin, etc) are used to evaluate the function of 125P5C8 as an ion channel. When 125P5C8 functions as an ion channel, it is used as a target for diagnostic, preventative and therapeutic purposes.

Example 13

Involvement of 125P5C8 in Cell-Cell Communication

Multi-transmembrane proteins have the ability to mediate intercellular communications. Cell expressing 125P5C8 are compared to cells lacking 125P5C8 using two types of assays (J. Biol. Chem. 2000, 275:25207). In the first assay, cells loaded with a fluorescent dye are incubated in the presence of unlabeled recipient cells and the cell populations are examined under fluorescent microscopy. This qualitative assay measures the exchange of dye between adjacent cells. In the second assay system, donor and recipient cell populations are treated as above and quantitative measurements of the recipient cell population are performed by FACS analysis. Using these two assay systems, we can determine whether 125P5C8 enhances or suppresses cell communications, and whether small molecules and/or specific antibodies modulate the function of 125P5C8.

When 125P5C8 function in cell-cell communication, it is used as a target for diagnostic, preventative and therapeutic purposes Example 14

Regulation of Transcription by 125P5C8

The 125P5C8 protein can play a role in transcriptional regulation of eukaryotic genes. Regulation of gene expression can be evaluated by studying gene expression in cells expressing or lacking 125P5C8. For this purpose, two types of experiments are performed. In the first set of experiments, RNA from parental and 125P5C8-expressing NIH3T3 and PC3 cells, respectively, are extracted and hybridized to commercially available gene arrays (Clontech). Resting cells as well as cells treated with FBS or androgen are compared. Differentially expressed genes are identified in accordance with procedures known in the art. The differentially expressed genes are then mapped to biological pathways.

In the second set of experiments, specific transcriptional pathway activation is evaluated using commercially available (Stratagene) luciferase reporter constructs including: NFkB-luc, SRE-luc, ELK1-luc, ARE-luc, p53-luc, and CRE-luc. These transcriptional reporters contain consensus binding sites for known transcription factors that lie downstream of well-characterized signal transduction pathways, and represent a good tool to ascertain pathway activation and screen for positive and negative modulators of pathway activation.

When 125P5C8 plays a role in gene regulation, 125P5C8 is used as a target for diagnostic, prognostic, preventative and therapeutic purposes.

Example 15

In Vivo Assay for 125P5C8 Tumor Growth Promotion

The effect of the 125P5C8 protein on tumor cell growth can be evaluated in vivo by gene overexpression in tumor-bearing mice. For example, SCID mice can be injected SQ on each flank with $1 \times 10^6$ of either PC3, TSUPR1, or DU145 cells containing tkNeo empty vector or 125P5C8. At least two strategies may be used: (1) Constitutive 125P5C8 expression under regulation of a promoter such as a constitutive promoter obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems. (2) Regulated expression under control of an inducible vector system, such as ecdysone, tet, etc., can be used provided such promoters are compatible with the host cell systems. Tumor volume is then monitored at the appearance of palpable tumors and is followed over time to determine if 125P5C8-expressing cells grow at a faster rate and whether tumors produced by 125P5C8-expressing cells demonstrate characteristics of altered aggressiveness (e.g. enhanced metastasis, vascularization, reduced responsiveness to chemotherapeutic drugs). Additionally, mice can be implanted with $1 \times 10^5$ of the same cells orthotopically to determine if 125P5C8 has an effect on local growth in the prostate or on the ability of the cells to metastasize, specifically to lungs, lymph nodes, and bone marrow. Also see Saffran et al, "Anti-PSCA mAbs inhibit tumor growth and metastasis formation and prolong the survival of mice bearing human prostate cancer xenografts" PNAS 10:1073-1078 or www.pnas.org/cgi/doi/10.1073/pnas.051624698.

The assay is also useful to determine the 125P5C8 inhibitory effect of candidate therapeutic compositions, such as for example, 125P5C8 intrabodies, 125P5C8 antisense molecules and ribozymes.

Example 16

125P5C8 Monoclonal Antibody-Mediated Inhibition of Prostate Tumors In Vivo

The significant expression of 125P5C8, in cancer tissues, together with its restrictive expression in normal tissues along with its expected cell surface expression makes 125P5C8 an excellent target for antibody therapy. Similarly, 125P5C8 is a target for T cell-based immunotherapy. Thus, the therapeutic efficacy of anti-125P5C8 mAbs in human prostate cancer xenograft mouse models is evaluated by using androgen-independent LAPC-4 and LAPC-9 xenografts (Craft, N., et al., Cancer Res, 1999. 59(19): p. 5030-6) and the androgen independent recombinant cell line PC3-125P5C8 (see, e.g., Kaighn, M. E., et al., Invest Urol, 1979. 17(1): p. 16-23).

Antibody efficacy on tumor growth and metastasis formation is studied, e.g., in a mouse orthotopic prostate cancer xenograft model. The antibodies can be unconjugated, as discussed in this Example, or can be conjugated to a therapeutic modality, as appreciated in the art. We demonstrate that anti-125P5C8 MAbs inhibit formation of both the androgen-dependent LAPC-9 and androgen-independent PC3-125P5C8 tumor xenografts. Anti-125P5C8 mAbs also retard the growth of established orthotopic tumors and prolonged survival of tumor-bearing mice. These results indicate the utility of anti-125P5C8 mAbs in the treatment of local and advanced stages of prostate cancer. (See, e.g., (Saffran, D., et al., PNAS 10:1073-1078 or www.pnas.org/cgi/doi/10.1073/pnas.051624698)

Administration of the anti-125P5C8 mAbs led to retardation of established orthotopic tumor growth and inhibition of metastasis to distant sites, resulting in a significant prolongation in the survival of tumor-bearing mice. These studies indicate that 125P5C8 as an attractive target for immunotherapy and demonstrate the therapeutic potential of anti-125P5C8 mAbs for the treatment of local and metastatic prostate cancer. This example demonstrates that unconjugated 125P5C8 monoclonal antibodies are effective to inhibit the growth of human prostate tumor xenografts grown in SCID mice; accordingly a combination of such efficacious monoclonal antibodies is also effective.

Tumor Inhibition using Multiple Unconjugated 125P5C8 mAbs

Materials and Methods

125P5C8 Monoclonal Antibodies:

Monoclonal antibodies are raised against 125P5C8 as described in Example 6. The antibodies are characterized by ELISA, Western blot, FACS, and immunoprecipitation for their capacity to bind 125P5C8. Epitope mapping data for the anti-125P5C8 mAbs, as determined by ELISA and Western analysis, recognize epitopes on the 125P5C8 protein. Immunohistochemical analysis of prostate cancer tissues and cells with these antibodies is performed.

The monoclonal antibodies are purified from ascites or hybridoma tissue culture supernatants by Protein-G Sepharose chromatography, dialyzed against PBS, filter sterilized, and stored at −20° C. Protein determinations are performed by a Bradford assay (Bio-Rad, Hercules, Calif.). A therapeutic monoclonal antibody or a cocktail comprising a mixture of individual monoclonal antibodies is prepared and used for the treatment of mice receiving subcutaneous or orthotopic injections of LAPC-9 prostate tumor xenografts.

Prostate Cancer Xenografts and Cell Lines.

The LAPC-9 xenograft, which expresses a wild-type androgen receptor and produces prostate-specific antigen (PSA), is passaged in 6- to 8-week-old male ICR-severe combined immunodeficient (SCID) mice (Taconic Farms) by s.c. trocar implant (Craft, N., et al., supra). Single-cell suspensions of LAPC-9 tumor cells are prepared as described in Craft, et al. The prostate carcinoma cell line PC3 (American Type Culture Collection) is maintained in DMEM supplemented with L-glutamine and 10% (vol/vol) FBS.

A PC3-125P5C8 cell population is generated by retroviral gene transfer as described in Hubert, R. S., et al., *STEAP: a prostate-specific cell-surface antigen highly expressed in human prostate tumors*. Proc Natl Acad Sci USA, 1999. 96(25): p. 14523-8. Anti-125P5C8 staining is detected by using an FITC-conjugated goat anti-mouse antibody (Southern Biotechnology Associates) followed by analysis on a Coulter Epics-XL flow cytometer.

Xenograft Mouse Models.

Subcutaneous (s.c.) tumors are generated by injection of $1 \times 10^6$ LAPC-9, PC3, or PC3-125P5C8 cells mixed at a 1:1 dilution with Matrigel (Collaborative Research) in the right flank of male SCID mice. To test antibody efficacy on tumor formation, i.p. antibody injections are started on the same day as tumor-cell injections. As a control, mice are injected with either purified mouse IgG (ICN) or PBS; or a purified monoclonal antibody that recognizes an irrelevant antigen not expressed in human cells. In preliminary studies, no difference is found between mouse IgG or PBS on tumor growth. Tumor sizes are determined by vernier caliper measurements, and the tumor volume is calculated as length×width×height. Mice with s.c. tumors greater than 1.5 cm in diameter are sacrificed. PSA levels are determined by using a PSA ELISA kit (Anogen, Mississauga, Ontario). Circulating levels of anti-125P5C8 mAbs are determined by a capture ELISA kit (Bethyl Laboratories, Montgomery, Tex.). (See, e.g., (Saffran, D., et al., PNAS 10:1073-1078 or www.pnas.org/cgi/doi/10.1073/pnas.051624698)

Orthotopic injections are performed under anesthesia by using ketamine/xylazine. An incision is made through the abdominal muscles to expose the bladder and seminal vesicles, which then are delivered through the incision to expose the dorsal prostate. LAPC-9 cells ($5 \times 10^5$) mixed with Matrigel are injected into each dorsal lobe in a 10-µl volume. To monitor tumor growth, mice are bled on a weekly basis for determination of PSA levels. Based on the PSA levels, the mice are segregated into groups for the appropriate treatments. To test the effect of anti-125P5C8 mAbs on established orthotopic tumors, i.p. antibody injections are started when PSA levels reach 2-80 ng/ml.

Anti-125P5C8 mAbs Inhibit Growth of 125P5C8-Expressing Prostate-Cancer Tumors

We next test the effect of anti-125P5C8 mAbs on tumor formation by using the LAPC-9 orthotopic model. As compared with the s.c. tumor model, the orthotopic model, which requires injection of tumor cells directly in the mouse prostate, results in a local tumor growth, development of metastasis in distal sites, deterioration of mouse health, and subsequent death (Saffran, D., et al., PNAS supra; Fu, X., et al., Int J Cancer, 1992. 52(6): p. 987-90; Kubota, T., J Cell Biochem, 1994. 56(1): p. 4-8). The features make the orthotopic model more representative of human disease progression and allowed us to follow the therapeutic effect of mAbs on clinically relevant end points.

Accordingly, LAPC-9 tumor cells are injected into the mouse prostate, and 2 days later, the mice are segregated into two groups and treated with either up to 200 µg, usually 10-50 µg, of anti-125P5C8 Ab or PBS three times per week for two to five weeks. Mice are monitored weekly for circulating PSA levels as an indicator of tumor growth.

A major advantage of the orthotopic prostate-cancer model is the ability to study the development of metastases. Formation of metastasis in mice bearing established orthotopic tumors is studies by IHC analysis on lung sections using an antibody against a prostate-specific cell-surface protein STEAP expressed at high levels in LAPC-9 xenografts (Hubert, R. S., et al., Proc Natl Acad Sci USA, 1999. 96(25): p. 14523-8).

Mice bearing established orthotopic LAPC-9 tumors are administered 11 injections of either anti-125P5C8 mAb or PBS over a 4-week period. Mice in both groups are allowed to establish a high tumor burden (PSA levels greater than 300 ng/ml), to ensure a high frequency of metastasis formation in mouse lungs. Mice then are killed and their prostate and lungs are analyzed for the presence of LAPC-9 cells by anti-STEAP IHC analysis.

These studies demonstrate a broad anti-tumor efficacy of anti-125P5C8 antibodies on initiation and progression of prostate cancer in xenograft mouse models. Anti-125P5C8 antibodies inhibit tumor formation of both androgen-dependent and androgen-independent tumors as well as retarding the growth of already established tumors and prolong the survival of treated mice. Moreover, anti-125P5C8 mAbs demonstrate a dramatic inhibitory effect on the spread of local prostate tumor to distal sites, even in the presence of a large tumor burden. Thus, anti-125P5C8 mAbs are efficacious on major clinically relevant end points/PSA levels (tumor growth), prolongation of survival, and health.

Example 17

Androgen Regulation of 125P5C8

Since 125P5C8 was derived from a LAPC-9 AD (14 days post-castration) minus LAPC-9 AD (no castration) subtraction, androgen regulation of 125P5C8 expression is studied (FIG. 11). LAPC-4 AD and LAPC-9 AD cells are grown in charcoal-stripped medium and stimulated with the synthetic androgen mibolerone, for either 14 or 24 hours. Expression of 125P5C8 is studied before and after stimulation with mibolerone. The experimental samples are confirmed by testing for the expression of the androgen-regulated prostate cancer gene PSA. In another experiment, 125P5C8 expression is analyzed in LAPC-9 AD and LAPC-9 AI tumors grown in castrated mice. Only, androgen independent tumors will grow in castrated mice.

When 125P5C8 expression is regulated by androgen, 125P5C8 is a target for diagnostic, preventative and therapeutic purposes.

Throughout this application, various publications and applications are referenced (within parentheses for example). The disclosures of these publications and applications are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

Tables

TABLE I

Tissues that Express 125P5C8 When Malignant

Prostate
Bladder
Kidney
Colon

TABLE II

AMINO ACID ABBREVIATIONS

| SINGLE LETTER | THREE LETTER | FULL NAME |
| --- | --- | --- |
| F | Phe | phenylalanine |
| L | Leu | leucine |
| S | Ser | serine |
| Y | Tyr | tyrosine |
| C | Cys | cysteine |
| W | Trp | tryptophan |
| P | Pro | proline |
| H | His | histidine |
| Q | Gln | glutamine |
| R | Arg | arginine |
| I | Ile | isoleucine |
| M | Met | methionine |
| T | Thr | threonine |
| N | Asn | asparagine |
| K | Lys | lysine |
| V | Val | valine |
| A | Ala | alanine |
| D | Asp | aspartic acid |
| E | Glu | glutamic acid |
| G | Gly | glycine |

TABLE III

AMINO ACID SUBSTITUTION MATRIX

Adapted from the GCG Software 9.0 BLOSUM62 amino acid substitution matrix (block substitution matrix). The higher the value, the more likely a substitution is found in related, natural proteins.

| A | C | D | E | F | G | H | I | K | L | M | N | P | Q | R | S | T | V | W | Y | |
|---|---|---|---|---|---|---|---|---|---|---|---|---|---|---|---|---|---|---|---|---|
| 4 | 0 | −2 | −1 | −2 | 0 | −2 | −1 | −1 | −1 | −1 | −2 | −1 | −1 | −1 | 1 | 0 | 0 | −3 | −2 | A |
|   | 9 | −3 | −4 | −2 | −3 | −3 | −1 | −3 | −1 | −1 | −3 | −3 | −3 | −3 | −1 | −1 | −1 | −2 | −2 | C |
|   |   | 6 | 2 | −3 | −1 | −1 | −3 | −1 | −4 | −3 | 1 | −1 | 0 | −2 | 0 | −1 | −3 | −4 | −3 | D |
|   |   |   | 5 | −3 | −2 | 0 | −3 | 1 | −3 | −2 | 0 | −1 | 2 | 0 | 0 | −1 | −2 | −3 | −2 | E |
|   |   |   |   | 6 | −3 | −1 | 0 | −3 | 0 | 0 | −3 | −4 | −3 | −3 | −2 | −2 | −1 | 1 | 3 | F |
|   |   |   |   |   | 6 | −2 | −4 | −2 | −4 | −3 | 0 | −2 | −2 | −2 | 0 | −2 | −3 | −2 | −3 | G |
|   |   |   |   |   |   | 8 | −3 | −1 | −3 | −2 | 1 | −2 | 0 | 0 | −1 | −2 | −3 | −2 | 2 | H |
|   |   |   |   |   |   |   | 4 | −3 | 2 | 1 | −3 | −3 | −3 | −3 | −2 | −1 | 3 | −3 | −1 | I |
|   |   |   |   |   |   |   |   | 5 | −2 | −1 | 0 | −1 | 1 | 2 | 0 | −1 | −2 | −3 | −2 | K |
|   |   |   |   |   |   |   |   |   | 4 | 2 | −3 | −3 | −2 | −2 | −2 | −1 | 1 | −2 | −1 | L |
|   |   |   |   |   |   |   |   |   |   | 5 | −2 | −2 | 0 | −1 | −1 | −1 | 1 | −1 | −1 | M |
|   |   |   |   |   |   |   |   |   |   |   | 6 | −2 | 0 | 0 | 1 | 0 | −3 | −4 | −2 | N |
|   |   |   |   |   |   |   |   |   |   |   |   | 7 | −1 | −2 | −1 | −1 | −2 | −4 | −3 | P |
|   |   |   |   |   |   |   |   |   |   |   |   |   | 5 | 1 | 0 | −1 | −2 | −2 | −1 | Q |
|   |   |   |   |   |   |   |   |   |   |   |   |   |   | 5 | −1 | −1 | −3 | −3 | −2 | R |
|   |   |   |   |   |   |   |   |   |   |   |   |   |   |   | 4 | 1 | −2 | −3 | −2 | S |
|   |   |   |   |   |   |   |   |   |   |   |   |   |   |   |   | 5 | 0 | −2 | −2 | T |
|   |   |   |   |   |   |   |   |   |   |   |   |   |   |   |   |   | 4 | −3 | −1 | V |
|   |   |   |   |   |   |   |   |   |   |   |   |   |   |   |   |   |   | 11 | 2 | W |
|   |   |   |   |   |   |   |   |   |   |   |   |   |   |   |   |   |   |   | 7 | Y |

TABLE IV (A)

HLA CLASS I SUPERMOTIFS

| SUPERMOTIF | POSITION 2 | C-TERMINUS |
|---|---|---|
| A2 | L, I, V, M, A, T, Q | L,. I, V, M, A, T |
| A3 | A, V, I, L, M, S, T | R, K |
| B7 | P | A, L, I, M, V, F, W, Y |
| B44 | D, E | F, W, Y, L, I, M, V, A |
| A1 | T, S, L, I, V, M | F, W, Y |
| A24 | F, W, Y, L, V, I, M, T | F, I, Y, W, L, M |
| B27 | R, H, K | A, L, I, V, M, Y, F, W |
| B58 | A, S, T | F, W, Y, L, I, V |
| B62 | L, V, M, P, I, Q | F, W, Y, M, I, V |

TABLE IV (B)

HLA CLASS II SUPERMOTIF

| 1 | 6 | 9 |
|---|---|---|
| W, F, Y, V, .I, L | A, V, I, L, P, C, S, T | A, V, I, L, C, S, T, M, Y |

TABLE V

Peptide Scoring Results - 125P5C8 A1 9-mers

| Rank | Start Position | Subsequence Residue Listing | Score (Estimate of Half Time of Disassociation of A Molecule Containing This Subsequence) |
|---|---|---|---|
| 1 | 41 | GLEGFSIAF | 45.000 |
| 2 | 635 | DSEIQMAKF | 27.000 |
| 3 | 490 | YTDFGPSTR | 12.500 |
| 4 | 371 | NLDLLLQTK | 10.000 |
| 5 | 583 | TSAPGSRDY | 7.500 |
| 6 | 514 | KSEHHLLPS | 6.750 |
| 7 | 231 | GPDPNPFGG | 6.250 |
| 8 | 22 | YHDLGPMIY | 6.250 |
| 9 | 602 | DIDSTDHDR | 5.000 |
| 10 | 541 | LVDFVVTHF | 5.000 |
| 11 | 213 | FGEVSLVSR | 4.500 |
| 12 | 36 | TLELTGLEG | 4.500 |
| 13 | 249 | LMLPSCLWF | 2.500 |
| 14 | 269 | TASAAGLLY | 2.500 |
| 15 | 132 | VLVVLRIWY | 2.500 |
| 16 | 431 | AIWPFRFGY | 2.500 |
| 17 | 24 | DLGPMIYYF | 2.000 |
| 18 | 611 | WCEYIMYRG | 1.800 |
| 19 | 466 | ESDASKPYM | 1.500 |
| 20 | 388 | KSEKYMKLF | 1.350 |
| 21 | 315 | TMTIAMIFY | 1.250 |
| 22 | 314 | KTMTIAMIF | 1.250 |
| 23 | 645 | IPDDPTNYR | 1.250 |
| 24 | 562 | AIAVSKLLK | 1.000 |
| 25 | 413 | KAYERKLGK | 1.000 |
| 26 | 54 | FLTITPFWK | 1.000 |
| 27 | 9 | LLESLLGCV | 0.900 |
| 28 | 324 | LLEIFFCAW | 0.900 |
| 29 | 551 | NHEDDLDRK | 0.900 |
| 30 | 630 | HAELSDSEI | 0.900 |
| 31 | 159 | LSAIATLDR | 0.750 |
| 32 | 141 | TSLNPIWSY | 0.750 |
| 33 | 348 | RSDVLLGTM | 0.750 |
| 34 | 112 | WSGSHLQRY | 0.750 |
| 35 | 633 | LSDSEIQMA | 0.750 |
| 36 | 573 | SNQVIFLGY | 0.625 |
| 37 | 358 | LIIGLNMLF | 0.500 |
| 38 | 49 | FLSPIFLTI | 0.500 |
| 39 | 429 | SAAIWPFRF | 0.500 |
| 40 | 644 | RIPDDPTNY | 0.500 |
| 41 | 407 | GLGLRHKAY | 0.500 |
| 42 | 482 | WLGEKLGFY | 0.500 |
| 43 | 614 | YIMYRGLIR | 0.500 |
| 44 | 76 | ITIGSIASF | 0.500 |
| 45 | 199 | GAAFGSLVF | 0.500 |
| 46 | 594 | LTEHGNVKD | 0.450 |
| 47 | 524 | EGEIAPAIT | 0.450 |
| 48 | 522 | SPEGEIAPA | 0.450 |
| 49 | 559 | KLQAIAVSK | 0.400 |
| 50 | 463 | TILESDASK | 0.400 |

TABLE VI

HLA Peptide Scoring Results-125P5C8-A1 10-mers

| Rank | Start Position | Subsequence Residue Listing | Score (Estimate of Half Time of Disassociation of A Molecule Containing This Subsequence) |
|---|---|---|---|
| 1 | 633 | LSDSEIQMAK | 75.000 |
| 2 | 605 | STDHDRWCEY | 62.500 |

TABLE VI-continued

HLA Peptide Scoring Results-125P5C8-A1 10-mers

| Rank | Start Position | Subsequence Residue Listing | Score (Estimate of Half Time of Disassociation of A Molecule Containing This Subsequence) |
|---|---|---|---|
| 3 | 490 | YTDFGPSTRY | 62.500 |
| 4 | 464 | ILESDASKPY | 45.000 |
| 5 | 635 | DSEIQMAKFR | 13.500 |
| 6 | 440 | DNEGWSSLER | 11.250 |
| 7 | 659 | VIDHREVSEK | 10.000 |
| 8 | 36 | TLELTGLEGF | 9.000 |
| 9 | 22 | YHDLGPMIYY | 6.250 |
| 10 | 268 | GTASAAGLLY | 6.250 |
| 11 | 314 | KTMTIAMIFY | 6.250 |
| 12 | 572 | SSNQVIFLGY | 3.750 |
| 13 | 171 | DGDCSKPEEK | 2.500 |
| 14 | 430 | AAIWPFRFGY | 2.500 |
| 15 | 131 | IVLVVLRIWY | 2.500 |
| 16 | 458 | GADFITILES | 2.500 |
| 17 | 662 | HREVSEKIHF | 2.250 |
| 18 | 594 | LTEHGNVKDI | 2.250 |
| 19 | 41 | GLEGFSIAFL | 1.800 |
| 20 | 324 | LLEIFFCAWC | 1.800 |
| 21 | 466 | ESDASKPYMG | 1.500 |
| 22 | 665 | VSEKIHFNPR | 1.350 |
| 23 | 140 | YTSLNPIWSY | 1.250 |
| 24 | 309 | GTNPGKTMTI | 1.250 |
| 25 | 582 | ITSAPGSRDY | 1.250 |
| 26 | 231 | GPDPNPFGGA | 1.250 |
| 27 | 524 | EGEIAPAITL | 1.125 |
| 28 | 182 | TGEVATGMAS | 1.125 |
| 29 | 454 | LNETGADFIT | 1.125 |
| 30 | 57 | ITPFWKLVNK | 1.000 |
| 31 | 505 | MALSRYPIVK | 1.000 |
| 32 | 561 | QAIAVSKLLK | 1.000 |
| 33 | 462 | ITILESDASK | 1.000 |
| 34 | 9 | LLESLLGCVS | 0.900 |
| 35 | 630 | HAELSDSEIQ | 0.900 |
| 36 | 611 | WCEYIMYRGL | 0.900 |
| 37 | 428 | VSAAIWPFRF | 0.750 |
| 38 | 348 | RSDVLLGTMM | 0.750 |

TABLE VI-continued

HLA Peptide Scoring Results-125P5C8-A1 10-mers

| Rank | Start Position | Subsequence Residue Listing | Score (Estimate of Half Time of Disassociation of A Molecule Containing This Subsequence) |
|---|---|---|---|
| 39 | 388 | KSEKYMKLFL | 0.675 |
| 40 | 329 | FCAWCTAFKF | 0.500 |
| 41 | 541 | LVDFVVTHFG | 0.500 |
| 42 | 158 | TLSAIATLDR | 0.500 |
| 43 | 531 | ITLTVNISGK | 0.500 |
| 44 | 320 | MIFYLLEIFF | 0.500 |
| 45 | 13 | LLGCVSWSLY | 0.500 |
| 46 | 371 | NLDLLLQTKN | 0.500 |
| 47 | 56 | TITPFWKLVN | 0.500 |
| 48 | 526 | EIAPAITLTV | 0.500 |
| 49 | 383 | KVLFRKSEKY | 0.500 |
| 50 | 357 | MLIIGLNMLF | 0.500 |

TABLE VII

HLA Peptide Scoring Results - 125P5C8-A2 9-mers

| Rank | Start Position | Subsequence Residue Listing | Score (Estimate of Half Time of Disassociation of A Molecule Containing This Subsequence) |
|---|---|---|---|
| 1 | 323 | YLLEIFFCA | 3820.380 |
| 2 | 62 | KLVNKKWML | 560.763 |
| 3 | 204 | SLVFLTHWV | 382.536 |
| 4 | 126 | FILGQIVLV | 374.369 |
| 5 | 277 | YLHTWAAAV | 319.939 |
| 6 | 8 | ILLESLLGC | 294.675 |
| 7 | 13 | LLGCVSWSL | 272.371 |
| 8 | 92 | RLMVLALGV | 257.342 |
| 9 | 211 | WVFGEVSLV | 238.235 |
| 10 | 275 | LLYLHTWAA | 202.694 |
| 11 | 615 | IMYRGLIRL | 193.040 |
| 12 | 254 | CLWFRGTGL | 177.308 |
| 13 | 392 | YMKLFLWLL | 162.824 |
| 14 | 351 | VLLGTMMLI | 150.931 |
| 15 | 364 | MLFGPKKNL | 134.369 |
| 16 | 241 | VLLCLASGL | 134.369 |
| 17 | 127 | ILGQIVLVV | 111.499 |

TABLE VII-continued

HLA Peptide Scoring Results - 125P5C8-A2 9-mers

| Rank | Start Position | Subsequence Residue Listing | Score (Estimate of Half Time of Disassociation of A Molecule Containing This Subsequence) |
|---|---|---|---|
| 18 | 398 | WLLVGVGLL | 108.713 |
| 19 | 133 | LVVLRIWYT | 105.168 |
| 20 | 274 | GLLYLHTWA | 101.099 |
| 21 | 49 | FLSPIFLTI | 91.183 |
| 22 | 188 | GMASRPNWL | 84.856 |
| 23 | 357 | MLIIGLNML | 83.527 |
| 24 | 56 | TITPFWKLV | 61.780 |
| 25 | 258 | RGTGLIWWV | 43.075 |
| 26 | 316 | MTIAMIFYL | 37.007 |
| 27 | 68 | WMLTLLRII | 24.186 |
| 28 | 356 | MMLIIGLNM | 22.569 |
| 29 | 216 | VSLVSRWAV | 21.418 |
| 30 | 28 | MIYYFPLQT | 21.182 |
| 31 | 120 | YLRIWGFIL | 17.760 |
| 32 | 319 | AMIFYLLEI | 17.330 |
| 33 | 261 | GLIWWVTGT | 17.140 |
| 34 | 352 | LLGTMMLII | 16.725 |
| 35 | 473 | YMGNNDLTM | 16.505 |
| 36 | 149 | YQMSNKVIL | 15.114 |
| 37 | 200 | AAFGSLVFL | 13.887 |
| 38 | 90 | KLRLMVLAL | 13.070 |
| 39 | 504 | IMALSRYPI | 12.809 |
| 40 | 156 | ILTLSAIAT | 12.668 |
| 41 | 150 | QMSNKVILT | 12.379 |
| 42 | 284 | AVSGCVFAI | 12.178 |
| 43 | 376 | LQTKNSSKV | 11.988 |
| 44 | 97 | ALGVSSSLI | 10.433 |
| 45 | 47 | IAFLSPIFL | 10.264 |
| 46 | 540 | KLVDFVVTH | 9.346 |
| 47 | 42 | LEGFSIAFL | 8.933 |
| 48 | 560 | LQAIAVSKL | 8.469 |
| 49 | 34 | LQTLELTGL | 8.469 |
| 50 | 154 | KVILTLSAI | 7.349 |

TABLE VIII

HLA Peptide Scoring Results - 125P5C8 A2 10-mers

| Rank | Start Position | Subsequence Residue Listing | SEQ ID NO: | Score (Estimate of Half Time of Disassociation of a Molecule Containing This Subsequence) |
|---|---|---|---|---|
| 1 | 482 | WLGEKLGFYT | 165 | 4483.377 |
| 2 | 394 | KLFLWLLVGV | 166 | 2071.606 |
| 3 | 54 | FLTITPFWKL | 167 | 1400.305 |
| 4 | 132 | VLVVLRIWYT | 168 | 1201.914 |
| 5 | 315 | TMTIAMIFYL | 169 | 1131.982 |
| 6 | 567 | KLLKSSSNQV | 170 | 900.698 |
| 7 | 396 | FLWLLVGVGL | 171 | 815.616 |
| 8 | 12 | SLLGCVSWSL | 172 | 592.807 |
| 9 | 8 | ILLESLLGCV | 173 | 536.309 |
| 10 | 356 | MMLIIGLNML | 174 | 223.203 |
| 11 | 453 | LLNETGADFI | 175 | 195.971 |
| 12 | 559 | KLQAIAVSKL | 176 | 171.967 |

TABLE VIII-continued

HLA Peptide Scoring Results - 125P5C8 A2 10-mers

| Rank | Start Position | Subsequence Residue Listing | SEQ ID NO: | Score (Estimate of Half Time of Disassociation of a Molecule Containing This Subsequence) |
|---|---|---|---|---|
| 13 | 384 | VLFRKSEKYM | 177 | 171.868 |
| 14 | 126 | FILGQIVLVV | 178 | 153.491 |
| 15 | 274 | GLLYLHTWAA | 179 | 137.862 |
| 16 | 49 | FLSPIFLTIT | 180 | 122.836 |
| 17 | 375 | LLQTKNSSKV | 181 | 118.238 |
| 18 | 188 | GMASRPNWLL | 182 | 115.713 |
| 19 | 614 | YIMYRGLIRL | 183 | 114.985 |
| 20 | 330 | CAWCTAFKFV | 184 | 83.786 |
| 21 | 399 | LLVGVGLLGL | 185 | 83.527 |
| 22 | 156 | ILTLSAIATL | 186 | 83.527 |
| 23 | 207 | FLTHWVFGEV | 187 | 79.025 |
| 24 | 351 | VLLGTMMLII | 188 | 61.882 |
| 25 | 536 | NISGKLVDFV | 189 | 59.279 |
| 26 | 363 | NMLFGPKKNL | 190 | 57.085 |
| 27 | 504 | IMALSRYPIV | 191 | 52.518 |
| 28 | 275 | LLYLHTWAAA | 192 | 45.944 |
| 29 | 62 | KLVNKKWMLT | 193 | 44.339 |
| 30 | 591 | YLQLTEHGNV | 194 | 41.592 |
| 31 | 69 | MLTLLRIITI | 195 | 40.792 |
| 32 | 296 | SMWPQTLGHL | 196 | 38.289 |
| 33 | 68 | WMLTLLRIIT | 197 | 37.557 |
| 34 | 323 | YLLEIFFCAW | 198 | 37.545 |
| 35 | 28 | MIYYFPLQTL | 199 | 36.752 |
| 36 | 242 | LLCLASGLML | 200 | 36.316 |
| 37 | 95 | VLALGVSSSL | 201 | 36.316 |
| 38 | 150 | QMSNKVILTL | 202 | 35.485 |
| 39 | 127 | ILGQIVLVVL | 203 | 34.246 |
| 40 | 20 | SLYHDLGPMI | 204 | 33.385 |
| 41 | 149 | YQMSNKVILT | 205 | 29.577 |
| 42 | 97 | ALGVSSSLIV | 206 | 28.516 |
| 43 | 137 | RIWYTSLNPI | 207 | 27.385 |
| 44 | 342 | GVYARERSDV | 208 | 19.475 |
| 45 | 134 | VVLRIWYTSL | 209 | 17.636 |
| 46 | 41 | GLEGFSIAFL | 210 | 17.295 |
| 47 | 46 | SIAFLSPIFL | 211 | 16.155 |

TABLE VIII -continued

HLA Peptide Scoring Results - 125P5C8 A2 10-mers

| Rank | Start Position | Subsequence Residue Listing | SEQ ID NO: | Score (Estimate of Half Time of Disassociation of a Molecule Containing This Subsequence) |
|---|---|---|---|---|
| 48 | 619 | GLIRLGYARI | 212 | 15.649 |
| 49 | 392 | YMKLFLWLLV | 213 | 13.748 |
| 50 | 355 | TMMLIIGLNM | 214 | 13.276 |

TABLE IX

HLA Peptide Scoring Results - 125P5C8 A3 9-mers

| Rank | Start Position | Subsequence Residue Listing | SEQ ID NO: | Score (Estimate of Half Time of Disassociation of a Molecule Containing This Subsequence) |
|---|---|---|---|---|
| 1 | 506 | ALSRYPIVK | 215 | 120.000 |
| 2 | 418 | KLGKVAPTK | 216 | 90.000 |
| 3 | 559 | KLQAIAVSK | 217 | 90.000 |
| 4 | 54 | FLTITPFWK | 218 | 60.000 |
| 5 | 619 | GLIRLGYAR | 219 | 54.000 |
| 6 | 361 | GLNMLFGPK | 220 | 54.000 |
| 7 | 41 | GLEGFSIAF | 221 | 54.000 |
| 8 | 409 | GLRHKAYER | 222 | 36.000 |
| 9 | 371 | NLDLLLQTK | 223 | 30.000 |
| 10 | 532 | TLTVNISGK | 224 | 30.000 |
| 11 | 593 | QLTEHGNVK | 225 | 30.000 |
| 12 | 431 | AIWPFRFGY | 226 | 27.000 |
| 13 | 384 | VLFRKSEKY | 227 | 20.000 |
| 14 | 375 | LLQTKNSSK | 228 | 20.000 |
| 15 | 250 | MLPSCLWFR | 229 | 18.000 |
| 16 | 315 | TMTIAMIFY | 230 | 12.000 |
| 17 | 132 | VLVVLRIWY | 231 | 12.000 |
| 18 | 90 | KLRLMVLAL | 232 | 10.800 |
| 19 | 413 | KAYERKLGK | 233 | 9.000 |
| 20 | 615 | IMYRGLIRL | 234 | 9.000 |
| 21 | 249 | LMLPSCLWF | 235 | 9.000 |
| 22 | 383 | KVLFRKSEK | 236 | 9.000 |
| 23 | 392 | YMKLFLWLL | 237 | 8.100 |
| 24 | 319 | AMIFYLLEI | 238 | 8.100 |
| 25 | 540 | KLVDFVVTH | 239 | 8.100 |
| 26 | 478 | DLTMWLGEK | 240 | 8.100 |

TABLE IX-continued

HLA Peptide Scoring Results - 125P5C8 A3 9-mers

| Rank | Start Position | Subsequence Residue Listing | SEQ ID NO: | Score (Estimate of Half Time of Disassociation of a Molecule Containing This Subsequence) |
|---|---|---|---|---|
| 27 | 62 | KLVNKKWML | 241 | 8.100 |
| 28 | 49 | FLSPIFLTI | 242 | 8.100 |
| 29 | 323 | YLLEIFFCA | 243 | 6.075 |
| 30 | 407 | GLGLRHKAY | 244 | 6.000 |
| 31 | 338 | FVPGGVYAR | 245 | 5.400 |
| 32 | 120 | YLRIWGFIL | 246 | 5.400 |
| 33 | 463 | TILESDASK | 247 | 4.500 |
| 34 | 24 | DLGPMIYYF | 248 | 4.050 |
| 35 | 351 | VLLGTMMLI | 249 | 4.050 |
| 36 | 261 | GLIWWVTGT | 250 | 4.050 |
| 37 | 562 | AIAVSKLLK | 251 | 4.000 |
| 38 | 364 | MLFGPKKNL | 252 | 3.375 |
| 39 | 275 | LLYLHTWAA | 253 | 3.000 |
| 40 | 453 | LLNETGADF | 254 | 3.000 |
| 41 | 205 | LVFLTHWVF | 255 | 3.000 |
| 42 | 405 | LLGLGLRHK | 256 | 3.000 |
| 43 | 296 | SMWPQTLGH | 257 | 3.000 |
| 44 | 254 | CLWFRGTGL | 258 | 3.000 |
| 45 | 691 | HMNTPKYFL | 259 | 2.700 |
| 46 | 404 | GLLGLGLRH | 260 | 2.700 |
| 47 | 482 | WLGEKLGFY | 261 | 2.700 |
| 48 | 13 | LLGCVSWSL | 262 | 2.700 |
| 49 | 394 | KLFLWLLVG | 263 | 2.700 |
| 50 | 188 | GMASRPNWL | 264 | 1.800 |

TABLE X

HLA Peptide Scoring Results - 125P5C8 A3 10-mers

| Rank | Start Position | Subsequence Residue Listing | SEQ ID NO: | Score (Estimate of Half Time of Disassociation of a Molecule Containing This Subsequence) |
|---|---|---|---|---|
| 1 | 361 | GLNMLFGPKK | 265 | 180.000 |
| 2 | 409 | GLRHKAYERK | 266 | 60.000 |
| 3 | 540 | KLVDFVVTHF | 267 | 40.500 |
| 4 | 249 | LMLPSCLWFR | 268 | 40.500 |
| 5 | 374 | LLLQTKNSSK | 269 | 30.000 |

TABLE X-continued

HLA Peptide Scoring Results - 125P5C8 A3 10-mers

| Rank | Start Position | Subsequence Residue Listing | SEQ ID NO: | Score (Estimate of Half Time of Disassociation of a Molecule Containing This Subsequence) |
|---|---|---|---|---|
| 6 | 404 | GLLGLGLRHK | 270 | 20.250 |
| 7 | 480 | TMWLGEKLGF | 271 | 20.000 |
| 8 | 248 | GLMLPSCLWF | 272 | 18.000 |
| 9 | 204 | SLVFLTHWVF | 273 | 9.000 |
| 10 | 188 | GMASRPNWLL | 274 | 8.100 |
| 11 | 54 | FLTITPFWKL | 275 | 8.100 |
| 12 | 158 | TLSAIATLDR | 276 | 8.000 |
| 13 | 12 | SLLGCVSWSL | 277 | 6.075 |
| 14 | 659 | VIDHREVSEK | 278 | 6.000 |
| 15 | 357 | MLIIGLNMLF | 279 | 6.000 |
| 16 | 559 | KLQAIAVSKL | 280 | 5.400 |
| 17 | 394 | KLFLWLLVGV | 281 | 4.500 |
| 18 | 396 | FLWLLVGVGL | 282 | 4.500 |
| 19 | 319 | AMIFYLLEIF | 283 | 4.500 |
| 20 | 351 | VLLGTMMLII | 284 | 4.050 |
| 21 | 323 | YLLEIFFCAW | 285 | 4.050 |
| 22 | 399 | LLVGVGLLGL | 286 | 4.050 |
| 23 | 41 | GLEGFSIAFL | 287 | 4.050 |
| 24 | 13 | LLGCVSWSLY | 288 | 4.000 |
| 25 | 20 | SLYHDLGPMI | 289 | 3.000 |
| 26 | 452 | HLLNETGADF | 290 | 3.000 |
| 27 | 500 | HTWGIMALSR | 291 | 3.000 |
| 28 | 36 | TLELTGLEGF | 292 | 3.000 |
| 29 | 58 | TPFWKLVNKK | 293 | 3.000 |
| 30 | 150 | QMSNKVILTL | 294 | 2.700 |
| 31 | 619 | GLIRLGYARI | 295 | 2.700 |
| 32 | 315 | TMTIAMIFYL | 296 | 2.700 |
| 33 | 142 | SLNPIWSYQM | 297 | 2.700 |
| 34 | 274 | GLLYLHTWAA | 298 | 2.700 |
| 35 | 314 | KTMTIAMIFY | 299 | 2.700 |
| 36 | 531 | ITLTVNISGK | 300 | 2.250 |
| 37 | 296 | SMWPQTLGHL | 301 | 2.025 |
| 38 | 167 | RIGTDGDCSK | 302 | 2.000 |
| 39 | 464 | ILESDASKPY | 303 | 2.000 |
| 40 | 320 | MIFYLLEIFF | 304 | 2.000 |
| 41 | 305 | LINSGTNPGK | 305 | 2.000 |

TABLE X-continued

HLA Peptide Scoring Results - 125P5C8 A3 10-mers

| Rank | Start Position | Subsequence Residue Listing | SEQ ID NO: | Score (Estimate of Half Time of Disassociation of a Molecule Containing This Subsequence) |
|---|---|---|---|---|
| 42 | 383 | KVLFRKSEKY | 306 | 1.800 |
| 43 | 505 | MALSRYPIVK | 307 | 1.800 |
| 44 | 69 | MLTLLRIITI | 308 | 1.800 |
| 45 | 145 | PIWSYQMSNK | 309 | 1.500 |
| 46 | 57 | ITPFWKLVNK | 310 | 1.500 |
| 47 | 462 | ITILESDASK | 311 | 1.500 |
| 48 | 127 | ILGQIVLVVL | 312 | 1.350 |
| 49 | 284 | AVSGCVFAIF | 313 | 1.350 |
| 50 | 140 | YTSLNPIWSY | 314 | 1.350 |

TABLE XI

HLA Peptide Scoring Results - 125P5C8 A11 9-mers

| Rank | Start Position | Subsequence Residue Listing | SEQ ID NO: | Score (Estimate of Half Time of Disassociation of a Molecule Containing This Subsequence) |
|---|---|---|---|---|
| 1 | 383 | KYLFRKSEK | 315 | 9.000 |
| 2 | 413 | KAYERKLGK | 316 | 2.400 |
| 3 | 54 | FLTITPFWK | 317 | 1.200 |
| 4 | 418 | KLGKVAPTK | 318 | 1.200 |
| 5 | 361 | GLNMLFGPK | 319 | 1.200 |
| 6 | 559 | KLQAIAVSK | 320 | 1.200 |
| 7 | 506 | ALSRYPIVK | 321 | 0.800 |
| 8 | 562 | AIAVSKLLK | 322 | 0.800 |
| 9 | 338 | FVPGGVYAR | 323 | 0.800 |
| 10 | 619 | GLIRLGYAR | 324 | 0.720 |
| 11 | 463 | TILESDASK | 325 | 0.600 |
| 12 | 129 | GQIVLVVLR | 326 | 0.540 |
| 13 | 409 | GLRHKAYER | 327 | 0.480 |
| 14 | 371 | NLDLLLQTK | 328 | 0.400 |
| 15 | 532 | TLTVNISGK | 329 | 0.400 |
| 16 | 375 | LLQTKNSSK | 330 | 0.400 |
| 17 | 58 | TPFWKLVNK | 331 | 0.400 |
| 18 | 593 | QLTEHGNVK | 332 | 0.400 |
| 19 | 614 | YIMYRGLIR | 333 | 0.320 |
| 20 | 329 | FCAWCTAFK | 334 | 0.200 |

TABLE XI -continued

| | | HLA Peptide Scoring Results - 125P5C8 A11 9-mers | | |
|---|---|---|---|---|
| Rank | Start Position | Subsequence Residue Listing | SEQ ID NO: | Score (Estimate of Half Time of Disassociation of a Molecule Containing This Subsequence) |
| 21 | 490 | YTDFGPSTR | 335 | 0.200 |
| 22 | 250 | MLPSCLWFR | 336 | 0.160 |
| 23 | 314 | KTMTIAMIF | 337 | 0.120 |
| 24 | 402 | GVGLLGLGL | 338 | 0.120 |
| 25 | 655 | NQKVVIDHR | 339 | 0.120 |
| 26 | 478 | DLTMWLGEK | 340 | 0.120 |
| 27 | 354 | GTMMLIIGL | 341 | 0.120 |
| 28 | 184 | EVATGMASR | 342 | 0.120 |
| 29 | 649 | PTNYRDNQK | 343 | 0.100 |
| 30 | 154 | KVILTLSAI | 344 | 0.090 |
| 31 | 581 | YITSAPGSR | 345 | 0.080 |
| 32 | 362 | LNMLFGPKK | 346 | 0.080 |
| 33 | 205 | LVFLTHWVF | 347 | 0.080 |
| 34 | 380 | NSSKVLFRK | 348 | 0.060 |
| 35 | 172 | GDCSKPEEK | 349 | 0.060 |
| 36 | 284 | AVSGCVFAI | 350 | 0.060 |
| 37 | 84 | FQAPNAKLR | 351 | 0.060 |
| 38 | 173 | DCSKPEEKK | 352 | 0.060 |
| 39 | 550 | GNHEDDLDR | 353 | 0.048 |
| 40 | 66 | KKWMLTLLR | 354 | 0.048 |
| 41 | 379 | KNSSKVLFR | 355 | 0.048 |
| 42 | 92 | RLMVLALGV | 356 | 0.048 |
| 43 | 391 | KYMKLFLWL | 357 | 0.048 |
| 44 | 316 | MTIAMIFYL | 358 | 0.045 |
| 45 | 688 | HHFHMNTPK | 359 | 0.040 |
| 46 | 386 | FRKSEKYMK | 360 | 0.040 |
| 47 | 671 | FNPRFGSYK | 361 | 0.040 |
| 48 | 405 | LLGLGLRHK | 362 | 0.040 |
| 49 | 400 | LVGVGLLGL | 363 | 0.040 |
| 50 | 306 | INSGTNPGK | 364 | 0.040 |

TABLE XII

| | | | | Score (Estimate of Half Time of Disassociation of a Molecule Containing This Subsequence) |
|---|---|---|---|---|
| Rank | Start Position | Subsequence Residue Listing | SEQ ID NO: | |
| 1 | 462 | ITILESDASK | 365 | 1.500 |
| 2 | 531 | ITLTVNISGK | 366 | 1.500 |
| 3 | 409 | GLRHKAYERK | 367 | 1.200 |
| 4 | 361 | GLNMLFGPKK | 368 | 1.200 |
| 5 | 402 | GVGLLGLGLR | 369 | 1.200 |
| 6 | 167 | RIGTDGDCSK | 370 | 1.200 |
| 7 | 57 | ITPFWKLVNK | 371 | 1.000 |
| 8 | 53 | IFLTITPFWK | 372 | 0.900 |
| 9 | 592 | LQLTEHGNVK | 373 | 0.900 |
| 10 | 500 | HTWGIMALSR | 374 | 0.800 |
| 11 | 374 | LLLQTKNSSK | 375 | 0.600 |
| 12 | 561 | QAIAVSKLLK | 376 | 0.600 |
| 13 | 505 | MALSRYPIVK | 377 | 0.600 |
| 14 | 305 | LINSGTNPGK | 378 | 0.400 |
| 15 | 58 | TPFWKLVNKK | 379 | 0.400 |
| 16 | 659 | VIDHREVSEK | 380 | 0.400 |
| 17 | 385 | LFRKSEKYMK | 381 | 0.400 |
| 18 | 379 | KNSSKVLFRK | 382 | 0.360 |
| 19 | 337 | KFVPGGVYAR | 383 | 0.360 |
| 20 | 580 | GYITSAPGSR | 384 | 0.360 |
| 21 | 249 | LMLPSCLWFR | 385 | 0.240 |
| 22 | 644 | RIPDDPTNYR | 386 | 0.240 |
| 23 | 670 | HFNPRFGSYK | 387 | 0.200 |
| 24 | 328 | FFCAWCTAFK | 388 | 0.200 |
| 25 | 81 | IASFQAPNAK | 389 | 0.200 |
| 26 | 370 | KNLDLLLQTK | 390 | 0.180 |
| 27 | 404 | GLLGLGLRHK | 391 | 0.180 |
| 28 | 158 | TLSAIATLDR | 392 | 0.160 |
| 29 | 550 | GNHEDDLDRK | 393 | 0.120 |
| 30 | 342 | GVYARERSDV | 394 | 0.120 |
| 31 | 427 | EVSAAIWPFR | 395 | 0.120 |
| 32 | 314 | KTMTIAMIFY | 396 | 0.120 |
| 33 | 558 | RKLQAIAVSK | 397 | 0.090 |
| 34 | 417 | RKLGKVAPTK | 398 | 0.090 |
| 35 | 383 | KVLFRKSEKY | 399 | 0.090 |
| 36 | 154 | KVILTLSAIA | 400 | 0.090 |

TABLE XII-continued

HLA Peptide Scoring Results - 125P5C8 A11 10-mers

| Rank | Start Position | Subsequence Residue Listing | SEQ ID NO: | Score (Estimate of Half Time of Disassociation of a Molecule Containing This Subsequence) |
|---|---|---|---|---|
| 37 | 145 | PIWSYQMSNK | 401 | 0.080 |
| 38 | 489 | FYTDFGPSTR | 402 | 0.080 |
| 39 | 613 | EYIMYRGLIR | 403 | 0.072 |
| 40 | 172 | GDCSKPEEKK | 404 | 0.060 |
| 41 | 268 | GTASAAGLLY | 405 | 0.060 |
| 42 | 421 | KVAPTKEVSA | 406 | 0.060 |
| 43 | 131 | IVLVVLRIWY | 407 | 0.060 |
| 44 | 648 | DPTNYRDNQK | 408 | 0.060 |
| 45 | 99 | GVSSSLIVQA | 409 | 0.060 |
| 46 | 309 | GTNPGKTMTI | 410 | 0.060 |
| 47 | 129 | GQIVLVVLRI | 411 | 0.054 |
| 48 | 119 | RYLRIWGFIL | 412 | 0.054 |
| 49 | 183 | GEVATGMASR | 413 | 0.054 |
| 50 | 248 | GLMLPSCLWF | 414 | 0.048 |

TABLE XIII

HLA Peptide Scoring Results - 125P5C8 A24 9-mers

| Rank | Start Position | Subsequence Residue Listing | SEQ ID NO: | Score (Estimate of Half Time of Disassociation of a Molecule Containing This Subsequence) |
|---|---|---|---|---|
| 1 | 391 | KYMKLFLWL | 415 | 864.000 |
| 2 | 29 | IYYFPLQTL | 416 | 240.000 |
| 3 | 119 | RYLRIWGFI | 417 | 210.000 |
| 4 | 148 | SYQMSNKVI | 418 | 75.000 |
| 5 | 613 | EYIMYRGLI | 419 | 75.000 |
| 6 | 21 | LYHDLGPMI | 420 | 72.000 |
| 7 | 31 | YFPLQTLEL | 421 | 33.000 |
| 8 | 83 | SFQAPNAKL | 422 | 33.000 |
| 9 | 125 | GFILGQIVL | 423 | 30.000 |
| 10 | 548 | HFGNHEDDL | 424 | 20.000 |
| 11 | 62 | KLVNKKWML | 425 | 12.000 |
| 12 | 321 | IFYLLEIFF | 426 | 12.000 |
| 13 | 328 | FFCAWCTAF | 427 | 10.000 |
| 14 | 498 | RYHTWGIMA | 428 | 10.000 |
| 15 | 471 | KPYMGNNDL | 429 | 9.600 |

TABLE XIII-continued

HLA Peptide Scoring Results - 125P5C8 A24 9-mers

| Rank | Start Position | Subsequence Residue Listing | SEQ ID NO: | Score (Estimate of Half Time of Disassociation of a Molecule Containing This Subsequence) |
|---|---|---|---|---|
| 16 | 533 | LTVNISGKL | 430 | 9.240 |
| 17 | 475 | GNNDLTMWL | 431 | 8.640 |
| 18 | 314 | KTMTIAMIF | 432 | 8.400 |
| 19 | 96 | LALGVSSSL | 433 | 8.400 |
| 20 | 151 | MSNKVILTL | 434 | 8.400 |
| 21 | 397 | LWLLVGVGL | 435 | 8.400 |
| 22 | 561 | QAIAVSKLL | 436 | 8.400 |
| 23 | 128 | LGQIVLVVL | 437 | 8.400 |
| 24 | 414 | AYERKLGKV | 438 | 8.250 |
| 25 | 90 | KLRLMVLAL | 439 | 8.000 |
| 26 | 55 | LTITPFWKL | 440 | 7.920 |
| 27 | 479 | LTMWLGEKL | 441 | 7.920 |
| 28 | 276 | LYLHTWAAA | 442 | 7.500 |
| 29 | 580 | GYITSAPGS | 443 | 7.500 |
| 30 | 322 | FYLLEIFFC | 444 | 7.500 |
| 31 | 247 | SGLMLPSCL | 445 | 7.200 |
| 32 | 445 | SSLERSAHL | 446 | 7.200 |
| 33 | 357 | MLIIGLNML | 447 | 7.200 |
| 34 | 241 | VLLCLASGL | 448 | 7.200 |
| 35 | 354 | GTMMLIIGL | 449 | 7.200 |
| 36 | 317 | TIAMIFYLL | 450 | 6.720 |
| 37 | 85 | QAPNAKLRL | 451 | 6.000 |
| 38 | 388 | KSEKYMKLF | 452 | 6.000 |
| 39 | 584 | SAPGSRDYL | 453 | 6.000 |
| 40 | 243 | LCLASGLML | 454 | 6.000 |
| 41 | 149 | YQMSNKVIL | 455 | 6.000 |
| 42 | 26 | GPMIYYFPL | 456 | 6.000 |
| 43 | 297 | MWPQTLGHL | 457 | 6.000 |
| 44 | 366 | FGPKKNLDL | 458 | 6.000 |
| 45 | 157 | LTLSAIATL | 459 | 6.000 |
| 46 | 350 | DVLLGTMML | 460 | 6.000 |
| 47 | 489 | FYTDFGPST | 461 | 6.000 |
| 48 | 691 | HMNTPKYFL | 462 | 6.000 |
| 49 | 210 | HWVFGEVSL | 463 | 6.000 |
| 50 | 139 | WYTSLNPIW | 464 | 6.000 |

TABLE XIV

| | | HLA Peptide Scoring Results - 125P5C8 A24 10-mers | | |
|---|---|---|---|---|
| Rank | Start Position | Subsequence Residue Listing | SEQ ID NO: | Score (Estimate of Half Time of Disassociation of a Molecule Containing This Subsequence) |
| 1 | 391 | KYMKLFLWLL | 465 | 600.000 |
| 2 | 119 | RYLRIWGFIL | 466 | 600.000 |
| 3 | 498 | RYHTWGIMAL | 467 | 400.000 |
| 4 | 148 | SYQMSNKVIL | 468 | 300.000 |
| 5 | 30 | YYFPLQTLEL | 469 | 264.000 |
| 6 | 624 | GYARISHAEL | 470 | 220.000 |
| 7 | 343 | VYARERSDVL | 471 | 200.000 |
| 8 | 438 | GYDNEGWSSL | 472 | 200.000 |
| 9 | 651 | NYRDNQKVVI | 473 | 60.000 |
| 10 | 683 | NYENNHHFHM | 474 | 37.500 |
| 11 | 365 | LFGPKKNLDL | 475 | 24.000 |
| 12 | 559 | KLQAIAVSKL | 476 | 13.200 |
| 13 | 322 | FYLLEIFFCA | 477 | 12.600 |
| 14 | 48 | AFLSPIFLTI | 478 | 12.600 |
| 15 | 388 | KSEKYMKLFL | 479 | 12.000 |
| 16 | 316 | MTIAMIFYLL | 480 | 10.080 |
| 17 | 540 | KLVDFVVTHF | 481 | 10.080 |
| 18 | 689 | HFHMNTPKYF | 482 | 10.000 |
| 19 | 327 | IFFCAWCTAF | 483 | 10.000 |
| 20 | 414 | AYERKLGKVA | 484 | 9.000 |
| 21 | 12 | SLLGCVSWSL | 485 | 8.400 |
| 22 | 570 | KSSSNQVIFL | 486 | 8.000 |
| 23 | 590 | DYLQLTEHGN | 487 | 7.500 |
| 24 | 276 | LYLHTWAAAV | 488 | 7.500 |
| 25 | 401 | VGVGLLGLGL | 489 | 7.200 |
| 26 | 445 | SSLERSAHLL | 490 | 7.200 |
| 27 | 474 | MGNNDLTMWL | 491 | 7.200 |
| 28 | 187 | TGMASRPNWL | 492 | 7.200 |
| 29 | 233 | DPNPFGGAVL | 493 | 7.200 |
| 30 | 240 | AVLLCLASGL | 494 | 7.200 |
| 31 | 356 | MMLIIGLNML | 495 | 7.200 |
| 32 | 616 | MYRGLIRLGY | 496 | 7.000 |
| 33 | 677 | SYKEGHNYEN | 497 | 6.600 |
| 34 | 532 | TLTVNISGKL | 498 | 6.160 |
| 35 | 614 | YIMYRGLIRL | 499 | 6.000 |
| 36 | 611 | WCEYIMYRGL | 500 | 6.000 |

TABLE XIV -continued

HLA Peptide Scoring Results - 125P5C8 A24 10-mers

| Rank | Start Position | Subsequence Residue Listing | SEQ ID NO: | Score (Estimate of Half Time of Disassociation of a Molecule Containing This Subsequence) |
|---|---|---|---|---|
| 37 | 363 | NMLFGPKKNL | 501 | 6.000 |
| 38 | 510 | YPIVKSEHHL | 502 | 6.000 |
| 39 | 63 | LVNKKWMLTL | 503 | 6.000 |
| 40 | 21 | LYHDLGPMIY | 504 | 6.000 |
| 41 | 399 | LLVGVGLLGL | 505 | 6.000 |
| 42 | 397 | LWLLVGVGLL | 506 | 6.000 |
| 43 | 134 | VVLRIWYTSL | 507 | 6.000 |
| 44 | 366 | FGPKKNLDLL | 508 | 6.000 |
| 45 | 524 | EGEIAPAITL | 509 | 6.000 |
| 46 | 25 | LGPMIYYFPL | 510 | 6.000 |
| 47 | 253 | SCLWFRGTGL | 511 | 6.000 |
| 48 | 41 | GLEGFSIAFL | 512 | 6.000 |
| 49 | 4 | LWREILLESL | 513 | 5.760 |
| 50 | 127 | ILGQIVLVVL | 514 | 5.600 |

TABLE XV

HLA Peptide Scoring Results - 125P5C8 B7 9-mers

| Rank | Start Position | Subsequence Residue Listing | SEQ ID NO: | Score (Estimate of Half Time of Disassociation of a Molecule Containing This Subsequence) |
|---|---|---|---|---|
| 1 | 26 | GPMIYYFPL | 515 | 240.000 |
| 2 | 344 | YARERSDVL | 516 | 120.000 |
| 3 | 625 | YARISHAEL | 517 | 120.000 |
| 4 | 367 | GPKKNLDLL | 518 | 80.000 |
| 5 | 235 | NPFGGAVLL | 519 | 80.000 |
| 6 | 471 | KPYMGNNDL | 520 | 80.000 |
| 7 | 86 | APNAKLRLM | 521 | 60.000 |
| 8 | 90 | KLRLMVLAL | 522 | 40.000 |
| 9 | 120 | YLRIWGFIL | 523 | 40.000 |
| 10 | 135 | VLRIWYTSL | 524 | 40.000 |
| 11 | 200 | AAFGSLVFL | 525 | 36.000 |
| 12 | 402 | GVGLLGLGL | 526 | 20.000 |
| 13 | 350 | DVLLGTMML | 527 | 20.000 |
| 14 | 400 | LVGVGLLGL | 528 | 20.000 |
| 15 | 512 | IVKSEHHLL | 529 | 20.000 |
| 16 | 189 | MASRPNWLL | 530 | 18.000 |

TABLE XV-continued

HLA Peptide Scoring Results - 125P5C8 B7 9-mers

| Rank | Start Position | Subsequence Residue Listing | SEQ ID NO: | Score (Estimate of Half Time of Disassociation of a Molecule Containing This Subsequence) |
|---|---|---|---|---|
| 17 | 584 | SAPGSRDYL | 531 | 18.000 |
| 18 | 270 | ASAAGLLYL | 532 | 12.000 |
| 19 | 85 | QAPNAKLRL | 533 | 12.000 |
| 20 | 197 | LAGAAFGSL | 534 | 12.000 |
| 21 | 47 | IAFLSPIFL | 535 | 12.000 |
| 22 | 561 | QAIAVSKLL | 536 | 12.000 |
| 23 | 354 | GTMMLIIGL | 537 | 12.000 |
| 24 | 294 | TASMWPQTL | 538 | 12.000 |
| 25 | 149 | YQMSNKVIL | 539 | 12.000 |
| 26 | 479 | LTMWLGEKL | 540 | 12.000 |
| 27 | 96 | LALGVSSSL | 541 | 12.000 |
| 28 | 88 | NAKLRLMVL | 542 | 12.000 |
| 29 | 298 | WPQTLGHLI | 543 | 8.000 |
| 30 | 55 | LTITPFWKL | 544 | 6.000 |
| 31 | 691 | HMNTPKYFL | 545 | 6.000 |
| 32 | 1 | MTSLWREIL | 546 | 6.000 |
| 33 | 364 | MLFGPKKNL | 547 | 6.000 |
| 34 | 284 | AVSGCVFAI | 548 | 6.000 |
| 35 | 423 | APTKEVSAA | 549 | 6.000 |
| 36 | 64 | VNKKWMLTL | 550 | 4.000 |
| 37 | 392 | YMKLFLWLL | 551 | 4.000 |
| 38 | 254 | CLWFRGTGL | 552 | 4.000 |
| 39 | 2 | TSLWREILL | 553 | 4.000 |
| 40 | 366 | FGPKKNLDL | 554 | 4.000 |
| 41 | 571 | SSSNQVIFL | 555 | 4.000 |
| 42 | 151 | MSNKVILTL | 556 | 4.000 |
| 43 | 109 | VTWWSGSHL | 557 | 4.000 |
| 44 | 357 | MLIIGLNML | 558 | 4.000 |
| 45 | 620 | LIRLGYARI | 559 | 4.000 |
| 46 | 237 | FGGAVLLCL | 560 | 4.000 |
| 47 | 34 | LQTLELTGL | 561 | 4.000 |
| 48 | 128 | LGQIVLVVL | 562 | 4.000 |
| 49 | 268 | GTASAAGLL | 563 | 4.000 |
| 50 | 316 | MTIAMIFYL | 564 | 4.000 |

TABLE XVI

| | | | | Score (Estimate of Half Time of Disassociation of a Molecule Containing This Subsequence) |
|---|---|---|---|---|
| Rank | Start Position | Subsequence Residue Listing | SEQ ID NO: | |
| 1 | 585 | APGSRDYLQL | 565 | 240.000 |
| 2 | 344 | YARERSDVLL | 566 | 120.000 |
| 3 | 510 | YPIVKSEHHL | 567 | 80.000 |
| 4 | 367 | GPKKNLDLLL | 568 | 80.000 |
| 5 | 233 | DPNPFGGAVL | 569 | 80.000 |
| 6 | 108 | AVTWWSGSHL | 570 | 60.000 |
| 7 | 240 | AVLLCLASGL | 571 | 60.000 |
| 8 | 528 | APAITLTVNI | 572 | 24.000 |
| 9 | 423 | APTKEVSAAI | 573 | 24.000 |
| 10 | 134 | VVLRIWYTSL | 574 | 20.000 |
| 11 | 311 | NPGKTMTIAM | 575 | 20.000 |
| 12 | 16 | CVSWSLYHDL | 576 | 20.000 |
| 13 | 63 | LVNKKWMLTL | 577 | 20.000 |
| 14 | 86 | APNAKLRLMV | 578 | 18.000 |
| 15 | 82 | ASFQAPNAKL | 579 | 18.000 |
| 16 | 187 | TGMASRPNWL | 580 | 12.000 |
| 17 | 246 | ASGLMLPSCL | 581 | 12.000 |
| 18 | 269 | TASAAGLLYL | 582 | 12.000 |
| 19 | 199 | GAAFGSLVFL | 583 | 12.000 |
| 20 | 614 | YIMYRGLIRL | 584 | 12.000 |
| 21 | 496 | STRYHTWGIM | 585 | 10.000 |
| 22 | 188 | GMASRPNWLL | 586 | 6.000 |
| 23 | 363 | NMLFGPKKNL | 587 | 6.000 |
| 24 | 28 | MIYYFPLQTL | 588 | 6.000 |
| 25 | 583 | TSAPGSRDYL | 589 | 6.000 |
| 26 | 54 | FLTITPFWKL | 590 | 6.000 |
| 27 | 288 | CVFAIFTASM | 591 | 5.000 |
| 28 | 560 | LQAIAVSKLL | 592 | 4.000 |
| 29 | 353 | LGTMMLIIGL | 593 | 4.000 |
| 30 | 4 | LWREILLESL | 594 | 4.000 |
| 31 | 1 | MTSLWREILL | 595 | 4.000 |
| 32 | 84 | FQAPNAKLRL | 596 | 4.000 |
| 33 | 253 | SCLWFRGTGL | 597 | 4.000 |
| 34 | 242 | LLCLASGLML | 598 | 4.000 |
| 35 | 570 | KSSSNQVIFL | 599 | 4.000 |
| 36 | 399 | LLVGVGLLGL | 600 | 4.000 |

TABLE XVI -continued

HLA Peptide Scoring Results 125P5C8 B7 10-mers

| Rank | Start Position | Subsequence Residue Listing | SEQ ID NO: | Score (Estimate of Half Time of Disassociation of a Molecule Containing This Subsequence) |
|---|---|---|---|---|
| 37 | 293 | FTASMWPQTL | 601 | 4.000 |
| 38 | 396 | FLWLLVGVGL | 602 | 4.000 |
| 39 | 127 | ILGQIVLVVL | 603 | 4.000 |
| 40 | 266 | VTGTASAAGL | 604 | 4.000 |
| 41 | 12 | SLLGCVSWSL | 605 | 4.000 |
| 42 | 532 | TLTVNISGKL | 606 | 4.000 |
| 43 | 376 | LQTKNSSKVL | 607 | 4.000 |
| 44 | 150 | QMSNKVILTL | 608 | 4.000 |
| 45 | 124 | WGFILGQIVL | 609 | 4.000 |
| 46 | 46 | SIAFLSPIFL | 610 | 4.000 |
| 47 | 366 | FGPKKNLDLL | 611 | 4.000 |
| 48 | 474 | MGNNDLTMWL | 612 | 4.000 |
| 49 | 112 | WSGSHLQRYL | 613 | 4.000 |
| 50 | 315 | TMTIAMIFYL | 614 | 4.000 |

TABLE XVII

HLA Peptide Scoring Results - 125P5C8 B35 9-mers

| Rank | Start Position | Subsequence Residue Listing | SEQ ID NO: | Score (Estimate of Half Time of Disassociation of a Molecule Containing This Subsequence) |
|---|---|---|---|---|
| 1 | 367 | GPKKNLDLL | 615 | 60.000 |
| 2 | 86 | APNAKLRLM | 616 | 40.000 |
| 3 | 471 | KPYMGNNDL | 617 | 40.000 |
| 4 | 229 | HPGPDPNPF | 618 | 30.000 |
| 5 | 26 | GPIYYFPL | 619 | 20.000 |
| 6 | 235 | NPFGGAVLL | 620 | 20.000 |
| 7 | 344 | YARERSDVL | 621 | 18.000 |
| 8 | 676 | GSYKEGHNY | 622 | 15.000 |
| 9 | 644 | RIPDDPTNY | 623 | 12.000 |
| 10 | 112 | WSGSHLQRY | 624 | 10.000 |
| 11 | 445 | SSLERSAHL | 625 | 10.000 |
| 12 | 494 | GPSTRYHTW | 626 | 10.000 |
| 13 | 583 | TSAPGSRDY | 627 | 10.000 |
| 14 | 141 | TSLNPIWSY | 628 | 10.000 |
| 15 | 570 | KSSSNQVIF | 629 | 10.000 |

TABLE XVII -continued

HLA Peptide Scoring Results - 125P5C8 B35 9-mers

| Rank | Start Position | Subsequence Residue Listing | SEQ ID NO: | Score (Estimate of Half Time of Disassociation of a Molecule Containing This Subsequence) |
|---|---|---|---|---|
| 16 | 88 | NAKLRLMVL | 630 | 9.000 |
| 17 | 625 | YARISHAEL | 631 | 9.000 |
| 18 | 298 | WPQTLGHLI | 632 | 8.000 |
| 19 | 181 | KTGEVATGM | 633 | 8.000 |
| 20 | 90 | KLRLMVLAL | 634 | 6.000 |
| 21 | 348 | RSDVLLGTM | 635 | 6.000 |
| 22 | 269 | TASAAGLLY | 636 | 6.000 |
| 23 | 17 | VSWSLYHDL | 637 | 5.000 |
| 24 | 2 | TSLWREILL | 638 | 5.000 |
| 25 | 270 | ASAAGLLYL | 639 | 5.000 |
| 26 | 571 | SSSNQVIFL | 640 | 5.000 |
| 27 | 285 | VSGCVFAIF | 641 | 5.000 |
| 28 | 151 | MSNKVILTL | 642 | 5.000 |
| 29 | 512 | IVKSEHHLL | 643 | 4.500 |
| 30 | 192 | RPNWLLAGA | 644 | 4.000 |
| 31 | 632 | ELSDSEIQM | 645 | 4.000 |
| 32 | 233 | DPNPFGGAV | 646 | 4.000 |
| 33 | 482 | WLGEKLGFY | 647 | 4.000 |
| 34 | 197 | LAGAAFGSL | 648 | 3.000 |
| 35 | 96 | LALGVSSSL | 649 | 3.000 |
| 36 | 330 | CAWCTAFKF | 650 | 3.000 |
| 37 | 520 | LPSPEGEIA | 651 | 3.000 |
| 38 | 423 | APTKEVSAA | 652 | 3.000 |
| 39 | 120 | YLRIWGFIL | 653 | 3.000 |
| 40 | 466 | ESDASKPYM | 654 | 3.000 |
| 41 | 64 | VNKKWMLTL | 655 | 3.000 |
| 42 | 85 | QAPNAKLRL | 656 | 3.000 |
| 43 | 392 | YMKLFLWLL | 657 | 3.000 |
| 44 | 561 | QAIAVSKLL | 658 | 3.000 |
| 45 | 587 | GSRDYLQLT | 659 | 3.000 |
| 46 | 377 | QTKNSSKVL | 660 | 3.000 |
| 47 | 388 | KSEKYMKLF | 661 | 3.000 |
| 48 | 294 | TASMWPQTL | 662 | 3.000 |
| 49 | 135 | VLRIWYTSL | 663 | 3.000 |
| 50 | 199 | GAAFGSLVF | 664 | 3.000 |

TABLE XVIII

| | | | | Score (Estimate of Half Time of Disassociation of a Molecule Containing This Subsequence) |
|---|---|---|---|---|
| Rank | Start Position | Subsequence Residue Listing | SEQ ID NO: | |
| 1 | 367 | GPKKNLDLLL | 665 | 60.000 |
| 2 | 311 | NPGKTMTIAM | 666 | 40.000 |
| 3 | 585 | APGSRDYLQL | 667 | 30.000 |
| 4 | 233 | DPNPFGGAVL | 668 | 20.000 |
| 5 | 510 | YPIVKSEHHL | 669 | 20.000 |
| 6 | 51 | SPIFLTITPF | 670 | 20.000 |
| 7 | 344 | YARERSDVLL | 671 | 18.000 |
| 8 | 19 | WSLYHDLGPM | 672 | 15.000 |
| 9 | 307 | NSGTNPGKTM | 673 | 10.000 |
| 10 | 445 | SSLERSAHLL | 674 | 10.000 |
| 11 | 572 | SSNQVIFLGY | 675 | 10.000 |
| 12 | 570 | KSSSNQVIFL | 676 | 10.000 |
| 13 | 528 | APAITLTVNI | 677 | 8.000 |
| 14 | 423 | APTKEVSAAI | 678 | 8.000 |
| 15 | 430 | AAIWPFRFGY | 679 | 6.000 |
| 16 | 496 | STRYHTWGIM | 680 | 6.000 |
| 17 | 348 | RSDVLLGTMM | 681 | 6.000 |
| 18 | 85 | QAPNAKLRLM | 682 | 6.000 |
| 19 | 428 | VSAAIWPFRF | 683 | 5.000 |
| 20 | 45 | FSIAFLSPIF | 684 | 5.000 |
| 21 | 246 | ASGLMLPSCL | 685 | 5.000 |
| 22 | 583 | TSAPGSRDYL | 686 | 5.000 |
| 23 | 444 | WSSLERSAHL | 687 | 5.000 |
| 24 | 112 | WSGSHLQRYL | 688 | 5.000 |
| 25 | 829 | ASFQAPNAKL | 689 | 5.000 |
| 26 | 176 | KPEEKKTGEV | 690 | 4.800 |
| 27 | 383 | KVLFRKSEKY | 691 | 4.000 |
| 28 | 471 | KPYMGNNDLT | 692 | 4.000 |
| 29 | 314 | KTMTIAMIFY | 693 | 4.000 |
| 30 | 540 | KLVDFVVTHF | 694 | 4.000 |
| 31 | 86 | APNAKLRLMV | 695 | 4.000 |
| 32 | 192 | RPNWLLAGAA | 696 | 4.000 |
| 33 | 281 | WAAAVSGCVF | 697 | 3.000 |
| 34 | 117 | LQRYLRIWGF | 698 | 3.000 |
| 35 | 377 | QTKNSSKVLF | 699 | 3.000 |
| 36 | 199 | GAAFGSLVFL | 700 | 3.000 |

TABLE XVIII -continued

HLA Peptide Scoring Results - 125P5C8 B35 10-mers

| Rank | Start Position | Subsequence Residue Listing | SEQ ID NO: | Score (Estimate of Half Time of Disassociation of a Molecule Containing This Subsequence) |
|---|---|---|---|---|
| 37 | 388 | KSEKYMKLFL | 701 | 3.000 |
| 38 | 64 | VNKKWMLTLL | 702 | 3.000 |
| 39 | 269 | TASAAGLLYL | 703 | 3.000 |
| 40 | 675 | FGSYKEGHNY | 704 | 3.000 |
| 41 | 102 | SSLIVQAVTW | 705 | 2.500 |
| 42 | 522 | SPEGEIAPAI | 706 | 2.400 |
| 43 | 413 | KAYERKLGKV | 707 | 2.400 |
| 44 | 131 | IVLVVLRIWY | 708 | 2.000 |
| 45 | 235 | NPFGGAVLLC | 709 | 2.000 |
| 46 | 355 | TMMLIIGLNM | 710 | 2.000 |
| 47 | 114 | GSHLQRYLRI | 711 | 2.000 |
| 48 | 298 | WPQTLGHLIN | 712 | 2.000 |
| 49 | 406 | LGLGLRHKAY | 713 | 2.000 |
| 50 | 582 | ITSAPGSRDY | 714 | 2.000 |

TABLE XIX

Motif-bearing Subsequences of the 125P5C8 Protein

| No | N terminal | transmembrane region | C terminal |
|---|---|---|---|
| 1 | 1 | MTSLWREILLESLLGCVSWSLYH | 23 |
| 2 | 42 | LEGFSIAFLSPIFLTTTPFWKLV | 64 |
| 3 | 94 | MVLALGVSSSLIVQAVTWWSGSH | 116 |
| 4 | 120 | YLRIWGFILGQIVLVVLRIWYTS | 142 |
| 5 | 189 | MASRPNWLLAGAAFGSLVFLTHW | 211 |
| 6 | 238 | GGAVLLCLASGLMLPSCLWFRGT | 260 |
| 7 | 269 | TASAAGLLYLHTWAAAVSGCVFA | 291 |
| 8 | 318 | LAMIFYLLEIFFCAWCTAFKFVP | 340 |
| 9 | 350 | DVLLGTMMLIIGLNMLFGP | 368 |
| 10 | 390 | EKYMKLFLWLLVGVGLLGLGLR | 411 |

TABLE XX

Frequently Occurring Motifs

| Name | av. % identity | Description | Potential Function |
|---|---|---|---|
| zf-C2H2 | 34% | Zinc finger, C2H2 type | Nucleic acid-binding protein functions as transcription factor, nuclear location probable |
| cytochrome_b_N | 68% | Cytochrome b(N-terminal)/b6/petB | membrane bound oxidase, generate superoxide |
| ig | 19% | Immunoglobulin domain | domains are one hundred amino acids long and include a conserved intradomain disulfide bond. |
| WD40 | 18% | WD domain, G-beta repeat | tandem repeats of about 40 residues, each containing a Trp-Asp motif. Function in signal transduction and protein interaction |

TABLE XX-continued

Frequently Occurring Motifs

| Name | av. % identity | Description | Potential Function |
| --- | --- | --- | --- |
| PDZ | 23% | PDZ domain | may function in targeting signaling molecules to sub-membranous sites |
| LRR | 28% | Leucine Rich Repeat | short sequence motifs involved in protein-protein interactions |
| pkinase | 23% | Protein kinase domain | conserved catalytic core common to both serine/threonine and tyrosine protein kinases containing an ATP binding site and a catalytic site |
| PH | 16% | PH domain | pleckstrin homology involved in intracellular signaling or as constituents of the cytoskeleton |
| EGF | 34% | EGF-like domain | 30-40 amino-acid long found in the extracellular domain of membrane-bound proteins or in secreted proteins |
| rvt | 49% | Reverse transcriptase (RNA-dependent DNA polymerase) | |
| ank | 25% | Ank repeat | Cytoplasmic protein, associates integral membrane proteins to the cytoskeleton |
| oxidored_q1 | 32% | NADH-Ubiquinone/plastoquinone (complex I), various chains | membrane associated. Involved in proton translocation across the membrane |
| efhand | 24% | EF hand | calcium-binding domain, consists of a12 residue loop flanked on both sides by a 12 residue alpha-helical domain |
| rvp | 79% | Retroviral aspartyl protease | Aspartyl or acid proteases, centered on a catalytic aspartyl residue |
| Collagen | 42% | Collagen triple helix repeat (20 copies) | extracellular structural proteins involved in formation of connective tissue. The sequence consists of the G-X-Y and the polypeptide chains forms a triple helix. |
| fn3 | 20% | Fibronectin type III domain | Located in the extracellular ligand-binding region of receptors and is about 200 amino acid residues long with two pairs of cysteines involved in disulfide bonds |
| 7tm_1 | 19% | 7 transmembrane receptor (rhodopsin family) | seven hydrophobic transmembrane regions, with the N-terminus located extracellularly while the C-terminus is cytoplasmic. Signal through G proteins |

The invention claimed is:

1. An isolated or purified antibody or fragment thereof that specifically binds to a protein comprising the amino acid sequence of SEQ ID NO:2.

2. The antibody or fragment thereof of claim 1, that binds to a portion of the protein, wherein the portion consists of amino acid residues 412-699 of SEQ ID NO:2.

3. The antibody or fragment thereof of claim 1, that binds to a portion of the protein, wherein the portion is selected from the group consisting of amino acid residues 24-41, 117-119, 212-237, 292-317, and 369-389 of SEQ ID NO: 2.

4. The antibody or fragment thereof of claim 1, which is monoclonal.

5. The antibody or fragment thereof of claim 1, which is labeled with a detectable marker.

6. The antibody or fragment thereof of claim 1, which is an Fab, F(ab')2, Fv or Sfv fragment.

7. The antibody or fragment thereof of claim 1, which is a human antibody.

8. The antibody or fragment thereof of claim 1, which is conjugated with a cytotoxic agent.

9. The antibody or fragment thereof of claim 8, wherein the cytotoxic agent is selected from the group consisting of radioactive isotopes, chemotherapeutic agents and toxins.

10. The antibody or fragment thereof of claim 9, wherein the radioactive isotope is selected from the group consisting of $^{211}$At, $^{131}$I, $^{125}$I, $^{90}$Y, $^{186}$Re, $^{188}$Re, $^{153}$Sm, $^{212}$Bi, $^{32}$P and radioactive isotopes of Lu.

11. The antibody or fragment thereof of claim 9, wherein the chemotherapeutic agent is selected from the group consisting of taxol, actinomycin, mitomycin, etoposide, tenoposide, vincristine, vinblastine, colchicine, gelonin, and calicheamicin.

12. The antibody or fragment thereof of claim 9, wherein the toxin is selected from the group consisting of diphtheria toxin, enomycin, phenomycin, Pseudomonas exotoxin (PE) A, PE40, abrin, abrin A chain, mitoge in, modeccin A chain, and alpha-sarcin.

13. The antibody or fragment thereof of any one of claim 1, wherein the antibody or fragment thereof further comprises a pharmaceutically acceptable carrier.

14. A hybridoma that produces an antibody of claim 4.

15. An isolated or purified single chain antibody, the variable domains of which comprise the heavy and light chains of the monoclonal antibody of claim 4.

* * * * *